US010017818B2

(12) United States Patent
Gromminger et al.

(10) Patent No.: US 10,017,818 B2
(45) **Date of Patent: *Jul. 10, 2018**

(54) MULTIPLEX DETECTION OF DNA THAT ORIGINATES FROM A SPECIFIC CELL-TYPE

(71) Applicant: LifeCodexx AG, Constance (DE)

(72) Inventors: Sebastian Gromminger, Constance (DE); Wera Hofmann, Constance (DE); Hamed Said, Constance (DE)

(73) Assignee: LifeCodexx AG, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/707,363

(22) Filed: May 8, 2015

(65) Prior Publication Data

US 2015/0322512 A1 Nov. 12, 2015

(30) Foreign Application Priority Data

May 9, 2014 (EP) .................................... 14167769

(51) Int. Cl.
*C12Q 1/68* (2018.01)
*C12Q 1/6881* (2018.01)
*C12Q 1/6883* (2018.01)

(52) U.S. Cl.
CPC ......... *C12Q 1/6881* (2013.01); *C12Q 1/6883* (2013.01); *C12Q 2600/118* (2013.01); *C12Q 2600/154* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 5,804,375 | A | 9/1998 | Gelfand et al. | |
| 5,994,056 | A | 11/1999 | Higuchi | |
| 6,200,756 | B1 | 3/2001 | Herman et al. | |
| 6,258,569 | B1 | 7/2001 | Livak et al. | |
| 6,331,393 | B1 | 12/2001 | Laird et al. | |
| 6,727,356 | B1 | 4/2004 | Reed et al. | |
| 6,929,907 | B2 | 8/2005 | Agris | |
| 2012/0252015 | A1* | 10/2012 | Hindson ............. | C12Q 1/6883 435/6.11 |

FOREIGN PATENT DOCUMENTS

| | | | |
|---|---|---|---|
| EP | 0 512 334 | B1 | 9/1999 |
| EP | 0 706 649 | B1 | 1/2001 |
| EP | 0 792 374 | B1 | 1/2001 |
| EP | 0 954 608 | B1 | 5/2006 |
| EP | 1 185 695 | B1 | 7/2006 |
| EP | 0 543 942 | B2 | 11/2006 |
| EP | 1 235 938 | B1 | 2/2012 |
| WO | 2005/118852 | A2 | 12/2005 |
| WO | 2007/132166 | A3 | 11/2007 |
| WO | 2007/132167 | A3 | 11/2007 |
| WO | 2010/033639 | A9 | 3/2010 |
| WO | 2011/018600 | A1 | 2/2011 |
| WO | 2011/034631 | A1 | 3/2011 |
| WO | 2012/092592 | A1 | 7/2012 |

OTHER PUBLICATIONS

Sperling et al., "Twin pregnancy: the role of ultrasound in management", Acta Obstet Gynecol Scand, 2001, vol. 80, pp. 287-299.

Sorenson et al., "Soluble Normal and Mutated DNA Sequences from Single-Copy Genes in Human Blood", Cancer Epidemiology, Biomarkers & Prevention, Jan./Feb. 1994, vol. 3, pp. 67-71.

Vasioukhin et al., "Point mutations of the N-ras gene in the blood plasma DNA of patients with myelodysplastic syndrome or acute myelogenous leukaemia", British Journal of Haematology, 1994, vol. 86, pp. 774-779.

Lo et al., "Presence of fetal DNA in maternal plasma and serum", The Lancet, Aug. 16, 1997, vol. 350, pp. 185-487.

Muller et al., "Methylated DNA as a possible screening marker for neoplastic disease in several body fluids", Expert Rev. Mol. Diagn., 2003, vol. 3(4), pp. 443-458.

Lo et al., "Quantitative Analysis of the Bidirectional Fetomatemal Transfer of Nucleated Cells and Plasma DNA", Clinical Chemistry, 2000, vol. 46:9, pp. 1301-1309.

Smid et al., "Correlation of fetal DNA levels in maternal plasma with Doppler status in pathological pregnancies", Prenat Diag, 2006, pp. 785-790.

Lo et al., "Rapid Clearance of Fetal DNA from Maternal Plasma", Am. J. Hum. Genet, 1999, vol. 64, pp. 218-224.

Kawai et al., "Methylation profiles of genomic DNA of mouse developmental brain detected by restriction landmark jenomic scanning (RLGS) method", Nucleic Acids Research, 1993, vol. 21:24, pp. 5604-5608.

(Continued)

*Primary Examiner* — James Martinell
(74) *Attorney, Agent, or Firm* — MH2 Technology Law Group, LLP

(57) ABSTRACT

The present invention relates to methods to detect an amount of DNA that originates from cells of a given type, where the sample comprising such DNA in admixture with DNA that does not originate from such cells. Such methods are based on different methylation, at certain regions, of the DNA that originates from the given type of cells compared to the admixed DNA. Such methods have particular application in the detection, from a biological fluid from a pregnant female, of cell free DNA that originates from a foetus or the placenta of a foetus, or the detection, from a biological fluid from an individual, of cell free DNA that originates from cells of a tumor. Accordingly, such methods have diagnostic, prognostic and/or predictive utility for detecting an increased risk of an individual suffering from or developing a medical condition such as preeclampsia or cancer, and/or to aid subsequent diagnostic, prognostic and/or predictive methods such as the detection of chromosomal trisomy in a foetus, including for twin-pregnancies. The present invention also relates to compositions, kits, computer program products and other aspects that are used in, useful for or related to the practice of such methods.

40 Claims, 3 Drawing Sheets

(56) References Cited

OTHER PUBLICATIONS

Masuzaki et al., "Detection of cell free placental DNA in maternal plasma: direct evidence from three cases of confined placental mosaicism", J. Med. Genet, 2004, vol. 41, pp. 289-292.
Flori et al., "Circulating cell-free fetal DNA in maternal serum appears to originate from cyto- and syncytio-trophoblastic cells. Case Report", Human Reproduction, Jan. 29, 2004, vol. 19:3, pp. 723-724.
Chim et al., "Detection of the placental epigenetic signature of the maspin gene in maternal plasma", Proc. Natl. Acad. Sci. USA, Oct. 11, 2005, vol. 102:41, pp. 14753-14758.
Chiu et al., "Hypermethylation of RASSF1A in Human and Rhesus Placentas", The American Journal of Pathology, Mar. 2007, vol. 170:3, pp. 941-950.
Old, et al., "Candidate epigenetic biomarkders for non-invasive prenatal diagnosis of Down syndrome", Reproductive BioMedicine Online, Jun. 21, 2007, vol. 15:2, pp. 227-235.
Chim et al., "Systematic Search for Placental DNA-Methylation Markers on Chromosome 21: Toward a Maternal Plasma-Based Epigenetic Test for Fetal Trisomy 21", Clinical Chemistry, 2008, vol. 54:3, pp. 500-511.
Lo et al., "Prenatal Diagnosis of Fetal RhD Status by Molecular Analysis of Maternal Plasma", The New England Journal of Medicine, Dec. 10, 1998, vol. 339, pp. 1734-1738.
Go et al., "Non-invasive aneuploidy detection using free fetal DNA and RNA in maternal plasma: recent progress and future possibilities", Human Reproduction update, 2011, vol. 17:3, pp. 372-382.
Lo et al., "Quantitative Analysis of Fetal DNA in Maternal Plasma and Serum: Implications for Noninvasive Prenatal Diagnosis", Am. J. Hum. Genet., 1998, vol. 62, pp. 768-775.
Lo et al., "Quantitative Abnormalities of Fetal DNA in Maternal Serum in Preeclampsia", Clinical Chemistry, 1999, vol. 45:2, pp. 184-188.
Yu et al., "Quantification of Maternal Serum Cell-Free Fetal DNA in Early-Onset Preeclampsia", Int. J. Mol. Sci, Apr. 8, 2013, vol. 4, pp. 7571-7582.
Hahn et al., "Cell-Free Nucleic Acids as Potential Markers for Preeclampsia", Placenta, 2011, vol. 32, pp. S17-S20.
Li et al., "Hypermethylation of multiple tumor-related genes associated with DMNT3b upregulation served as a biomarker for early diagnosis of esophageal squamous cell carcinoma", Epigenetics, Mar. 2011, vol. 6:3, pp. 307-316.
Ha et al., "Elevated Levels of Cell-Free Circulating DNA in Patients with Acute Dengue Virus Infection", PLoS One, Oct. 7, 2011, vol. 6:10, e25969, pp. 1-7.
Outinen et al., "Plasma Cell-Free DNA Levels Are Elevated in Acute Puumula Hantavirus Infection", PLoS One, Feb. 7, 2012, vol. 7:2, e31455, pp. 1-7.
Forsblom et al., "High Cell-Free DNA Predicts Fatal Outcome among *Staphylococcus aureus* Bacteraemia Patients with Intensive Care Unit Treatment", PloS One, Feb. 10, 2014, vol. 9:2, e87741, pp. 1-9.
Chan et al., "Size Distributions of Maternal and Fetal DNA in Maternal Plasma", Clinical Chemistry, 2004, vol. 50:1, pp. 88-92.
Kimura et al., "Fragment Size Analysis of Free Fetal DNA in Maternal Plasma Using Y-STR Loci and SRY Gene Amplification", Nagoya J. Med. Sci., 2011, vol. 73, pp. 129-135.
Lo et al., "Maternal Plasma DNA Sequencing Reveals the Genome-Wide Genetic and Mutational Profile of the Fetus", Science Translational Medicine, Dec. 8, 2010, vol. 2:61, 61ra91 pp. 1-14.
Elshimali et al., "The Clinical Utilization of Circulating Cell Free DNA (CCFDNA) in Blood of Cancer Patients", International Journal of Molecular Sciences, 2013, vol. 14, pp. 18925-18958.
Sacha Zeerleder, "The struggle to detect circulating DNA", Critical Care, 2006, vol. 10:142, pp. 1-3.
Kirsch et al., "An Improved Method for the Isolation of Free-Circulating Plasma DNA and Cell-Free DNA from Other Body Fluids", Ann. N.Y. Acad. Sci., 2008, vol. 1137, pp. 135-139.
Struble et al., "Fetal Fraction Estimate in Twin Pregnancies Using Directed Cell-Free DNA Analysis", Fetal Diagnosis and Therapy, Dec. 7, 2013, pp. 1-5.
Gauthier et al., "Blood Clearance Kinetics and Liver Uptake of Mononucleosomes in Mice", The Journal of Immunology, 1996, vol. 156, pp. 1151-1156.
Lo et al., "Quantitative Analysis of Aberrant p16 Methylation Using Real-Time Quantitative Methylation-specific Polymerase Chain Reaction", Cancer Research, Aug. 15, 1999, vol. 59, pp. 3899-3903.
Birch et al., "Accurate and Robust Quantification of Circulating Fetal and Total DNA in Maternal Plasma from 5-41 Weeks of Gestation", Clinical Chemistry, 2005, vol. 51:2, pp. 312-320.
Papageorgiou et al., "Fetal-specific DNA methylation ratio permits non-invasive prenatal diagnosis of trisomy 21", Nat. Med., Apr. 7, 2011, vol. 17:4, pp. 1-13.
Tong et al., "Technical concerns about immunoprecipitation of methylated fetal DNA for noninvasive trisomy 21 diagnosis", Nature Medicine, Sep. 2012, vol. 18:9, pp. 1327-1328.
Hindson et al., "High-Throughput Droplet Digital PCR System for Absolute Quantitation of DNA Copy Number", Anal. Chem., 2011, vol. 83, pp. 8604-8610.
White et al., "Evaluation of a Novel Assay for Detection of the Fetal Marker RASSF1A: Facilitating Improved Diagnostic Reliability of Noninvasive Prenatal Diagnosis", PLoS One, Sep. 14, 2012, vol. 7:9, e45073 pp. 1-5.
Qu et al., "Noninvasive Prenatal Determination of Twin Zygosity by Maternal Plasma DNA Analysis", Clinical Chemistry, 2013, vol. 59:2, pp. 427-435.
Lim et al., "Disease specific characteristics of fetal epigenetic markers for non-invasive prenatal testing of trisomy 21", BMC Medical Genomics, 2014, vol. 7:1, pp. 1-11.
Poon et al., "Differential DNA Methylation between Fetus and Mother as a Strategy for Detecting Fetal DNA in Maternal Plasma", Clinical Chemistry, 2002, vol. 48:1, pp. 35-41.
Yegnasubramanian et al., "Combination of methylated-DNA precipitation and methylation-sensitive restriction enzymes (COMPARE-MS) for the rapid, sensitive and quantitative detection of DNA methylation", Nucleic Acids Research, 2006, vol. 34:3, e19 pp. 1-14.
Papantoniou et al., "RASSF1A in maternal plasma as a molecular marker of preeclampsia", Prenatal Diagnosis, 2013, vol. 33, pp. 682-687.
Zeybek et al., "Clinical evaluations of cell-free fetal DNA quantities in pre-eclamptic pregnancies", J. Obstet Gynaecol Res., Mar. 2013, vol. 39:3, pp. 632-640.
Jakobsen et al., "Identifying mild and severe preeclampsia in asymptomatic pregnant women by levels of cell-free fetal DNA", Transfusion, Sep. 2013, vol. 53, pp. 1956-1964.
Chen et al., "Chimerism in Monochorionic Dizygotic Twins: Case Study and Review", Am. J. Med. Genet. Part A, May 22, 2013, vol. 161A, pp. 1817-1824.
Chan et al., "Hypermethylated RASSF1A in Maternal Plasma: A Universal Fetal DNA Marker that Improves the Reliability of Noninvasive Prenatal Diagnosis", Clinical Chemistry, 2006, vol. 52:12, pp. 2211-2218.
Stumm et al., "Diagnostice accuracy of random massively parallel sequencing for non-invasive prenatal detection of common autosomal aneuploidies: a collaborative study in Europe", Prenatal Diagnosis, 2014, vol. 34, pp. 185-191.
Leung et al., "Noninvasive twin zygosity assessment and aneuploidy detection by maternal plasma DNA sequencing", Prenatal Diagnosis, 2013, vol. 33, pp. 675-681.
Tong et al., "Noninvasive Prenatal Detection of Fetal Trisomy I8 by Epigenetic Allelic Ratio Analysis in Maternal Plasma: Theoretical and Empirical Considerations", Clinical Chemistry, 2006, vol. 52, No. 12, pp. 2194-2202.
Papageorgiou et al., "Sites of Differential DNA Methylation between Placenta and Peripheral Blood", The American Journal of Pathology, May 2009, vol. 174, No. 5, pp. 1609-1618.
He et al., "Development of a multiplex MethyLight assay for the detection of multigene methylation in human colorectal cancer", Cancer Genetics and Cytogenetics, Oct. 1, 2010, vol. 202:1, pp. 1-10.

(56) References Cited

OTHER PUBLICATIONS

Olkhov-Mitsel et al., "Novel Multiplex MethyLight Protocol for Detection of DNA Methylation in Patient Tissues and Bodily Fluids", Scientific Reports, Mar. 21, 2014, vol. 4: 4432, pp. 1-8.
Snellenberg et al., "Development of a multiplex methylation-specific PCR as candidate triage test for women with an HPV-positive cervical scrape", BMC Cancer, Nov. 23, 2012, vol. 12:551, pp. 1-10.
Nygren et al., "Quantification of Fetal DNA by Use of Methylation-Based DNA Discrimination", Clinical Chemistry, Aug. 20, 2010, vol. 56:10, pp. 1627-1635.
Campan et al., "MethyLight", DNA Methylation: methods and Protocols, Second Edition , 2009, vol. 57, pp. 325-337.
Swift-Scanalan et al., "Two-color quantitative multiplex methylation-specific PCR", ' BioTechniques, Feb. 1, 2006, vol. 40:2, pp. 210-219.
Weisenberger et al., "Analysis of repetitive element DNA methylation by MethyLight", Nucleic Acids Research, Dec. 2, 2005, vol. 33:21, pp. 6823-6836.
Weisenberger et al., "DNA methylation analysis by digital bisulfite genomic sequencing and digital MethyLight", Nucleic Acids Research, Aug. 1, 2008, vol. 36:14, pp. 4689-4698.

* cited by examiner

SEQUENCE LISTING

```
<160> NUMBER OF SEQ ID NOS: 199

<210> SEQ ID NO 1
<211> LENGTH: 20
<212> TYPE: DNA
<213> ORGANISM: Artificial Sequence
<220> FEATURE:
<223> OTHER INFORMATION: Primer
```

<400> SEQUENCE: 1
attgagctgc gggagctggc 20

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
tgccgtgtgg ggttgcac 18

<210> SEQ ID NO 3
<211> LENGTH: 15
<212> TYPE: DNA
<213> ORGANISM: Artificial Sequence
<220> FEATURE:
<223> OTHER INFORMATION: Probe

<400> SEQUENCE: 3
acccggctgg agcgt 15

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ggtcatccac caccaagaac 20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tgcccaagga tgctgtcaag 20

<210> SEQ ID NO 6
<211> LENGTH: 20
<212> TYPE: DNA
<213> ORGANISM: Artificial Sequence
<220> FEATURE:
<223> OTHER INFORMATION: Probe

<400> SEQUENCE: 6
gggcctcaat gacttcacgt 20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggtgcgaact cctctttgtc 20

<210> SEQ ID NO 8
<211> LENGTH: 20

<212> TYPE: DNA
<213> ORGANISM: Artificial Sequence
<220> FEATURE:
<223> OTHER INFORMATION: Primer

<400> SEQUENCE: 8
ttaatcaccc agcgcatggc 20

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
ccctcccggt gggtgataaa 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tgttcactgg aggactcatc 20

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
cagtccatga gggtgtttg 19

<210> SEQ ID NO 12
<211> LENGTH: 18
<212> TYPE: DNA
<213> ORGANISM: Artificial Sequence
<220> FEATURE:
<223> OTHER INFORMATION: Probe

<400> SEQUENCE: 12
gaggtcccat tctccttt 18

<210> SEQ ID NO 13
<211> LENGTH: 18151
<212> TYPE: DNA
<213> ORGANISM: Homo sapiens
<220> FEATURE:
<221> NAME/KEY: misc_feature
<223> OTHER INFORMATION: RASSF1

<400> SEQUENCE: 13
gacttggcgt ctgaggacag agtccagacc acaaggatct ggagctcagg agagactcgt 60
gggccacagc ccgagaaagc gctgggaatc caaatactat ggcgattggc agtcgcgtag 120
gcgaggcggg ctagagaccc gcccggattt aggcgcgagc cacctccagg ggcggggccc 180
aggccgcact gcgcaggcgc ggctaacccg tttccatggc tgcgagaact gacgctcccc 240
aaccgtcccg caactgtcct gtcccagact ttggcaccgt cggggtccgt cgtccccgaa 300
tgtgacagca tccccacccc ggctgctgcc caggatccgc cggaccccgg cctcgatatg 360

```
ggagacctgg aactgctgct gcccggggaa gctgaagtgc tggtgcgggg tctgcgcagc    420
ttcccgctac gcgagatggg ctccgaaggg tgaggcaccc gggtcaggcg gagtcccgga    480
gtcattgtcc ttgagtcggg gagctggggc ctgactcggg ggaggggctg cccagtgtgg    540
aggggctccc aaatgggggga gcagagcgtt ccgagacagg agtattactg ctcctgagcc    600
ccctgtgtcc cctcaggatc aggttaggct tcagtaggat ccagcccccca tccccactcc    660
taatgcacac acgtggacgc acatgcactt accctctgag gcaggtggaa ccagcagcat    720
gagaacctgg agaagctgaa catgcaagcc atcctcgatg ccacagtcag ccagggcgag    780
cccattcagg agctgctggt cacccatggg aaggtacccc gaggtcacag gcagggttcc    840
tgccttcccc catacctcac ctactctacc cctccggagt cccctgtgtg cccttcccct    900
ctggcctggt acacctgttc tccctgaagg acaaagagga atgtgttaca tgtttcattt    960
tgtatcccta ttggacagga ctctggcaca ccaggctggg tgcagggcat gagttgatta   1020
gggagaaagc tgtaggtcct agaacagctt aggcttcaag gggaaggccc aaatgctaaa   1080
ggcatctgtg aattgactgt aaggctggtg gtggggaagg ggtggggagg ggttggggag   1140
ggcgggaggg aggggagata acctaactgg aggtggaact tcggcatgga aggaagcagc   1200
cttcccaaca tgaaaggggg aagttagaaa ccagggagat gcctggctgg aacatggacc   1260
agggagtgtc accagcagat gacctgagat atcaattgac caaaaaaaaa aaaaaaaaag   1320
ccgggcatgg tagctcatgc ctgttatccc agcattttgg gaggccaaga cgggtggatc   1380
atctgaggtc aggagttcaa ggccagcctg gccaacatgg tgaaacccca cctctactaa   1440
aaatacaaaa atttgcagag catggtggtg cacacctgta atcccagcta ctcgggaggc   1500
tgaggcagga gaatcgcttg aacctgggag gcagaggtta cagagagcca agatcatgcc   1560
actgcactcc agcctgggtg acaagagtga aactccgtct caaaaaaaaa aaaaaaaaaa   1620
agaaaggtcc tttgcaaaag aaagatggaa ctcatactag gggataggat aggaacaggg   1680
cactgtgaag ggtcctgagt aggagtgagg ccaaggcaca caagagcttt ggaggaccac   1740
agacagggac tagagggagg gcatgaggag aagggctggc ttgaaaggga tgcctgaatg   1800
ggcgggcaga ggataagggt gcaggtgcag gcagggcaag gcagtctggg aactgggcag   1860
gagccagtca cataagcatg agggacatcc acagaggtgt tgggagcagc tggtaatgaa   1920
ggtccaaggt gcaagagaga agtcaggaag gatactcatg ggtctggaat agtttagggg   1980
cccagcagtg tttggggata tcagggttga gctgagccgg ggatgggagg gttgccaggc   2040
aaaggtaggc ccatctcatc cctgtccttt accctaccct tcaaaggtcc caacactggt   2100
ggaggagctg atcgcagtgg agatgtggaa gcagaaggtg ttccctgtgt tctgcagggt   2160
ggaggacttc aagccccaga acaccttccc catctacatg gtggtgagct gggcccctgg   2220
ttcatacctc ttctcactcc ttcagagggc tctggaccgg ggaggagagc tggtagcccc   2280
tatcccttcc tcaggccctg tccttctctt tatctgacag gtgcaccacg aggcctccat   2340
catcaacctc ttggagacag tgttcttcca caaggtgagg gactatctct gcccatgggc   2400
cacagttccg ggtcagggcc tggcaggaag ggagattgtg tctgtgtggg gaaggcatca   2460
gacacagaaa gtttccctcc tccttttccc aggaggtgtg tgagtcagca gaagacactg   2520
tcttggactt ggtagactat tgccaccgca aactgaccct gctggtggcc cagagtggct   2580
gtggtggccc ccctgagggg gagggatccc aggacagcaa ccccatgcag gtgggttgag   2640
gttacctagg gttgtgaaag cctaggtctg ggttccccaa ggcctgcgca ggtgagggtg   2700
```

-continued

```
gcccagcgtg aacactgtgt gacctcccag gagctgcaga agcaggcaga gctgatggaa   2760
tttgagattg cactgaaggc cctctcagta ctacgctaca tcacagactg tgtggacagg   2820
tgagcagtcc gactgggcct gggcctactg tggagggctg gaagaccggg cctgtagcct   2880
gcctctactc acctccttca caacgtccct gcccctagcc tctctctcag caccttgagc   2940
cgtatgctta gcacacacaa cctgccctgc ctcctggtgg aactgctgga gcatagtccc   3000
tggagccggc gggaaggagg tagggtcctc ccccaccagc ctaagcccca ggctactgct   3060
tcagggtatc tttttgatag aggggggcag cttgcacaca cgaagacaaa ccctgtcccc   3120
aagcccactg aggataccag gatgcctcag ccaaggttgg cctagacctg agctctgcag   3180
caggccaggc ccatgtgtcc actactgagg ctcaccctgc tctggggtca gcagccctat   3240
agcctgggca agtcctgcag cccaggttct cccattccca ggcagtggtc agtctcccag   3300
cccccacagc tggctcactt gaagagaatt caacgtctgc acccagtgtg ctggttcctc   3360
tccccaggca agctgcagca gttcgagggc agccgttggc atactgtggc cccctcagag   3420
cagcaaaagc tgagcaagtt ggacgggcaa gtgtggatcg ccctgtacaa cctgctgcta   3480
agccctgagg ctcaggcgcg ctactgcctc acaagttttg ccaagggacg gctactcaag   3540
gtcagactcc ctccgcacca gcccccacag ccccagtacc gccctcccca tcctaccccg   3600
actgcgtccc tgctgtttat ctttgcccac ccacctcaac cccagtgctc ttttcagtcc   3660
ttgggcctca ggtgacacac cagctagtgg gacatgggcc cccacaggca ttctcagccc   3720
aacccagccc cttccttttc cttggccccc tggccagcac ctgcatcaca ctggcctcca   3780
ctggacaccc ttgcagcttc gggccttcct cacagacaca ctgctggacc agctgcccaa   3840
cctggcccac ttgcagagtt tcctggccca tctgacccta actgaaaccc agcctcctaa   3900
gaaggacctg gtgttggaac aggtaggcac tggaaagtta gctgctcagg accactgtcc   3960
cactttacca gcaccttcct gccactctcc acttctctct cctagatccc agaaatctgg   4020
gagcggctgg agcgagaaaa cagaggcaag tggcaggcaa ttgccaagca ccagctccag   4080
catgtgttca gcccctcaga gcaggacctg cggctgcagg cgcgaaggta aggcctgtgg   4140
aaatggcagg gagggtggag gggatgcagg aggcatggat gtgggtgggg tgcccccacc   4200
ttccagggcc agtcagacct tcctgacttt cccccaggtg ggctgagacc tacaggctgg   4260
atgtgctaga ggcagtggct ccagagcggc cccgctgtgc ttactgcagt gcagaggctt   4320
ctaagcgctg ctcacgatgc cagaatgagt ggtattgctg caggtgaggg tatcctagaa   4380
ccttggacct ctaagcccta ctcccacatc ccccacatgc attgccatcc tcaataccca   4440
cctgcctgca gggagtgcca agtcaagcac tgggaaaagc atggaaagac ttgtgtcctg   4500
gcagcccagg gtgacagagc caaatgaggg ctgcagttgc tgagggccga ccacccatgc   4560
caagggaatc cacccagaat gcacccctga acctcaagat cacggtccag cctctgccgg   4620
agccccagtc tccgcagtgg agagcagagc gggcggtaaa gctgctgacc gatctccctc   4680
ctcctcaccc caagtgaagg ctcgagactt cctgccccac ccagtgggta ggccaagtgt   4740
gttgcttcag caaaccggac caggagggcc agggccggat gtggggaccc tcttcctcta   4800
gcacagtaaa gctggcctcc agaaacacgg gtatctccgc gtggtgcttt gcggtcgccg   4860
tcgttgtggc cgtccggggt ggggtgtgag gaggggacga aggagggaag gaagggcaag   4920
gcgggggggg ctctgcgaga gcgcgcccag ccccgccttc gggccccaca gtccctgcac   4980
ccaggtttcc attgcgcggc tctcctcagc tccttcccgc cgcccagtct ggatcctggg   5040
ggaggcgctg aagtcggggc ccgccctgtg gccccgcccg gcccgcgctt gctagcgccc   5100
```

```
aaagccagcg aagcacgggc ccaaccgggc catgtcgggg gagcctgagc tcattgagct   5160
gcgggagctg gcacccgctg ggcgcgctgg gaagggccgc acccggctgg agcgtgccaa   5220
cgcgctgcgc atcgcgcggg gcaccgcgtg caacccccaca cggcagctgg tccctggccg   5280
tggccaccgc ttccagcccg cggggcccgc cacgcacacg tggtgcgacc tctgtggcga   5340
cttcatctgg ggcgtcgtgc gcaaaggcct gcagtgcgcg cgtgagtagt ggccccgcgc   5400
gcctacgaga gcggaagggg cagccaaggg gcagcgcagt cgccgcgggt caagtcgcgg   5460
cagaggggt cggcggggac agctcccgag gactaggtcc gttactttcg ccccatcgct   5520
gaagagtgcg cgaaaatggt ttatcccttg tcgcactcca ctcgtatctg ggccacagat   5580
gagcagaggt ggctgcttat atgtaaaaat acgctgattt taagtttctt atctttaaaa   5640
tgccttggcc cttcttgaga aagggtttgt gcctactgtc ctcggagtcc atcttcccag   5700
gcttgcctct tctcaaacac tcatgacccc ctccagaacc tttagggtga agggaaatta   5760
ccacctatgg gagggagcct ggaaaaattt agaacctttg gtgggccccc tgcaagcagg   5820
agttttgttg agtctttatt tagcaaacac ccttttctga cccagtgaat cagatgctaa   5880
aatatgcacg cagccacaca cccagcagtc cttctgcacc cctgggaatc gccagcaagc   5940
aaaggttgct ctcccctggg tagacaccag ctggaatcac caggggtgct tttacagtcc   6000
tccccgctag cctggatccc accgcagacc tgttgaatca actgctggga gtggacccta   6060
ggcatcagta aattttaaaa actccccaaa ttattgtaac atggagtctg ggttgagcat   6120
cactgctctg gcctatttag gaacttgtgg atggatagtg tcccaggtct gtgtgtgcat   6180
ggagaccctc tcatccggta caagaggaca tcacaaattc agctgggggg agcacaaagt   6240
tgtgacagaa tgcaaagaat gaacaagggg ccgagcgcgg tggctcatgc ctgtaatccc   6300
agcacttcgg aaggcggagg cgggtggatc acctgaggtc aggagttcaa gaccagcctg   6360
gccaacatgg tgaaacctca tgtctactaa aaaataaaaa aaaatgagcc aggcgtagtg   6420
gcgggtgcct gtaatcccag ctactcggga ggctgaggtg ggagaattgc ttgaacacag   6480
gaggcggagg ttgcagtgag ccgagatcgt gccactgccc tccagccttg gcgacagagt   6540
gagactctgt ctcaaaaaaa aaaaaaaaaa aaaaaagaac aaggctggga cattgcagcg   6600
ttctcaaaga gaaataaagt agccatggag ataagaagca ggatgatttg ggcatgttta   6660
tcagaggtag agacaaggga gaaatcaaag ataagtttgg gcttttgtct ccagtaactg   6720
ggagcctagt ggccattttt gctgcaaaga ggaagctggg caagtgtagc agtgaggctg   6780
aagaaaaggg aattaaattt tggccatgtt cacttgaaac gtcttttaga catcctagtg   6840
aaggtactgg cacggaggat ctagtctgag ggtttaggtc agtgtttcag ccgtggatct   6900
ggggcagatg aatgtagaca gaccaggcca gtgatcagga ctgagcccag acttcatcgt   6960
gagatatgga agttgagtca gaatctgcaa aggagctgag caggagctgc agggggtagg   7020
aggaaaactg ggagagtgta gcccctggga gtcaaaggga gcaagcttca aatgatgctg   7080
agggggtgag aatggagaat ggaacactgg attccatttg gtagtacaca gatcgctgag   7140
gaccctgtcc cgggcagttt cctggaggaa gaggcaagcc tggctggagt gggtagaggg   7200
gagagtgaag gcgaaggatt agagtgtata gagaccagtg tcttggtctg aggggagtag   7260
agacaggtga caaccacagg gcagacgtag gttaaaggtg tttagttttt ccttcaagta   7320
aatgggcaga tgtattccat atacgttccc agtgaagggc cgggtgcggt ggctcaagcc   7380
tgtagtccca gcactttgga aggccgaggc gggtggatca cctgagatca ggagtttgag   7440
```

-continued

```
accagcctgg ctaacatggt gaaaccccgt ctctactaaa aatacaaaaa ttagctgggc   7500
atggtggcgg gcgcctgtaa tcctaggtac tcaggaggct gaggcagaag aatcgcttga   7560
acccaggagg cggaggttgc ggtgagccga aatcgcgcca ttgcactcca gcctgggtga   7620
caaaagcaag acgcagtttt ttgttgttgt ttttttaatt gccaatgagg aaaggggaag   7680
ttctgtgcta ggcgatagag atccaactgt tgagcaggcc tctctgcctg tggccttccg   7740
gccggtttcc agacgcccag gtggccaaca ttagagtccg cgtagcagtg tgaggtaacc   7800
cactgagata ggtcgggcct gcggagcctg gcgagcagcg gccctctccc tggggcttcc   7860
cttcaatctc cgggacattt ccccgacctg gagctcctcc gcctcaccgc caggcctctc   7920
tgcagattgc aagttcacct gccactaccg ctgccgcgcg ctcgtctgcc tggactgttg   7980
cgggccccgg gacctgggct gggaacccgc ggtggagcgg gacacgaacg tggtgagcgc   8040
ggggccgagg gcgtatggga agggcgagga tgggcaggcc acagtgcagg cattctcgag   8100
ggctgcctgg gtgccgcgcg caaggagcgt tctaattgcc gatttcccgg cggcacagag   8160
aggctaattc tgcgcggggg ctgggagggg agcctggatt gccggctccg caagtactcc   8220
acccgctgca agcggacccg ggcccaggct gacccaggct ccgcgcacgc gcacttcccg   8280
caccttcccg ccctcgcctc cggccagagg ccactcttgt gcgcttgccc ggacgctggc   8340
acccgccccc gttccctgtg gtaggtgggg tctgtgagtg gagctccgga gcgatgaggt   8400
cattcctggg ggcgaagcgt gcgtgtcccc gccccggcgt tcctgcccca atgagacaag   8460
agctagatcc cggcgatcta cgtttcagtc ttaacggttg cggcgcggct ctggcccggg   8520
cgcacgcgca cactgacacg cgtacacgca cgcacgcgac cggggcggtg gttggcggct   8580
acggacgcgc aggactgggg gacgggcggg tacggctatg ggcgaggcgg aggcgccttc   8640
tttcgaaatg acctggagca gcacgacgag cagtggctac tgcagccaag aggactcgga   8700
ctcggagctc gagcagtact tcaccgcgcg aacctcgcta gctcgcaggc cgcgccggga   8760
ccaggtggga gccagggggt gccggcgggc gggaggggaa gcggtcgctg gagctccgcc   8820
ctccccggtc cgttgccgcg tcctgggtcg gtgggcagcc ccaccctcct ggctacgtgg   8880
ctccccgcgg gtcctggccg gggacctgcc cgcggaaccg tgcgtaagac cccgattcca   8940
ccgcctagat gctgggtgcc ggggccccct tggtttctgt cacagacagg ttgaacacgg   9000
aaaaagcagc tgtatggctt gtggtagacc tgagccgggc attatccagc tatgactaaa   9060
gccgaccgag cagtttggac tagcacctcg atttccgcgt tcgaatgctc ctgctccctc   9120
cttggggaga ctaggggagg atgtggagag ggaagagtcc tcgccaggaa ttgagaagta   9180
tgtttaggaa aacttgagag gcagagagag atcctgctcc tccatctgca ctcctgtatg   9240
gagccagctg agccctcacc tcttccctgt tctggcctgt caccagctgc tggaatgtgg   9300
aagattctgt tcccttcctc tagggtggat ctggagaaag atttgggaat agataggaaa   9360
gaagtcttgt tttggaccat aagcattcag gagcacttta cccacaggaa gggggaaagc   9420
tagattataa aatgcctaaa gaggtggaaa aagagatcca ggttactaac ccaggactgt   9480
aaggtgtctc ggaacctcct aggtatcccc attatcggag aactgtgtgc cagatgccat   9540
tggtgtgacc accaggctca gagaaccagg cctaggcacc aggaaaaaga aacagggact   9600
gtgaagctca gtatgcctgg cagaaatggg gcggaaatcc ttatttaagt aaagaaagtg   9660
gagttgtgag tgatgcttca gataaaattt tacaaaattc cttacaaaat gggtggtgct   9720
cagcacgcca aaatcttagc ccagagcttg ggtgcaaggg ttgagttgag tgtagacccc   9780
tgggcttgtc ttcatgtcag tcagtcctga gccattttcc actgtggaaa ggtgggaaaa   9840
```

```
ccacaagaca ctaaccaatt gaaaaggagg gctagccacg gaggtgcaca cctgtaatcc   9900
cagctacttg ggagggtgag gcagaaggat cacttgaacc tgggaggcag aggttgcagt   9960
gagccaagat cgtgccactg cactccagcc tgagtgacag agtgagactc tgtctcaaaa  10020
atagaaaagg aagccaagta cggtggctca cacctctaat gccaatgctt tgggaggcca  10080
aggcaggtgg atcatttgca atcaggaatt cgaggtcagc ctggccaaca tggtgaaacc  10140
ctatctctac taaacataca aaaattagcc gggcatggtg gtgtgtgact gtagtcccag  10200
ctacttggga gactgaatca cttcaaccgg gaggcaaagg ttgcagtgag ccaagatcgt  10260
gccactgcac tccaacctgg gtgacagggt gaggctctgt ctcaaaaaaa agaaagaagg  10320
ctgggcttgg tgactcatgc ctgtaatctc agcattttgg gaggccaagg caggcagatc  10380
acttgaggcc aagagttcga gacctgccag gccaacatag caaaaccccg tctgtactga  10440
aaatacaaaa aaattatctg gccatggtgg tgtgtgcctg taatcccagc tactggggag  10500
gctgaggcag gagtatcact tgaacccaga agacagaggt tgcagtgagt cgagactggg  10560
ccactgcatt ccagcctgga tgagagagca agactctgtc tcaaaaaaaa aaaaaaaaaa  10620
aaagaaagaa taggaggctg agaagtccca agttatatgt taaaaaaaaa gaaaaaaaca  10680
tcagttttag gccaggtgca gtggctcaca ccctttaatcc cagcactttg gaaagccgag  10740
gtgggtggat catgaggtca ggagttcaag accagcctgg ccaaaatggt gaaaccccgt  10800
ctcgactaaa aatacaaaaa attagccagt tgtggtggca ggcacctgta atcccagcta  10860
cttgggaggc tgaagcagag aattgcttga acccaggagg cagagattgc aatgagccaa  10920
gatcgcacca ctgcactcca gcctggaaaa cagagcgaga ctctgtctca aaaaaaaaac  10980
catcagtttt tatggacagt ggtagagtgg agggtgggtc cctatggtgc agaagggaaa  11040
ttccatggtc ctgctgtgca tccgactggg atggctgttg aaatcctctt ccagcaggca  11100
gctttggaaa cagaaaaaga aactcttcct cctttagaat cctggaaggg ctgtgcagtg  11160
cctctaatcc aagtctgttt tctgagtgaa gatagggagg ttcatcacca gaagggaagg  11220
ggctggaaat gaggtcactg catcccagcc cagggctcct gggtcatcca ggaagggaag  11280
aaggagcaag ctttctcatt gttaggtagg agctcagagc catcacaaga acaagttagc  11340
accatccctg tgccctccct gttctgcaaa caaaatgatc ttccttcttg ccctggcact  11400
agagtctgtc tggcatttct cctgccccta gtactcctcc catctgggta cttcttcccg  11460
ttggtgtact gaacaaacac atccactgct ttattcacag cctccagccc tcattttcca  11520
gggcccacac catttgtttt tactaacccg acaaggttgc ccactgtccc cagtaaggtt  11580
tgtactgggg tttttactcc agtgctcttc tccatccagg agacctttgg atacttgggg  11640
aagaaaatga gcttaaattc ccacccctcc ccctttacct ttttcctgta aggccctggc  11700
cttagttctt agccccacat ccttgctggc tgcagaatag cagcgggttc tgggtaagga  11760
gcattctgct aaaacgctcc accctgctcc ctcatctgtc ctctccattt gtccccatca  11820
gatggtttaa gtgcttaagg ggactccagg gcggagtcag ggagaaccct ggctctcctg  11880
ggctaggcac aagatcattc tacaggaaac cttgtgggaa ttcttctggg acaaagtatt  11940
ggtcagcgct gagcttagct gtgtctgtga cactcgcatt ctaactaggg cctatctgac  12000
gtcaacagga agtaaggctg atgcagtggg gccaagggag tctgggagaa gaaagtcggt  12060
tcagagccct ggctgccctg tcccacactc cacccttccg gcaagaatcc agtccctaga  12120
tgaggtgggg agtgagtggt cgagttaaaa atctctgggt cgggtacgat ggttcacgcc  12180
```

```
tgtaatccca gcactttggg aggtgaaggc aggcggatca cttgaggtca ggagttcaag  12240
accaacctgg ccaatgtggt gaaatcccat ctctactaaa aatacaaaaa ttagccgggt  12300
gttgttgtgg cacgcgcctg tagtcccagc tactcgggag tctgaggcag gagaatcgct  12360
tgaacccagg aggcagaact tgcagtgagc caagatccag ccactgcact acagcctggg  12420
cgacagagtg aggcttcgtc tcaaaaaaaa aaaaaatctt tgggccaaat ctccagacag  12480
cacaggcagg tgcagaaacc caccaggaag ctgcctgtgt acctctggca gattggagcc  12540
tggcctaaag ctgcctttta tgcagcttgg gtcaaggtta aacatcatgt cacagtgatt  12600
tttctcacta tgtgtgagac atggagaact ggctccaagt actactctgt ccactggtgg  12660
ctggactact gatgtgcacc actctccact cctctcaccc tgcagtgggt catggccccg  12720
tgccggggca gaggagaaaa atgggctgcc ttctccagga caaaccctca ctccaactca  12780
actagggtgc tgtgatcaga atgtgcaatt gaggtgtgat tttactgatt tttttttttt  12840
ttgagaccga gtttcgctct tgttgcccag gctggagtgc gatggcacga tctcagttca  12900
ctgcaacctc cacctcccga gtttgagcaa ttctcctgcc tcagcctcct aagtagctgg  12960
gattacaggc atgtgccacc acgcctggct aattttgtat ttttagtaga gacggggttt  13020
ctccatgttg gtcaggctgg tctcaaactc ctgacctcag gtgatccacc cgcctcggcc  13080
tcccaaagtg ctagaattac aggcgtgagc caacgtgccc agcctgtttt tgtttttttgt  13140
gttttgaagc agggtctcac tcagttcccc aggctggagt gcagtgacac gataatagct  13200
tactgtagct gcaatctccc gggctcaaac gatcctccca cctcagcctc ctgaacagtt  13260
gggactacag gcacaccacc acacctggct aatttttttt tttctttttt tagtagagat  13320
gaggtcttgc tatgttgccc aagctggtct caaactcctg aggatcaagt gatcctccta  13380
ccttagcctc ccaaaatgct gggattgcag atgtgagcca ccacacccag cctgatttta  13440
ctttaaatga gagtccctct tcagagtccc tcagctgttc ctggcccctg gccatgtgcc  13500
ttcagttgcc cctgcttctg tggtatcctt aaggctacat tcagtgctga ggccctaggc  13560
aggcagcaga gagaagccaa atgattctgt ctttccctta tccacccaga gcatgcaaaa  13620
ccaggagcag tggtgggttc agggtgggca ccagctatgt atatgtacat cagggacagg  13680
gggccaaagg cagtcagttt ccaaagactg ccccagaggc catttttcag agaagccctg  13740
ggttcctcaa gggccctgtg tccatgctgg cccatcttgc aggacgagcc tgtggagtgg  13800
gagacacctg acctttctca agctgagatt gagcagaaga tcaaggagta caatgcccag  13860
atcaacagca acctcttcat gagcttggtg agttgactgc tcaggaaggg ggcgtgggga  13920
ggagcaggta cccagctatg tgcctgatac tcagagggtc acaactgagg ttatcttggg  13980
tgggcgcaag cagtaatttg tgcataccca gcctagcccc aagtagactg acatctcacc  14040
tggaacctat tatcaaggtt tggtttctct atttctttag aacaaggacg gttcttacac  14100
aggcttcatc aaggttcagc tgaagctggt gcgccctgtc tctgtgccct ccagcaagaa  14160
gccaccctcc ttgcaggatg cccggcgggg cccaggacgg ggcacaagtg tcaggcgccg  14220
cacttccttt tacctgccca aggatgctgt caagcacctg catgtgctgt cacgcacaag  14280
ggcacgtgaa gtcattgagg ccctgctgcg aaagttcttg gtggtggatg acccccgcaa  14340
gtttgcactc tttgagcgcg ctgagcgtca cggccaaggt gggcttccca ccccaccctg  14400
ccctatgtga gggtatatac gcatgcacct gagcatgcag gggctgagca gctggccctg  14460
tctctgatca ttacttcccc ttcacagtgt acttgcggaa gctgttggat gatgagcagc  14520
ccctgcggct gcggctcctg gcagggccca gtgacaaggc cctgagcttt gtcctgaagg  14580
```

```
aaaatgactc tggggaggtg aacgtgagta catagttctt agtttcttgg ttgtcactag  14640
acaggactga tgggctgtag ctacagtaag gcttggagga ggaattgtgc tggaagacaa  14700
gccctgcaaa acagttccag gagtgtatag gcattgtaac taaagcaaag gcttccagac  14760
cactcatgcc aaagcctagg gttgtcccaa gaagccagga agaattgcct tggtgctttg  14820
atctttcctg gtgtggaaaa tcttctggag atgcaggagt ccatctaatg acatgaggag  14880
gccccccttca gactttttac ctggaagctt tctggctcca aggtattagg cctgtggagt  14940
gaaattagac tcagaatatg cctgacctgt ccacaggtaa ttggggaaca tctgacttgg  15000
ttgtctcagt aaggtgaccg ttttgtaggg cccatcttcc atacaaactg ctgtcaggga  15060
tcctaccaga gatcattcag ccaagagcct gacatcagaa agcccagtcc tagcttgtgt  15120
gaacatgagg tgctagtctt ctctggggag ggtctgctgg cttggccatc ccttctgcag  15180
cctgtacact cccctttgc cccttgcagt gggacgcctt cagcatgcct gaactacata  15240
acttcctacg tatcctgcag cgggaggagg aggagcacct ccgccagatc ctgcagaagt  15300
actcctattg ccgccagaag atccaagagg ccctgcacgc ctgccccctt gggtgacctc  15360
ttgtaccccc aggtggaagg cagacagcag gcagcgccaa gtgcgtgccg tgtgagtgtg  15420
acagggccag tggggcctgt ggaatgagtg tgcatggagg ccctcctgtg ctgggggaat  15480
gagcccagag aacagcgaag tagcttgctc cctgtgtcca cctgtgggtg tagccaggta  15540
tggctctgca cccctctgcc ctcattactg ggccttagtg ggccagggct gccctgagaa  15600
gctgctccag gcctgcagca ggagtggtgc agacagaagt ctcctcaatt tttgtctcag  15660
aagtgaaaat cttggagacc ctgcaaacag aacagggtca tgtttgcagg ggtgacggcc  15720
ctcatctatg aggaaaggtt ttggatcttg aatgtggtct caggatatcc ttatcagagc  15780
taagggtggg tgctcagaat aaggcaggca ttgaggaaga gtcttggttt ctctctacag  15840
tgccaactcc tcacacaccc tgaggtcagg gagtgctggc tcacagtaca gcatgtgcct  15900
taatgcttca tatgaggagg atgtccctgg gccagggtct gtgtgaatgt gggcactggc  15960
ccaggttcat accttatttg ctaatcaaag ccagggtctc tccctcaggt gtttttttatg  16020
aagtgcgtga atgtatgtaa tgtgtggtgg cctcagctga atgcctcctg tggggaaagg  16080
ggttggggtg acagtcatca tcagggcctg gggcctgaga gaattggctc aataaagatt  16140
tcaagatcct cctgctgttg gaatctttta tacatataaa gtttttgtag agacatgagt  16200
ctctctgtgt tgcccaggat cctcccaact tggcctccca aagtgttggg attacaggtg  16260
tgagccaccc tgcccagcct ggactcttta ttattatagg cgcagagctg cagttgcccc  16320
tcatggtgcc agaagttgcc aagggtgatg gacaggctcc caggtgtctt gcaaagtcac  16380
catggaccaa tttgtgaaga tgtagtatgc atacatactt ggtcatcact cagctccctg  16440
gggctcaggt tgtggtggag acaaaaatgg actgcagtta gaacttaggg aaactggctg  16500
ggcatagtgg ctcacacctg taatcccaac actttggttg ggctaggtgg gcagatcact  16560
tgaggccagg agttcgaggc cagcctggcc agcatggcga aaccccatct ctaccaaaaa  16620
tacaaaaaaa atttagctgg gcgtggtggt gggcgcttgt agtcccagct actcagaagg  16680
ctgaggcagg agaatcgctt gaacccggca ggcagaggtt gcagtgagtg gagatcacac  16740
cactgcactc cgatagagca agactccaac tcaaaaaaaa aaaaaacggc cgggcgcagt  16800
ggctcaggcc tgtaatccca gcactttggg aggccaaggc gggtggatca cctgaggtcc  16860
ggagttcaag actgcctgac caacatggtg aaaccccgtc tctactagaa atacaaaaaa  16920
```

```
attagccggc atggtggcag atgcctgtaa tcccaagtac tcgggaggct gaggcaggag  16980
aatcgcttga accctggagg cagaggctgc agtgagccga gatcgtgcca ctgcacatta  17040
tcctgggcga caagagtgaa actccatctc aaaaaaaaaa aaaaacaaaa ccatcccttc  17100
aacacacaca caccacgctc tgggagaagg tgtggcataa ctccttcacc aaatacagag  17160
ctgccaccgt ggaccagaca ctgctcgtga taccgagggt atagctgtta acaattcttg  17220
ctttcattaa gcatggactc tgctgggttt gaaaacactg aattcgaagt tcttcagaac  17280
tgaatgtaac tatgtgaatc tggccagttc cttaattttc tttcaacttg gttagttcac  17340
ataagcgtgg caatcgcaaa aatacagctg tgaaaataga agccagatgg gcacccggcg  17400
gtctggcctt aggccctgaa gtgcaggttt gaggattggt gcttgcgaag tcctgctagg  17460
cctgaactca ggtgttgggg gacgtcagag ccgccaaata cacccaaaag accgggagga  17520
ctcacggcca ccactttcct cggtgggagc tgtcccagct ggtcagatcg cgcttgctgg  17580
gacctgggat ctcgcaacgc atgctgggat gcccagcatc taagggcgcc cattggtccc  17640
gcccccacga cttgagcaac agccaatcag aggtggcagc gtgcggaagc ggaagtgagg  17700
tttccgtgga gacagccgag cctgcggaag gcggcggcgg cggcacctgc gatcagcggc  17760
tggggcaggt tatggtagtg cggactgcgg tgtgagcaga gcggccacgg ggcccgccat  17820
gcgccggcgg ccctgacatg ggcgccagcg ggtccaaagc tcggggcctg tggcccttcg  17880
cctcggcggc cggaggcggc ggctcagagg cagcaggagc tgagcaagct ttggtgcggc  17940
ctcggggccg agctgtgccc cccttcgtat tcacgcgccg cgggtaaggg catgggttcc  18000
accctggcgg ggggaacagg cgggcggcca ggcgtcccgc gccacggggg aacttccacc  18060
gctgtacccc actacagcca agccaggacg acccccatat tttgagcctc attggagctg  18120
ggggtggaga aagccgggca gtggtctcct g                                 18151
```

```
<210> SEQ ID NO 14
<211> LENGTH: 20911
<212> TYPE: DNA
<213> ORGANISM: Homo sapiens
<220> FEATURE:
<221> NAME/KEY: misc_feature
<223> OTHER INFORMATION: TBX3

<400> SEQUENCE: 14

agggatctcc aggctgtcat ggttgctggg aaagatgagg gagggaaagg gggcagagta     60
cggaggcacc aggtcagaaa gacaggagag aattcagaca ggaccaaaac agccagaaaa    120
aataggataa agaaggtaga aaaaaaaaaa aaacaaaaca aaacatgaga agttaaagcc    180
tgggaaatag atacaagaca agaaagagaa atagaaacca agaacaagat tgatgaaagg    240
aggagaagag aaagtagaag gaaaaagaat aagaaagatt ccagacacgc attcaaataa    300
tcctaaatgg ggatgagcag aaagacaagg agaccaaaag aaaagggggg gggggggtgg    360
tggggaggag aaagaaagga atggaaaaag aaacaaaagg tgaatgtcct gccctgtctg    420
tctggtccaa ccaagaagct agtgtctgcc ctggagggag gaaaggtggg ggagtccagc    480
ctgtctccaa gggactgaca ggcagcttct ggaccagaga ggaactaagc tctcaaagca    540
agctttgggg aggaggaagg gatgggggtg catggtgagt ggagactcct ggaggaagag    600
caagcctcca ctgggttcag cactgccagg gggagagtca gggttcaggg tagcatagca    660
gtgctaatgt atgtacccca gaggggtagg gggtgctagg gcaatttgca ggaggaccac    720
aaacagtaaa ctagagagct acttccctgg gatccgtgat aagaaaatca cttcctcagg    780
```

```
tgggagaatt gagcccgaaa gagaatggga gcccttgggg ggcaggcacc tggtcagttt    840
caaagctcgt caatatcaaa agaggctggg atcctgagat caaatgggct ggggcactgg    900
gcagaaacga ggagccattg ccaaactgcc aggatgacca gaacgcccct cccccaggaa    960
aagttcatat atgaacccac ccctgtatga aacttcttaa ttaggtctca tacccccggt   1020
gaatcttgga tgcccttctg tcaacagaat tcccaattta gtgacacctc ggactgaaaa   1080
gagctctgcg gcaaacgggg gtgaaagttt aagagggaat aagcatataa tactcccttg   1140
ccagacctca cacatgctga agggaatatt tacagcaaac tggccaaagc aaacgacccc   1200
gcctacccac catcctttta ccctcctccc cgcccttttt gtaaactcca gataaacacc   1260
atttgatcac aaaagggtcg gtttgtcccc tttatagttt gaggcaggca gtgcggcagg   1320
gaaaagtggc gtgggctaag cttccgtctc gggcaaggcc agcttctttg ctggcaccgt   1380
ggcctgggct aaggacagtt gatttggttt tgtttccccc gacccccacc ccgaccccac   1440
ccccacaaag gaacattatt ttcagggtcc tccccccacc cagctttaac actcgcctac   1500
ttgcacccgc actactttaa atgctgcggg cattgcagat agagaggttt ttcagttaat   1560
ttactttttt aattctagag ctacaattaa gtgaaaactc tttttgcgaa aaggtggagg   1620
aatatttcag agacgccaga aattatctgg gtcttttctg acccggaatc tgccctcttt   1680
ctcccttctc ctccccttaa gtcacccttt tctgggactc tgttgaaggg caggctcttt   1740
caacgtctct agtctgtctt ttgttgagtg tgagaccgaa ggaaagagga tcgaggggtc   1800
tgcagagaga aaaagaccgc agatagccgg cagctggcgc ctaatgccgg ggtccgggga   1860
gcgctggcct cgtgggttct cctggaggcc aggcccagca caagccttcg gaacacgctg   1920
gccaatgttt aacccgaatg cagtggccac caggccgctt ttgtttgttc gcaaattaat   1980
cacccagcgc atggccggcg ccagagtggg tttatcaccc accgggaggg gggcgcgccg   2040
ggcacgcaga gacaaagagg agttcgcacc ttcccgcttt tgatcccaga attacggcgg   2100
cctccctgcc taatacgagc ctcctggggc cgagtctggg aggtcagtca taattggcgg   2160
aagtttgcag accattagca agatgtcgac attttcgatt cgaaccccgc aaactttcct   2220
ctcgttctct gcttcgcgcg ctggaggttg gtgtgggaga ggagatgggg gtcagaagta   2280
gcgatctggg gtgatcacag ggttaagtta gagctatggg caaaaaatag gcaattgagg   2340
gaggaggaca gtgtgagggg cagaactccc tctcagtcca cccgcggagc caaaaacaaa   2400
tctagacatt tttaagtaaa atccgcaagc tcccctccca tttccaaagc tgacagctgg   2460
ccagaatgca gaggaatgtc tctctgctgt gcgtgggacg cttgggggca ccgagtgggt   2520
gaggaggagg tcggtcacag tgtggttgta gaactacttt gcttccaccc caagtagtgg   2580
ggcagagatt ggcctgcgag ggcaggcagg caaaaccaga tcgctgggat ttggggccgc   2640
tcttgaaaga gcagcgaagg ggccccaggc cccggaggcg agcagtctgg gggagggggt   2700
gcactttttt tttctatttc tttcttttct tttcttttc tttttttgg ggcgggggtc   2760
cccagagact catgaaaccc tgcagtgact tccgtgttct gtgtaaggcg ggaaatggcc   2820
tggcctttcg cacccttcag gtggggagga ggggatgcgg gagggggtgt tatgagccaa   2880
cactctgggg caccaccacc tcgtaatttt ccctctctct cctttctcta ttttaaccac   2940
tggcagagac agagaggacg ccagagaaag acagactgaa agggaaagaa aggggcgaga   3000
tggcgagcca gacggagttc gcagaaccac actattctct ctggtgactt cagggaattc   3060
tcaacgctgg cgccaagctc tcttaaccat gtgcgtcaaa aatgcgaggc tggagaagcc   3120
tgtcgcctca aaagatcctc ccctatctca gcgtggttgg cccacaagag cacttcattt   3180
```

```
tcacccttcc cttggtgcca cgttggggtt tcggggttgc tgggggttgc gcgggtgcac   3240
aaggcaaaat gcgagagagg cctgtgctgg cctacagaga cacacacatc caaagccctg   3300
agtctcttaa accccctaagc ccccagatca gccctttctc cgttcccttt ccatcgaaga   3360
agctttcatc tcaggaaaga taaaagaaca ttgttttcaa gatttccctc catctaagca   3420
aggatggtcc aagacattgg cccccagaat caagaactgt gggcttaggc gaatcctctg   3480
accccgaccg ggcgctgcgg taacagagtt ggtaattcgg cgattggtaa gatccggtcg   3540
tttccctccc gtccgcctaa gaggaggccc ccaccctacc cgtactaaaa acagtcaact   3600
cgcctctgag gtgggggcgt ttcacggttt gttttacaaa ttcaccctcc ctccccgact   3660
tctggccaga ttaagtcccc ggggtggaga aagaactgag gcaccgagag ataagtgcga   3720
tgcctagaga agataccagg ctggcgcgcc tccccccaacc caatcgccca ccccttaccc   3780
tgtgctgtgc acccagccgg gcctcgaggt gagggcagcg gcttggaggg gacaggctca   3840
gaacccagtc tctcgctgtg ctcgctttgt ccagatcctc cattctcttc tctacaccca   3900
cacccacatc caggtggaat atgggggccc gcatgcaaat gaaagacgag atccaaaagg   3960
gctggtaaat gcatttcata aaaatcccaa atccatcttc cccaggagct caggcagggc   4020
cagccgcgca ggctgtgtac gtgtttgtgt gtacgtgttt ttcggtgtgt gtttcagtcc   4080
cagtgtgttg gcgcgtgttc gagtacagat acaccggggg tgtttgggta cccgcacatg   4140
gctgcgggtg gggcgcagtg gagaggaagc ccacacatgc gtgtgctgag atatggccgc   4200
atccttgtgc tcccccagcc cagacgcagg ggagaccagc accgagacac ccgagctcgg   4260
gagcccttca gcggcggccg ggcggagctt ggctccacgt ggggctggag agcacgcaag   4320
cctggagtct cggcgctcgc ttctcggctg ccgccggctt ttgtagaacc gagtggccgg   4380
atggcagctc gcggggaggc tcggccaccc gcccggctcg cccggggcgg ggagaagaag   4440
gagagctgga gagagaaccg gccgcggcgg tcggagaggc gagcggagtg caagagaggc   4500
gagcgcccct gcccggcgcc cgggcgcgct ctccgccttc cccgcccggc tcgcctgctc   4560
gctggctccc tccctctctc cctccccctt cctccttggc cctgcctcct ccctcgatcc   4620
ccggctggat gactgaggca tttcagacgt gggctgaacc agagcgagcg agcgagctca   4680
ggggctgcag cgatctctcg ataagccacc tagaggcgac tctgtgcgcg cgcgctcccc   4740
agtggctccc gcccgccctc tgatcatgtt gacatattca caggacaggc agtagtaccg   4800
atgcggcgct gcgacgttac agtttccgac accttctttt tataactcag ctctatcccc   4860
cagcactcga cctgtgaaaa ccacgcctat gcagcaacac aattggtccg aaagcgtcaa   4920
agagccaatc aagaggcctc cggctccccg cagcccacag cgcagcccga ccttctagag   4980
ccgccgagca gacgcccggt gaattctaga ggcggcggag ggtggcgagg agctctcgct   5040
ttctctcgct ccctccctct ccgactccgt ctctctctct ctctctctct ctcccctccc   5100
tctctttccc tctgttccat tttttccccc tctaaatcct ccctgccctg cgcgcctgga   5160
cacagattta ggaagcgaat tcgctcacgt tttaggacaa ggaagagaga gaggcacggg   5220
agaagagccc agcaagattt ggattgaaac cgagacaccc tccggaggct cggagcagag   5280
gaaggaggag gagggcggcg aacggaagcc agtttgcaat tcaagttttg atagcgctgg   5340
tagaaggggg tttaaatcag attttttttt ttttaaagga gagagacttt ttccgctctc   5400
tcgctccctg ttaaagccgg gtctagcaca gctgcagacg ccaccagcga gaaagaggga   5460
gaggaagaca gatagggggc gggggaagaa gaaaaagaaa ggtaaaaagt cttctaggag   5520
```

```
aacctttcac atttgcaaca aaagacctag gggctggaga gagattcctg ggacgcaggg   5580
ctggagtgtc tatttcgagc tcagcggcag ggctcgggcg cgagtcgaga ccctgctcgc   5640
tcctctcgct tctgaaaccg acgttcagga gcggcttttt aaaaacgcaa ggcacaagga   5700
cggtcacccg cgcgactatg tttgctgatt tttcgccttg ccctctttaa aagcggcctc   5760
ccattctcca aaagacactt cccctcctcc ctttgaagtg cattagttgt gatttctgcc   5820
tccttttctt ttttcttct tttttgtttt gctttttccc cccttttgaa ttatgtgctg    5880
ctgttaaaca acaacaaaaa aacaacaaaa cacagcagct gcggacttgt ccccggctgg   5940
agcccagcgc cccgcctgga gtggatgagc ctctccatga gagatccggt cattcctggg   6000
acaagcatgg cctaccatcc gttcctacct caccgggcgc cggacttcgc catgagcgcg   6060
gtgctgggtc accagccgcc gttcttcccc gcgctgacgc tgcctcccaa cggcgcggcg   6120
gcgctctcgc tgccgggcgc cctggccaag ccgatcatgg atcaattggt gggggcggcc   6180
gagaccggca tcccgttctc ctccctgggg ccccaggcgc atctgaggcc tttgaagacc   6240
atggagcccg aagaagaggt ggaggacgac cccaaggtgc acctggaggc taaagaactt   6300
tgggatcagt ttcacaagcg gggcaccgag atggtcatta ccaagtcggg aaggtaagca   6360
gtgggggcct cctcccctaa gctgttggag agtttttttcc tccctttatt tctctgctcc   6420
cagaacagtc ggttggtcgg ttattacggc ttggacgaaa agttagttcc cctagaaatg   6480
tatgcacaga cttccaggcc ctgccccggt ggcaggaaat ttcagcttac ctgggcatct   6540
gcatgggtct tgcatttggt ctgcatcctg ggttccctcc cgaacagaca gaatttttca   6600
gtggagcaca gacatccctg cagggagcag gaaagaaaaa aaaaaaaggc actctactgc   6660
aagaaactca ctcttcaaac cctcctggaa catccttatt tctttgttga tgttgtgttg   6720
tctgttttat tttgttctca gagagaaaaa cttaaagccc tttccttttg tgtgggtatt   6780
gggaggcctg acaccattcc ccggcccttt ctgccctcca gtctagcctc tgggtctaaa   6840
ggggcctgct gctgccctgg tcagagagaa atcgaagggc attttggttt gtttgcccac   6900
actacttcac gtgtctgtaa cccaagggcg agttcagcag gcaattttgc ataatttaag   6960
attatgtttg cagacttaag gagccagtga ggagacacac accttttttt taatgtgtga   7020
atattatcaa ccatatttta cataatgttt aaaggtcctt gcctgaccaa aacctgcctg   7080
gaagagaaga tcctgtaata gtcatttaaa atcactgatt ttttttttgt aatagcattg   7140
aagcctgtaa aggcataaag ttgatacaaa aataaaatcc ccttcatgat atcttaagcg   7200
ttctgtctcc ttccaagcta aatgaggcca aagtttggca taaaatcctc ctcaaactca   7260
caagacattt agtcagtttt ccagcaaagt gcttccttgc ttccttttaa gtcaagacta   7320
cagaatgcca acccttctgt gaaattaaca gcaatgtggt ggcacagtct tgcggttttg   7380
gactggccta agaagtgggg gaatgtgtta gcagctccac gggcagatcg gttatcaggc   7440
ccaggagtgc accgaagtct gcaaaattcg ttctgggaac tcactgaagt ccagtttcac   7500
ttcgcccaca gcgggattgc tattctgcag cagggagggg tgcaacttga cgttcatttc   7560
cttgataagt ttaacatttt ctcatcaatg ggtggtggaa aattctagtc ttaactgacc   7620
gcgctttaca aaaatcttac cccaacctgt ttagatctag atacccacag aaaaagacat   7680
gggcaagaat ttgctctcag gagggcaatc tgtaaagtca agcaaggaca aaaaaaaatat  7740
tgaagaaatt gttagacaat gtagagaatt gcagtgccac aatgcatttg ttttgaacct   7800
tgggacgtct aaatatggcg aaactgagaa tatttaatac gttagttgtg gaagaaaacg   7860
attttgcaac cagttgcctc actctgaaac atgtaagctt atcagtcaca atataaagtc   7920
```

```
ttagacttgg tttcaatatt atgtgataca taggaaatca aacccaagat tacgggtggt   7980

ttatctttct ttttcttttc tattctttcg ttttataggc gaatgtttcc tccatttaaa   8040

gtgagatgtt ctgggctgga taaaaaagcc aaatacattt tattgatgga cattatagct   8100

gctgatgact gtcgttataa atttcacaat tctcggtgga tggtggctgg taaggccgac   8160

cccgaaatgc caaagaggat gtacattcac ccggacagcc ccgctactgg ggaacagtgg   8220

atgtccaaag tcgtcacttt ccacaaactg aaactcacca acaacatttc agacaaacat   8280

ggatttgtaa gtttcattgc tctcttcagt aaaatttttct cctccttcac tcagtcaaag   8340

gcagtgcttc ccatttcatg agtttcagcc cagacttctc ctttgcttct ccctaagcat   8400

agcaaacttg tcctcgtctg gaaaaaggat tcggggtgtt tctctccaaa taatggaagg   8460

cctggcgttc taaaagaaat ggggcaagaa aacttaccgg cttgtgttct atagcaattc   8520

cagctctttg gtagattcct gacctgagag tgaagttaaa aaccattttt taagagctaa   8580

aatcaatttc aaggctatgt attcctaaag gatttgtttt gttttaaaat atcatacttc   8640

tgttttgaaa ccagtgatat tattttctca ggagagttta cgtttcggag ccttgactct   8700

gttggttaaa tggtgtgaat acatttttaa aaactcgttc ttttactaaa aaaagaattg   8760

ggcttaggtg ggagtccggc ttaccctaaa tgaggcttag atcttcagaa aaaaatggtt   8820

tgtgtgttgg gagtgtatat atggattcag tgacagtgct tagaaactta gaaaactttc   8880

attgcttgta gatatcaggc aaaggacctt ttgcgccttt tcctacccct ccccaacatt   8940

tcaataaaat aaacagcgtg ataagcaagg agtaagcaga aagattaggc ccaggaagac   9000

gcgaatggcg cggaaatatc ttcagcgggc aggaattgca tttgaagccc ttgatttgat   9060

taaggcataa atattcctct ctagagttca gcctttcagg gctttaagtg gattgggctc   9120

gtcaattagt gggcgcttaa agtactgaat cattttgtaa attaaaatgc atgtttttct   9180

ctatctttta agactttggc cttcccaagt gatcacgcta cgtggcaggg gaattatagt   9240

tttggtactc aggtaggcta gggttcaagg tatgaatgat ccttagatgg tgagggtggg   9300

gggggccctt tggcaactga ggagcaattt ggattctcca gaagataaca tctgtggagc   9360

gaaacgtacc cagggggtac tccaaggagg tgggctcggt acaagcgtgg taccctgcgg   9420

tggggaagat ttcagcctgg caggggtcct aagatcccgt ttgttctgct aaatccttgt   9480

tttatgtatg tctcctcttc cctgcccctg cagactatat tgaactccat gcacaaatac   9540

cagccccggt tccacattgt aagagccaat gacatcttga aactccctta tagtacattt   9600

cggacatact tgttccccga aactgaattc atcgctgtga ctgcatacca gaatgataag   9660

gtaaactcaa ggggctttcc tttttaatgg tgatattttg ccttcccctt aaaagctgct   9720

ttaagtcagg atgagaaagt tacaagagag tggagacgag agtcttgagt tgtcttttgt   9780

gatttgtgga gcatttgggg ggaaaggaca atgacacctc gaggagacag aaaaacacct   9840

tgactaggta ggaacaatgc tgagcaaaaa aacgccatac taattttgcc acagagaaac   9900

tcctagaact gctgtcattg atgccaccca ctcctccccc cctcttgggc tttgtcctgt   9960

ctgttttaag gttcatcttc ttccccttgg ggaagaagga tcaagaagtc acattcaaaa  10020

ggaaccagct aaaaatttaa ggcaaaagcc atttgggatc ctgggaggag aatcctagta  10080

gagaccagct tttctcccct agccagaaat cctgagtagc tggtctggtt tttattacct  10140

tttatgctgc tgtgttatga tgtgtgtgtg tgtgtgcatg tgtgtgcatg catgcgtgtg  10200

gttggaaaaa cctaccctga tcacagggtc atattaatcg agttgtctga ggcttttgag  10260
```

```
ttggggtggc caaagtcacc acttcatttg aattcccccc ctcccccagg cctgaatctg  10320
gaggttagaa ggatccccaa aagggaaagc acctgatatc tagagctatg gtggcctgaa  10380
ggtcatgggc acagaaaaag tgacccttac tgctgattca ccagttccca gattggctgt  10440
tagcagttat ggggtgggag gagggactga agacccctgc tctgcaatcc tggacttcaa  10500
agagagtcca ttttacctga caacacactt cattttgaac tcactgtcat tgtcactgtc  10560
cttgggtcct ctgtggactt catgatgggg atgttccagc taaatttctt tagtgtgaat  10620
accaaaacat gatcttctct ccctgtgaaa cctgaagtct tcaatagagc aatttattcc  10680
aagaacatga atccaaccaa gggtccccct ttccacctct gagtaactct gtgtatataa  10740
cttcttcttc ccaccaaggg gaagggattt gaaagattac acactatagc atttttctca  10800
aagtgcaaaa tgcatgtgcc ctctagaccc agaatcctgt gaaatgaagt tgttaatgta  10860
ataataaaat gtagcatttt tgatcagaca aaaaggccat gggccttctc cacctaatgg  10920
ccatggcaga gcatataaat gaaaacagat gtttccagtg gtcattcagt actgtaactg  10980
tcaatattgt aatttcctca aaccaccccc caggcaaaga aaaaaaaaat taaactcact  11040
cccgcactca ctcccgcaca agggtagtga aaccccataa atcatttatt ggattcatgg  11100
aaaaggagtg tgtgtgtgtg tgtgtgtgtg tgtgtgtgtg tgtgaaggga gtatgctata  11160
atttatgatt aattgcactg tataaaaatc aaaatgaaag cataatttta agatctacag  11220
gttttccctc ttgatgactt tgacaacact tccatgtcta aacccaaact gttggctgcc  11280
caaagaaaag aatttctttg aataatttca tccccaaatc cctggtttgg cctcatatag  11340
gagatacaag ccctgccaca gtttccttat tatctccttt ccctggcata tctatatgac  11400
ttctgttggc agtcacatct ctagacttgt tgagttggga aaaacaccct caaaacattc  11460
tagaaaatga gaacaatgtc tctgtcttgc ttgtgtctct tccaatagat aacccagtta  11520
aaaatagaca acaacccttt tgcaaaaggt ttccgggaca ctggaaatgg ccgaagagaa  11580
aaaaggtgag ttgaaacaat tatttattag atagtttaga aaaatccctt tttttaggat  11640
ccaactctga agtgttagaa gtgagatgca ggcacttatc ctaagagcgg gtggaaatca  11700
ttcactttcc ccactgctac atgcttgccg ctatcagtat acccaggaca agtacttttc  11760
ctacctcctt acctttaagg aaattaacta ggctacacca tacttatctc tggaagagaa  11820
gcatcaggga taatagatta tacagggatg cctattaatt cctaattaat ttaagttcat  11880
cctaggcagg tcccagaaag aaccatgcca ttgagaaaat acttgggaat ttttgcaatc  11940
ctgtcttcca aataccatca gacagagctg ggacttcgg aaagatgtat ggctctctcc  12000
ctccttcgtg gggacatgta tcattttgca ttacgtagac agctggagag tatatgaaag  12060
agggtctccc ctcccccacc ccctttcaaa gaatttctaa aatccagaaa atcacccccca  12120
aatttttaac ctatcccctt ggggcgggca ttaaaaaata attgctaaca gctaaatata  12180
tttttattcc aattaatttg ttagtaaaac gattacagta aagtgcagca tgaaataacc  12240
acttcctccc aatcttagcc accatccaaa atttgggtat gctggggaca gacagcgttg  12300
tgtttgcagg attggacacc cggttctccc tatataaggc tggcagtcca gctgtctctg  12360
actagatcca gcctcttctc ctgcttttaa ataaaatttc acagcccaag caaatgcctt  12420
ttcctaatga aaccccatct tgaataaatg caactgaagc ctccttcctt tctccctaac  12480
cctctgccac actcttcagc ccagttagag ggtcaaggac aaagcttggg tctatgtggc  12540
tgccctgggg caagcagatt tcagtgaatt agcgttgtcc ctgggcagca ggcagggtgt  12600
gaggtatgtg tgtgccgctt tggaaagggt aagggaaaca aagaggggaa atgtatgtta  12660
```

```
cattctgtaa cctgggtgtg ggcttctgcc acagaaaaca gctcaccctg cagtccatga  12720
gggtgtttga tgaaagacac aaaaaggaga atgggacctc tgatgagtcc tccagtgaac  12780
aagcagcttt caactgcttc gcccaggctt cttctccagc cgcctccact gtagggacat  12840
cgaacctcaa aggtaaacca tgtcaccttt gtgatcactg gactccagtc cctcgtggcc  12900
tggaagagtt gaagggggat ggggcaccaa ccagggcact tgccctttaa aagctagaag  12960
ccttctaaac atccttaaac agaagccaga gttcaaaaag ggctatcagg tgtgtctccc  13020
cttccccgct aaggcagtag aaggagagca cagaggcctt tctcccagat ccttatttgg  13080
ctggtgggga ggggaggtgg gtgtctgttt gcatactacc tcttggcaag cagctttgaa  13140
aacttgcttg aagcgcttct ctcttttctc tctgtctctg tttctttctc ctcccattct  13200
ctccaaccaa cagaggctcc aactgctgac ttttcactgt ctttgaactc taggttacaa  13260
tgtgttggac tgggtggggg ggaagcaagg gactctgcca cctggaaccg agaaggtggc  13320
ctagaaaaca tccagctata aagcaacaat tgacctggga gaggaggtgg agcactgggg  13380
atctgcggtg ggggtagagc tgggggaggt gggtgaggag tggacaagat ggctcaaatc  13440
ccccctcagt tacctgtgtt taaagagcaa gcagtattta tttggaaaga cacacacaca  13500
cacacacaca cacacacaca cacacacaca ctctcaacgg gaagaaacct gtttttttagt  13560
gaaataaaat gcaagtcctt tatgtcttca atccatttaa gctttaaaca taaaatagga  13620
tcccttttttc ttttcttctg gtggaacacc cacagagggt gtggtaaaag cgaaaaaaga  13680
atctatgatc gtccccgggc tgtgagccat ctgtccgaca ctcatctctc tctgcaggga  13740
ctggggcaaa tacaaacggt tcaactgagt actggtgttg aaggacaggt gtccgttctg  13800
ccattatcaa ttcagatgtc agggttcttg ccaaacaaat ccttccagag taattcacaa  13860
atttgtggaa ggtgctgctc tctgtcattc actgattttt tgatagtaat tagaatatgt  13920
tccagctgtg agttttaatg ttacttttta cttttaaaaa gttaatttgc aatcgaatgg  13980
ggagatgcat gtgaaatctg ccactgtagg aactcaaaaa aagaagtaaa attcattaaa  14040
ataagaagag ctactgatta ggggattgtc catctaaggg aaagtttaaa ctctgggtaa  14100
atactttaaa ttcataatcg cttattgaat tttccagcaa tgttgttggg cacgattatc  14160
cccattttgc agatgacaac actgaggtgc agagaggcta aggggctttc cccgggatta  14220
cacagccact aagccacgag ctgggattcc aacttgggaa ctggagttcc gttggctcat  14280
actggagata acgcccttct gccttggttt tttccttcgc ctgtggtaga tttatgtccc  14340
agcgagggtg agagcgacgc cgaggccgag agcaaagagg agcatggccc cgaggcctgc  14400
gacgcggcca agatctccac caccacgtcg gaggagccct gccgtgacaa gggcagcccc  14460
gcggtcaagg ctcacctttt cgctgctgag cggccccggg acagcgggcg gctggacaaa  14520
gcgtcgcccg actcacgcca tagccccgcc accatctcgt ccagcactcg cggcctgggc  14580
gcggaggagc gcaggagccc ggttcgcgag ggcacagcgc cggccaaggt ggaagaggcg  14640
cgcgcgctcc cgggcaagga ggccttcgcg ccgctcacgg tgcagacgga cgcggccgcc  14700
gcgcacctgg cccagggccc cctgcctggc ctcggcttcg ccccgggcct ggcgggccaa  14760
cagttcttca acgggcaccc gctcttcctg caccccagcc agtttgccat ggggggcgcc  14820
ttctccagca tggcggccgc tggcatgggt cccctcctgg ccacggtttc tggggcctcc  14880
accggtgtct cgggcctgga ttccacggcc atggcctctg ccgctgcggc gcagggactg  14940
tccggggcgt ccgcggccac cctgcccttc cacctccagc agcacgtcct ggcctctcag  15000
```

```
gtatggatcc ttcttcctgc ctccaccagt ctttccacct ttcgtccagt ttccctgtcc  15060
tttgccagca gaccctcacc cgatcccttt ggcctagtag ctgtaataat ttttactgag  15120
ccattaccgg gttcaaggct tagctcatgg agttattatg acttcattct ccccattcac  15180
cccaaaaatc tttaaaattt ttccgaagtt aaaggctgtt tccagcagag tagataggta  15240
gtaacaaaga taacagctgg acacagcact tactttcagg cattcttcta agtgcttgct  15300
ctgtattgac tcatttgacc taacccttca ggggtactat tatcacctcc actttacaga  15360
tgaaggcgaa gacgcccaga gatgttgagt gacttgtcca aggtcacaca gcgggtacat  15420
ggtggagctg agactcaacc ccaggctatc tgactccagg gcctctttga gggtttctga  15480
ttttagcttc agagctgaca tgtctcttaa gtgtctcata gccaaccctt ccccaggaat  15540
gggactctag gcctggggag gggaagtgac tacttcctga gtaggagttc agtcttgatt  15600
cctccagcct ttcctcccag ttcgaagctc ttctccccac ccccaacccc aagcaggcca  15660
gcctattcct cgaagggtta atggtttgtg cacacgtggg aaatgtcaga ggacagggat  15720
aagcagggac tggggcaggc ctggaggcct gtgtgtggct cagacagctg tgctgggggg  15780
aggtctcagg cggctggaaa caccctgaac tcgatgaaaa ggttctatga ggttttgcat  15840
gctgttgcct tttgttttgt ctgagcacat tcgtctggtc tcccttccct gcgccaagaa  15900
accagattgg cctccccact ccagggagga gggagctgag gaaaggcttg gcttctggca  15960
tttctcaatt cctcccatct cctctgctgg cttctccggg agaccctgtc ctaggtgggc  16020
aggtggttgg tacaccaagg actacctgaa cagacaaaac cttaagggca cctcaaggca  16080
tgatgcagag aactggccca ggccagggtg cctgcatctt aaatgctgct tctgccaatt  16140
cccagcttag tgcactcctg aactcctgcg gcctacctcg gcttctcacc tggaacacca  16200
gtgaatcatg ctggacgatt tctttgtctc tgtttataac aaatgccctt tttccctccc  16260
ccagccccag tttccttttg cttaagatct tcactgtctg tttttttgt tttgttttgt  16320
tttgtttgga gaaacttcta ggattggggt gggaggatgg gggttgggga agaagaaaga  16380
tttaaaaaat tattcctact aatttatgtc ctccggcttc cccttggtta cctctgtggg  16440
gtaaactgaa tctgtatccc catttaacag gtgcaaggag atttcctggg ggctgcacac  16500
actgtgtgca gcatattgca ggctttcact catttaatat ctacaaagtc ctcaataagt  16560
atatgaatta cttatgattt ccctgttttt tcttcctata aggaagctga ggcacaagtt  16620
aatcaaagtc tcttggccta gggtgacaca gctaagattt gtacctagag atttctgagt  16680
gttgacttct ctcctgcccc cacctatctc ccccccaaa aaaaaaaaca caacaacaac  16740
aacaacagaa cataccaggg attcatggct tgcccaatgt tggaggggga gaagagagga  16800
gagggatgag ataagctcct cccacccggc tgactcgctg tgtgtctctt ttctcacccc  16860
agggcctggc catgtcccct ttcggaagcc tgttccctta cccctacacg tacatggccg  16920
cagcggcggc cgcctcctct gcggcagcct ccagctcggt gcaccgccac cccttcctca  16980
atctgaacac catgcgcccg cggctgcgct acagccccta ctccatcccg gtgccggtcc  17040
cggacggcag cagtctgctc accaccgccc tgccctccat ggcggcggcc gcggggcccc  17100
tggacggcaa agtcgccgcc ctggccgcca gcccggcctc ggtggcagtg gactcgggct  17160
ctgaactcaa cagccgctcc tccacgctct cctccagctc catgtccttg tcgcccaaac  17220
tctgcgcgga gaaagaggcg gccaccagcg aactgcagag catccagcgg ttggttagcg  17280
gcttggaagc caagccggac aggtcccgca gcgcgtcccc gtagacccgt cccagacacg  17340
tcttttcatt ccagtccagt tcaggctgcc gtgcactttg tcggatataa aataaaccac  17400
```

```
gggcccgcca tggcgttagc ccttcctttt gcagttgcgt ctgggaaggg gccccggact  17460
ccctcgagag aatgtgctag agacagcccc tgtcttcttg gcgtggttta tatgtccggg  17520
atctggatca gattctgggg gctcagaaac gtcggttgca ttgagctact gggggtagga  17580
gttccaacat ttatgtccag agcaacttcc agcaaggctg gtctgggtct ctgcccacca  17640
ggcggggagg tgttcaaaga catctccctc agtgcggatt tatatatata tttttccttc  17700
actgtgtcaa gtggaaacaa aaacaaaatc tttcaaaaaa aaaatcggga caagtgaaca  17760
cattaacatg attctgtttg tgcagattaa aaactttata gggacttgca ttatcggttc  17820
tcaataaatt actgagcagc tttgtttggg gagggaagtc cctaccatcc ttgtttagtc  17880
tatattaaga aaatctgtgt ctttttaata ttcttgtgat gttttcagag ccgctgtagg  17940
tctcttcttg catgtccaca gtaatgtatt tgtggttttt attttgaacg cttgctttta  18000
gagagaaaac aatatagccc cctacccttt tcccaatcct ttgccctcaa atcagtgacc  18060
caagggaggg ggggatttaa agggaaggag tgggcaaaac acataaaatg aatttattat  18120
atctaagctc tgtagcagga ttcatgtcgt tctttgacag ttctttctct ttcctgtata  18180
tgcaataaca aggttttaaa aaaataataa agaagtgaga ctattagaca aagtatttat  18240
gtaattattt gataactctt gtaaataggt ggaatatgaa tgcttggaaa attaaacttt  18300
aatttattga cattgtacat agctctgtgt aaatagaatt gcaactgtca ggttttgtgt  18360
tcttgttttc ctttagttgg gtttatttcc aggtcacaga attgctgtta acactagaaa  18420
acacacttcc tgcaccaaca ccaataccct ttcaaaagag ttgtctgcaa catttttgtt  18480
ttcttttta atgtccaaaa gtgggggaaa gtgctatttc ctattttcac caaaattggg  18540
gaaggagtgc cactttccag ctccacttca aattccttaa aatataactg agattgctgt  18600
ggggagggag gagggcagag gctgcggttt gactttttaa tttttctttt gttatttgta  18660
tttgctagtc tctgatttcc tcaaaacgaa gtggaattta ctactgttgt cagtatcggt  18720
gttttgaatt ggtgcctgcc tatagagata tattcacagt tcaaaagtca ggtgctgaga  18780
gatggtttaa agacaaattc atgaaggtat attttgtgtt atagttgttg atgagttctt  18840
tggttttctg tatttttccc cctctcttta aaacatcact gaaatttcaa taaattttta  18900
ttgaaatgtc tttgggcctt gtgttaaatg tttttttcttt gggaaccttt cctgaagatg  18960
gacagtcagg ggagggttta gtatcttctt gttctgagtt taccccccttc ccttcgcctt  19020
taaataatta agaccgcccc cagcgaacca aaatgagatg tcactcaagt tacaaagcta  19080
aaaacaaaag tcccttactt gagcgaaggg agccacttca atctgaaatt acttttcctt  19140
taaattaggg agcaaagcag ggagacggaa aggggcctga tgagaataca gaaagaaggg  19200
taatttcaga tacttttaag ttttaatgga aaaagactga tgtgctccct aagtcaggtt  19260
ttcccacccg aatccgacca aaagtaagct cggcaagtac gaatgttttt cgttttaagc  19320
tcgccctcag ttttgacatc aatctggcga atccaagtcg aaaatacctt cttgcaccag  19380
tgtgtttggc tcggggaaaa ggccagcaga atgccccagc agtccgagcg ggcttggcta  19440
ggcagcaacc ctccaggttg tagaagtgga caagacgcaa cgcctttcca ctcggcaacc  19500
ccccacacag cctgcagtcc ctggtgcctc aaattgaacc cggctggccc aaggcgcccc  19560
tacgaggccc catccatccc gagttgtgcg tgcaaagcgc ggccagctcc gcgaaaactt  19620
agctgtgtca cgcgagggag gagggaaatt atccccgaaa ggggaaaggt aattccaggg  19680
tgcacatttc accccctcca cggcaaaagt cacccaggag gctgacatcc tcccctagtc  19740
```

```
tccccttcaa acccgtctcc aggctgttcg gggagttgcc ttttgaagtt caatttatct  19800

ttgaaacatt caataaaaaa tgatgaggca ctgtcagtct tttggtctcc cgaccccccag  19860

cctcgcctcc gaggtgtgtg tctgttgggg ggcgggggcg gcacgggaag gttcgagggt  19920

tagtccttag cccttttctt gccctggggg ccatgacgtg aagacccagc tggagcctgc  19980

ctggcggctg cctccctccc caccccccac ccgccacccc ctggagcccg ccagcccggc  20040

cccaagtccc tgtcaccttc aggcctcttg aatgaccgga gaggaggacg ccccctccct  20100

tccctcatcc tgtacttgga agggatcgag gtcgagacct tttggagagc ggggcaaagc  20160

cccttccatc tctggccagg cacgtgggga cccctacagc ctcctctgcg atgtctccgg  20220

gggtgggagg gaagacagac aaccagagta tgttggtgcg gagtcgcggg gggggggagg  20280

ggcggggtgc gctgcggggg tggcagggcc tgagctgaga cgggccctgg ggacctttga  20340

ggctggggct cccccgagga ctgggagatt tccagggcgc gctccttctg cgcagcggct  20400

acagcctgaa gggggcagct ctggatccag cgacaacgcg cggtgtccgc gcctctgaga  20460

aggtggtagt tggctggttg cgctctcccg aattggggaa aaaagaactc agcctccaaa  20520

agggaagaaa tgctttgctt ttctcttctt tctcagtcca aatttgctta cctcctccct  20580

tctctccccc cgcccccgat ttggggaccc tgctcagact tgtgtccagc ctctcttact  20640

ggcgttcctc tttttttttt tttttttttt ttaatctcct gtgtatctca tttgtatatt  20700

gtgatgttaa tgagtaactc ctgtagcgct gatgggcggg gggtggaggg gatgaacggc  20760

tcgcagtctc tctggatttt gctgcctatt actcacctgg cgccggtcgc aatctcgccg  20820

caggctttat ggtggctgcg gccgccccag aggccactca gggcaggcgc cttcgccttt  20880

tttctgggct tcgagtgcca cctatctgtc t                                20911
```

<210> SEQ ID NO 15
<211> LENGTH: 305
<212> TYPE: DNA
<213> ORGANISM: Homo sapiens

<400> SEQUENCE: 15

```
cagcaggcgc gctcccggcg aatctgcctg aatcgccgtg aatgcggtgg ggtgcagggc     60

aggggctggt tttctcagcc ggtcttggct tttctctttc tctcctgctc caccagcagc    120

ccctccgcgg gtcccatggg ctccgcgctc agaacagccc ggaaccaggc gccgctcgcc    180

gctcgctggg ggccacccgc ctctccccgg aacagcctcc cgcgggcctc ttggcctcgc    240

actggcgccc tcacccacac atcgtccctt tatccgctca gacgctgcaa agggccttct    300

gtctc                                                               305
```

<210> SEQ ID NO 16
<211> LENGTH: 336
<212> TYPE: DNA
<213> ORGANISM: Homo sapiens

<400> SEQUENCE: 16

```
gctttggatt tatcctcatt ggctaaatcc ctcctgaaac atgaaactga aacaaagccc     60

tgaacccccct caggctgaaa agacaaaccc cgcctgaggc cgggtcccgc tccccacctg    120

gagggaccca attctgggcg ccttctggcg acggtccctg ctagggacgc tgcgctctcc    180

gagtgcgagt tttcgccaaa ctgataaagc acgcagaacc gcaatcccca aactaacact    240

gaacccggac ccgcgatccc caaactgaca agggacccgg aacagcgacc cccaaaccga    300

cacgggactc gggaaccgct atctccaaag ggcagc                             336
```

<210> SEQ ID NO 17
<211> LENGTH: 139
<212> TYPE: DNA
<213> ORGANISM: Homo sapiens

<400> SEQUENCE: 17
tttccacaac agggagccag cattgaggcg cccagatggc atctgctgga aatcacgggc 60
cgctggtgaa gcaccacgcc ttacccgacg tggggaggtg atcccccacc tcatcccacc 120
cccttctgtc tgtctcctt 139

<210> SEQ ID NO 18
<211> LENGTH: 292
<212> TYPE: DNA
<213> ORGANISM: Homo sapiens

<400> SEQUENCE: 18
gctggacaag gagcgctcac tgtagctctg ctgtggattg tgttggggcg aagagatggg 60
taagaggtca aagtcgtagg attctggcga ccgcctacca agggattggg tccacagcac 120
agaggtctga tcgcttcctt ctctgctctg ccacctccag acagcagctc taaccagctg 180
cccagcagca agaggatgcg cacggctttc accagcacgc agctgctaga gctggagcgc 240
gagttcgctt ctaatatgta cctgtcccgc ctacgtcgca tcgagatcgc ga 292

<210> SEQ ID NO 19
<211> LENGTH: 190
<212> TYPE: DNA
<213> ORGANISM: Homo sapiens

<400> SEQUENCE: 19
tgcctgacac tgaccccagg cgcagccagg aggggctttg tgcgggagag ggagggggac 60
cccagcttgc ctggggtcca cgggactctc ttcttcctag ttcactttct tgctaaggcg 120
aaggtcctga ggcaggacga gggctgaact gcgctgcaat cgtccccacc tccagcgaaa 180
cccagttgac 190

<210> SEQ ID NO 20
<211> LENGTH: 706
<212> TYPE: DNA
<213> ORGANISM: Homo sapiens

<400> SEQUENCE: 20
tcggcggaga gacctcgagg agagtatggg gaaaggaatg aatgctgcgg agcgcccctc 60
tgggctccac ccaagcctcg gaggcgggac ggtgggctcc gtcccgaccc cttaggcagc 120
tggaccgata cctcctggat cagaccccac aggaagactc gcgtggggcc cgatatgtgt 180
acttcaaact ctgagcggcc accctcagcc aactggccag tggatgcgaa tcgtgggccc 240
tgaggggcga gggcgctcgg aactgcatgc ctgtgcacgg tgccgggctc tccagagtga 300
gggggccgta aggagatctc caaggaagcc gaaaaaagca gccagttggg cttcgggaaa 360
gacttttctg caaaggaagt gatctggtcc cagaactcca gggttgaccc cagtacctga 420
cttctccggg agctgtcagc tctcctctgt tcttcgggct tggcgcgctc ctttcataat 480
ggacagacac cagtggcctt caaaaggtct ggggtggggg aacggaggaa gtggccttgg 540
gtgcagagga agagcagagc tcctgccaaa gctgaacgca gttagcccta cccaagtgcg 600
cgctggctcg gcatatgcgc tccagagccg gcaggacagc ccggccctgc tcaccccgag 660

```
gagaaatcca acagcgcagc ctcctgcacc tccttgcccc agagac                706

<210> SEQ ID NO 21
<211> LENGTH: 325
<212> TYPE: DNA
<213> ORGANISM: Homo sapiens

<400> SEQUENCE: 21

agatcccggt gcatttaaag gccggcgtga tctgcaccac gtacctatct cggattctca  60

gtttcacttc gctggtgtct gccaccatct ttaccacatc ccggtagcta catttgtcta 120

ccgcttgagc caccagcgtc tgaaacctgg accggatttt gcgcgccgag aggtagccgg 180

aggcggtaat gaattccacc cagagggaca tgctcctctt gcgcccgtcg ctcaacttca 240

gcaccgcgca gccgggcagt gagccatcgt ccacgaagtt gaacaccccc atttggttga 300

gataaagcac cacttcaaat tcggt                                      325

<210> SEQ ID NO 22
<211> LENGTH: 663
<212> TYPE: DNA
<213> ORGANISM: Homo sapiens

<400> SEQUENCE: 22

actatgcctt gagggtcaaa acgtctggat ttcctgatcg atgctgtcgt cgctgtccac  60

ggagctactg tcgccgtcag agcgggaagg cacgttcagg gagtagaagc gtgggcttgc 120

agaaagggac ctgttgctgc cttacatggg ggccggcagg gtagtcttgg aaatgcccaa 180

gattgcttcc gcgcgcgtca gttcagcgga cgtgtctgcc tggcacgagg accgttctac 240

aaactcgttc ctggaagccg ggctcgctgg aggcggagct ttggtttcct tcgggagctt 300

gtggggaatg gtcagcgtct aggcaccccg ggcaagggtc tgtggccttg gtggccactg 360

gcttcctcta gctgggtgtt ttcctgtggg tctcgcgcaa ggcacttttt tgtggcgctg 420

cttgtgctgt gtgcggggtc aggcgtcctc tctcctcccg gcgctgggcc ctctggggca 480

ggtccccgtt ggcctccttg cgtgtttgcc gcagctagta cacctggatg gcctcctcag 540

tgccgtcgtt gctgctggag tctgacgcct cgggcgcctg cgccgcactt gtgacttgct 600

ttccccttct cagggcgcca gcgctcctct tgaccccgct tttattctgt ggtgcttctg 660

aag                                                              663

<210> SEQ ID NO 23
<211> LENGTH: 1985
<212> TYPE: DNA
<213> ORGANISM: Homo sapiens

<400> SEQUENCE: 23

gcaagtcggg tagctaccgg gtgctggaga actccgcacc gcacctgctg gacgtggacg  60

cagacagcgg gctcctctac accaagcagc gcatcgaccg cgagtccctg tgccgccaca 120

atgccaagtg ccagctgtcc ctcgaggtgt tcgccaacga caaggagatc tgcatgatca 180

aggtagagat ccaggacatc aacgacaacg cgccctcctt ctcctcggac cagatcgaaa 240

tggacatctc ggagaacgct gctccgggca cccgcttccc cctcaccagc gcacatgacc 300

ccgacgccgg cgagaatggg ctccgcacct acctgctcac gcgcgacgat cacggcctct 360

ttggactgga cgttaagtcc cgcggcgacg gcaccaagtt cccagaactg gtcatccaga 420

aggctctgga ccgcgagcaa cagaatcacc atacgctcgt gctgactgcc ctggacggtg 480

gcgagcctcc acgttccgcc accgtacaga tcaacgtgaa ggtgattgac tccaacgaca 540
```

```
acagcccggt cttcgaggcg ccatcctact tggtggaact gcccgagaac gctccgctgg    600

gtacagtggt catcgatctg aacgccaccg acgccgatga aggtcccaat ggtgaagtgc    660

tctactcttt cagcagctac gtgcctgacc gcgtgcggga gctcttctcc atcgacccca    720

agaccggcct aatccgtgtg aagggcaatc tggactatga ggaaaacggg atgctggaga    780

ttgacgtgca ggcccgagac ctggggccta accctatccc agcccactgc aaagtcacgg    840

tcaagctcat cgaccgcaac gacaatgcgc cgtccatcgg tttcgtctcc gtgcgccagg    900

gggcgctgag cgaggccgcc cctcccggca ccgtcatcgc cctggtgcgg gtcactgacc    960

gggactctgg caagaacgga cagctgcagt gtcgggtcct aggcggagga gggacgggcg   1020

gcggcggggg cctgggcggg cccggggggtt ccgtcccctt caagcttgag gagaactacg  1080

acaacttcta cacggtggtg actgaccgcc cgctggaccg cgagacacaa gacgagtaca   1140

acgtgaccat cgtggcgcgg gacgggggct ctcctcccct caactccacc aagtcgttcg   1200

cgatcaagat tctagacgag aacgacaacc cgcctcggtt caccaaaggg ctctacgtgc   1260

ttcaggtgca cgagaacaac atcccgggag agtacctggg ctctgtgctc gcccaggatc   1320

ccgacctggg ccagaacggc accgtatcct actctatcct gccctcgcac atcggcgacg   1380

tgtctatcta cacctatgtg tctgtgaatc ccacgaacgg ggccatctac gccctgcgct   1440

cctttaactt cgagcagacc aaggcttttg agttcaaggt gcttgctaag gactcggggg   1500

cgcccgcgca cttggagagc aacgccacgg tgagggtgac agtgctagac gtgaatgaca   1560

acgcgccagt gatcgtgctc cccacgctgc agaacgacac cgcggagctg caggtgccgc   1620

gcaacgctgg cctgggctat ctggtgagca ctgtgcgcgc cctagacagc gacttcggcg   1680

agagcgggcg tctcacctac gagatcgtgg acggcaacga cgaccacctg tttgagatcg   1740

acccgtccag cggcgagatc cgcacgctgc accctttctg ggaggacgtg acgcccgtgg   1800

tggagctggt ggtgaaggtg accgaccacg gcaagcctac cctgtccgca gtggccaagc   1860

tcatcatccg ctcggtgagc ggatcccttc ccgagggggt accacgggtg aatggcgagc   1920

agcaccactg ggacatgtcg ctgccgctca tcgtgactct gagcactatc tccatcatcc   1980

tccta                                                               1985
```

<210> SEQ ID NO 24
<211> LENGTH: 213
<212> TYPE: DNA
<213> ORGANISM: Homo sapiens

<400> SEQUENCE: 24

```
atgcgccctc tgcaccccta gagccagaag acgctaggtg ggctgcgcgc tctgccaggc     60

gaaggctgga gcgcagacgg caaagccgcg cgtttcagcc gtggtcgggt ccgcaggacc    120

tgggcgtggg gacaccacca ggcaggagca gaggcaggac tgggacgcca aaagctgaga    180

atcctcgatg cccgcgcgag agccccgtgt tat                                 213
```

<210> SEQ ID NO 25
<211> LENGTH: 1558
<212> TYPE: DNA
<213> ORGANISM: Homo sapiens

<400> SEQUENCE: 25

```
ttctggaaac cgggccccac ttgcaggccc ggccaccttg ggttctggtg gccgaagccg     60

gagctgtgtt tctcgcagac tcggggagct acattgtgcg taggcaattg tttagtttga    120
```

```
aaggaggcac atttcaccac gcagccagcg ccctgcatgc aggagaagcc cccagggccc    180
agggtcggct ggctttagag gccacttagg ttgttttaag cacatgtgaa agggcagaca    240
gcaggggagc aggatatggg taagatcttc gggtctcaga acaggggctg cccttgggct    300
gtcccggcgc cctgggctct gacactgaag ggtggaatgg aggaaggaat ggagaaagga    360
cggtggaact ttcgcttccc ctctgggccg ccttcccagg gtcatgcctg agctgctttg    420
atcccagtgt cgcgcatctt ggtccgctac ctcccaggcg atagctactg ggctcctcgc    480
tggcctcact gggggccatc ccgggcagtg gcctgccctc cgaggcccgc gggacccagc    540
ccagagctga ggttggagtt ctccgggcca cgttccgggt cgcttaggct cggagatttc    600
ccggagaccg tcgtcctccc tttctgcttg gcactgcgga gctccctcgg cctctctcct    660
cctctggtcc ctaaggcccg gagtggttgg cggtactggg gcccgtcgtc atctctgctt    720
ctaaggcatt cagactgggc tccagctggg accggcagag gaggttctca aggaaactgg    780
tgggaaatat agttttcttt cgtctggtcg tttaatttaa atgcaacttc ccttggggac    840
attttcctgg acgttaacca gaccaccttg agatgtcgtt gatgacctag agacccagat    900
gatgcgtccc aggaaagttc actgctgact attgtcactc ttggcgttat atctatagat    960
atagacctat gtacatatct ccaccctgat ctctccgtgg acatgaaacc cacctacctt   1020
gtgaaagccc tacgggtgac acatgactac tacgtctctg tcccaacagg ggctgggcct   1080
cccctgccta atagttgcca ggagtttcgc agcccaagtg aataatgtct tatggctgaa   1140
cgtggccaag gactcctgtg atttaggtcc caggaggagc agagacgtcc ccgcccccgcc   1200
tgggccctgc cgcattcaaa gctggaagaa ggcgctgatc agagaagggg cttccaggtc   1260
ctgggttaga acaacaacaa acaaacgaaa ctccacaaca gacacgcctg cccatgaccc   1320
cacgcaagga cataggaagt tctgtcgcct tcctgctccg cggatagccg cctgccgtct   1380
gctgccacca gaacgcacgg acgctcgggg tggaggtagt caatgggcag caggggaccc   1440
ccagcccccca caagcgcggc tccgaggacc tggaagcggg tgcctgtcgc tctccgcagg   1500
ctccgctctg cctccaggag caagatcccc aaaagggtct ggaagctgtg gagaaaac     1558
```

<210> SEQ ID NO 26
<211> LENGTH: 1264
<212> TYPE: DNA
<213> ORGANISM: Homo sapiens

<400> SEQUENCE: 26

```
tttttaaac acttcttttc cttctcttcc tcgttttgat tgcaccgttt ccatctgggg      60
gctagaggag caaggcagca gccttcccag ccagcccttg ttggcttgcc atcgtccatc    120
tggcttataa aagtttgctg agcgcagtcc agagggctgc gctgctcgtc ccctcggctg    180
gcagaagggg gtgacgctgg gcagcggcga ggagcgcgcc gctgcctctg gcgggctttc    240
ggcttgaggg gcaaggtgaa gagcgcaccg gccgtggggt ttaccgagct ggatttgtat    300
gttgcaccat gccttcttgg atcggggctg tgattcttcc cctcttgggg ctgctgctct    360
ccctccccgc cggggcggat gtgaaggctc ggagctgcgg agaggtccgc caggcgtacg    420
gtgccaaggg attcagcctg gcggacatcc cctaccagga gatcgcaggt aagcgcgggc    480
gcgctgcagg ggcaggctgc agccctcggc tgccgcacgt cccactggcc gcccggcgtc    540
cccttccttc cccctgttgc tgagttggtg ctcactttct gccaccgcta tgggactccg    600
cgtctccgtg ttgggcggcg gatgctcctg cggcttcttc ggcgggggaa ggtgtgcgtc    660
tccgccgcct cattgtgtgc acacgcggga gcaccctggc tcccgcctcc cgctgctctc    720
```

```
gcgcccttct accccttagt tgatggctca ggcccggctg gccagggagc ccgggtcact    780

ccggggcggc tgcaaggcgc agacggagag ccgagccggg cgctcactcc gcgttctggt    840

tcgggcaaac ttggaagaac tgcgaccgca gtttgcccag cgccacagtc tgagtggcgc    900

cttctccact cccgcccttg cgccggcagg ggcggtggag agacgcggag ggctccccca    960

gcccctctct cccctatccg tccttcgggc gacagagcgc ccggcgctcg ggccgggggc   1020

gggcaaggct gggagggacc ctcgccgggg acctggcctc tggacgccgg cgtttcaagg   1080

ctggtttggg gacttcacgg gctgcctgtt tcagatgtgg ggcgggcttt cccgttaggg   1140

ttcctcagtg cttccccagt tgctgttggc cactcagggc ccggggacac cctgccaccc   1200

ggtctggagc cggcctcgtc tgccagcgaa cagccaactt tagcgggtgg ctcagctggg   1260

gatt                                                                1264
```

<210> SEQ ID NO 27
<211> LENGTH: 761
<212> TYPE: DNA
<213> ORGANISM: Homo sapiens

<400> SEQUENCE: 27

```
cactcagtgt gtgcatatga gagcggagag acagcgacct ggaggccatg ggtgggggcg     60

ggtggtgaag ctgccgaagc ctacacatac acttagcttt gacacttctc gtaggttcca    120

aagacgaaga cacggtggct tcagggagac aagtcgcaag ggcgactttt ccaagcggga    180

gatggtgaag tctttggacg tgtagtgggt aggtgatgat ccccgcagcc gcctgtaggc    240

ccgcagactt cagaaaacaa gggccttctg tgagcgctgt gtcctccccg gaatccgcgg    300

cttaacacat tctttccagc tgcggggcca ggatctccac cccgcgcatc cgtggacaca    360

cttagggtcg cctttgtttt gcgcagtgat tcaagttggg taacccttgc tcaacacttg    420

ggaaatgggg agaatctccc ccacccgcaa cctcccgcac cccaggttcc caaaatctga    480

atctgtatcc tagagtggag gcagcgtcta gaaagcaaag aaacggtgtc caaagacccc    540

ggagagttga gtgagcgcag atccgtgacg cctgcggtac gctagggcat ccaggctagg    600

gtgtgtgtgt gcgggtcggg gggcgcacag agaccgcgct ggtttaggtg gacccgcagt    660

cccgcccgca tctggaacga gctgcttcgc agttccggct cccggcgccc cagagaagtt    720

cggggagcgg tgagcctagc cgccgcgcgc tcatgtttat t                        761
```

<210> SEQ ID NO 28
<211> LENGTH: 1198
<212> TYPE: DNA
<213> ORGANISM: Homo sapiens

<400> SEQUENCE: 28

```
agtcactcca ggatcagagg ccgcgtcggt tctgcttggg gcatgggcag agggaggctg     60

ctggggccaa gccccggctg gacgcgaggg aagaaactcg tcccaggacc cgcacgccca    120

tacctggctg tcccagagct cttccctagg ccggcacctt cgctcttcct cttccccacc    180

ccctagccct tttgtctctt tttcagacgg atgttttcag tctcaagtgg ttttattttc    240

cgcacaaaac cctgagatca agggcagatc acagactgta ccggaggctc gggtttccct    300

ggactctgtg ctgttctgcg tcccagggtt ggctaggaag gaaggcctgg gccggcgagg    360

tgacgggtct cccgcccagg tcggcaggac ggggggaggt gtgtcccggt aggtccctgg    420

tgagctcacc cgtggcatcg gggacccgcg ggaacccacc gggcgcccac tagagactcg    480
```

```
ggtcctaccc tcccccacac tactccaccg aaatgatcgg aagggcgcgc taggcctgct     540

tccaagggct cagtgataaa ggcctcaaaa tcacactcca tcaagacttg gttgaagctt     600

tgggtaggtt tgttgttgtt gttgttgttg tttgtttgtt tgttttagca gacacgtcct     660

ggaaagaggt cctcagaacc caaaggttca ataatgattt gtggatggat tgattatagt     720

ctgatatcgc tctggttcca cagaaacccg gagctccttg gcccactgtt accccagcag     780

acctaaatgg acggtttctg tttttcactg gcagctcaga actggaccgg aagaagttcc     840

cctccacttc ccccctcccg acaccagatc attgctgggt ttttattttc gggggaaaaa     900

caacaacaac aacaacaaaa aaaacactag gtccttccag actggatcag gtgatcgggc     960

aaaaaccctc aggctagtcc ggctgggtgc ccgagcatga aaaggcctcc gtggccgttt    1020

gaacagggtg ttgcaaatga gaacttttgt aagccataac cagggcatcc tgagggtctg    1080

agttcacggt caaggctgtg ggctactagg tccagcgagt ccaggcctcg ccccgccccc    1140

gagctgccac agccaagatc ttcggcaggg aattcgagac cagggtcctc ccactcct      1198


<210> SEQ ID NO 29
<211> LENGTH: 377
<212> TYPE: DNA
<213> ORGANISM: Homo sapiens

<400> SEQUENCE: 29

tttcgtgccg ctgttttcaa tgcgctaacg aggcacgtta ttcttagccg cgtccgggag      60

gggatcacat tcctgcgcag ttgcgctgct ggcggaagtg acttgttttc taacgaccct     120

cgtgacagcc agagaatgtc cgtttctcgg agcgcagcac agcctgtccc atcgagaagc     180

ctcgggtgag ggcccggtg ggcgcccgga ggccgctgga gggctgtggg agggacggtg     240

gctccccact cccgtggcga agggcaggca aaccagaagc ctcttttgag agccgtttgg     300

gattgagacg agtaagccac agcgagtggt tagaagtagg ttaggaagaa ggggaggtaa     360

gaaagccgag tagggtt                                                    377


<210> SEQ ID NO 30
<211> LENGTH: 256
<212> TYPE: DNA
<213> ORGANISM: Homo sapiens

<400> SEQUENCE: 30

gttcggtgga caaggggggca gcgcccacag caagccggaa agagggaggc gcggggccgc      60

gcttggggcc tgccgctgca cgccagcctg ggcaaagagc tgccaccttc tgcgggcgaa     120

gcgggtcggg acgcaggacg gcagcggggc tggaggcagc tacgtgggtc cacaccccca     180

tgccctgcaa ggctccttgg ccctgcttct cctctgtctc ggcgggagag gagcagcctc     240

ggttttacag aatttc                                                     256


<210> SEQ ID NO 31
<211> LENGTH: 189
<212> TYPE: DNA
<213> ORGANISM: Homo sapiens

<400> SEQUENCE: 31

tgtgccattt agtgagaggt gttttgggca aagaatcaat ttaactgtga ctgaccgacg      60

ggcttgactg tattaattct gctaccgaaa aaaaaaaaaa aaaaaaagca atgagccgca     120

agccttggac tcgcagagct gccggtgccc gtccgagagc cccaccagcg cggctcacgc     180

ctcagtctc                                                             189
```

<210> SEQ ID NO 32
<211> LENGTH: 707
<212> TYPE: DNA
<213> ORGANISM: Homo sapiens

<400> SEQUENCE: 32

```
agagtcccag ttctgcaggc cgctccaggg ctaggggtag agatggtggc aggtggtgcg     60
tcaactctct agggaagagg aacttgcatt acaaagactt gtctttctga gctgaagtca    120
aaacgggggc gtcaagcgcg ctccgtttgg cggcggtgga ggggccgcgc gcccgcgctg    180
tcccagccgg agctgccctg gctggtgatt ggaggtttaa cgtccggaat tcaggcgctt    240
ctgcagctca gatttgccgg ccaaggggcc tcagttgcaa cttttcaaaa tggtgtttct    300
ggaaaataac aaattcagac tcaactggtg acagcttttg gctatagaga atgaaactgc    360
ttccctttgg cggtggaact cttaaacttc gaagagtgaa agaatacaat gaaataaaat    420
gccataagat cactggattt ttcagaaaaa ggaagacccc aaattactcc caaaatgagg    480
ctttgtaaat tcttgttaaa aatctttaaa tctcgaattt cccccctacaa catctgatga    540
gtgctttaag agcaaacgag caaatcccac ctcgagaatc aacaaaccca agctctggcc    600
aaggctctcc ccgcgttttc ttctcgtgac ctggggaatg tcccgcccca tcgctcacct    660
ggctcttgtc atctcgctca tcttgaagtg acccgtggac aatgctg                  707
```

<210> SEQ ID NO 33
<211> LENGTH: 182
<212> TYPE: DNA
<213> ORGANISM: Homo sapiens

<400> SEQUENCE: 33

```
agctgccctc tgtggccatg agcgggtgtc cagccccttc caaggctgca ccggggagac     60
gctggttttc tgctcgctgt gaccgaacaa agcccctaag agtcagtgcg cggaacagaa    120
gagccggacc ccgacgggcc gagtcccaac gtgaggcacc cggcagagaa aacacgttca    180
cg                                                                   182
```

<210> SEQ ID NO 34
<211> LENGTH: 179
<212> TYPE: DNA
<213> ORGANISM: Homo sapiens

<400> SEQUENCE: 34

```
cctcggcagc accggcatgg ctggaggcca gtacggccag gtgtggcggg agggagcgcc     60
gtctggcttg ggtcgtccat cctgacagga cgctgcaagg gcaggagccc cgcgccccgt    120
gtcctgcgcc cccgctcgag gacaagcccc agccgccggt ctccgctggg ttccgacag     179
```

<210> SEQ ID NO 35
<211> LENGTH: 369
<212> TYPE: DNA
<213> ORGANISM: Homo sapiens

<400> SEQUENCE: 35

```
ctttaagagg ctgtgcaggc agacagacct ccaggcccgc taggggatcc gcgccatgga     60
ggccgcccgg gactatgcag gagccctcat caggcgagtg ccccgcgtcc ccctgattgc    120
cgtgcgcttc caatcgcctt gcgttcggtg gcctcatatt cccctgtgcg cctctagtac    180
cgtaccccgc tcccttcagc cccctgctcc ccgcattctc ttgcgctccg cgaccccgcg    240
```

cacacaccca tccgccccac tggtgcccaa gccgtccagc cgcgcccgcg ggcagagccc 300
aatcccgtcc cgcgcctcct caccctcttg cagctgggca caggtaccag gtgtggctct 360
tgcgaggtg 369

<210> SEQ ID NO 36
<211> LENGTH: 176
<212> TYPE: DNA
<213> ORGANISM: Homo sapiens

<400> SEQUENCE: 36
agacttgcag aactcgggcc ccctggagga gacctaaccg ccacggtctt ggggaggttc 60
cggagggcct cggttgtctg cactcccaac accaagaaac ccctgagacg cgaagctgcc 120
agcgtgctgc cctcagagca gggcgacgca aagccagcgg accccggggt ggcggg 176

<210> SEQ ID NO 37
<211> LENGTH: 167
<212> TYPE: DNA
<213> ORGANISM: Homo sapiens

<400> SEQUENCE: 37
tgctcggctg gggggctcgc tccgcacttt cggtgccaga aaatgcccag aggagcgggg 60
cggccccaga gcctcctttc ggggcgcgag gcccggcgcg tgtgtacgga gtccagtccc 120
cccagggagt ggggtgcccg caccttcccc tccgcgctcg gagccac 167

<210> SEQ ID NO 38
<211> LENGTH: 1205
<212> TYPE: DNA
<213> ORGANISM: Homo sapiens

<400> SEQUENCE: 38
tcttgcacac ctgcttgtag ttctgcaccg agatctggtc gttgaggaac tgcacgcaga 60
gcttggtgac ctgggggatg tgcaggatct tgctgaccga cagcacctcc tccaccgtgt 120
ccagggacag ggtcacgttg gccgtgtaga ggtactcgag caccaggcgc agcccgatgg 180
acgagcagcc ctgcagcacc aggttgttga tggcccgggg gctggtcagc agcttgtcgt 240
cgggggagga agaaggagtc ccgggctcct cctgcggcgg cggctgctgc tgctgtgacg 300
gctgctgctg cggcggctgc tgctggtcct tgggggcccc caggccgtcc tggccgccga 360
cccctccccc gagagggggg tggctggaga agagcgatcg gaagtactgc gagcaggagg 420
ccagcacggc cttgtggcaa tggaactgct ggccctgggc cgtcagggtc acgtcgcaaa 480
acagctgctt cctccacagc aggttgaggc cgtgcagcag gttgtcgctg tggctggggt 540
cgaaggtgga ggtcctgtcc ccggatctgg acatggcgag ctgactcggt gcacctggct 600
ttaaaccctc ctccaacctg gcagacaggg gtgggggatg ggagggaggg gagcagggtg 660
gtggagcggg tggggtgtgg tcggggtggg gaagggtgtg gaggggaggg gagggcgaag 720
aacaagaatc aaggctcagc ttgactccct cctggcgcgc tccggacccc gaccctagga 780
ggaaagtccg aagacgctgg atccgtgagc gccaccagaa gggccctgtc tggggtcccg 840
gcgccggttc tgcgccctgc ggctcctctc gccacctccc acacacttcg tccctcactt 900
tcctaaaacc aaccacctca gctcggctgt tggcagcaac agcagtggca gcagcgacgg 960
caaagtggcg gctgaggccg aggcacctcg tgggctcgtg tccatgccgg gccagatgaa 1020
gggaaaggcc gggaagtggg gagccggggg tgccctgaaa gctcagaggc gaccgacggc 1080
gaaggttcca ggtcaacttg tgcccgaagc tttgcttttc gcagttggcc cagtttgggg 1140
gagggggtag gaacaggggc ccgaccagcg tgcggggtgt gcgaatctta gctctccaaa 1200
agctg 1205

<210> SEQ ID NO 39
<211> LENGTH: 44
<212> TYPE: DNA
<213> ORGANISM: Homo sapiens

<400> SEQUENCE: 39
cctctgtgtt agtgccctcg ggaatttggt tgatggggtg tttg 44

<210> SEQ ID NO 40
<211> LENGTH: 5002
<212> TYPE: DNA
<213> ORGANISM: Homo sapiens

<400> SEQUENCE: 40
tgatgtcgca cctgaacggc ctgcaccacc cgggccacac tcagtctcac gggccggtgc 60
tggcacccag tcgcgagcgg ccaccctcgt cctcatcggg ctcgcaggtg gccacgtcgg 120
gccagctgga agaaatcaac accaaagagg tggcccagcg catcacagcg gagctgaagc 180
gctacagtat cccccaggcg atctttgcgc agagggtgct gtgccggtct caggggactc 240
tctccgacct gctccggaat ccaaaaccgt ggagtaaact caaatctggc agggagacct 300
tccgcaggat gtggaagtgg cttcaggagc ccgagttcca gcgcatgtcc gccttacgcc 360
tggcaggtaa ggccggggct agccaggggc caggctgctg ggaagagggc tccgggtccg 420
gtgcttgtgg cccaagtctg cgcgccgagt cacttctctt gattctttcc ttctctttcc 480
tatacacgtc ctctttcttc tcgtttttat ttcttcttcc attttctctt tctcttccgc 540
tcttccccta ctttcccttc tcccttttct ttttctttct tactctctcc ttgtccctga 600
gctttcattg accgaccccc ccccatttca ttcgccctcc cctcaatgtg ccaacctttg 660
ccctatttcc gatcttccca ggtactggga ggcgggatgg gggtgtgcgt tttcctctag 720
gagccctgtc tttccaagac ccacagaaac caggacctgc ccttattcaa aaccccatgc 780
acttcaagtc tcttttagac aacacatttc aattttccgg gctgactagt ctccctgtgc 840
agaggcagtt gagaggcttt gctctgcaga gggaaaagag ctctctactc tcccacccac 900
catataggca aacttatttg gtcattggct gaaggcacag ccttgccccc gcggggaacc 960
ggcggccagg atacaacagc gctcctggag cccatctctg gccttggcgt tggcgcaggg 1020
actttctgac cgggcttgag ggctcgggc cagctccaat gtcactacct acagcgaggg 1080
cagggtgtaa ggttgagaag gtcacattca ccgctttggg aggacgtggg agaagagact 1140
gaggtggaaa gcgctttgcc ttgctcaccg gccgtccttg ccccggtccc agcgtttgct 1200
gggatttgcc aggatttgcc ggggctccgg gagaccctga gcactcgcag gaagaggtgc 1260
tgagaaatta aaaattcagg ttagttaatg catccctgcc gccggctgca ggctccgcct 1320
ttgcattaag cgggcgctga ttgtgcgcgc ctggcgaccg cggggaggac tggcggcccg 1380
cgggagggga cgggtagagg cgcgggttac attgttctgg agccggctcg gctctttgtg 1440
cctcctctag cggccaagct gcgaggtaca gccctctatt gttctaggag cacagaaacc 1500
tcctgtgtgg gcggcgggtg cgcgagctag agggaaagat gcagtagtta ctgcgactgg 1560
cacgcagttg cgcgcttttg tgcgcacgga ccccgcgcgg tgtgcgtggc gactgcgctg 1620
cccctaggag caagccacgg gcccagaggg gcaaaatgtc caggtccccc gctgggaagg 1680

```
acacactata ccctatggca agccagggtg ggcgacttcc catggatcgg gtggaggggg   1740
gtatctttca ggatcggcgg gcggtctagg ggaacaattc gtggtggcga tgatttgcat   1800
agcgcgggtc ttgggatgcg cgcggttccg agccagcctc gcacagctcg cttccggagc   1860
tgcgagctca ggtttccacc cccgatcccc cgggctttcc tcgcaccgct gagcccagct   1920
tgtggggtgc actcgaccaa cgcccgacag ggctggggaa tgtgacaggc agcaggttca   1980
cccgggcttg gggaggggga gtttccgctt tgacagcatt ttcctttgcc gtctgctggt   2040
ggattcctat tcccagtcgg taatcgcccc gcagtgttga tctaagaagg taaagaaaac   2100
taggtttccc tgcaaagagc ctcccccaaa tcggcggact ccggatactt tgagtggatt   2160
tagaaattta tgtaatcttt ctcctttagt ttatttttca tcctctccta cagttttctc   2220
tgatttgctg ttggttcggg gcaagataaa gcagccagta gagagcgata ataatagcgg   2280
cgggaaatga actggagact ggctgacagt tcttaacatt ttgtcataga tccccccgaa   2340
tgtcccaggc tgtctctggt gggttttagt acccgccggc ttcttgggca ccggggacca   2400
gaaggaactt ggcagctggt cttaggggta cagttaaagg caggatgaca gctattctcc   2460
tgctcatctc agagcgctgc cgccccctca tgccggtcgc gcaaagaaca cagcttttaa   2520
aaaacacgtg ccttctgccc atataggtct gaaagtgatg aggaaagtaa tgcttcgcct   2580
attagcgagt ttcagctttt aaaatgatcc caagcgttgc tgagatgaga aagcgtggca   2640
tcccgggggt cctcagcccc acccgcgccc atggtgcaag tctgcaggga caggcccggg   2700
acagcactgc ccacgctgct agattttccg cagaggatcg ctgaagctgc cttcgtggga   2760
gacagaatgc ctcctccagc gagtggaaaa ggcctgctga ggaccccgct ttgctcgagc   2820
attcaaatgt gtgtctgttt tattaccctg ggttgaaaag ggacaagagc tttagccttt   2880
ttatctggcc attttatcag caactacaag tgtgttgagt ggttattatt acataggagg   2940
cttttcagtt tggggtcagt agatcagtct cttcagacac tgatgcagaa gctgggactg   3000
gtaagtaggt attatgtgct cggagcgcta ggggacagga gcaaatggag aagaaaagcg   3060
gaggctttct ccgcccggag tatcgatcgg aatccccgcc ggtacgccgc agagggccct   3120
cgccgttggg ccccgggggt ttaacaagcc cagccgctcc gcaggcggct cggccggact   3180
ctcagaccgg tgcctggaag acaccgtccc tgccccccctc ccgccaaacc tgcctcttct   3240
ctttctctca taggttatag gttccctttc tctctcattt tggccccgcc cccgggtcct   3300
gccaaacagc caagcaggcc ggggtttagg gggctcagaa tgaagaggtc tgatttggcc   3360
agcgccggca aagctcaccc ttaggcgagg tcacaacaga ggcaggtcct tcctgcccag   3420
cctgccggtg tagtcacagc caagggtggc acttgaaagg aaaagggaga aaacttcgga   3480
gaaatttaga ttgccccaac gttagatttc agagaaattg actccaaatg cacggattcg   3540
ttcggaaagg gcggctaagt ggcaggtggt tgcaaccccg cccggtcggg ccttcgcaga   3600
ggttccccaa gaccagccct tgcagggcgg ttttcagcaa cctgacaaga ggcggccaag   3660
acaaatttct gcgggttcga gcacacactc tcgggcgttg ggccccagag acctctaaac   3720
caagcacaaa caagaaggga gtgagagaac ccaggctaga acttgcacgg gcatcccact   3780
gaggaaaagc gaggcctcgg tggcaggcat gttttcttcc gacgcccgaa aatcgagccg   3840
agcgcccgac tacatttact gcagaggttt ccgcctccag tgagcccgga tcccccagcg   3900
gcctgcccgg agctggtctc cagtccccgc cgtagtccga cgcacggccc tctcctggca   3960
gcaagctccc agcggccagt ctgaagccaa ttctgttcag gcggccgagg gcccttagcc   4020
aacccaccat gatgtcgcct gggccacctg atgcccgcag cggcgggaca cggcccgggc   4080
```

```
agtgcgcagt ggctcctgct aggggcaccg cgtgcgtgct tgtctcccgc tgcgccgggg   4140

acgtccttgg gtgacacggg ccgctgggca cctcccaagc cgaggaaacg gaccccccttc   4200

gcagagtctc gcgcccaccc cccaacctcc cacctcgttt ctcgctgcta gggctcccga   4260

ctcagcccac ctctcctggc ggtttagtta gggatcagag ctggagaggc tgaacgcaac   4320

ccgtgccagt acggaacaga cgatatgttt gcctgctagc tgcttggatg aataattgaa   4380

aagttcgctg cagtctgtgc ttcgtcaagt cccgggtgcc gggagaacac cttcccaaca   4440

cgcatcaggg tgggcgggag cgggcagagg aggcgggacc cgagggagga gagtgaaccc   4500

gagcaggaga agcagcccag gcagccaggc gccctcgatg cgagaggctg ggcatttatt   4560

tttattccag gctttccact gtgtggttat gtcactttct caaacaaatg tgtatatgga   4620

gggagatcga tgctgataat gtttagaaga ttaaaagagc attaatgctg gcaacaataa   4680

cgtaaacgtg tggacccaga tttcattgat ctggaacttg atccggcgcg tttccagtaa   4740

gcccgacggc gcgctcttcc cagcagagcg ctcaccagcg ccacggcccc gcggttttcc   4800

agcggtgccg cttcgccagc tctgcgcggg ttctcccgtc tgaccgcagc tcctcccccg   4860

cgaggcccca gcccgcctta cttccccgag gttttctcct cctctcgcgg ggctctctgc   4920

cctctgcacc ccctccccccg acctctgcac cacccgcccc tgtgcgcaca caccgctact   4980

tgcgcttccg gcgatccgcc tg                                             5002
```

<210> SEQ ID NO 41
<211> LENGTH: 150
<212> TYPE: DNA
<213> ORGANISM: Homo sapiens

<400> SEQUENCE: 41

```
aaccggagat ctgcttggtg aactgagagg agtccttagg agagcgggga cgccaggggc     60

cgggggacac ttcgctctcg ccctagggaa ggtggtcttg acgctttcta ttgaagtcaa    120

acttgaaaat atcagctgcc gctggactat                                    150
```

<210> SEQ ID NO 42
<211> LENGTH: 339
<212> TYPE: DNA
<213> ORGANISM: Homo sapiens

<400> SEQUENCE: 42

```
cgtgagcaga acgcccgccc tggagcagtt aggaccgaag gtctccggag agtcgccggc     60

ggtgccaggt aacgcagagg gctcgggtcg ggccccgctt ctggggcttg ggactccggg    120

cgcgcggagc cagccctctg gggcgaaatc cccgggcggc gtgcgcggtc cctctccgcg    180

ctgtgctctc ccagcaactc cctgccacct cgacgagcct accggccgct ccgagttcga    240

cttcctcgga cttagtggga gaaggggttg gaaatgggct gccgggactg gggagctgc     300

tctctggaag cagggaagct ggggcgcacc ggggcaggt                           339
```

<210> SEQ ID NO 43
<211> LENGTH: 1961
<212> TYPE: DNA
<213> ORGANISM: Homo sapiens

<400> SEQUENCE: 43

```
tagaagagga agactcctct ggccccacta ggtatcatcc gcgctctccc gctttccacc     60

tgcgccctcg cttgggccaa tctctgccgc acgtgtccat ccctgaactg cacgctatcc    120
```

```
tccacccccg gggggttcct gcgcactgaa agaccgttct ccggcaggtt ttgggatccg    180

gcgacggctg accgcgcgcc gcccccacgc ccggttccac gatgctgcaa tacagaaagt    240

ttacgtcggc cccgacccgc gcgggactgc agggtccgcc ggagcgcggc gcagaggctt    300

ttcctgcgcg ttcggccccg ggaaaggggc gggagggctg gctccgggag cgcacgggcg    360

cggcggggag ggtactcact gtgaagcacg ctgcgcccat ggatcatgtc tgtgcgttac    420

accagaggct ccgggctcca ctaattccat ttagagacgg gaagacttcc agtggcgggg    480

ggaggacagg gtcgagaggt gttaaagacg caaagcaaga aggaaataaa ggggggccga    540

gagggagacc gagaggaagg gggagctccg agcccacgct gcagccagat ccggatgagt    600

ccgtcctccg ccccgggcgg gctctcgctc tcgctggccc tcagcgccgc gcagccagca    660

gcatccccac cgtgacgctc gcatcacacc cgggcgccgg ccgccaccat ccgcgccgcc    720

gccgtcagga ccctcctccc gggcatcgtc gccgccgcgg ggtcgggagg acgcggcgcg    780

cgggaggcgg cggtcgcagg gcgagccccg ggacgccccg agccggggcc ggggccgggg    840

agagggcgca gcgaggtggg ggccagtcca gaccgacggc agcgacggag cgggcggcgg    900

cggcggcgcc ggcggcggcg gggtggctca gtccccagtc tcagacgcgc cgcgcagcag    960

gtcggagcag cctccccggg aggatgtcca gcggcagcgc tcctcgctcc agcccttggg   1020

gatcttccgc tgaggcattg aaggcaggaa gaaggggtcc gtcatcggct cgccgggctg   1080

cgcgccacct ctgctatctt gcggaaagag gagcgggtgg gtgggcgtct gggaggcggg   1140

ctggagggcg gtgcagggga gcggggcggc cggggggggg gccgggggc ggggaaggga    1200

gggaggagaa aggagccgga agagggcaga gttaccaaat gggctcctta gtcatggctt   1260

ggggctccac gaccctcctg gaagcccgga gcctgggtgg gatagcgagg ctgcgcgcgg   1320

ccggcgcccc ggggctggtg cgcggcagaa tggggccgcg gcggcggcag caaggacatc   1380

ccagccgcgc ggatctgggg gaggggcggg gagggggtga ggacccggct gggatccgcg   1440

gctcggcccg ccagggcgca gagagaggat gcagccgcaa atcccgagcc ggatcctcgt   1500

gccggacgga aggcgtggaa gcgggagggg ccttcgtgtg aaaatccctt gtggggtttg   1560

gtgtttcact ttttaaaggt tagaccttgc gggctctctg cctcccaccc cttcttttcc   1620

atccgcgtaa aggaactggg cgccccctct ccctccctcc ctggggcgca ggtttcgccg   1680

cggactccgc gctcagcttg ggagacacgg caggggcgcg ccccagggaa aggcggccgt   1740

aaaagtttcg cggttgagca ctgggcctga tgtccagtcc ccccaccaaa ttactcctgc   1800

aaagacgcgg gcttcttgca attgagcccc ccacctcgag gtatttaaaa ccaccccaag   1860

gcacacacgg acccccgttc ccccgcgcca cttcctccta caggctcgcg cggcgcgtta   1920

aagtctggga gacacgagtt gcggggaaac agcaccggaa g                       1961
```

<210> SEQ ID NO 44
<211> LENGTH: 314
<212> TYPE: DNA
<213> ORGANISM: Homo sapiens

<400> SEQUENCE: 44

```
aagaaacagc tcatttcgga gctgaggaca aggcgtggga agaagacgcg tttggtttca     60

cccaggcggg tggcggcaaa gctgtgggat gcgcgctgca cactccttcc gtcatcccgt    120

tcccaccttc cacacacacc tgcgggaggt cggacatgtc ctgattgcgt gttcatcacg    180

atggcaaacc gaacatgagg agaacgccac tgacgctggg tgcgccggct ttcccagccc    240

tcgtgcataa cggggaggga gatgcagaag ttttttccaa catcggtgca aaggggaagc    300
```

```
tgaggttttc ctat                                                  314


<210> SEQ ID NO 45
<211> LENGTH: 584
<212> TYPE: DNA
<213> ORGANISM: Homo sapiens

<400> SEQUENCE: 45

tctgtcagct gctgccatgg ggcagcggga aggccctgga gggtgcctgg gctgtgtctg     60

gtcccggcca cgcgtccctg cagcgtctga gaccttgtgg aacacacttg acccggcgct    120

gggacggggt cggcccacac gcaccgccag cccgcaggag tgaggtgcag gctgccgctg    180

gctccttagg cctcgacagc tctcttgagg tcggccctcc tcccctcccg agagctcagc    240

agccgcagac ccaggcagag agagcaaagg aggctgtggt ggcccccgac gggaacctgg    300

gtggccgggg gacacaccga ggaactttcc gccccccgac gggctctccc accgaggctc    360

aggtgctcgt gggcagcaag gggaagcccc atggccatgc cgcttccctt tcaccctcag    420

cgacgcgccc tcctgtgccc gcggggaaca agacggctct cggcggccat gcaggcggcc    480

tgtcccacga acacgatgga gacctcagac gccgtcccca ccctgtcact gtcaccatca    540

cccatcctgt cccctcacgc ctccccacat cccatcatta ctac                     584


<210> SEQ ID NO 46
<211> LENGTH: 349
<212> TYPE: DNA
<213> ORGANISM: Homo sapiens

<400> SEQUENCE: 46

gaagtagaat cacagtaaat gaggagttag ggaatttagg gtagagatta aagtaatgaa     60

cagaggagga ggcctgagac agctgcagag agaccctgtg ttccctgtga ggtgaagcgt    120

ctgctgtcaa agccggttgg cgctgagaag aggtaccggg ggcagcaccc gcctcctggg    180

agagggatgg gcctgcgggc acctggggga accgcacgga cacagacgac actataaacg    240

cgggcgagac atcagggacc gggaaacaga aggacgcgcg tttcgagcag ctgcccagtg    300

ggccacaagc cccgccacgc cacagcctct tcccctcagc acgcagaga                349


<210> SEQ ID NO 47
<211> LENGTH: 3510
<212> TYPE: DNA
<213> ORGANISM: Homo sapiens

<400> SEQUENCE: 47

tactccggcg acgggaggat gttgagggaa gcctgccagg tgaagaaggg gccagcagca     60

gcacagagct tccgactttg ccttccaggc tctagactcg cgccatgcca agacgggccc    120

ctcgactttc acccctgact cccaactcca gccactggac cgagcgcgca aagaacctga    180

gaccgcttgc tctcaccgcc gcaagtcggt cgcaggacag acaccagtgg gcagcaacaa    240

aaaaagaaac cgggttccgg gacacgtgcc ggcggctgga ctaacctcag cggctgcaac    300

caaggagcgc gcacgttgcg cctgctggtg tttattagct acactggcag gcgcacaact    360

ccgcgccccg actggtggcc ccacagcgcg caccacacat ggcctcgctg ctgttggcgg    420

ggtaggcccg aaggaggcat ctacaaatgc ccgagccctt tctgatcccc acccccccgc    480

tccctgcgtc gtccgagtga cagattctac taattgaacg gttatgggtc atccttgtaa    540

ccgttggacg acataacacc acgcttcagt tcttcatgtt ttaaatacat atttaacgga    600
```

```
tggctgcaga gccagctggg aaacacgcgg attgaaaaat aatgctccag aaggcacgag    660
actggggcga aggcgagagc gggctgggct tctagcggag accgcagagg gagacatatc    720
tcagaactag gggcaataac gtgggtttct ctttgtattt gtttattttg taactttgct    780
acttgaagac caattattta ctatgctaat ttgtttgctt gtttttaaaa ccgtacttgc    840
acagtaaaag ttccccaaca acggaagtaa cccgacgttc ctcacactcc ctaggagact    900
gtgtgcgtgt gtgcccgcgc gtgcgctcac agtgtcaagt gctagcatcc gagatctgca    960
gaaacaaatg tctgaattcg aaatgtatgg gtgtgagaaa ttcagctcgg ggaagagatt   1020
agggactggg ggagacaggt ggctgcctgt actataagga accgccaacg ccagcatctg   1080
tagtccaagc agggctgctc tgtaaaggct tagcaatttt ttctgtaggc ttgctgcaca   1140
cggtctctgg cttttcccat ctgtaaaatg ggtgaatgca tccgtacctc agctacctcc   1200
gtgaggtgct tctccagttc gggcttaatt cctcatcgtc aagagttttc aggtttcaga   1260
gccagcctgc aatcggtaaa acatgtccca acgcggtcgc gagtggttcc atctcgctgt   1320
ctggcccaca gcgtggagaa gccttgccca ggcctgaaac ttctctttgc agttccagaa   1380
agcaggcgac tgggacggaa ggctctttgc taacctttta cagcggagcc ctgcttggac   1440
tacagatgcc agcgttgccc ctgccccaag gcgtgtggtg atcacaaaga cgacactgaa   1500
aatacttact atcatccggc tcccctgcta ataaatggag gggtgtttaa ctacaggcac   1560
gaccctgccc ttgtgctagc gcggttaccg tgcggaaata actcgtccct gtacccacac   1620
catcctcaac ctaaaggaga gttgtgaatt ctttcaaaac actcttctgg agtccgtccc   1680
ctccctcctt gcccgccctc tacccctcaa gtccctgccc ccagctgggg gcgctaccgg   1740
ctgccgtcgg agctgcagcc acggccatct cctagacgcg cgagtagagc accaagatag   1800
tggggacttt gtgcctgggc atcgtttaca tttggggcgc caaatgccca cgtgttgatg   1860
aaaccagtga gatgggaaca ggcggcggga aaccagacag aggaagagct agggaggaga   1920
ccccagcccc ggatcctggg tcgccagggt tttccgcgcg catcccaaaa ggtgcggctg   1980
cgtggggcat caggttagtt tgttagactc tgcagagtct ccaaaccatc ccatccccca   2040
acctgactct gtggtggccg tattttttac agaaatttga ccacgttccc tttctccctt   2100
ggtcccaagc gcgctcagcc ctccctccat cccccttgag ccgcccttct cctccccctc   2160
gcctcctcgg gtccctcctc cagtccctcc ccaagaatct cccggccacg ggcgcccatt   2220
ggttgtgcgc agggaggagg cgtgtgcccg gcctggcgag tttcattgag cggaattagc   2280
ccggatgaca tcagcttccc agccccccgg cgggcccagc tcattggcga ggcagcccct   2340
ccaggacacg cacattgttc cccgcccccg cccccgccac cgctgccgcc gtcgccgctg   2400
ccaccgggct ataaaaaccg gccgagcccc taaaggtgcg gatgcttatt atagatcgac   2460
gcgacaccag cgcccggtgc caggttctcc cctgaggctt ttcggagcga gctcctcaaa   2520
tcgcatccag agtaagtgtc cccgccccac agcagccgca gcctagatcc cagggacaga   2580
ctctcctcaa ctcggctgtg acccagaatg ctccgataca gggggtctgg atccctactc   2640
tgcgggccat ttctccagag cgactttgct cttctgtcct ccccacactc accgctgcat   2700
ctccctcacc aaaagcgaga agtcggagcg acaacagctc tttctgccca agccccagtc   2760
agctggtgag ctccccgtgg tctccagatg cagcacatgg actctgggcc ccgcgccggc   2820
tctgggtgca tgtgcgtgtg cgtgtgtttg ctgcgtggtg tcgatggaga taaggtggat   2880
ccgtttgagg aaccaaatca ttagttctct atctagatct ccattctccc caaagaaagg   2940
ccctcacttc ccactcgttt attccagccc gggggctcag ttttcccaca cctaactgaa   3000
```

agcccgaagc ctctagaatg ccacccgcac cccgagggtc accaacgctc cctgaaataa 3060
cctgttgcat gagagcagag gggagataga gagagcttaa ttataggtac ccgcgtgcag 3120
ctaaaaggag ggccagagat agtagcgagg gggacgagga gccacgggcc acctgtgccg 3180
ggaccccgcg ctgtggtact gcggtgcagg cgggagcagc ttttctgtct ctcactgact 3240
cactctctct ctctctccct ctctctctct ctcattctct ctcttttctc ctcctctcct 3300
ggaagttttc gggtccgagg gaaggaggac cctgcgaaag ctgcgacgac tatcttcccc 3360
tggggccatg gactcggacg ccagcctggt gtccagccgc ccgtcgtcgc cagagcccga 3420
tgaccttttt ctgccggccc ggagtaaggg cagcagcggc agcgccttca ctgggggcac 3480
cgtgtcctcg tccaccccga gtgactgccc 3510

<210> SEQ ID NO 48
<211> LENGTH: 333
<212> TYPE: DNA
<213> ORGANISM: Homo sapiens

<400> SEQUENCE: 48
ttaattcgaa aatggcagac agagctgagc gctgccgttc ttttcaggat tgaaaatgtg 60
ccagtgggcc aggggcgctg ggacccgcgg tgcggaagac tcggaacagg aagaaatagt 120
ggcgcgctgg gtgggctgcc ccgccgccca cgccggttgc cgctggtgac agtggctgcc 180
cggccaggca cctccgagca gcaggtctga gcgtttttgg cgtcccaagc gttccgggcc 240
gcgtcttcca gagcctctgc tcccagcggg gtcgctgcgg cctggcccga aggatttgac 300
tctttgctgg gaggcgcgct gctcagggtt ctg 333

<210> SEQ ID NO 49
<211> LENGTH: 385
<212> TYPE: DNA
<213> ORGANISM: Homo sapiens

<400> SEQUENCE: 49
ccggtcccca gtttggaaaa aggcgcaaga agcgggcttt tcagggaccc cggggagaac 60
acgagggctc cgacgcggga gaaggattga agcgtgcaga ggcgccccaa attgcgacaa 120
tttactggga tccttttgtg gggaaaggag gcttagaggc tcaagctata ggctgtccta 180
gagcaactag gcgagaacct ggccccaaac tccctcctta cgccctggca caggttcccg 240
gcgactggtg ttcccaaggg agcccccctga gcctaccgcc cttgcagggg gtcgtgctgc 300
ggcttctggg tcataaacgc cgaggtcggg ggtggcggag ctgtagaggc tgcccgcgca 360
gaaagctcca ggatcccaat atgtg 385

<210> SEQ ID NO 50
<211> LENGTH: 105
<212> TYPE: DNA
<213> ORGANISM: Homo sapiens

<400> SEQUENCE: 50
gcgcaggtcc ccccagtccc cgagggagtg cgcccgacgg aaacgcccct agcccgcggg 60
cctcgctttc ctctcccggg ttcctgggtc acttcccgct gtctc 105

<210> SEQ ID NO 51
<211> LENGTH: 147
<212> TYPE: DNA
<213> ORGANISM: Homo sapiens

<400> SEQUENCE: 51
ttccctcgcg gctttggaaa gggggtgcaa atgcaccctt ctgcgggccc gctacccgct 60
gcaacacctg tgtttccttt ctgggcacct tctaggtttc tagatattgc tgtgaatacg 120
gtcctccgct gtacagttga aaacaaa 147

<210> SEQ ID NO 52
<211> LENGTH: 365
<212> TYPE: DNA
<213> ORGANISM: Homo sapiens

<400> SEQUENCE: 52
tgggaattta ggtcgggcac tgccgatatg tcgccttcca caaggcgggc ccgggcctct 60
gctgaccgtg caccggtcct ggggctgggt aattctgcag cagcagcgca gcccatgccg 120
gggaatttgc gggcagagga gacagtgagg cccgcgttct gtgcgggaac tcccgagctc 180
acagagccca agaccacacg gctgcatctg cttggctgac tgggccaggc ccacgcgtag 240
taacccggac gtctctctct cacagtcccc ttgcgtctgg ccagggagct gccaggctgc 300
accccgcggt ggggatcggg agaggggcag tgtcgcccat ccccggaagg ctgagcctgg 360
tgcag 365

<210> SEQ ID NO 53
<211> LENGTH: 418
<212> TYPE: DNA
<213> ORGANISM: Homo sapiens

<400> SEQUENCE: 53
cggttttctc ctggaggact gtgttcagac agatactggt ttccttatcc gcaggtgtgc 60
gcggcgctcg caagtggtca gcataacgcc gggcgaattc ggaaagcccg tgcgtccgtg 120
gacgacccac ttggaaggag ttgggagaag tccttgttcc cacgcgcgga cgcttccctc 180
cgtgtgtcct tcgagccaca aaaagcccag accctaaccc gctcctttct cccgccgcgt 240
ccatgcagaa ctccgccgtt cctgggaggg gaagcccgcg aggcgtcggg agaggcacgt 300
cctccgtgag caaagagctc ctccgagcgc gcggcgggga cgctgggccg acaggggacc 360
gcgggggcag ggcggagagg acccgccctc gagtcggccc agccctaaca ctcaggac 418

<210> SEQ ID NO 54
<211> LENGTH: 906
<212> TYPE: DNA
<213> ORGANISM: Homo sapiens

<400> SEQUENCE: 54
agggaatcgg gctgaccagt cctaaggtcc cacgctcccc tgacctcagg gcccagagcc 60
tcgcattacc ccgagcagtg cgttggttac tctccctgga aagccgcccc cgccggggca 120
agtgggagtt gctgcactgc ggtctttgga ggcctaggtc gcccagagta ggcggagccc 180
tgtatccctc ctggagccgg cctgcggtga ggtcggtacc cagtacttag ggagggagga 240
cgcgcttggt gctcagggta ggctgggccg ctgctagctc ttgatttagt ctcatgtccg 300
cctttgtgcc ggcctctccg atttgtgggt ccttccaaga aagagtcctc tagggcagct 360
agggtcgtct cttgggtctg gcgaggcggc aggccttctt cggacctatc cccagaggtg 420
taacggagac tttctccact gcagggcggc ctggggcggg catctgccag gcgagggagc 480
tgccctgccg ccgagattgt ggggaaacgg cgtggaagac accccatcgg agggcaccca 540
atctgcctct gcactcgatt ccatcctgca acccaggaga aaccatttcc gagttccagc 600

```
cgcagaggca cccgcggagt tgccaaaaga gactcccgcg aggtcgctcg gaaccttgac    660

cctgacacct ggacgcgagg tctttcagga ccagtctcgg ctcggtagcc tggtccccga    720

ccaccgcgac caggagttcc ttcttccctt cctgctcacc agccggccgc cggcagcggc    780

tccaggaagg agcaccaacc cgcgctgggg gcggaggttc aggcggcagg aatggagagg    840

ctgatcctcc tctagccccg gcgcattcac ttaggtgcgg gagccctgag gttcagcctg    900

actttc                                                               906
```

<210> SEQ ID NO 55
<211> LENGTH: 860
<212> TYPE: DNA
<213> ORGANISM: Homo sapiens

<400> SEQUENCE: 55

```
cactacggat ctgcctggac tggttcagat gcgtcgttta aaggggggg ctggcactcc      60

agagaggagg gggcgctgca ggttaattga tagccacgga agcacctagg cgccccatgc    120

gcggagccgg agccgccagc tcagtctgac ccctgtcttt tctctcctct tccctctccc    180

acccctcact ccgggaaagc gagggccgag gtaggggcag atagatcacc agacaggcgg    240

agaaggacag gagtacagat ggagggacca ggacacagaa tgcaaaagac tggcaggtga    300

gaagaaggga gaaacagagg gagagagaaa gggagaaaca gagcagaggc ggccgccggc    360

ccggccgccc tgagtccgat ttccctcctt ccctgaccct tcagtttcac tgcaaatcca    420

cagaagcagg tttgcgagct cgaatacctt tgctccactg ccacacgcag caccgggact    480

gggcgtctgg agcttaagtc tgggggtctg agcctgggac cggcaaatcc gcgcagcgca    540

tcgcgcccag tctcggagac tgcaaccacc gccaaggagt acgcgcggca ggaaacttct    600

gcggcccaat ttcttcccca gctttggcat ctccgaaggc acgtacccgc cctcggcaca    660

agctctctcg tcttccactt cgacctcgag gtggagaaag aggctggcaa gggctgtgcg    720

cgtcgctggt gtggggaggg cagcaggctg cccctccccg cttctgcagc gagttttccc    780

agccaggaaa agggagggag ctgtttcagg aatttcagtg ccttcaccta gcgactgaca    840

caagtcgtgt gtataggaag                                                860
```

<210> SEQ ID NO 56
<211> LENGTH: 452
<212> TYPE: DNA
<213> ORGANISM: Homo sapiens

<400> SEQUENCE: 56

```
ggagcctgaa gtcagaaaag atggggcctc gttactcact ttctagccca gcccctggcc     60

ctgggtcccg cagagccgtc atcgcaggct cctgcccagc ctctggggtc gggtgagcaa    120

ggtgttctct tcggaagcgg gaagggctgc gggtcgggga cgtcccttgg ctgccacccc    180

tgattctgca tccttttcgc tcgaatccct gcgctaggca tcctccccga tcccccaaaa    240

gcccaagcac tgggtctggg ttgaggaagg gaacgggtgc ccaggccgga cagaggctga    300

aaggaggcct caaggttcct ctttgctaca aagtggagaa gttgctctac tctggagggc    360

agtggccttt tccaaacttt tccacttagg tccgtaagaa aagcaattca tacacgatca    420

gcgctttcgg tgcgaggatg gaaagaaact tc                                  452
```

<210> SEQ ID NO 57
<211> LENGTH: 1992
<212> TYPE: DNA

<213> ORGANISM: Homo sapiens

<400> SEQUENCE: 57

```
ttttcctgtt acagagctga gcccactcat gtggtgccaa gtagcgacta tctctcggcc     60
acctccaccc agagcaatgt gggcgccccc agcgggtggg agcgattgcc gagcggcgca    120
agggcgttta acgcctaacc ccctcctcct gggttgccaa gccgctaggt cgccgtttcc    180
aacgtggctg cgcgggactg aagtccgacg actcctcgtc ctcagtagga gacacacctc    240
ccactgcccc cagccacgcg agctatgggc agaatcgggg caacggtaat atctggatgg    300
ggcaggctcc cctgaggctg tgcttaagaa aaaaggaatc tggagtagcc tgaggggccc    360
cacgaggggg cctcctttgc gatcgtctcc cagccttagg ccaaggctac ggaggcaggc    420
ggccgagtgt tggcgcccag cccggccgag gactggatgg aggacgagaa gcagcctgcc    480
tctgggcgac agctgcggac gcagcctcgc cgcctcgccg cctcagcctc ggtcccagcg    540
tctctaaagc cgcgcccatt ttacagatgc agggcaggga gacaagaggc atctccgggg    600
gccgagtaga atgatggcgc gggttctccc ggcgccctga tttcgaggct gcgcccgggg    660
ccctacatgc aggcggggag gcctgggccg aaggcgtctg caaggagggg cgagtctgcc    720
cggtccgggc agggagtgag gccacagtca gttctcccta ggaggccgcg cagcgggtag    780
ggtatgggac tgggggacgc aacggggacc tggccgaatc agagccctca gcagagaacg    840
ccgaaaactc tggggccggc cgctcgcttc ccgctagtgg gaatggtttc cggtcatccg    900
ttcccagtcc agccccgggt agggagctct gatttgcaat gcacagcact tgcgaggttc    960
gaatgccccc gcaatttgca gatggaaata ctaagcctag gccgggcgtg gtggctcaag   1020
cctatcatct cagccctttg ggaggccaag ccgggaggat tgtttgagcc caagaattca   1080
aaaccagcct gagcaacata gcgaccccgt ctctacaaaa taaaataaaa taaattatcc   1140
gggcgtggtg gcacgcgcct gtggttccag ctactccgga ggctgaggtg ggaggatcgc   1200
ttgagtccgg gaggtcgagg ctacagtgag ccgtgatcgc accactgcac tccagcctgg   1260
gcgacagagt gagaccttgt ctcaaaaaag gaaaaaaaga aaaagaaagt aagcttcaaa   1320
gaagctctga taatagttct gggtcgtgca gcggtggcgg ccccgcgctc tcgcccctaa   1380
agcaagcgct ctttgtactg ggtggaggag ctttgagtag tgagggtgga gatgcagctt   1440
cggggtggcg cagccaccct gacactaggc ccggggtcgc agtgggacag aagagtctgc   1500
cgctctgact tgggctctga gttccaaggg cgcccggcac ttctagcctc ccaggcttgc   1560
gcgctggcgc ctttgccatc cgtgccgaag tggggagacc tagccgcgac caccacgagc   1620
gcagcggtga cacccagagg tcccaccggg cccctgggca gggtaacctt agcctgtccg   1680
cttcggcagc tttgcgaaga gtggcgcgca gctagggctg aggctcttgc ggacctgcgg   1740
tcgaagcagg cggctgagcc agttcgatcg ccaaggcctg ggctgccgac agtggtgcgc   1800
gctctgttcc gccgcggccg ggccaggcgc tctggaatag cgatgggggg acacggcctc   1860
caactttctg cagagaccat cgggcagctc cgggcctaag cagcgacctc accgaaggtt   1920
cctgggaacc tttgccaaaa tcccagcctc tgcctcggtc cagctaaacc gtgtgtaaac   1980
aagtgcacca ag                                                       1992
```

<210> SEQ ID NO 58
<211> LENGTH: 448
<212> TYPE: DNA
<213> ORGANISM: Homo sapiens

<400> SEQUENCE: 58

```
ataaaggacc gggtaatttc gcggaatgcg gattttgaga caggcccaga cggcggcgga     60
ttccctgtgt cccccaactg gggcgatctc gtgaacacac ctgcgtccca ccccgatcct    120
aggttggggg gaaagggtat gggaaccctg agcccagagc gcgccccgct ctttcctttg    180
ctccccggct tccctggcca gccccctccc ggctggtttc ctcgctcact cggcgcctgg    240
cgtttcgggc gtctggagat caccgcgtgt ctggcacccc aacgtctagt ctccccgcag    300
gttgaccgcg gcgcctggag ccgggaatag gggtggggag tccggagaac caaacccgag    360
cctgaagttg ccattcgggt gactcccgag aaagcccggg agcattttgg ccaatgcggg    420
tttttacctg aacttcagca tcttcacc                                        448
```

<210> SEQ ID NO 59
<211> LENGTH: 395
<212> TYPE: DNA
<213> ORGANISM: Homo sapiens

<400> SEQUENCE: 59

```
aattggaaaa ccctggtatt gtgcctgttt gggggaagaa aacgtcaata aaaattaatt     60
gatgagttgg cagggcgggc ggtgcgggtt cgcggcgagg cgcagggtgt catggcaaat    120
gttacggctc agattaagcg attgttaatt aaaaagcgac ggtaattaat actcgctacg    180
ccatatgggc ccgtgaaaag gcacaaaagg tttctccgca tgtggggttc cccttctctt    240
ttctccttcc acaaaagcac cccagcccgt gggtccccccc tttggcccca aggtaggtgg    300
aactcgtcac ttccggccag ggaggggatg gggcggtctc cggcgagttc caagggcgtc    360
cctcgttgcg cactcgcccg cccaggttct ttgaa                                395
```

<210> SEQ ID NO 60
<211> LENGTH: 491
<212> TYPE: DNA
<213> ORGANISM: Homo sapiens

<400> SEQUENCE: 60

```
gggaagcgat cgtctcctct gtcaactcgc gcctgggcac ttagcccctc ccgtttcagg     60
gcgccgcctc cccggatggc aaacactata aagtggcggc gaataaggtt cctcctgctg    120
ctctcggttt agtccaagat cagcgatatc acgcgtcccc cggagcatcg cgtgcaggag    180
ccatggcgcg ggagctatac cacgaagagt tcgcccgggc gggcaagcag gcggggctgc    240
aggtctggag gattgagaag ctggagctgg tgcccgtgcc ccagagcgct cacggcgact    300
tctacgtcgg ggatgcctac ctggtgctgc acacggccaa gacgagccga ggcttcacct    360
accacctgca cttctggctc ggtaagggac ggcgggcggc gggaccccga cgcaccaagg    420
ccggcgaggg gagggcgtag ggtctgaga tttgcaggcg tgggagtaaa ggggaccgca    480
aactgagcta g                                                          491
```

<210> SEQ ID NO 61
<211> LENGTH: 1284
<212> TYPE: DNA
<213> ORGANISM: Homo sapiens

<400> SEQUENCE: 61

```
ctcaggggcg ggaagtggcg ggtgggagtc acccaagcgt gactgcccga ggcccctcct     60
gccgcggcga ggaagctcca taaaagccct gtcgcgaccc gctctctgca ccccatccgc    120
tggctctcac ccctcggaga cgctcgcccg acagcatagt acttgccgcc cagccacgcc    180
```

```
cgcgcgccag ccaccgtgag tgctacgacc cgtctgtcta ggggtgggag cgaacggggc     240

gcccgcgaac ttgctagaga cgcagcctcc cgctctgtgg agccctgggg ccctgggatg     300

atcgcgctcc actccccagc ggactatgcc ggctccgcgc cccgacgcgg accagccctc     360

ttggcggcta aattccactt gttcctctgc tcccctctga ttgtccacgg cccttctccc     420

gggcccttcc cgctgggcgg ttcttctgag ttacctttta gcagatatgg agggagaacc     480

cgggaccgct atcccaaggc agctggcggt ctccctgcgg gtcgccgcct tgaggcccag     540

gaagcggtgc gcggtaggaa ggtttccccg gcagcgccat cgagtgagga atccctggag     600

ctctagagcc ccgcgccctg ccacctccct ggattcttgg gctccaaatc tctttggagc     660

aattctggcc cagggagcaa ttctctttcc ccttccccac cgcagtcgtc accccgaggt     720

gatctctgct gtcagcgttg atcccctgaa gctaggcaga ccagaagtaa cagagaagaa     780

acttttcttc ccagacaaga gtttgggcaa gaagggagaa aagtgaccca gcaggaagaa     840

cttccaattc ggttttgaat gctaaactgg cggggccccc accttgcact ctcgccgcgc     900

gcttcttggt ccctgagact tcgaacgaag ttgcgcgaag ttttcaggtg gagcagaggg     960

gcaggtcccg accggacggc gcccggagcc cgcaaggtgg tgctagccac tcctgggttc    1020

tctctgcggg actgggacga gagcggattg gggtcgcgt gtggtagcag gaggaggagc    1080

gcggggggca gaggagggag gtgctgcgcg tgggtgctct gaatccccaa gcccgtccgt    1140

tgagccttct gtgcctgcag atgctaggta acaagcgact ggggctgtcc ggactgaccc    1200

tcgccctgtc cctgctcgtg tgcctgggtg cgctggccga ggcgtacccc tccaagccgg    1260

acaacccggg cgaggacgca ccag                                           1284
```

<210> SEQ ID NO 62
<211> LENGTH: 554
<212> TYPE: DNA
<213> ORGANISM: Homo sapiens

<400> SEQUENCE: 62

```
tggagaacct tgggctctgt ggcctcaaag gtaggggtga tttcgagggg ccggcacctc      60

acagggcagg ttccaccgcg gaaacgcagt catcgcccag cgaccctgct cctggccctc     120

agcctccccc caggtttctt tttctcttga atcaagccga ggtgcgccaa tggccttcct     180

tgggtcggat ccggggggcc agggccagct tacctgcttt caccgagcag tggatatgtg     240

ccttggactc gtagtacacc cagtcgaagc cggcctccac cgccaggcgg gccagcatgc     300

cgtacttgct gcggtcgcgg tcagacgtgg tgatgtccac tgcgcggccc tcgtagtgca     360

gagactcctc tgagtggtgg ccatcttcgt cccagccctc ggtcacccgc agtttcactc     420

ctggccactg gttcatcacc gagatggcca aagcgttcaa cttgtcctta cacctctgcg     480

aagacaaggg gacccccacc gacggacacg ttagcctggg caaccgccac ccctcccggc     540

ccctccatca gcct                                                       554
```

<210> SEQ ID NO 63
<211> LENGTH: 772
<212> TYPE: DNA
<213> ORGANISM: Homo sapiens

<400> SEQUENCE: 63

```
tctcacgacc catccgttaa cccaccgttc ccaggagctc cgaggcgcag cggcgacaga      60

ggttcgcccc ggcctgctag cattggcatt gcggttgact gagcttcgcc taacaggctt     120

ggggagggtg ggctgggctg ggctgggctg ggctgggtgc tgcccggctg tccgcctttc     180
```

```
gttttcctgg gaccgaggag tcttccgctc cgtatctgcc tagagtctga atccgacttt    240

ctttcctttg ggcacgcgct cgccagtgga gcacttcttg ttctggcccc gggctgatct    300

gcacgcggac ttgagcaggt gccaaggtgc cacgcagtcc cctcacggct ttcggggggt    360

cttggagtcg ggtggggagg gagacttagg tgtggtaacc tgcgcaggtg ccaaagggca    420

gaaggagcag ccttggatta tagtcacggt ctctccctct cttccctgcc atttttaggg    480

ctttctctac gtgctgttgt ctcactgggt tttgtcgga  gccccacgcc ctccggcctc    540

tgattcctgg aagaaagggt tggtcccctc agcaccccca gcatcccgga aaatggggag    600

caaggctctg ccagcgccca tcccgctcca cccgtcgctg cagctcacca attactcctt    660

cctgcaggcc gtgaacacct tcccggccac ggtggaccac ctgcagggcc tgtacggtct    720

cagcgcggta cagaccatgc acatgaacca ctggacgctg ggtatccca at             772
```

```
<210> SEQ ID NO 64
<211> LENGTH: 1362
<212> TYPE: DNA
<213> ORGANISM: Homo sapiens

<400> SEQUENCE: 64

tggtttcctt tcgcttctcg cctcccaaac acctccagca agtcggaggg cgcgaacgcg     60

gagccagaaa cccttcccca aagtttctcc cgccaggtac ctaattgaat catccatagg    120

atgacaaatc agccagggcc aagatttcca gacacttgag tgacttcccg gtccccgagg    180

tgacttgtca gctccagtga gtaacttgga actgtcgctc ggggcaaggt gtgtgtctag    240

gagagagccg gcggctcact cacgctttcc agagagcgac ccgggccgac ttcaaaatac    300

acacagggtc atttataggg actggagccg cgcgcaggac aacgtctccg agactgagac    360

attttccaaa cagtgctgac attttgtcgg gccccataaa aatgtaaac  gcgaggtgac    420

gaacccggcg gggagggttc gtgtctggct gtgtctgcgt cctggcggcg tgggaggtta    480

tagttccaga cctggcggct gcggatcgcc gggccggtac ccgcgaggag tgtaggtacc    540

ctcagcccga ccacctcccg caatcatggg gacaccggct tggatgagac acaggcgtgg    600

aaaacagcct tcgtgaaact ccacaaacac gtggaacttg aaaagacaac tacagccccg    660

cgtgtgcgcg agagacctca cgtcacccca tcagttccca cttcgccaaa gtttcccttc    720

agtggggact ccagagtggt gcgccccatg cccgtgcgtc ctgtaacgtg ccctgattgt    780

gtacccctct gcccgctcta cttgaaatga aaacacaaaa actgttccga attagcgcaa    840

ctttaaagcc ccgttatctg tcttctacac tgggcgctct taggccactg acagaaacat    900

ggtttgaacc ctaattgttg ctatcagtct cagtcagcgc aggtctctca gtgacctgtg    960

acgccgggag ttgaggtgcg cgtatcctta aacccgcgcg aacgccaccg gctcagcgta   1020

gaaaactatt tgtaatccct agtttgcgtc tctgagcttt aactccccca cactctcaag   1080

cgcccggttt ctcctcgtct ctcgcctgcg agcaaagttc ctatggcatc cacttaccag   1140

gtaaccggga tttccacaac aaagcccggc gtgcgggtcc cttcccccgg ccggccagcg   1200

cgagtgacag cgggcggccg gcgctggcga ggagtaactt ggggctccag cccttcagag   1260

cgctccgcgg gctgtgcctc cttcggaaat gaaaaccccc atccaaacgg ggggacggag   1320

cgcggaaacc cggcccaagt gccgtgtgtg cgcgcgcgtc tg                      1362
```

```
<210> SEQ ID NO 65
<211> LENGTH: 476
<212> TYPE: DNA
```

<213> ORGANISM: Homo sapiens

<400> SEQUENCE: 65

```
gaaagccatc cttaccattc ccctcaccct ccgccctctg atcgcccacc cgccgaaagg      60
gtttctaaaa atagcccagg gcttcaaggc cgcgcttctg tgaagtgtgg agcgagcggg     120
cacgtagcgg tctctgccag gtggctggag ccctggaagc gagaaggcgc ttcctccctg     180
catttccacc tcaccccacc cccggctcat ttttctaaga aaaagttttt gcggttccct     240
ttgcctccta cccccgctgc cgcgcggggt ctgggtgcag accccctgcca ggttccgcag     300
tgtgcagcgg cggctgctgc gctctcccag cctcggcgag ggttaaaggc gtccggagca     360
ggcagagcgc cgcgcgccag tctattttta cttgcttccc ccgccgctcc gcgctccccc     420
ttctcagcag ttgcacatgc cagctctgct gaaggcatca atgaaaacag cagtag         476
```

<210> SEQ ID NO 66
<211> LENGTH: 300
<212> TYPE: DNA
<213> ORGANISM: Homo sapiens

<400> SEQUENCE: 66

```
atcgaaaatg tcgacatctt gctaatggtc tgcaaacttc cgccaattat gactgacctc      60
ccagactcgg ccccaggagg ctcgtattag gcagggaggc cgccgtaatt ctgggatcaa     120
aagcgggaag gtgcgaactc ctctttgtct ctgcgtgccc ggcgcgcccc cctcccggtg     180
ggtgataaac ccactctggc gccggccatg cgctgggtga ttaatttgcg aacaaacaaa     240
agcggcctgg tggccactgc attcgggtta aacattggcc agcgtgttcc gaaggcttgt     300
```

<210> SEQ ID NO 67
<211> LENGTH: 1246
<212> TYPE: DNA
<213> ORGANISM: Homo sapiens

<400> SEQUENCE: 67

```
atcaacatcg tggctttggt cttttccatc atggtgagtg aatcacggcc agaggcagcc      60
tgggaggaga gacccgggcg gctttgagcc cctgcagggg agtccgcgcg ctctctgcgg     120
ctcccttcct cacggcccgg cccgcgctag gtgttctttg tcctcgcacc tcctcctcac     180
ctttctcggg ctctcagagc tctccccgca atcatcagca cctcctctgc actcctcgtg     240
gtactcagag ccctgatcaa gcttccccca ggctagcttt cctcttcttt ccagctccca     300
gggtgcgttt cctctccaac ccggggaagt tcttccgtgg actttgctga ctcctctgac     360
cttcctaggc acttgcccgg ggcttctcaa ccctcttttc tagagcccca gtgcgcgcca     420
ccctagcgag cgcagtaagc tcataccccg agcatgcagg ctctacgttc ctttccctgc     480
cgctccgggg gctcctgctc tccagcgccc aggactgtct ctatctcagc ctgtgctccc     540
ttctctcttt gctgcgccca agggcaccgc ttccgccact ctccgggggg tccccaggcg     600
attcctgatg ccccctcctt gatcccgttt ccgcgctttg gcacggcacg ctctgtccag     660
gcaacagttt cctctcgctt cttcctacac ccaacttcct ctccttgcct ccctccggcg     720
ccccctttttt aacgcgcccg aggctggctc acacccacta cctctttagg cctttcttag     780
gctccccgtg tgcccccctc accagcaaag tgggtgcgcc tctcttactc tttctaccca     840
gcgcgtcgta gttcctcccc gtttgctgcg cactggccct aacctctctt ctcttggtgt     900
cccccagagc tcccaggcgc ccctccaccg ctctgtcctg cgcccggggc tctcccggga     960
atgaactagg ggattccacg caacgtgcgg ctccgcccgc cctctgcgct cagacctccc    1020
```

gagctgcccg cctctctagg agtggccgct ggggcctcta gtccgccctt ccggagctca 1080
gctccctagc cctcttcaac cctggtagga acacccgagc gaaccccacc aggagggcga 1140
cgagcgcctg ctaggccctc gccttattga ctgcagcagc tggcccgggg gtggcggcgg 1200
ggtgaggttc gtaccggcac tgtcccggga caacccttgc agttgc 1246

<210> SEQ ID NO 68
<211> LENGTH: 984
<212> TYPE: DNA
<213> ORGANISM: Homo sapiens

<400> SEQUENCE: 68
acaaataaaa caccctctag cttcccctag actttgttta actggccggg tctccagaag 60
gaacgctggg gatgggatgg gtggagagag ggagcggctc aaggacttta gtgaggagca 120
ggcgagaagg agcacgttca ggcgtcaaga ccgatttctc cccctgcttc gggagacttt 180
tgaacgctcg gagaggcccg gcatctcacc actttacttg gccgtagggg cctccggcac 240
ggcaggaatg agggaggggg tccgattgga cagtgacggt ttggggccgt tcggctatgt 300
tcagggacca tatggtttgg ggacagcccc agtagttagt aggggacggg tgcgttcgcc 360
cagtccccgg atgcgtaggg aggcccagtg gcaggcagct gtcccaagca gcgggtgcgc 420
gtccctgcgc gctgtgtgtt cattttgcag agccagcctt cggggaggtg aaccagctgg 480
gaggagtgtt cgtgaacggg aggccgctgc ccaacgccat ccggcttcgc atcgtggaac 540
tggcccaact gggcatccga ccgtgtgaca tcagccgcca gctacgggtc tcgcacggct 600
gcgtcagcaa gatcctggcg cgatacaacg agacgggctc gatcttgcca ggagccatcg 660
ggggcagcaa gccccgggtc actacccccca ccgtggtgaa acacatccgg acctacaagc 720
agagagaccc cggcatcttc gcctgggaga tccgggaccg cctgctggcg gacggcgtgt 780
gcgacaagta caatgtgccc tccgtgagct ccatcagccg cattctgcgc aacaagatcg 840
gcaacttggc ccagcagggt cattacgact catacaagca gcaccagccg acgccgcagc 900
cagcgctgcc ctacaaccac atctactcgt accccagccc tatcacggcg gcggccgcca 960
aggtgcccac gccacccggg gtgc 984

<210> SEQ ID NO 69
<211> LENGTH: 545
<212> TYPE: DNA
<213> ORGANISM: Homo sapiens

<400> SEQUENCE: 69
aggaggcgca acgcgctgcc agggcggctt tatcctgccg ccacagggcg gggaccagcc 60
cggcagccgg gtgtccagcg ccgctcacgt gcctcgcctg gagcttagct ctcagactcc 120
gaagagggcg actgagactt gggcctggga gttggcttcg gggtacccaa ggcgacgaca 180
gctgagttgt accacgaagc tcaggccgag gcctcctccc ttgtctggcc ttcgaatcca 240
tactggcagc ctctcctctc aggcactccg cgggccgggc cactaggccc cctgctcctg 300
gagctgcgct atgatccggg tcttgagatg cgcgcgattc tctctgaacc ggtggagagg 360
aggctctgcc ccgcgcggag cgaggacagc ggcgcccgag cttcccgcgc ctctccaggg 420
cccaatggca agaacagcct ccgaagtgcg cggatgacag gaaaagatct tcagttcttc 480
tgccgctaga gaagtgcggg atacaagcct ctattggatc cacaacctgg agtcctgcct 540
tcgga 545

<210> SEQ ID NO 70
<211> LENGTH: 1533
<212> TYPE: DNA
<213> ORGANISM: Homo sapiens

<400> SEQUENCE: 70
atctgcgtgc cctttttctgg gcgagccctg ggagatccag ggagaactgg gcgctccaga 60
tggtgtatgt ctgtaccttc acagcaaggc ttcccttgga tttgaggctt cctatttttgt 120 ctgggatcgg ggtttctcct tgtcccagtg gcagccccgc gttgcgggtt ccgggcgctg 180
cgcggagccc aaggctgcat ggcagtgtgc agcgcccgcc agtcgggctg gtgggttgtg 240
cactccgtcg gcagctgcag aaaggtggga gtgcaggtct tgcctttcct caccgggcgg 300
ttggcttcca gcaccgaggc tgacctatcg tggcaagttt gcggcccccg cagatcccca 360
gtggagaaag agggctcttc cgatgcgatc gagtgtgcgc ctccccgcaa agcaatgcag 420
accctaaatc actcaaggcc tggagctcca gtctcaaagg tggcagaaaa ggccagacct 480
aactcgagca cctactgcct tctgcttgcc ccgcagagcc ttcagggact gactgggacg 540
cccctggtgg cgggcagtcc catccgccat gagaacgccg tgcagggcag cgcagtggag 600
gtgcagacgt accagccgcc gtggaaggcg ctcagcgagt ttgccctcca gagcgacctg 660
gaccaacccg ccttccaaca gctggtgagg ccctgcccta cccgccccga cctcgggact 720
ctgcgggttg ggatttagc cacttagcct ggcagagagg ggaggggggtg gccttgggct 780 gaggggctgg gtacagccct aggcggtggg ggaggggggaa cagtggcggg ctctgaaacc 840
tcacctcggc ccattacgcg ccctaaacca ggtctccctg gattaaagtg ctcacaagag 900
aggtcgcagg attaaccaac ccgctccccc gccctaatcc ccccctcgtg cgcctgggga 960
cctggcctcc ttctccgcag ggcttgctct cagctggcgg ccggtcccca agggacactt 1020
tccgactcgg agcacgcggc cctggagcac cagctcgcgt gcctcttcac ctgcctcttc 1080
ccggtgtttc cgccgcccca ggtctccttc tccgagtccg gctccctagg caactcctcc 1140
ggcagcgacg tgacctccct gtcctcgcag ctcccggaca cccccaacag tatggtgccg 1200
agtcccgtgg agacgtgagg gggacccctc cctgccagcc cgcggacctc gcatgctccc 1260
tgcatgagac tcacccatgc tcaggccatt ccagttccga aagctctctc gccttcgtaa 1320
ttattctatt gttatttatg agagagtacc gagagacacg gtctggacag cccaaggcgc 1380
caggatgcaa cctgctttca ccagactgca gacccctgct ccgaggactc ttagtttttc 1440
aaaaccagaa tctgggactt accagggtta gctctgccct ctcctctcct ctctacgtgg 1500
ccgccgctct gtctctccac gccccacctg tgt 1533

<210> SEQ ID NO 71
<211> LENGTH: 702
<212> TYPE: DNA
<213> ORGANISM: Homo sapiens

<400> SEQUENCE: 71
aggtctcttc agactgccca ttctccgggc ctcgctgaat gcgggggctc tatccacagc 60
gcgcggggcc gagctcaggc aggctggggc gaagatctga ttctttcctt cccgccgcca 120
aaccgaatta atcagtttct tcaacctgag ttactaagaa agaaaggtcc ttccaaataa 180
aactgaaaat cactgcgaat gacaatacta tactacaagt tcgttttggg gccggtgggt 240
gggatggagg agaaagggca cggataatcc cggagggccg cggagtgagg aggactatgg 300
tcgcggtgga atctctgttc cgctggcaca tccgcgcagg tgcggctctg agtgctggct 360

```
cggggttaca gacctcggca tccggctgca ggggcagaca gagacctcct ctgctagggc    420

gtgcggtagg catcgtatgg agcccagaga ctgccgagag cactgcgcac tcaccaagtg    480

ttaggggtgc ccgtgataga ccgccaggga aggggctggt tcggagggaa ttcccgctac    540

cgggaaggtc ggaactcggg gtgatcaaac aaggaatgca tctcacctcc gtgggtgctt    600

gtgctgcgca aggaattatt accggagcgg ttgcgatggc ctttgcccgg cgacccaaga    660

agagtaagca aactaccgtc cacccagcgg atcaggtcca at                        702
```

<210> SEQ ID NO 72
<211> LENGTH: 3180
<212> TYPE: DNA
<213> ORGANISM: Homo sapiens

<400> SEQUENCE: 72

```
gatgtcctgt ttctagcagc ctccagagcc aagctaggcg agaggcgtag gaggcagaga     60

gagcgggcgc gggaggccag ggtccgcctg ggggcctgag gggacttcgt ggggtcccgg    120

gagtggccta gaaacaggga gctgggaggg ccgggaagag cttgaggctg agcgggggac    180

gaacgggcag cgcaaagggg agatgaacgg aatggccgag gagccacgca ttcgccttgt    240

gtccgcggac ccttgttccc gacaggcgac caagccaagg ccctccggac tgacgcggcc    300

tgagcagcag cgagtgtgaa gtttggcacc tccggcggcg agacggcgcg ttctggcgcg    360

cggctcctgc gtccggctgg tggagctgct gcgccctatg cggcctgccg agggcgccgc    420

cgagggcccg cgagctccgt ggggtcgggg tgggggggacc cgggagcgga cagcgcggcc    480

cgaggggcag gggcaggggc gcgcctggcc tggggtgtgt ctgggccccg gctccgggct    540

cttgaaggac cgcgagcagg aggcttgcgc aatcccttgg ctgagcgtcc acggagaaag    600

aaaaagagca aaagcagagc gagagtggag cgagggatgg gggcgggcaa agagccatcc    660

gggtctccac caccgccctg acacgcgacc cggctgtctg ttggggaccg cacgggggct    720

cgggcgagca ggggagggag gagcctgcgc ggggctcgtg ttcgcccagg aatcccggag    780

aagctcgaag acggtctggt gttgaacgca cacgtggact ccatttcatt accaccttgc    840

agctcttgcg ccacggaggc tgctgctgcc cggcggctgc tacccaccga gacccacgtg    900

gcccctcccc aggggtgtag ggtgacggt  tgtcttctgg tgacagcaga ggtgttgggt    960

ttgcgactga tctctaacga gcttgaggcg caaacctagg attccctgag tgttggggtg   1020

cggcgggggg gcaagcaagg tgggacgacg cctgcctggt ttccctgact agttgcgggg   1080

ggtgggggcc ggctctcagg ggccaccaga agctgggtgg gtgtacagga aaatattttt   1140

ctcctgccgt gtttggcttt ttcctggcat ttttgcccag ggcgaagaac tgtcgcgcgg   1200

ggcagctcca ccgcggaggg agaggggtcg cgaggctggc gcgggaagcg ctgtaggtgg   1260

cagtcatccg tccacgccgc acaggccgtc tgcgccgtcg gaccatcggg aggtctgcag   1320

caactttgtc ccggccagtc cccttgtccg ggaaggggct gagcttcccg acactctacc   1380

ctccccctct tgaaaatccc ctggaaaatc tgtttgcaat gggtgtttcc gcggcgtcca   1440

ggtctgggct gccgggggag gccgagcggc tgctgcagcc tccctgctgc caggggcgtc   1500

ggactccgct tcgctcacta cgcccaggcc cctcaggggc ccacgctcag gacttcgggg   1560

ccacacagca ggacccggtg ccccgacgac gagtttgcgc aggacccggg ctgggccagc   1620

cgcggagctg gggaggaagg ggcgggggtc ggtgcagcgg atctttttctg ttgctgcctg   1680

tgcggcggca ggaagcgtct tgaggctccc caagactacc tgaggggccg cccaagcact   1740
```

```
tcagaagccc aaggagcccc cggccacccc cgctcctggc ctttttgcca acgactttga   1800

aagtgaaatg cacaagcacc agcaattgac ttcccttccg tggttattta ttttgtcttt   1860

gtggatggtg ggcagatggg gagagaggcc cctacctaac ctcggtggct ggtccctaga   1920

ccacccctgc cagccggtgt ggggaggagc tcaggtccgc gggagagcga atgggcgcca   1980

ggaggtggga cagaatcctg ggaaggtaca gcggacgccc tggaagctcc cctgatgccc   2040

cagagggccc ttcctgggaa acctcccggg ggggtgcccc ataccatccc acccggctgt   2100

cttggcccct cccagggagc cgcaggagaa actagcccta cacctgggat tcccagagcc   2160

ttctgctggg gctcctgccc ccgacttcgg ataaccagct ccgcacaggt ccccgagaag   2220

ggccgctggc ctgcttattt gatactgccc cctcccagac aggggctggt cgagcccctg   2280

gttctgctgc cagactgaag ccttccagac gccacctcgg tttgggcccc cagggccctc   2340

aggggcccca ggagaggaga gctgctatct agctcagcca caggctcgct cctggtgggg   2400

gccaggctga aggagtggac cctggagagg tcgggaacct tttaacagcc gtgggctgga   2460

gggtggctac taagtgttcg gtctgggaag aggcatgacc cgcaccatcc cggggaaata   2520

aacgacttct taagggaatc ttctcgctga gcgggtgctc tgggccagga gattgccacc   2580

gccagcccac ggaacccaga tttgggctct gccttgagcg ggccgcctgt ggcttcccgg   2640

gtcgctcccc cgactcagaa agctctcaag ttggtatcgt ttcccggccc ctcggaggtg   2700

gattgcagat caccgagagg ggatttacca gtaaccacta cagaatctac ccgggcttta   2760

acaagcgctc atttctctcc cttgtcctta gaaaaacttc gcgctggcgt tgatcatatc   2820

gtacttgtag cggcagctta ggggcagcgg aactggtggg gttgtgcgtg caggggggagg   2880

ctgtgaggga gccctgcact ccgcccctcc acccttctgg aggagtggct ttgtttctaa   2940

gggtgccccc ccaacccccg ggtccccact tcaatgtttc tgctctttgt cccaccgccc   3000

gtgaaagctc ggctttcatt tggtcggcga agcctccgac gcccccgagt cccaccctag   3060

cgggccgcgc ggcactgcag ccgggggttc ctgcggactg gcccgacagg gtgcgcggac   3120

ggggacgcgg gccccgagca ccgcgacgcc agggtccttt ggcagggccc aagcacccct   3180
```

<210> SEQ ID NO 73
<211> LENGTH: 1038
<212> TYPE: DNA
<213> ORGANISM: Homo sapiens

<400> SEQUENCE: 73

```
tggcggccgg cgggcacagc cggctcattg ttctgcacta caaccactcg ggccggctgg     60

ccgggcgcgg ggggccggag gatggcggcc tgggggccct gcgggggctg tcggtggccg    120

ccagctgcct ggtggtgctg gagaacttgc tggtgctggc ggccatcacc agccacatgc    180

ggtcgcgacg ctgggtctac tattgcctgg tgaacatcac gctgagtgac ctgctcacgg    240

gcgcggccta cctggccaac gtgctgctgt cgggggcccg caccttccgt ctggcgcccg    300

cccagtggtt cctacgggag ggcctgctct tcaccgccct ggccgcctcc accttcagcc    360

tgctcttcac tgcaggggag cgctttgcca ccatggtgcg gccggtggcc gagagcgggg    420

ccaccaagac cagccgcgtc tacggcttca tcggcctctg ctggctgctg gccgcgctgc    480

tggggatgct gcctttgctg ggctggaact gcctgtgcgc ctttgaccgc tgctccagcc    540

ttctgcccct ctactccaag cgctacatcc tcttctgcct ggtgatcttc gccggcgtcc    600

tggccaccat catgggcctc tatggggcca tcttccgcct ggtgcaggcc agcgggcaga    660

aggccccacg cccagcggcc cgccgcaagg cccgccgcct gctgaagacg gtgctgatga    720
```

```
tcctgctggc cttcctggtg tgctggggcc cactcttcgg gctgctgctg gccgacgtct    780

ttggctccaa cctctgggcc caggagtacc tgcggggcat ggactggatc ctggccctgg    840

ccgtcctcaa ctcggcggtc aaccccatca tctactcctt ccgcagcagg gaggtgtgca    900

gagccgtgct cagcttcctc tgctgcgggt gtctccggct gggcatgcga gggcccgggg    960

actgcctggc ccgggccgtc gaggctcact ccggagcttc caccaccgac agctctctga   1020

ggccaaggga cagctttc                                                 1038


<210> SEQ ID NO 74
<211> LENGTH: 1200
<212> TYPE: DNA
<213> ORGANISM: Homo sapiens

<400> SEQUENCE: 74

gtcctaacat cccaggtggc ggcgcgctgg ctccctggag cggggcggga cgcggccgcg     60

cggactcacg tgcacaaccg cgcgggacgg ggccacgcgg actcacgtgc acaaccgcgg    120

gaccccagcg ccagcgggac cccagcgcca gcgggacccc agcgccagcg ggaccccagc    180

gccagcggga ccccagcgcc agcgggaccc cagcgccagc gggaccccag cgccagcggg    240

tctgtggccc agtggagcga gtggagcgct ggcgacctga gcggagactg cgccctggac    300

gccccagcct agacgtcaag ttacagcccg cgcagcagca gcaaagggga aggggcagga    360

gccgggcaca gttggatccg gaggtcgtga cccaggggaa agcgtgggcg gtcgacccag    420

ggcagctgcg gcggcgaggc aggtgggctc cttgctccct ggagccgccc ctccccacac    480

ctgccctcgg cgcccccagc agttttcacc ttggccctcc gcggtcactg cgggattcgg    540

cgttgccgcc agcccagtgg ggagtgaatt agcgccctcc ttcgtcctcg gcccttccga    600

cggcacgagg aactcctgtc ctgccccaca gaccttcggc ctccgccgag tgcggtactg    660

gagcctgccc cgccagggcc ctggaatcag agaaagtcgc tctttggcca cctgaagcgt    720

cggatcccta cagtgcctcc cagcctgggc gggagcggcg gctgcgtcgc tgaaggttgg    780

ggtccttggt gcgaaaggga ggcagctgca gcctcagccc caccccagaa gcggccttcg    840

catcgctgcg gtgggcgttc tcgggcttcg acttcgccag cgccgcgggg cagaggcacc    900

tggagctcgc agggcccaga cctgggttgg aaaagcttcg ctgactgcag gcaagcgtcc    960

gggaggggcg gccaggcgaa gccccggcgc tttaccacac acttccgggt cccatgccag   1020

ttgcatccgc ggtattgggc aggaaatggc agggctgagg ccgaccctag gagtataagg   1080

gagccctcca tttcctgccc acatttgtca cctccagttt tgcaacctat cccagacaca   1140

cagaaagcaa gcaggactgg tggggagacg gagcttaaca ggaatatttt ccagcagtga   1200


<210> SEQ ID NO 75
<211> LENGTH: 900
<212> TYPE: DNA
<213> ORGANISM: Homo sapiens

<400> SEQUENCE: 75

caccttcccc gaggtaatta ttttctgggg ggtaggggtg ggggttggga gggtgaagaa     60

aggaagaaaa agaaggccga tcacactggg caccggcgga ggaagcgtgg agtccattga    120

tctaggtact tgtggggagg ggagaacccg agcagcagct gcaaacggaa gggctgtgag    180

cgagcgggcg ggcgggtggc tggcagcgag gccaccagca ggggggggccc gggccgaggc    240

cgcgccacct cggcaccacg cgggcagccg gtgcggcggg gtcgccacgg ccaggggagc    300
```

gctgggtgcc caccatggca gttatgcaag cggtgacccc ctggtcttgc ctccccgccg 360
ccctgcactc cttcctcccc gctgccgaca cttggatctc tctagctctt tctctcccct 420
gtgttttcaa acaggaagtg cacggctgtc tataacgtgc tgccgggtct caggatggag 480
gagtgaagtc tcctgtcgcc gtggttccag cctccggagc tcgcccaagc cgcgtcccca 540
gagagcgccc tgagagaaca gggtggccgc ttggtccagg tgcgcggggt cgggtctggg 600
tccagggagc gggtcgggaa gtctgcggca cggagcactg ctagtgtcgg atctgcatct 660
ccagctctgt gctgcagctt cacttgcccg ccccccacca ctggcttctc acccggggtc 720
tctgccaaac tctggctgct gccgccctgg gttcgggccg gcggaaggcc ctgggcgtgc 780
gctgcggagc cgcctgcgag gactccacta gggcgctttc caggctggac tgccccgggc 840
tgcgctggag ctgccagtgc tcggggagtc ttcctggagt ccccagctgc cctctccacc 900

<210> SEQ ID NO 76
<211> LENGTH: 200
<212> TYPE: DNA
<213> ORGANISM: Homo sapiens

<400> SEQUENCE: 76
ctcttcccaa gttacgccac cggtcgagga cggcaggaga cccccgagtg cagagaaagc 60
tcaaaccggc agcgaagtcg gtcctagcca agctgaaaaa acgtctcgga tttcgcggac 120
agcggcctag acacagcccg atcttccagt cctagtgccc tggtcgagac ggttctatcc 180
ttttgcaaag aagccggaaa 200

<210> SEQ ID NO 77
<211> LENGTH: 400
<212> TYPE: DNA
<213> ORGANISM: Homo sapiens

<400> SEQUENCE: 77
tctcggttgc aatccccacc ctcctcaccc agcagggcag gaggcaccca acttggagga 60
gaaaggggtg ggggaggtga aacagagacc ggagagtcac gagggctggg ccgccgagag 120
caggagaata taccgtgtca cacacctcca ttctctcaca cacgttgcag acacaaatca 180
ctgacggttt ccacgtgctg cgctcgtgag cggaggtgtt caaagagggg gcagatgagt 240
tacttcccga gacggaaccg gggtcccac gtccgccgcc ttcagtagca caaccaatct 300
ctgaacactc aaaccgcgca tctctggcgc atcaccatcc tatttaaggc cacgggctcc 360
gcccttttcc tcccctccct tcttttccac tctttttcca 400

<210> SEQ ID NO 78
<211> LENGTH: 700
<212> TYPE: DNA
<213> ORGANISM: Homo sapiens

<400> SEQUENCE: 78
ctgccagaga tgtgtctgtc ttgcgccccg catgcactgc ctgcggggct gcgctgcact 60
ccccggcggc gccacgggtc tggcccccgc gcttctacgt gttgggggga tgcatggacc 120
ttggagatcc gtagttggcc ctaaccttct cggaatctcc tctgcacgcg ctgcctgttc 180
ctcctctgca cgctctgtcc gttcctttgc aacttctgtg ggaattgtcc tggcgtggga 240
aacgcccccg cgctctttgg cacttagggt gtgagtgttg cgccccttgc cgcagcgctc 300
agggcagcat cccgctcgag gatgcagggt tctcaccaag cagtgagggg gactcacgcg 360
ccgccgggga gcggagccag gctccgagaa gggagcaggc tcgagccgct gggttttcgc 420

```
aagccttggg gcctctggcc gcccttccat gcctccgggc gcgggcggct cagcaggtcc    480

ccggcttcgg gaagttttgt gcgcggatcg ctggtgggga gggcgcgcgg gccagtggct    540

gagcttgcag cgaagtttcc gtgaaggaaa ctgcatgtgc ctttggaggc gactcgggac    600

tgctgtaggg tggactgggt gtctatggag ttgcgggtca gagcgagtag ggtgggtcct    660

ttcctgggac aggactggga attggggctc gaagtagggg                          700


<210> SEQ ID NO 79
<211> LENGTH: 200
<212> TYPE: DNA
<213> ORGANISM: Homo sapiens

<400> SEQUENCE: 79

aggggtgtcc tccaacatct ctgaaccgcc ttcccttcct cctcactggc gccctcttgc     60

ctcagtcgtc ggagatggag aggcggctga agattggcag gcggcggcca gggtcgaggc    120

tgggagactc agagccgctg aggctgccgg agctcaggga gccgcttagg tagctgtcgc    180

ggtccgacag cgagtccggg                                                200


<210> SEQ ID NO 80
<211> LENGTH: 5000
<212> TYPE: DNA
<213> ORGANISM: Homo sapiens

<400> SEQUENCE: 80

tctgactctc gggctggagc agccgagaca gcgctcccca gcgggactac agaatcccgg     60

gtgtcggcct gggggccctg gattggcagt ggtggagtct tctgagccta acagctacta    120

ggaatgacag agttgcagat ggctttgtcg cccgcggggc ggctcaagcg tcctgggtcc    180

caggcctctg tcctacggcc aggccgccgg ctcaacgggc cgaagggaat cgggctgacc    240

agtcctaagg tcccacgctc ccctgacctc agggcccaga gcctcgcatt accccgagca    300

gtgcgttggt tactctccct ggaaagccgc ccccgccggg gcaagtggga gttgctgcac    360

tgcggtcttt ggaggcctag gtcgcccaga gtaggcggag ccctgtatcc ctcctggagc    420

cggcctgcgg tgaggtcggt acccagtact tagggaggga ggacgcgctt ggtgctcagg    480

gtaggctggg ccgctgctag ctcttgattt agtctcatgt ccgcctttgt gccggcctct    540

ccgatttgtg ggtccttcca agaaagagtc ctctagggca gctagggtcg tctcttgggt    600

ctggcgaggc ggcaggcctt cttcggacct atccccagag gtgtaacgga gactttctcc    660

actgcagggc ggcctggggc gggcatctgc caggcgaggg agctgccctg ccgccgagat    720

tgtggggaaa cggcgtggaa gacaccccat cggagggcac ccaatctgcc tctgcactcg    780

attccatcct gcaacccagg agaaaccatt tccgagttcc agccgcagag gcacccgcgg    840

agttgccaaa agagactccc gcgaggtcgc tcggaacctt gaccctgaca cctggacgcg    900

aggtctttca ggaccagtct cggctcggta gcctggtccc cgaccaccgc gaccaggagt    960

tccttcttcc cttcctgctc accagccggc cgccggcagc ggctccagga aggagcacca   1020

acccgcgctg gggcggaggg ttcaggcggc aggaatggag aggctgatcc tcctctagcc   1080

ccggcgcatt cacttaggtg cgggagccct gaggttcagc ctgactttcc cgactccgcc   1140

gggcgcttgg tgggctcctg ggcttctggg ctcaccctta cacctgtgta ctaaagggct   1200

gctaccctcc cgaggtgtac gtccgccgcc tcggcgctca tcggggtgtt ttttcaccct   1260

ctcgcggtgc acgctttttc tctcacgtca gctcacatct ttcagtacac agccactggg   1320
```

-continued

```
tctccctgcc cctccagcct ttcctaggca gctttgaggg cccagacgac tgaagtctta   1380
ctgctaggat gggaacacga tgaaaaagga aggggcccag tcaaaagtcc tctcctcttc   1440
ggtttttctt caactgtcct tcacaaaaac atttatttct gtcccagcgc cctggcggat   1500
ttcggcagat gggccctagg gggttgtgga ggccaaattc ccaggatgct ggtcctgcct   1560
ttttcattgg ccaaaactgt atttcctaca acgactaaag ataaccaaga actgagtaga   1620
ccctgttctc tcaccagatc tccctggctc tgtttaactt ttcctggtgc aatgcgatgg   1680
caccaccagc tccccaggca ggcaccactc cctcaagata ccatttgggg tagggatttg   1740
agtcctggag agggtcagcg gggcgccggg gtgggggtgg gaaggagact gacagggaca   1800
caccgcgagc tccgcatact ctcctctgcc ccctgtagcc cggggcttta atgaccccaa   1860
gcagatttcc tgtctctggt ctagccagct gcccctaggg ctggatttta tttcttcatg   1920
gggtttcacc ctaaagggcc ccctggtcat gggacctggt tgggaacaaa tgaaagatgt   1980
cttgtagcaa atgctttcag gggagcagaa aagaagattg ggcacttcca gtcacttggt   2040
cactttaggt ggctggaaca aaactggtga ctttcacgac tgctacaggg tgagggggtg   2100
aagggtggca gagaggtgac aagccactgg gaatcctatt cagtggggat gccgacaggg   2160
agtggctgta atcaactgag caacatctgt gtgaatgtta ttcacaggtc aggacagcag   2220
cttggtcttc ccaggtgagg aactgaggac tggcctgcat agatttgtgc agtaggtgag   2280
tagcttccaa atttattttc agaacttcca tgtagtacct gcctctccat ttaaatattt   2340
tttaaaattt tatttattta aatattttct tggttagctt tccaagaggg aggaaaagag   2400
gggagttgca acaagtagtg cccctatgct gggattcatt ttccagagta aagcctggga   2460
ctggcaccct gacccctacc ggcaggtgaa aactccaggc aaactgctga gatcccacct   2520
gggctggctg agatagtgcc tggggtgcat ccctcagcag ctgccacctg ggccctgggg   2580
ccatctcttt ctctggcatc aagcagccag gtgtcaaggc cttcccagca atccatgctg   2640
catggctggg tcttgttcta gcaggtcgat gggcagggac tggtagctta gccagggcac   2700
cagtgcgtgg ctgtgggttt gtgtgcttct gtggagaagc atgatgtgta tgtgtgtgtg   2760
tgggcacagg catgaggaag ggttcatttg tgcaggtatc tcccatgtat atcagtgtgg   2820
gagagtgcct gaggatgtgt ttgtgtgtct gaaaatgggc ggagggtctg ttgtgctaat   2880
gtgtgcaggg gtgaacatgt gtgtgacagt ctgtgtgttt ccctgagtgg tggctgcgtg   2940
agagggtgag gggatttggt gttgtctacc atgcccggca catagcaggc tcttaataat   3000
cttgaattta attaatgtta aatgtgtatg ttcccatcct tgtggaagtt ggtatagagc   3060
ctgttttcct gtgattgtga gactggaaaa tgggggacgg gcaggggcga gacaggatac   3120
agaggctact gttttcttcc tccctagaag taagtacata gaagagtggg ctctggcacc   3180
tcacgggaca tcaccaagtc ctgtgtggct ggctaggctg tcccaaggtg gcttcaggca   3240
tcacttgaat cttttgagac cttcaggcag tagcctgcca ttcaccctgt cagtcagcag   3300
aagttgggcc cacacaggcc atagaaacac agagcagttc ccgggaggac ctgagctgtc   3360
cctgagagca gagcttccag gagaggccgc aggaactgcc ttgaccggaa ttcctcttgg   3420
ggtgcaaagg tggagggaca catggtgcga ccccaggcag aggactgcag ccactccgtg   3480
cagtcccagc ctctggggta gccccttgac ctccaggcct gcacagatcc aaggccgagg   3540
tccaggctcc agcgccaaat tagctggcct agcagcctgc agccgctcta atctcaacta   3600
ggaaggaatc cttgcgctta gaaagtccaa gcgaaagggt attctgattt tatcccggtt   3660
ttaccagaaa atgctgaaag gaaaagcccc gagaggacac agtgctctag gaactcgggg   3720
```

```
cgccacgagc gcctcatccc ctcccttccg cccggccgcg gtgccctggt cgctgaggga   3780

cgcggtcagt acctaccgcc actgcgaccc gagaagggaa agcctcaact tcttcctctc   3840

ggagtcctgc ccactacgga tctgcctgga ctggttcaga tgcgtcgttt aaaggggggg   3900

gctggcactc cagagaggag ggggcgctgc aggttaattg atagccacgg aagcacctag   3960

gcgccccatg cgcggagccg gagccgccag ctcagtctga cccctgtctt ttctctcctc   4020

ttccctctcc cacccctcac tccgggaaag cgagggccga ggtaggggca gatagatcac   4080

cagacaggcg gagaaggaca ggagtacaga tggagggacc aggacacaga atgcaaaaga   4140

ctggcaggtg agaagaaggg agaaacagag ggagagagaa agggagaaac agagcagagg   4200

cggccgccgg cccggccgcc ctgagtccga tttccctcct tccctgaccc ttcagtttca   4260

ctgcaaatcc acagaagcag gtttgcgagc tcgaatacct ttgctccact gccacacgca   4320

gcaccgggac tgggcgtctg gagcttaagt ctgggggtct gagcctggga ccggcaaatc   4380

cgcgcagcgc atcgcgccca gtctcggaga ctgcaaccac cgccaaggag tacgcgcggc   4440

aggaaacttc tgcggcccaa tttcttcccc agctttggca tctccgaagg cacgtacccg   4500

ccctcggcac aagctctctc gtcttccact tcgacctcga ggtggagaaa gaggctggca   4560

agggctgtgc gcgtcgctgg tgtggggagg gcagcaggct gcccctcccc gcttctgcag   4620

cgagttttcc cagccaggaa aagggaggga gctgtttcag gaatttcagt gccttcacct   4680

agcgactgac acaagtcgtg tgtataggaa ggcgtctggc tgtttcggga ctcaccagag   4740

agcatcgcca accagaacgg cccacccggg gtgtcgagtc ttggtaggga aatcagacac   4800

agctgcactc ccggcccgcg ggccttgtgg catataacca tttatatatt tatgatttct   4860

aattttatta taaaataaaa gcagaaatat ttcccgaaga acattcacat gagggcatta   4920

cggggagacg gcaagtcggc ggctcggggg gcgcgctcag ccgggagcgc tgtagtcaca   4980

gtcccgggag gaagagcgcg                                               5000
```

<210> SEQ ID NO 81
<211> LENGTH: 1500
<212> TYPE: DNA
<213> ORGANISM: Homo sapiens

<400> SEQUENCE: 81

```
tggaacaagt gtcagagagt aagcaaacga ctttctgagc tgtgactctg ctcctcgact     60

gcccacgtgc tctccgctgt ctgcactcct gcctcacctg ggctgactcg gactctccac    120

ctcctttgct gcttccggca tgagctaccc aggagcctaa ggcgctcctt cccgcaactc    180

cggtccccgc gccccgggac tgcaaatcct ttaaacagag gccccagagc taggggtttt    240

cccaggctct ggtgggcgtg ggctgacagt cgctgggagc cccgcaacag gggggatgtc    300

caggcaggta tgcacccagc tcccggcgtt tcccggagtc accacaatgt ttccctttct    360

ctctccccca cgtatgctgc taggggtact ccccagatag gattttcttt gtcttttctc    420

ctagtaacac cgaagccctc tcgtgcccgg ggactgcaga ggaacgccag accatccgga    480

ccttgcggga tggctcggtg tgtgtgtttt actgtgtgtc ggagtgtcgc gcatgtgtgc    540

gtgttggggc gcgttatcaa caggggccta gggcaccccc actctttctt gctctcttcc    600

cccatcactt catggacctc cgaggcgcaa agcgctcgac cctctcctgg gctcagtggc    660

ttgggtactc cgggctgagc tcagctgggg agtcccctta cccagcccgc accggcaccc    720

cgaagcttca aagttgcggc aaacagttgc ggggagcaga ggaactgagg tccaggccag    780
```

cgcgcccgcg gtcgctcgcc ttggggagca ggctgagccg agggtcgtgc gggtgcgcgg 840
cagaggcggt aggaggcgga ggagaggggg gagaaagagg gggcggtggg gaacagctgc 900
cggggtaggc gaggcgcaag gtggctcccc gcggccccgc gccccgcggc tctcggacgc 960
accaggcagc caatggctgc gcagaggtgt acagcagatg gcgtctgact gcgccgttcc 1020
ttcctcctcc tcctcctcct ccttctcttc ctcctcctcc ttctcttcct cctcctcctc 1080
cttcagtgct gaggagccag agtcgccgcc gggttgccag acgctggaat gggtggtctt 1140
ccgacacaca ccaccatctt tcttgcgctc gggaagctcg gggctcagcg gctcccagag 1200
gttacggcgg cggctctggc gagacgggtg agtgcaagca cgcggagccc cgagtcgggg 1260
atgccgggcc ccctggccgg ccgactgggg cgcggggtgg cagcgccggg gaagggggcg 1320
cgctgccggc gcagactttg ctctttcctc gccggacagc catcgtcgcc ccttctccca 1380
gccagacgcg ggaacttgga agcggatctt ctcggacgcc tctggcttgg ggctgcggga 1440
agcgtgggct gcccggggcg cagtgtgcgg agaccctcta ggcgggcggg gacgccccac 1500

<210> SEQ ID NO 82
<211> LENGTH: 800
<212> TYPE: DNA
<213> ORGANISM: Homo sapiens

<400> SEQUENCE: 82
gttattatcc acggggtcct aattaaagct tgattaaaat gcccttcttt ctctaaaaaa 60
ttacgaacta ggcaacttca tacattttga atggcgcagt gtttcctctt ccaactgttt 120
agtttgtagt atactatgta agcaacatca attatcaacc cttgcaagat gacaacatga 180
gcctgtgggg gaagcacttg aggggaggga ggagaaactt ctctttttta ataatcagcc 240
ggaaacaatg tttaacaaga atctgatgag gtcactgcag taaatatttt tcctcttaca 300
gagccaatca tcacggaggg atcccctgaa tttaaagtcc tggaggatgc atggactgtg 360
gtctccctag acaatcaaag gtgtttgctt tctgctctgt tgcttttaaa ttgtatggga 420
aaggaagatt ggtccgacgg cgcgcttgtg gcccggccgg agcttgcgtg cgcgttctga 480
cggctgggtg ctgtgttaca ggtcggcgca gttcgagcac acggttctga tcacgtcgag 540
gggcgcgcag atcctgacca aactacccca tgaggcctga ggagccgccc gaaggtcgcg 600
gtgacctggt gcctttttaa ataaattgct gaaatttggc tggagaactt ttagaagaaa 660
cagggaaatg accggtggtg cggtaacctg cgtggctcct gatagcgttt ggaagaacgc 720
gggggagact gaagagcaac tgggaactcg gatctgaagc cctgctgggg tcgcgcggct 780
ttggaaaaac aaatcctggc 800

<210> SEQ ID NO 83
<211> LENGTH: 40
<212> TYPE: DNA
<213> ORGANISM: Homo sapiens

<400> SEQUENCE: 83
tccctgctgt gggacccgag gagaggagaa ctggttcgct 40

<210> SEQ ID NO 84
<211> LENGTH: 500
<212> TYPE: DNA
<213> ORGANISM: Homo sapiens

<400> SEQUENCE: 84
tctctctctc tctcttgctt ggtttctgta atgaggaagt tctccgcagc tcagtttcct 60

```
ttccctcact gagcgcctga aacaggaagt cagtcagtta agctggtggc agcagccgag    120

gccaccaaga ggcaacgggc ggcaggttgc agtggagggg cctccgctcc cctcggtggt    180

gtgtgggtcc tgggggtgcc tgccggcccg gccgaggagg cccacgccca ccatggtccc    240

ctgctggaac catggcaaca tcacccgctc caaggcggag gagctgcttt ccaggacagg    300

caaggacggg agcttcctcg tgcgtgccag cgagtccatc tcccgggcat acgcgctctg    360

cgtgctgtga gtacaacctg ctccctcccc gggcacagat atgacagagg ggcttagagg    420

gggcccagct ttgagatggg ttgttcttat gtcacaggac agagtgatct gacatgcaca    480

cttccccgcc accctgtcat                                                500
```

<210> SEQ ID NO 85
<211> LENGTH: 500
<212> TYPE: DNA
<213> ORGANISM: Homo sapiens

<400> SEQUENCE: 85

```
tgtcctcgaa gaagggcctg agcagcagca gaggacccca ggcgaccgtg cctgagccgg     60

gcgccgacga cgactgagca cctgatatgt ccccggcact cgcagccccg cggccggagt    120

cgctgtgggt gagcggtcgt cgagcttcac agaggccggg ctctgtgcca gggccccgac    180

agggcaggaa gcagatagag tcccacaagc acaagcccag tgcgcagaaa gggttactta    240

aaaaataagt tctgtgataa aatcaaacag ggtgaagggc tggaaacagg tcatgagggc    300

gcaaacaggt cgtgagggcg caaacaggtc gtgagggcgc aaacaggtcg tgagggcgca    360

aacaggtcgt gagggcgcaa acaggtcgtg agggcgcaaa cagatcgtga gggcgcaaac    420

aggtcgtgag ggcgcaaaca ggtcgtgagg gtgcaaacag gtcgtgaggg cgcaaacagg    480

tcgtgagggt gcaaacaggt                                                500
```

<210> SEQ ID NO 86
<211> LENGTH: 300
<212> TYPE: DNA
<213> ORGANISM: Homo sapiens

<400> SEQUENCE: 86

```
aaatgagacc tctggggaga ctgtcaaccc caggggtaaa acaaaaattc tgatcagaaa     60

ctgagtttcc caaagaaggg gctaaatgtt ttccaacact ttcggggctc agggaagatg    120

actctgtaag gacactgaga atcttcctcg cgtgccacgg ggaggaggac tgggggcgtt    180

tgaggggctc agcgcaccag aggagtgagg tggaggaggg cgttcccgcg tcctcctctt    240

caatccagag cagctcaacg acgtggctcc ctttctatgt atccctcaaa gccttcgcgt    300
```

<210> SEQ ID NO 87
<211> LENGTH: 600
<212> TYPE: DNA
<213> ORGANISM: Homo sapiens

<400> SEQUENCE: 87

```
taggctctag tggacctagc agtgggagag ctacttgggc tggtttcttt cctgacgctg     60

cagggatggg catcggcctg gaaccagaag cgcaggagct gggccacggc agagtaatta    120

agaaaataat gaaattgatg gcggatgggg gcgctagaaa tcctggggcg tctacttaaa    180

accagagatt cgcggtcggc cccacggaat cccggctctg tgtgcgccca ggttccgggg    240

cttgggcgtt gccggttctc acactaggaa ggagcctgaa gtcagaaaag atggggcctc    300
```

gttactcact ttctagccca gcccctggcc ctgggtcccg cagagccgtc atcgcaggct 360
cctgcccagc ctctggggtc gggtgagcaa ggtgttctct tcggaagcgg gaagggctgc 420
gggtcgggga cgtcccttgg ctgccacccc tgattctgca tccttttcgc tcgaatccct 480
gcgctaggca tcctccccga tcccccaaaa gcccaagcac tgggtctggg ttgaggaagg 540
gaacgggtgc ccaggccgga cagaggctga aaggaggcct caaggttcct ctttgctaca 600

<210> SEQ ID NO 88
<211> LENGTH: 800
<212> TYPE: DNA
<213> ORGANISM: Homo sapiens

<400> SEQUENCE: 88
gaggttgctg actcaggagc caggagctga gaaactccta ggctagcagc cgttgagcct 60
aattttattt tctggctttc tccgaaatgt ctcgtttccc tcatctttct ggtccttttc 120
gtctctctta ttttccccaa aacgtctacc tcacttcgtc ttcctttctc ctcccctccc 180
cctctctttc ctctatactc tcttcccatt tagccttgca ggcccctcct ccccggtgtt 240
ggagagctca aagacgcgcg aaactcaagg atctggccct gaccagggac gggattaggc 300
gggaagtggt gacggcctga aaaggctggg ctcgaacccg tgccttcctg aaaggactct 360
ccccgccaca agtcacaccc acccgcaggc ctgctggcca aagaaacaaa ggagtcgggc 420
gtggatccag gagaaacagg ttttcgctct cggatctccc tgggcaaatc agggatcctg 480
agcgctatac cccgcagtcg tacggagcct ctgggaaagg ggatttaagg gtgacttcca 540
ctttcagctt cggctacttg ttgcctgcgg tccaagcctt ctctgcttcc tcctacctcg 600
tcttaggcct ctgtagaaag tgcacgccgc gtttcccctt ccaggctctg agagggcctg 660
caggcccgtg gccgcctccg acaagatgcc ttccagtgct aggggggcca ctttggcggg 720
atgggggtcg gttggttaaa aaaaacttaa gttctggctc agtcgagtgt ggcaaaagcc 780
gagggtcggg ggttgggggg 800

<210> SEQ ID NO 89
<211> LENGTH: 2000
<212> TYPE: DNA
<213> ORGANISM: Homo sapiens

<400> SEQUENCE: 89
tactgacctg gtctccgcct caccggcctc ttgcggccgc tgcagaagcg cactttgctg 60
aacaccccga ggacgtgcct ctcgcacagg gagcgcccgt ctttgctggg gctggagcgg 120
cgcttggagg ccgacactcg gtcgctgttg gactccctcg cctgccgctt ctgccggatc 180
aaggagctgg ctatcgccgc agccatagct gctcagcgag ggcctcaggc cccagcctct 240
actgcgccct ccggcttgcg ctccgccggg gcgagggcag gacctgggcg gccagggaaa 300
gggcagtcgc ggggaggcag tgctaaaatt tgaggaggct gcagtatcga aaacccggcg 360
ctcacaaggt tagtcaaagt ctgggcagtg gcgacaaaat gtgtgaaaat ccagatgtaa 420
acttccccaa cctctggcgg ccggggggcg gggcggggcg gtcccaggcc ctcttgcgaa 480
gtagacgttt gcaccccaaa cttgcacccc aaggcgatcg gcgtccaagg ggcagtgggg 540
agtttagtca cactgcgttc ggggtaccaa gtggaagggg aagaacgatg cccaaaataa 600
caagacgtgc ctctgttgga gaggcgcaag cgttgtaagg tgtccaaagt atacctacac 660
atacatacat agaaaacccg tttacaaagc agagtctgga cccaggcggg tagcgcgccc 720
ccggtagaaa atactaaaaa gtgaataaaa cgttcctttta gaaaacaagc caccaaccgc 780

```
acgagagaag gagaggaagg cagcaattta actccctgcg gcccgcggtt ctgaagatta    840

ggaggtccgt cccagcaggg tgaggtctac agaatgcatc gcgccggctg cggctttcca    900

ggggccggcc acccgagttc tggaattccg agaggcgcga agtgggagcg gttacccgga    960

gtctgggtag gggcgcgggg cgggggcagc tgtttccagc tgcggtgaga gcaactcccg   1020

gccagcagca ctgcaaagag agcgggaggc gagggagggg ggagggcgcg agggagggag   1080

ggagatcctc gagggccaag cacccctcgg ggagaaacca gcgagaggcg atctgcgggg   1140

tcccaagagt gggcgctctt tctctttccg cttgctttcc ggcacgagac gggcacagtt   1200

ggtgattatt tagggaatcc taaatctgga atgactcagt agtttaaata agccccctca   1260

aaaggcagcg atgccgaagg tgtcctctcc agctcggcgc ccacacgcct ttaactggag   1320

ctccccgcca tggtccaccc ggggccgccg caccgagctg gtctccgcac aggctcagag   1380

ggagcgaggg aagggaggga aggaaggggc gccctggcgg gctcgggatc aggtcatcgc   1440

cgcgctgctg cccgtgcccc ctaggctcgc gcgccccggc agtcagcagc tcacaggcag   1500

cagatcagat ggggattacc cgccggacgc aaggccgatc actcagtccc gcgccgccca   1560

tcccggccga ggaaggaagt gacccgcgcg ctgcgaatac ccgcgcgtcc gctcgggtgg   1620

ggcgggggct ggctgcaggc gatgttggct cgcggcggct gaggctcctg gccggagctg   1680

cccaccatgg tctggcgcca ggggcgcagg cggggcccct aggcctcctg ggctacctc    1740

gcgaggcagc cgagggcgca acccgggcgc ttggggccgg aggcggaatc aggggccggg   1800

gccaggaggc aggtgcaggc ggctgccaac tcgcccaact tgctgcgcgg gtggccgctc   1860

agagccgcgg gcttgcgggg cgccccccgc cgccgcgccg ccgcctcccc aggcccggga   1920

gggggcgctc agggtggagt cccattcatg ggctgaggct ctgggcgcgc ggagccgccg   1980

ccgcccctcc ggctggctca                                               2000
```

<210> SEQ ID NO 90
<211> LENGTH: 800
<212> TYPE: DNA
<213> ORGANISM: Homo sapiens

<400> SEQUENCE: 90

```
gggggacaca gagaggaggg gttgcgggcc tgtgagaatg aagagcacag agcggagagg     60

gggaggagga gggaaaggaa ggcgtggcag tgagagagaa gaggaagaag agaggaggag    120

tggggagggg agggagagca agacagcagc gggtctggat tcccctccga gccacatctg    180

gtcaggttct aagtaattag aagattttcc cattggttta cccaagggct ctctctctga    240

ttaattttcg aaagagttgg ccaattttaa tcatagcaaa cacgatgatc acggtgatca    300

tggcctgaac agctaaaagc agaaaataaa acccccagaa cggactatga tcttgacctt    360

tgcccgtggt caccggctgg gcccacaccc agggttctga gctgttggga gccaaggctg    420

ggtggacagg ggcttccgag gagctgtccg cagcggggcg gggaggcggg ccccgggggc    480

ccgggcactc cgcgtcaccc cccggcaggg cccagagcgg caggccggcg tgcgccccag    540

ggcctgcgca ccgtgggggc tcttccccgc ccacgaggcc taggtgctgc cgcagccacc    600

ccaggaaggg ccccaggcca cagtcgcagc gccaggagtt gtgccccaac aggacctccg    660

tcagccgggg cagagcccca aacacgtcgc caggcagggt ctccagctgg ttgtggtcga    720

gctggacgct ctccaggctg ctgagattgc ggaagagggc acggggcagg gcgcgcagcc    780

tgttgcggcg cagggacacc                                                800
```

<210> SEQ ID NO 91
<211> LENGTH: 550
<212> TYPE: DNA
<213> ORGANISM: Homo sapiens

<400> SEQUENCE: 91

```
gccccggtgc accgcgcgtc cagccggccc aactcgagct agaagcccca accactgccc     60

agtgcctgag ttgcagtctt gggtccttta gaaacctgga gatgtgcgta aaattcagat    120

gccggtattc ccgaacttcc ccaggcctca gcatatctcg gcggcctgtg gacagatggg    180

aggctaccaa tcgctccggc gtccgcagcc cgacccctgc cgccagaccc cggacgtctt    240

ccggataata aagttcccgc tctaattcat tttccctaat ctggacgccc ctaatctaca    300

gcttttattg cgcccagtta aaagtcgagg gaattcgctg tccctccgcg ctcggataat    360

taccccctaaa tggccacggc agccccttgt gtttcctgga gattagaacc ccgcagtcat    420

caatggcagg gccgagtgag ccgccaatca cctccgctca ctccctgaga gccgctggcc    480

tgggccgcag gaggagaggc cataaagcga caggcgcaga aaatggccaa gccccgaccc    540

cgcttcaggc                                                           550
```

<210> SEQ ID NO 92
<211> LENGTH: 2000
<212> TYPE: DNA
<213> ORGANISM: Homo sapiens

<400> SEQUENCE: 92

```
agggtgcctc tgttcaaatt agaaaaaggc gccccctcag ggcagactca gcccagctgc     60

caggggacaa gtcctggcta acgggagctg gagctgggtt tcacctccag gtgcctcctt    120

ggcggggcgc cccgtgcagg ctacagccta cagctgtcag cgccggtccg gagccggagc    180

gcgggaatca ctcgctgcct cagcccaagc gggttcactg ggtgcctgcg gcagctgcgc    240

aggtggagag cgcccagcct gggaggcagt agtacgggta atagtaggag ggctgcagtg    300

gcagaagcga gggtggccgc agcacttcgc cgggcaggta ttgtctctgg tcgtcgcgca    360

ccagcacctt tacggccacc ttcttggcgg cgggcgccga ggccagcagg tcggctgcca    420

tctgccggcg ctttgtcttg tagcgacggt tctggaacca gattttcacc tgcgtctcgg    480

tgagcttcag cgacgcggcc aggtctgcgc gctcgggccc ggacaggtag cgctggtggt    540

taaagcggcg ctccagctcg aagacctgcg cgtgggagaa agcggcccgc gagcgcttct    600

tgcgtggctt gggcgccgcc ggctcctcct cctcctccgc gacgcctgcc ggcccgctgc    660

cgcccccgcc gccggccccg ctgcacagcg cggacacgtg tgcacctctg ggccaacac    720

cgtcgtcctc ggtccttggg ctgcggtcgc ctgcggaccc cggtgggaac agaaacaaga    780

gactgtcagc gccacagacg aggtgaggcc gggcctcaac tgcaggggtc acgggagtgg    840

ggcggaaata cactttgatc ccactcaagc ggagcggagg tctgggaggc cctgggcccg    900

ggagaccagt cttagactct tgccccactg ggtatcccat ctaggcctct tctggggagg    960

gcggcagact cagccgctgt gtcaacgctg tgttgtcgag accagctccc caccctctct   1020

gggccccagg ctcccctcag taacttgggg cactcgaccc gagcatccgc gaaagccctc   1080

ccggctctca gcgttgagca ttgggattct agactgcatt tccgtctctc tgcttgggtt   1140

cacgcgcctc tccacactta gttcacacgc acacacgcgc gcgtcctcgc agcacacact   1200

tgtctggtgc aggtaaggga aggtggaggc ggatcctggg gccaaaggta tttagaatct   1260

ttcaccctca gccgcctggg attgctgtga gagacatgga aacaggctga gccgaggcct   1320
```

tagatgagag gatggactgg agagtaaaga gggagggttg cccctgcatc gagtttttgg 1380
accctgatcc cacaccagct tctcggtctc gtacccgccc ttccgaagaa ctccagcaga 1440
aaggtccagc ggtcccctgt gcttgaggcc tacagaagct tgtacccaac tagggcaggc 1500
acccgggtct tccagaccac aggacaggac aggccacggc tgaggaggcc tctctcctgc 1560
ctccaggatg aactaaagac ccaatccggg atcttcggcc tagggctgct ctcccagacc 1620
tggggtctga gaaagccaaa ccagcccttt ccccaaagct ctagttctgc agattctcag 1680
ctctggccca ctcggaggtg ttcttcacca cctatccacc tactgtgggg cccggccctg 1740
ggaccttgaa ctggcaggtc tctggtccag agctaggtca ctggctacct gaggtctctg 1800
aacccctcac ttttccgctt ccctgatttt ggggatttgg ggacagacac ggcagaaagc 1860
actggcgacg aactcaaaaa ctcccgaacg caaggggcag cggttctccc aacccagtct 1920
aatgcacatt ggcccaggat gtctcaggcc tcaccccagg acgtagggct ctgaggagct 1980
actccggtct ctcgcgggct 2000

<210> SEQ ID NO 93
<211> LENGTH: 1000
<212> TYPE: DNA
<213> ORGANISM: Homo sapiens

<400> SEQUENCE: 93
gagaagggat gtggcggggg gctcctccgg ccctggactc cctgggtgga ctagaaaagg 60
gcaaagaagt ggtcacatct gtgggccaga ctggtgcgcg atctttggag gcgcagcagc 120
aaggccgcgc cagggctgag cccagaccgc ccacgaggag gcccgccagg cccggagcag 180
cggcgcgtgc gggggcgtgc cgagcgcagg ctctagggcc cctgcttcgc cccagctgga 240
ccccgcgggc ggtcggtgca gctcgagcgt gtgggctgcg atgccctgcc tgagacttcg 300
ggctagggat gcgggcggga agtgggggtg cggcggcagc tgcagattag attccttttt 360
tttttggccg gagggacgtg caaacttcta gtgcccgggc caagagggcg accccggagg 420
tgcgtaggtg gccctccggg ttcccgcttc tcctagtgcc tctgaaaata ccgtcagggt 480
aaagggagac aggcagtaag tcttaccacc accgcccttt ccccatgtca ttggccaaaa 540
actgaacatt aagataaagc agctgtttca gtcaatggaa agcggtaggg cgaggttgta 600
cccaaaaccc ggtttagacg gccaatgaag tcctaggaaa agccgccccg ggggcacgtt 660
caggtggagc ggctgcacct cgggtcgttc taagggatgg gctgcgtggt acccacggaa 720
ttcatgggtc caaaaggtcc tggtcacctg tccaaacatc catcccctgg cgcatggcgg 780
ttgacaagat ggcccggcca cccagaggaa ggaggatccg ggacggggaa cttcgcgccg 840
ggaagctgta gcccagagct gcagctcagc attcgcaaga gattcatctt ttttttctct 900
cgtgttcgga gaaacagata aacaagacac cgcctcatca gataagaacg tctccttcga 960
tgtcacggat ttcaagaggt agctggagaa actgacgtca 1000

<210> SEQ ID NO 94
<211> LENGTH: 1300
<212> TYPE: DNA
<213> ORGANISM: Homo sapiens

<400> SEQUENCE: 94
caggtcaggc agaacttctg cccttcccgc tactggcacc ccaagcaggg atgcactggg 60
atgcgtggca ggggcgggat ctcctgggag cgtctcagcc cagcagggag tggggaagca 120

```
agagggaagg cttaccttcc tcggtggctg gcaggaggtg gtcgctgcta gcgaggggga    180
tgcaaaggtc gttgtcctgg gggaaacggt cgcactcaag catgtcgggc caggggaagc    240
cgaaggcgga catgaccggg gcgcagcggt ccttcacctg cacgcagagc gagtggcatg    300
gctggatggt ctcgtctagg tcatcgaggc agacgggggc gaagagcgag cacaggaact    360
tcttggtgtc cgggtggcac tgcttcatga ccagcgggat ccaagcgccg gcctgctcca    420
gcacctcctt catggtctcg tggcccagca ggttgggcag ccgcatgttc tggtattcga    480
tgccgtggca cagctgcagg ttggcaggga tgggcttgca attgctgcgc ttgtaggaga    540
agtcgggctg gccaaagagg aagagcccgc gcgccgagcc caggcagcag tgcgaggcga    600
ggaagagcag cagcagcgag ccagggccct gcagcatcgt gggcgcgcga ccccgagggg    660
gcagagggag cggagccggg gaagggcgag gcggccggag ttcgagcttg tcccgggccc    720
gctctcttcg ctgggtgcga ctcggggccc cgaaaagctg gcagccggcg gctggggcgc    780
ggagaagcgg gacaccggga ggacagcgcg ggcgaggcgc tgcaagcccg cgcgcagctc    840
cggggggctc cgacccgggg gagcagaatg agccgttgct ggggcacagc cagagttttc    900
ttggcctttt ttatgcaaat ctggagggtg gggggagcaa gggaggagcc aatgaagggt    960
aatccgagga gggctggtca ctactttctg ggtctggttt tgcgttgaga atgcccctca   1020
cgcgcttgct ggaagggaat tctggctgcg ccccctcccc tagatgccgc cgctcgcccg   1080
ccctaggatt tctttaaaca acaaacagag aagcctggcc gctgcgcccc cacagtgagc   1140
gagcagggcg cgggctgcgg gagtgggggg cacgcagggc accccgcgag cggcctcgcg   1200
accaggtact ggcgggaacg cgcctagccc cgcgtgccgc cggggcccgg gcttgttttg   1260
ccccagtccg aagtttctgc tgggttgcca ggcatgagtg                         1300
```

<210> SEQ ID NO 95
<211> LENGTH: 500
<212> TYPE: DNA
<213> ORGANISM: Homo sapiens

<400> SEQUENCE: 95

```
tgcgatcatt aaaatcagtt ccttccctcc tgtcctgagg gtaggggcgg gcagatttta     60
ttacttctct tttcctgata gcagaactga ggcggggttg tggaggagcg acggaggacc    120
acctctaact tcccttcact tcctggattt gaagcctcag ggccaccggc ctcagtcctg    180
ttacggtggc ggactcgcga ggttttccag cagctcattc cgggacggcg gtgtctagtc    240
cagtccaggg taactgggct ctctgagagt ccgacctcca tcggtctggg agcgagtggt    300
tcgagttcag atgctgggaa ccgtcgcttc tccccggccg ggctcgctgt tttctcctcc    360
gctcgccgtc atcaagcccg gctatgagca gggctttaaa tcctccctcc ctcacccgca    420
ggtttaccga gcagccccgg agctctcaga catgctgcgc tgcggcggcc agaggagggg    480
tgggggcatt gccctctgca                                                500
```

<210> SEQ ID NO 96
<211> LENGTH: 500
<212> TYPE: DNA
<213> ORGANISM: Homo sapiens

<400> SEQUENCE: 96

```
gggcttgggc cgcaggcttc cctggacttc cgcagtcccc cttctcccca ttccagaacc     60
tgccgagccc ctgctgcatc tgggacccgc cttcaccgtt tcccaatccc agcggttagc    120
ccctgcgccc cctttttggt ctccactttg ccgttcgaaa atgcctaggt tggtggatcg    180
```

```
accctccgcg gagcaaagac ggatggctgg caggagcagg ttcaggagct gggccaaggt    240

attctctgct tccgcctttg tgtccgcccc cccgccccct gctccccgct tcccgccagc    300

atctctcctt ttctgctcag gagtgtttgg cccggcggtc caccccggct tcccgagata    360

cgctagagtt gcccccacgt cctgtccgcc gcgcccctac ccaccgggtt gccttcgggg    420

cccttcggtg ctgtgtagtc ggcgtggcgc tgtgagctag gcgaacagga acccccaggc    480

ccgccacgtc tacgctatta                                                500
```

<210> SEQ ID NO 97
<211> LENGTH: 600
<212> TYPE: DNA
<213> ORGANISM: Homo sapiens

<400> SEQUENCE: 97

```
ttctggggcc tggatgggtg cgagcgggac ccgggggagt gggagtcgcc aggctctgag     60

caagcaaggg ctgcacctgc acctctgccg ggcatgaaga aaggtaagga aggaaggagc    120

tcacccgggt gggagacaga gccggggcgc gcgagcttgg tgtgggggcg ccactccggg    180

gcggagggga ggggctacca gtgacttctc cgagtcggga gctagaaaga ggcttccggc    240

caggttccct tggaacaggt gtcggagttg ttgggagagg gggctgcaag aaagaggggt    300

gcagaaactg gttcattaga tggaggctct gggcggaacc gcgaggacac cctggcagcg    360

cgctgtgcct gcgttaggcc gggaggggag aggcctccgg acggcgaagt gtccctaggg    420

acccagacgc ctcgggagcg atccgggccg ctgcgaagcc ctgcccacca ggagtggatc    480

cccaggattc acctcccggc tgcctgctct gagctgagaa ggggatctgg ttcttcacaa    540

taccgtggat ggcggggaag gggagggagc ctggggtaaa atcccatctt ggtttcctcg    600
```

<210> SEQ ID NO 98
<211> LENGTH: 1300
<212> TYPE: DNA
<213> ORGANISM: Homo sapiens

<400> SEQUENCE: 98

```
tgtcacagaa accccagcag cgcagccacc ggactgggtt ctggaggccg agccgcagtc     60

cgtgcggcgg cgctgggaag agaaggcgcc ccggcagctc ccctgccacc ggccccgagg    120

agcggctggc tcccccagcc cagcgccgcc gccgcccggt aactccaggc gcaactgggc    180

gcaactgggg cagctgcgac accgaatccc tcacatctgc aacctgggtg ctgcggccac    240

tgagaaaatg gaggcgcaga ccaacgagcg gtgccgcgac cgagagacct cggctggcga    300

aatggtggtg ccgggagcct gcgagtgacg ccagccggcg gggttgtcaa ggacaacatt    360

cgttttgacg cagccaatgg cgccgtcacc aagaaaccat cgactctgag aaaaaagaga    420

ggttcggcca ccgagaaact ccgtacgaca agtgctgtgg cagaaaaacc gcctactccg    480

cgccacaggc aaaacagcca atggaaaccc caggtgctgc gaccgtgaca ccggcactag    540

agggtctcgg atggagaaag cggcgcacgg agaccaggaa actatgtgta gcacaactag    600

cagaaaaccg tctggtcggc catccgggag aaagcgcgga tcagaaacaa gcgacttcga    660

tgcagggaac cgcgcagcca ctgaagaaag tgacccacgt ggcagtggtg ccagcgaaac    720

actgcagttt ggacggcagc tgtggggatg ccacagagaa acatgcactg ccactgaagt    780

acatccagct ccgcggagct agtgttcata tgatcaagaa accgccagtt gggctctgct    840

agaaactttt agtcctccct taacggctat cctacccaca acagacaatg cctttaccca    900
```

```
gcacctagcg gtgctgagac ccgcctgggc cagcacagag cgcagagcag tacgggtacg    960

gagaaacgcc ggactcagtg aaaccagcct tgcctccagc ggattccccg gcttcgccgg   1020

acgccacagg cagagtgccg cggggaaacc tctggctccc taaaccgatt agattgtggg   1080

agtggggggg acactcacaa gttgtgtgga agggaaccag cggcaatggg acccggcgag   1140

cacttgcccg cagcaaatgc ctgcgctgct gcaaaaaaaa caacttttgg cgcaaagaat   1200

gttgcggcca gagagcatcc gctgtcgctg acaaaggagt agcaatggca atgagaaacc   1260

gccggcgcca cggccgaccg cggcggctca cgcctatgat                         1300


<210> SEQ ID NO 99
<211> LENGTH: 2100
<212> TYPE: DNA
<213> ORGANISM: Homo sapiens

<400> SEQUENCE: 99

caaacgctga gagacaaaaa gacaccaaca cccaccagga ctgcgtcctg ccagctcttc     60

actccgctga cctgaccttc cacgccccta gtcctcgagc ggacttgacc tgtgggggag    120

taccgaaccg tccccatgag gccctccaag cggccaggtg gcctccgcca ctctctccac    180

ccccacctcc tccacccccc agcccatcgg tccatcttcg atctgcaaaa cacgccgggt    240

cagcgacgca tcggtcccag gcttgtgacc acctctttct ctgttacttg gggagccagg    300

cccaccgctc aggatcacag tgaggagaaa aaagacacaa acgccaggac agggcggctg    360

gggaaggaaa ctgctaggga ccgctcattg tcagcctggc gtgtcccacg gatcgcagga    420

cccgtcgagg ctttgctctc tgcgacccga atactcctgg gcctctcgac ctcctcctcg    480

gactcaggcg tccgcgtctc cggtcatcac gggagaccaa ttggtttaca aatagtgatg    540

ataaacctgg gaccgacctt ggggctgtgt aaaagtctac tgacagatgt aatggagggt    600

tgttagcagt cacaaagcct gtcggacccg tagcattagt tcaagagact attttcgtgt    660

cgcaccaaaa ttactgcgcg tgtaaaccaa tttccccgac ggaagaataa acagagattc    720

gtttgaagcg cgagatgaaa acagatgggg tatcgcaaac agttccccaa aatacaacag    780

acttctgggc caattacacg tggttagctc tgaatggcag aggaaatagt tttctttgct    840

gctaaatgtc acaaaagtca cctaaaggca cagaggaggc cgctctgttt ttgcgaaact    900

tgctaaaatt aatctgcgct gggccacttg cagaaagcag aaccacctcc cgcccccacc    960

tcgcctccag ccgccggggt tcaggcgttt gtgaaagaca gaacctttgg gctagggacc   1020

cgggcactgg tgcttcgaag tccgaatccg ccggccgaga aaacgacaag agaaagaaaa   1080

tccagcgggc gctctctcca gcgccaggcc ggtgtaggag ggcgctgggg ctcggcctgc   1140

cacccctacc cgacattggg aagcagcccc tgcgctcccg cggcgcctca gcctccggtc   1200

cccgccccga ggtgcgcgtt cctcctcccg catgcccgtc tcgggcccca cggagcaaga   1260

agatagacga tgacgaggcg cgcccatcca tccgggccga cgaggtcagg cccgcgccac   1320

aggcaaaaat tgcgcaagcc cggccgcagg gatttcgcgg gcgcctgggt cccaggtgcg   1380

cggccgaaat cctcagggaa aatcccgagg ggccaacggt ctaggccaca gggctgctgg   1440

gcccgggcct ggctcagagc gcattcgggc ggggaggccg cacgccgcac ccgggcctct   1500

cctccgagcc cgaggcaggc actgagctcc gggccagcca ggtgcctccc ggctggtgcg   1560

agaccccggg cctgctggga ggcgtgggca gggcagggca gggctgaacc ccagcgactg   1620

aatctcgaag gcaggaggcc tcggaggtca tcggcccagc tcgcctgaaa ctgtccctgc   1680

tcgtgccagg gcgcgggcag aggagaaagg acagggcgga gcaagcccac tgcagaactg   1740
```

```
cggtcggtgg ctgcgaaggg tccgggtcac cgcgctcccg gacgccggaa gccgcgctgg   1800

cggggccgcg gggagggagg ctgggtaccg gggccgtccg gccggaggaa gcggctccgg   1860

ccgcgctgtc cgcgcttggg agccgcgtgc agggttcagc cgtgtttcag ttgccctctg   1920

acctgacccc gggcgcacaa aggcctcccg ggtgcgccgc catggcccag tcttccagtc   1980

gctgccaaat taatgagccc acgtcaggtt gggtttacag ctcggccggg aagcagccga   2040

gtggaaaatg agctcggggc cgctccagag gctcccgcac aactgcagag gctgcccgcg   2100
```

<210> SEQ ID NO 100
<211> LENGTH: 250
<212> TYPE: DNA
<213> ORGANISM: Homo sapiens

<400> SEQUENCE: 100

```
tttccaagac agaaggaggg aactaggcgc ctttttttcca ctccgctgac cccaacgtct     60

gggctgtgcg ttgtaacgca gttggcgggg ccttcagctt gggatgaggg cgaaggggct    120

cgggatgggt gggaaagcaa ggaccgggca acaggtgggg aggtggcgga cttttgtctc    180

ggggaaggaa atcggctgtg ctgaaagggc ggaaagcagt agcgcacaga actagtgtct    240

gcggggtccc                                                           250
```

<210> SEQ ID NO 101
<211> LENGTH: 250
<212> TYPE: DNA
<213> ORGANISM: Homo sapiens

<400> SEQUENCE: 101

```
ccctcctgtg gctgcttggg cagacgcctg tggcctgtcg gatgcggccc acatcgagag     60

cctgcaggag aagtcgcagt gcgcactgga ggagtacgtg aggagccagt accccaacca    120

gcccagccgt tttggcaaac tgctgctgcg actgccctcg ctgcgcaccg tgtcctcctc    180

cgtcatcgag cagctcttct tcgtccgttt ggtaggtaaa acccccatcg aaactctcat    240

ccgcgatatg                                                           250
```

<210> SEQ ID NO 102
<211> LENGTH: 2000
<212> TYPE: DNA
<213> ORGANISM: Homo sapiens

<400> SEQUENCE: 102

```
tcctcctttg tgtatgtcaa cccagaggat ggacggatct ttgcccagcg tacctttgac     60

tatgaattgc tgcagatgct gcagattgtg gtgggggttc gagactccgg ctctccccca    120

ttgcatgcca acacatctct gcatgtgttt gtcctagacg agaatgataa tgccccagct    180

gtgctgcacc cacggccaga ctgggaacac tcagcccccc agcgtctccc tcgctctgct    240

cctcctggct ccttggtcac caaggtgaca gccgtggatg ctgatgcagg ccacaatgcg    300

tggctctcct actcactgtt gccacagtcc acagccccag gactgttcct cgtgtctaca    360

cacactggtg aggtgcgcac agcccgggcc ttactggagg atgactctga cacccagcag    420

gtggtggtcc tggtgaggga caatggtgac ccttcactct cctccacagc cacagtgctg    480

ctggttctgg aggatgagga ccctgaggaa atgcccaaat ccagtgactt cctcatacac    540

cctcctgagc gttcagacct taccctttac ctcattgtgg ctctagcgac cgtcagtctc    600

ttatccctag tcaccttcac ctttctgtca gcgaagtgcc ttcagggaaa cgcagacggg    660
```

```
gacgggggtg gagggcagtg ctgcaggcgc caggactcac cctccccgga cttctataag    720
cagtccagcc ccaacctgca ggtgagctcg gacggcacgc tcaagtacat ggaggtgacg    780
ctgcggccca cagactcgca gagccactgc tacaggacgt gcttttcacc ggcctcggac    840
ggcagtgact tcacttttct aagacccctc agcgttcagc agcccacagc tctggcgctg    900
gagcctgacg ccatccggtc ccgctctaat acgctgcggg agcggagcca ggtgaggggc    960
tcggcgccgc cccgggcgac ccctggggc ggcactggag aagccgcccg tcctcataag    1020
ggattgaact tgcatccact cctctccggc cggcttggtc gctggctgcg ctccacccga    1080
ttctcgggat cattggaccg tttgcgcgaa accagagtgg ccgattaagg gatggggctc    1140
cgagcaccgg gggtggtggc gactgtgggc gaggggaggt gggaccgacc cccaccccta    1200
cactcaaaaa aggccggggc ctccttcgag cttccggtga atttcgggcg atttccgcgg    1260
gtgtcggggg tcccgggagg aggcagtcac agatccaccc ctgcagccag cctcctaggc    1320
gccggctccg gcacgcttcg ccggtctgta gatttcctct tcgatttctc cccagctccc    1380
agcatctgtg acttcactgt taccctccct atccccgcat cacccaaccg cacctgtctg    1440
cgggacttag gtgtgcgcgc ggggctcatg cgtgtcctcc ctgctggcca cccccacggc    1500
ccacacaagt tgcacgggct cgccacgccc cgccaacacg tgcgcggacg cacgcacgca    1560
ctcctcgcac gtgggcttac gcgaatacca gctttcactg ccactcgctc gcggccagat    1620
tcacaggcct gttccggtcc actcgcagct cccctctgcc gctccctccg ccgggctcag    1680
gagtactcgt agctgattgt gcgcgcctga gggtcccaga tcgcggccgc ccaggaccag    1740
gcgaggactc cggagcctcc tctcacctct cccacctgcg ccccgggctg ggccgggtcg    1800
cctgggggc ggcctgagcg aggcgcgggg ccaggagcgc tggagcgact gccgctctaa    1860
gtgccgggcg ggcaggactc tacgatcctt gggccagagg tccggatggt cccgggactc    1920
cgtctcaagg gtcggcgacc cctcaaccca gaagcctcga gcaggcggac aggcagagct    1980
gcccagtggc cgaggcgcgg                                                2000
```

<210> SEQ ID NO 103
<211> LENGTH: 1100
<212> TYPE: DNA
<213> ORGANISM: Homo sapiens

<400> SEQUENCE: 103

```
atttgtcgtt gtgccattgc tgccactgtt gttcttgtcc agggaaacac cggtggccaa     60
cccagatcgg atacaatggt gcggctctgg actgagcctc caaccacatt agccatgggc    120
agcattgttg ctgccgctgc tgttatttta attatgattg tacgttaacc accaccttcc    180
ttcctctgcc tcccttcagc tgcaatgatg tatgttactt tttggtaact ggatttcatt    240
aacatttatg aactctcata aagtagtaga aaaagcaatt tgtgtggaag aattttccac    300
ctcattaaac agtgttcttt tgggggtcaa gctgatattt tttttgttgt tagatttttt    360
ttataggtcc tttgtccttc cctaagccct gggggatgaa aggagagccg tccacccagc    420
gaggggcttg tgtgccctag agggcgctgg gccccgcgcg ctttcctggc tgtccccgcc    480
ggctttccac cctccccaaa gcccaggtgc ccaccgtggg tcgctgcggc ctttcccctt    540
cttggccaaa tccgattact tcgcagcctg cagatggcat cgccggctaa gggcagcctg    600
cggcaggtcc ccgagcctga gcactcctcc tatctggggc ctgagaggac gctctgggct    660
ttttcccagg cccagggtgc gcggcctgct agcgcctttc gaggcacagt cccaagatag    720
gctcttgtcc ttcgacgccc ccttggcaca agcgcactgg cgccctccgc tcaacccacc    780
```

```
ttgcctttgg ggcgggcttc aaccctggga agacaggcct gggggaagcg agaggagagg     840

cccgaataga ggttccggct caatctttcc cagacggagg cctggtgttt ccagctcagt     900

tgcatcttcc agccgcgggc tcctggccca aacagaatgt gtttgctttc acaccgggac     960

ggcaagcgga gtccgcctca gtgagcagcg agctgcgcag tccggacggg tgtcgccccc    1020

agagactcgc cagccgcccc cagacactcg ccagccgtcc ccatctctaa tccaccgtcc    1080

aggcccgggc cctgggaaga                                                1100
```

<210> SEQ ID NO 104
<211> LENGTH: 800
<212> TYPE: DNA
<213> ORGANISM: Homo sapiens

<400> SEQUENCE: 104

```
ccgtgtctcc cttaagaact ggggcctcat ctccactcca gctgcgcgtg cacgtgtgct      60

cccggcagga cgcgcgccca ggagcgcgct gggggctgcc ccgcccctct ctccctcccc     120

cgcgggtaaa ctccgggcat ccatcagtct gttaattgca ctaattagag atcgcagagg     180

tgttaattgg aaaaccctgg tattgtgcct gtttgggggga agaaaacgtc aataaaaatt    240

aattgatgag ttggcagggc gggcggtgcg ggttcgcggc gaggcgcagg gtgtcatggc     300

aaatgttacg gctcagatta agcgattgtt aattaaaaag cgacggtaat taatactcgc     360

tacgccatat gggcccgtga aaaggcacaa aaggtttctc cgcatgtggg gttccccttc     420

tcttttctcc ttccacaaaa gcaccccagc ccgtgggtcc cccctttggc cccaaggtag     480

gtggaactcg tcacttccgg ccagggaggg gatggggcgg tctccggcga gttccaaggg     540

cgtccctcgt tgcgcactcg cccgcccagg ttctttgaag agccaggagc ctccggggaa     600

gtgggagccc ccagcggccc gcagactgcc tcagagcgga agaggcagcc gcggctttga     660

cccagcttcc ttccgacggc atctgcagga gcctctaggc ctgacatagg ctccgaggtg     720

ccctggctcc cccacgggga atgctgaggg ttgggccact aggtcctgcc taagtgcagg     780

acctgagcct cagacaaatc                                                 800
```

<210> SEQ ID NO 105
<211> LENGTH: 300
<212> TYPE: DNA
<213> ORGANISM: Homo sapiens

<400> SEQUENCE: 105

```
gggattgccg gctttgagaa aatatgaaga aaccgatttc tccttccact ttgccagtgc      60

actttccttc cactttcact ggtgctgggg gcggcgcact ctttacgaca tataagcgga     120

aaattctgca aaagtggccc ccggggatcc ccgcccgacc cctgtctgtc gctaatgtgg     180

gcctgtctcc ggaaattcga ggttgggcct ttgcctgaat ctgttgctat tgctcccctt     240

gctaccgctg acacttggca ccgccgcctc ctagcagcgg ccagacgcgg ggctgggggc     300
```

<210> SEQ ID NO 106
<211> LENGTH: 400
<212> TYPE: DNA
<213> ORGANISM: Homo sapiens

<400> SEQUENCE: 106

```
gttgcgagcg cggcacaggt tgctggtagc ttctggactc tggaggcttg gccttccttc      60

taagccgatg gcggggaaag aacctcgttt ccacagcttc cccgaccccc gccgcttgcc     120
```

```
atttggggac gggaagcgcg cccgggtcgc ttcacgtccc tctgggccgg agccctttcc    180

atggctggct cctctggggg cccttgggcc tgtgagcagc gtctccttcc ctcagagaag    240

aatcctttcc ttcccccatc gaagtgtccc tttctgtatc ctgaaataac ccctcctggg    300

tgaggccagt tcccctctgt cgccctcctc ccgcaggcgt ccgggagcct cgtgaggacc    360

ccgtgcagtt gagtccaggc gacaggtgcc tccccaggtg                          400


<210> SEQ ID NO 107
<211> LENGTH: 800
<212> TYPE: DNA
<213> ORGANISM: Homo sapiens

<400> SEQUENCE: 107

cagtgcgccc cttaccggag cacccatggc ctcccgcgtt accccaaatt ttgtaggcag     60

actgtcagag ttcgaagcca gctgtgtcct ctgcgggccg tgtgacccta ggctatctgg    120

gctgctcgga gccttagttt ccctagttgt gaagagggag ggtgtgacca tggcccggag    180

ctctccgaaa ggctgtgcgg attgctcggt ggcgggatgt ggagcgcgtc ttctatgatg    240

ccaggtgctg gccaagcgct cgatgcaggc tgctccagtt aggtcgatgc gatggcggga    300

agcactttcc tctgcaatgg agagacgccg acaccccgag cccgaaggct tgcaaggcgc    360

gctctcgcca ctggggtcgg ggatccgtgg gttctctatc ccgcttaccc actccatcct    420

tagcagctgt cgtcggtccc agacctctac cttggagaga ccaaggcggc ccagagccca    480

ggagactact gcgcggtacg ccaggatcca gaagtggatt ctgacttcta aagacccctc    540

ccaagccaac gctatcaggg tccctgcaag cggttgactg tggcggaggc agaaccaaaa    600

cctttgctct gcccgcggcg ctccagcctc tcacccagga cagtgctctg ggctccagcc    660

gctgcagtgg ggtcgggaca cagacgccga gttagaagcc ccgccgctgc aggtccctgc    720

ttggtcggcg cggtgacggt gtcgctggcg gcggcggggg ccttcctttg gctgcccggc    780

catttaatca gagctattat                                                800


<210> SEQ ID NO 108
<211> LENGTH: 1000
<212> TYPE: DNA
<213> ORGANISM: Homo sapiens

<400> SEQUENCE: 108

tttagtattt aaggagaaaa gcctcatttt ccagaatcga ataagcgaat taatcgcaca     60

attgtgtaga atggaactca gtctgtaaaa aatcaagacc aacgtacttt ttaatattct    120

aacatctcca agtagtagtt acaagtattg tacccatgaa gtccaggtaa ttaatttgtt    180

caatgtcaca ctgttaaaag tcaggtgggc tccaaagcac agtcctaacc agcatgctct    240

actgcctcct ctgaggcaac agccgaagtg cagaccactg ggaataaata gctgcccggt    300

cttccccact cctaaattct cccgacagac cccaaagcct ctctgagagc ctctctgacc    360

gccctgcggc ccaccccgag ttcccggcat cctctgggat ccctcttcct ggagccaaaa    420

cctacgcagg ctcctttcct ccgagctggt tgctaggtga tctccgaagg ctgtccgaag    480

tctcgcgagg gcggacccgt tgcctgatga cgagagttgg gagtgtggct ggggctgcgg    540

atctccagca gtggcgttac ttctagcggc tggataccgg gttctccgcg agatcgcgag    600

atcccgagat attctccccg cacggaagcg acgactggcc tggccagagg actcgcgtgg    660

gagcgaggtg ccggccccga caggacggtg aggtatgcag aagtaaggcg gggcgccccc    720

tgcgggaagc gagcgcgccc cggaaaatga gcgcctcccc acaccaaggt gtccaggagt    780
```

```
gagtgcggga aggaactcgg ccgcccggag ttgtggcctc atcgtgcttc ccgccaaaaa    840

cgccttggta ctgtcgggac gcggctaagc gtggacgcgc ccgcatctgc ccctcctccg    900

cagtggtgga agacacccgc ggagcgccgg tggataaggg ccgtttcctg agaccagagc    960

tgtatccgca gcaggtcagc acttcgtgcg ccctgtgtgc                         1000
```

<210> SEQ ID NO 109
<211> LENGTH: 300
<212> TYPE: DNA
<213> ORGANISM: Homo sapiens

<400> SEQUENCE: 109

```
agcggcgctg ttcccgggct gggtgcagct gctaaggaca aggcccctgc tccgaagaac     60

gcggtggctc ggggataccc tgaaagggac ggccatggcg cacatgggat gccctagggt    120

tcgtgggagg gcatgcaggc gcagcccccg caggggttgg cctgccagag aaggcagggg    180

agagcactcg ggctgcaca aatggtgtgg ccggagggaa ggtgcagcct tgtgtgtgtc    240

tggatgaggg ctgggcatag gagcttggta tttgatcctg aaagctctgc gtttccaaag    300
```

<210> SEQ ID NO 110
<211> LENGTH: 600
<212> TYPE: DNA
<213> ORGANISM: Homo sapiens

<400> SEQUENCE: 110

```
gagtcatact tgtagtcaca tccttttcct ttctccaacc cactggttaa tcatgaaagg     60

ctcttctgat tggctgcctc ctggcagtag tgcctcagcg cgacggttcg ggagcaaata    120

aataattccc gctgggaagc tgtttctcag acaggagcag cgacacccct gccacgcctg    180

ccgcctggag ttgagtgggg taagcacgcc ggcctccagg aatcgacggt gccacgtggt    240

tcttcttgca cttctcttct tctccagttt caggggacac cgtggggtgt gcgagcccgg    300

gggagcgcag ggaagggcgg gttgggctgc aggtgggaat gtgcggtcct tctgcgccct    360

caacagagct tccttccttt ttgccaaggt ccccgtgccg ccttcagcgc gcctccttat    420

gcacctctac ctctgctgca gcgtacctct tccgcagccc tagcggcctc cccgaggggc    480

gccgcggcct cggctgtccc tcccctgcct ggcacgacca cctgaccccc agcgacccaa    540

gaagcaagtt gtgtttgcag acgcaaaggg gctgtcgttg gtatcggtgc actggtttga    600
```

<210> SEQ ID NO 111
<211> LENGTH: 1700
<212> TYPE: DNA
<213> ORGANISM: Homo sapiens

<400> SEQUENCE: 111

```
acactttctg tgtgggaggg cacaagacat gggctatgac atggccagag accccacctt     60

ctttacacat gtaaaaacca accaaatcaa gatgcgtcaa cggtgattct tcctcccaca    120

ttgtttccct ttttaaactg ttattttttc aatccatgga gcagttgaga aacgggtatg    180

catctctcct cccctcccct tctatcaaag cctgtaagac acataaggaa atccaaagcc    240

acagtaatag agagagagag agagagagag agagagagag agagagagag agagaaaaca    300

gaacaaaaga aatcctcctt ggcttgtttt tccagggtgg ccaggcaagg tgtgaaaatc    360

catatttccc tctgggctgg caggtagaag ttactgggaa ggctgcgctc ccttctctcc    420

caccggctct cacatccagg ctgttccctc accctcagcc tcccccagcg ccagcttcct    480
```

```
cctccgcctc tctgcagcca ggcctcccct gcaaggcgga ccttggccca ccttggttcc    540
gggccaaggc ggcgggaaag gcaccgctac ctgcagccgc acgactccac caccatgtcc    600
tcgtactgct tgtagaccac attattgccc gcgtcgatgt atagaatgct gatgggagtc    660
aatttggtgg gcacgcagca gctgggcggg gtggagccgg ggtccatgga gttcatcagc    720
gtctggatga tggcgtggtt ggtgggctcc aggtgcgagc gcagcgggaa gtcgcataca    780
ccctcgcagt gataggcctc gtactccagg ggcgcgataa tccagtcgtc ccagcccagc    840
tccttgaagt tcacgtgcag ggcttcttg ctgcagcgta gcctggactt cttgccgtgc    900
cgcttgccat ggcgactggc gaaggccgtg cgccgccgcc ggcggccggg cgagggcagc    960
caaggcctgg catccggggc gcccgacggc ggcggccacg acccctcggc gcccgcgccc   1020
gggcccgcag cctcggccga gcccagctgc tcgcgcatct ctgcgaacag gttcttgcgc   1080
tgggatctgg tgaataccac cagcagggcc cgctcctggg gaggccgcac cctccggccg   1140
aagcccagac tccgcaggtc cgggggcggc ggttgctggg gtccccgcgc gcgcgcctcg   1200
gcctccccgg cgtccagctc gccccatgcg gcccgcagct ccaagcacag ctgcttccag   1260
ggctggtggc gcaggccctg ccacacgtcg aagacttccc agccggccgg cggcgccccc   1320
tgcgggtcca gggtccgcgc gtccagcagt aggggcgaaa ggcaagggaa gagctgcacg   1380
tggagcggcc cggctggtgg cccccagggc gctgagggcg cctggcgaaa gagccgcagc   1440
tccgcgccca ccagctcttc tttgtctgag agcatggaca catcaaacaa atacttctgt   1500
ctccggagag gagtgtgcga gagatcgtct gcgagataaa aaataattac agtcagtttc   1560
acttaagggg gagatcagcc cggtgctctt cggccgcccc gggaggaaaa gggcggggag   1620
tgggggcagg tcggccgggc agtccagctt gcccggccca gggcctgacc accccggctc   1680
cccatctggc tggtgcatgg                                                1700
```

<210> SEQ ID NO 112
<211> LENGTH: 2000
<212> TYPE: DNA
<213> ORGANISM: Homo sapiens

<400> SEQUENCE: 112

```
gcccgctgtg aatgtaggtg aggtgatccc gggaacctgg gtctgaaatc agacctgtgt     60
tgccattggg agcacggaga gaggggaagc gccctgctta ggcccaggcc gggcgtcctg    120
gtggtgggac cgcagccgca ctcacctcca ggccaacgga caaggttcct gcaagccagc    180
agggccactc tgtgcttggc ctactgcagc tcccctgcag ctcctttcct ctccctcccc    240
ggagcgctct cctctctcct ctcccctctc ttctctctcc tctctcgtct cctggggcat    300
cccgggtgga gggatgtagg ggtcgctcct cggtgccagg ccgggaagca gctcaggcct    360
cccaagagct tggcgctcag tctgggaaaa ggggttcctc tggcctcagg gacgttctcc    420
gcccccaccc cacccccctgg gagcctgaac catctggaag ggatcttagt cgggggttgg    480
gaggagagcc cgtggatagg aggagggggc gattctaggc cgaatccagc ccctgaggtg    540
tcacttttct ttcctgcggc ccgtcaccgc tgatagatgg ggctgagggc agaggaagga    600
aaaagaaaac ctccgaggtc agtgcggggc gaggtgagcc cctcccaggg ccctctggcc    660
caggaggatg aagcgcgccg gcttcgctct tgcacgccgg cttgccatcc gggtaagcgc    720
gggaaaggcg gccacagggc gcggcggcag cgcagcgcgt gggatctcac gacccatccg    780
ttaacccacc gttcccagga gctccgaggc gcagcggcga cagaggttcg ccccggcctg    840
ctagcattgg cattgcggtt gactgagctt cgcctaacag gcttggggag ggtgggctgg    900
```

```
gctgggctgg gctgggctgg gtgctgcccg gctgtccgcc tttcgttttc ctgggaccga    960
ggagtcttcc gctccgtatc tgcctagagt ctgaatccga ctttctttcc tttgggcacg   1020
cgctcgccag tggagcactt cttgttctgg ccccgggctg atctgcacgc ggacttgagc   1080
aggtgccaag gtgccacgca gtcccctcac ggctttcggg gggtcttgga gtcgggtggg   1140
gagggagact taggtgtggt aacctgcgca ggtgccaaag ggcagaagga gcagccttgg   1200
attatagtca cggtctctcc ctctcttccc tgccattttt agggctttct ctacgtgctg   1260
ttgtctcact gggtttttgt cggagcccca cgccctccgg cctctgattc ctggaagaaa   1320
gggttggtcc cctcagcacc cccagcatcc cggaaaatgg ggagcaaggc tctgccagcg   1380
cccatcccgc tccacccgtc gctgcagctc accaattact ccttcctgca ggccgtgaac   1440
accttcccgg ccacggtgga ccacctgcag ggcctgtacg gtctcagcgc ggtacagacc   1500
atgcacatga accactggac gctggggtat cccaatgtgc acgagatcac ccgctccacc   1560
atcacggaga tggcggcggc gcagggcctc gtggacgcgc gcttcccctt cccggccctg   1620
ccttttacca cccacctatt ccaccccaag caggggggcca ttgcccacgt cctcccagcc   1680
ctgcacaagg accggccccg ttttgacttt gccaatttgg cggtggctgc cacgcaagag   1740
gatccgccta agatgggaga cctgagcaag ctgagcccag gactgggtag ccccatctcg   1800
ggcctcagta aattgactcc ggacagaaag ccctctcgag gaaggttgcc ctccaaaacg   1860
aaaaaagagt ttatctgcaa gttttgcggc agacacttta ccaaatccta caatttgctc   1920
atccatgaga ggacccacac ggacgagagg ccgtacacgt gtgacatctg ccacaaggcc   1980
ttccggaggc aagatcacct                                                2000

<210> SEQ ID NO 113
<211> LENGTH: 2000
<212> TYPE: DNA
<213> ORGANISM: Homo sapiens

<400> SEQUENCE: 113

cactcccccg ccgcctccgc ccctaaccct cggccccgtg cgcgagcgag cgagggagcg     60
aacgcagcgc aacaaaacaa actagtgccg gcttcctgtt gtgcaactcg ctcctgagtg    120
agtcgggggc cgaaagggtg ctgcggctgg gaagcccggg cgccggggac ctgcgcgcgc    180
tgcccggcct ggccggagcc tgtagcccgg gggcgccacg gccgggctcg cagtcccccc    240
acgccggccc cccggtcccc gccgagccag tgtcctcacc ctgtggtttc ctttcgcttc    300
tcgcctccca aacacctcca gcaagtcgga gggcgcgaac gcggagccag aaacccttcc    360
ccaaagtttc tcccgccagg tacctaattg aatcatccat aggatgacaa atcagccagg    420
gccaagattt ccagacactt gagtgacttc ccggtccccg aggtgacttg tcagctccag    480
tgagtaactt ggaactgtcg ctcggggcaa ggtgtgtgtc taggagagag ccggcggctc    540
actcacgctt tccagagagc gacccgggcc gacttcaaaa tacacacagg gtcatttata    600
gggactggag ccgcgcgcag gacaacgtct ccgagactga gacattttcc aaacagtgct    660
gacattttgt cgggccccat aaaaaatgta aacgcgaggt gacgaacccg gcggggaggg    720
ttcgtgtctg gctgtgtctg cgtcctggcg gcgtgggagg ttatagttcc agacctggcg    780
gctgcggatc gccgggccgg tacccgcgag gagtgtaggt accctcagcc cgaccacctc    840
ccgcaatcat ggggacaccg gcttggatga gacacaggcg tggaaaacag ccttcgtgaa    900
actccacaaa cacgtggaac ttgaaaagac aactacagcc ccgcgtgtgc gcgagagacc    960
```

```
tcacgtcacc ccatcagttc ccacttcgcc aaagtttccc ttcagtgggg actccagagt   1020

ggtgcgcccc atgcccgtgc gtcctgtaac gtgccctgat tgtgtacccc tctgcccgct   1080

ctacttgaaa tgaaaacaca aaaactgttc cgaattagcg caactttaaa gccccgttat   1140

ctgtcttcta cactgggcgc tcttaggcca ctgacagaaa catggtttga accctaattg   1200

ttgctatcag tctcagtcag cgcaggtctc tcagtgacct gtgacgccgg gagttgaggt   1260

gcgcgtatcc ttaaacccgc gcgaacgcca ccggctcagc gtagaaaact atttgtaatc   1320

cctagtttgc gtctctgagc tttaactccc ccacactctc aagcgcccgg tttctcctcg   1380

tctctcgcct gcgagcaaag ttcctatggc atccacttac caggtaaccg ggatttccac   1440

aacaaagccc ggcgtgcggg tcccttcccc cggccggcca gcgcgagtga cagcgggcgg   1500

ccggcgctgg cgaggagtaa cttggggctc cagcccttca gagcgctccg cgggctgtgc   1560

ctccttcgga aatgaaaacc cccatccaaa cggggggacg gagcgcggaa acccggccca   1620

agtgccgtgt gtgcgcgcgc gtctgcgagg gcagcggcgg caggggggagg aggaggcaga   1680

ggcggggtgg ctggaccctc ggcatcagct cattctcccc tgctacacac atacacacac   1740

aaataatgtt tctaaaaagt tcagttgcga ctttgtgcct cgcctgtcct gttcatcctc   1800

gtcctgggcc ggggaatgct tctgggggcc gaccccggga tgctggctaa ttgctgccgg   1860

cgggttccgt cgccggtgtg accctggacg gcgcggacgg cgtacagggg gtcccgggag   1920

gggcagtggc cgcggcactc gccgccggtg cccgtgcgcg ccgcgctctg ggctgcccgg   1980

gcggcgcagt gtggacgcgg                                               2000
```

<210> SEQ ID NO 114
<211> LENGTH: 800
<212> TYPE: DNA
<213> ORGANISM: Homo sapiens

<400> SEQUENCE: 114

```
ctgaaaagcc gtcagggaaa ccacacatgt tcaacccctg gcggctcccc caaacctctc     60

atttccagta actgtgtgtt tccgctcgtc aacagctgaa accgagcgga acttgggggg    120

ccccaccacg cggccctgct gtgcggcacg gggctcatct gtcccccggc tgcggggagt    180

cagctctcac cgcccacctc cttcccagat agtctctgtg cccactcgac ggcccggcaa    240

gcccagcccc tgcctgccac ggccacagca gcctcagaga gctgccctct ctggccaggg    300

tcagggcctg agctgctgcc tcccgcaggg tcgagggcag gacacttgtc tgaggcttgg    360

gtggggcaat ggcacctcct cagggcctca gcccccgggc aggctcggtg accatgggcc    420

tacagcaggg aaaattctgg gccaaaagct ccagcctcct actagggcat ctgtctgcaa    480

atgcacctta acctgaccgc ttgggctgtg ggggagcctg tttcagggaa agtgagggac    540

gcgccagttt cctcctttgg acttgatgag gcacgaacgc atctctaata aagccaggtc    600

tccccgccgt ggctccctgg gcgggtgcct gtggctcggg ccatgagtca cgctgggtaa    660

ccccactacg gggaagaggg caggaagctg ggagccaccg cctctgtgcc cggttgtcat    720

ctcggcacga gggcgaccgt cggcttcgtc ctgccctcat ggctgagggc ttttgggatg    780

tggcgggaga cgggggagtc                                                800
```

<210> SEQ ID NO 115
<211> LENGTH: 500
<212> TYPE: DNA
<213> ORGANISM: Homo sapiens

<400> SEQUENCE: 115

```
aaatcatcag aatggctaaa atgaaaaaga cagacaacag caagtgctga caagggtgtg     60

gggcggccaa atgctcctgc actgctggca ggggacctga gaactgcagg gcattccctg    120

gcttcctgcc cctcctggga ctggggaccc cccagggaca gcctaaggga actgcattta    180

tcttcacgtc tgccaaaaga taacacgaag atgttcaaag ctaagccccc aggctggtaa    240

gagctccaag gcaccagcag tgtgtgcaga actgggggga gtctgttctc ccagggatgc    300

tcccatcacc tgctgccagc agtggggcat gccggtcccc tggggtgtgg ccaaggggct    360

gtgtctcctg cccgggctgc cggcccctct caggttcact ttcccatctc taagcccacg    420

tctcgctgca gttcaagttt gccaggccac caacgggtga cacgcccggc gcagtggggg    480

actccgcact ttctgcgcac                                                500
```

```
<210> SEQ ID NO 116
<211> LENGTH: 1200
<212> TYPE: DNA
<213> ORGANISM: Homo sapiens

<400> SEQUENCE: 116

accctttgtg cctgggtccc ataaacaatg tgctttttaa aggggagccc cctcccagct     60

ccggcctttt tctccagcgt gggcagccaa tcagctgcgc agagctgcat agctggaccg    120

ctttccattc tgagtagcaa caacgtacta atttgatgca cacatggatg cctcgcgcac    180

tctgcaaatt catcacccgc atcttgcatt agtcatctga cggactgcca agtgtttcat    240

tttctttcca tgtgacttta ttattaccac ctctctcctc tcttccaaaa acctcccaaa    300

aagggcggtg gggcgggggg cggggcaggg agagggagag aaatccagca gacatctagc    360

tctgcctttc tttcccagcc acagccaggg tagggctgat aaggcgctga tgcgttgatg    420

gcagccttgc agagctagac ctgcacttaa cttgcagctg cctcccgagc ctccaagatg    480

tccacgccct gggtgacagg cggcagggcg ctgccccgtg ctcccccggc tctgctcgac    540

agcagcacgc agtgagagcc tcgccgccgc cgaggagcaa ctcatggtgc ctccgctttg    600

ttttagttca tcaaatttct acgactcatt aggcactttg ccactgctct tcttcctcct    660

ccttccgcct ccccgctccc ccaccccac tattttttct tcctgtccct catcgtgccg    720

ccctaactct ggctcccggt tccgtttttg acagtaacgg cacagccaac aagatgaacg    780

gagctttgga tcactcagac caaccagacc cagatgccat taagatgttt gtcggacaga    840

tcccccggtc atggtcggaa aaggagctga aagaactttt tgagccttac ggagccgtct    900

accagatcaa cgtcctccgg gaccggagtc agaaccctcc gcagagtaaa ggtacagagc    960

gcggggcggg ggtcgccagg cgtccaggtg ggcgtcgcgg ggcactgggg ctgtccgagc   1020

ccccagcctg caggaggaag ggcgggtagg caggagggct ggaagcagcc ggtgctggcg   1080

gcccctgtgc tccaggggct gctcccgact cctccccgca cccccgcccg cctgcccgcc   1140

gggacaggtt ggaggcggga gagagggacc gaggcagggc gggagcgcag aggctcggtc   1200
```

```
<210> SEQ ID NO 117
<211> LENGTH: 800
<212> TYPE: DNA
<213> ORGANISM: Homo sapiens

<400> SEQUENCE: 117

taacaaataa gccgcccgtg gtccgcgctg tgggtgaccc ttggcgcctt cgaggtctgg     60

agccctaggg taaataagga aacggggcgc ctctagagtt ttaaatgaac tctgttattg    120
```

```
gaagcttcag tagggaccct gaaaacaatt aacgtcttaa ttagcatttt aatgtctcca    180
ttattacggc gcgggctcta gctcagccct ttaccttacc ttctcaccgt taacagggga    240
gggggattgt atttttagtt catcttttta tgtttttgag ttgttatcct gtctgtctga    300
ttccagcctc gagggtttga tgatgcggcc cgagcctggc tgtggtcgcc tgtcggggct    360
ggagcgggac cctcagccgg gccgggcctg ggggctaacg ttttcacagt gcgccctgag    420
tttccttggg ttactgctgg gaccgcgcag gaggaagcaa agagtttttc gagctagacc    480
aacaggaaac acattgacgg aaatgttgcc atagcccatg ggtggcttt aactggccgc    540
ccccgcgggc tgggtgtgaa atcagaggag gccgcggctc ccccggccag gattggaggc    600
tcctcgcgca acctaatgcg ggtgtccggg cccgagcgct tcccgcgcag ccaggccttg    660
tcggtgcagc agccccgctc ctccccaaca cgcacacacc cggtgttcgc aagtgcggct    720
caccaaggga gatccaaggg ggcaaaaagt tatgtataaa tccgagagcc actggggaaa    780
gagggtcgtg gtattgtaag                                                 800
```

<210> SEQ ID NO 118
<211> LENGTH: 500
<212> TYPE: DNA
<213> ORGANISM: Homo sapiens

<400> SEQUENCE: 118

```
ctaccctgtg ctatcctgag ctgtagtctt ctgaaatgat cgtttggctt cccagccaag     60
gcagggctcc cccaaagttc attcccactc ttgcagtttc acctcgggat gcttccgcag    120
aatttcagcg cctaagcaga caaggtcaaa gtaaaccgct tcaccgctgc ttctggcgca    180
ggggcccaga gcgcgtgcag ctccccagca cagaccaaca gcaggagagg ggtccgggcg    240
ggagccctgg gctgtagata agcaaaacgc acccattttc tctcctattt actccagagg    300
cacctctcct cccccactcc tggcatctct ttatcactgg ctccctctcc ctgtggcata    360
tttttgggta gtagaatgct gaggtcacag ggagcggctc tttatccaag cagtggggac    420
atcagcctgg agccctgagc atgaaccagc aagatgcaga ctctcgctct tgactttggg    480
ctccaggagc tgccccgacc                                                 500
```

<210> SEQ ID NO 119
<211> LENGTH: 1100
<212> TYPE: DNA
<213> ORGANISM: Homo sapiens

<400> SEQUENCE: 119

```
cagtgctccg ctccgggaaa ttgcatcgtc acgacaaacg ggaccgtgat aaaacgaccc     60
tttccgtcct tatttgtaga tcactcagac gagattgaac tgcacttgtt tccccttcga    120
ggggagccgc gttttcaggg tagccgaagg cttggggctg aggggggggcc ctcaccaagg    180
cgcgggtggg ggccggagcc tcaactcgat gagaagtgac aggcgtttgg gggatctggg    240
ctccggccgg gaccagcgca agcagggact ttgcggggac accgcttctc caacagagca    300
aggcctggcc cacgtttccg gtttctccta acttcctttt attgccttcc tttgcttcgc    360
aagttccatc taccccctcca gctacagagc cccacctcta ggcacaggaa gcttcccgga    420
aaaagaaagg ctgtcccaga aagagaccga gagagacttt ccaaacttcg ggcatagcca    480
cggcaattcc cagtctgcta atgccaaggc gggcgcgtaa ggccgcctaa atctagacct    540
ccctcctcac tcatttcaaa aaataacaac gtgccagcca cctccgcaga taccgccggc    600
tggtgcttgc ccaggagacg ccagggccag agcgccactc ccagcatcga aatggcagag    660
```

```
agaaagcgca gctccaaatt ccccttcaga ggttaagcct caatcattgt gtcccttccc    720

tagggactgc tggcgctctc gcccactggc gatgattatg cgcctagaac tcgaccgcga    780

agcaactaat aggaaaacat atggtgtcaa tttggatgct ccgcgcctcg cgcacacccg    840

ggaacgagcg gcacaaagcc ctgccggccg gcccgcgacc ccgcgcccct cggggcctgc    900

cagccgggcc gcagcgacaa acgctcaggg ctgcgcgccc tggctggggc ccgcccgaga    960

gacagcctgc ggctggggag tctgagctcc aaggggagag cccagccgcc gaaggcgagc   1020

ctaccggcca agccctgggg tccggcaggt tctgcacaac tactcccgca aagctcgcca   1080

cctttgtgcc ctttcctcag                                               1100
```

<210> SEQ ID NO 120
<211> LENGTH: 500
<212> TYPE: DNA
<213> ORGANISM: Homo sapiens

<400> SEQUENCE: 120

```
gggccctcgc ggctcaagcg ccagcgctgg agagagagtc tgagggtacc acgggcgtgc     60

tggcctgggt gctcactccc gccctccttc atgagcggct ttcctctggg tgtgtccagg    120

gcatcacaga gctcttctgc ccaaacccgg aggcctacca gggcctgccc accttgcctc    180

cttccacact ctctgtagca gcagccgcag ccatggcggg gatgaagaca gcctccgggg    240

actacatcga ctcgtcatgg gagctgcggg tgtttgtggg agaggaggac ccagaggccg    300

agtcggtcac cctgcgggtc actggggagt cgcacatcgg cggggtgctc ctgaagattg    360

tggagcagat cagtgagtgt ccgctgcccg cttgctgaac tcggcaccat gggcggccgc    420

cacgggtgtc tctgggcact tccgggccat ccctgctgct cagctcccga taatggtgtc    480

acggtgactc aggcattagc                                                500
```

<210> SEQ ID NO 121
<211> LENGTH: 600
<212> TYPE: DNA
<213> ORGANISM: Homo sapiens

<400> SEQUENCE: 121

```
tgtttacgga atcgggatcg aggggccgat aagtagttta cacgccggcc agagcagagg     60

gctggaggtc ggagttgggg gctggaggaa cgggtggcgt tttaggatt cagtaacagg    120

atcacagctt tttcttgtgg tggaagctat tggaatttgg ggagggtagc acgaggggtc    180

ctgcagctcc gcgtgtgaaa aagcgtttag gtaggcgatg aaagtagttg atctgagcca    240

tggcaggcga gccccgaatt tttgctgctt ccccctgaaa gtgtttcttt aggaggagag    300

gacttgggcc acacaggacc cggtcctaag agagcgattc cgggaagcgg acagatcgaa    360

gagaccttct gggcgaagcg gcagggcagc ctcgcggggc tgggagtgga tctgaggtcc    420

cgacccaggc ggctcggagt gctccaggag ccacctgggt ctgcgggcgc agcgcggcgg    480

ggcgggagcg gtggcccgca ggggccgcgg cctgcgatga aggccggggg gcagcgctag    540

cagcgaggtg ccacagtggg ccgaggagtc tgggctgtgg cccagggtag gaccggctca    600
```

<210> SEQ ID NO 122
<211> LENGTH: 150
<212> TYPE: DNA
<213> ORGANISM: Homo sapiens

<400> SEQUENCE: 122

```
acctaaacca agctctccct ccctgccgtc tccttccctg gcctgggtct gaaggagagg     60

aggtgcccag aagttcagag cggcataacc acagagatac tacctaatta acataccaga    120

agcataaaga actcatttgc attggagagt                                     150
```

```
<210> SEQ ID NO 123
<211> LENGTH: 900
<212> TYPE: DNA
<213> ORGANISM: Homo sapiens

<400> SEQUENCE: 123

ataactacgg gggtgggggt ggggaaggaa gagatccaag gaggcagaag gctgcggtca     60

aaatattttg gggtggcaga gtcacgtagg atgtggctgt gggttctggc agcccagaga    120

ttcagctccc gcctcctccc tcagagcgag tccatagcta ccctcacgtc ccccgtggcg    180

gtcctcgcca cgctccggag cgggttaccc atgagggtgc tagacctggg cagcgggaac    240

ctcgaagagg tggagattgc aggctgggac tccagatttc gggcagggat gcggggaagg    300

gaagacgcct cgctggaggc ggaatggagg gcaaggcgaa ggaggatggt gcaggaaacg    360

gcgacaaggc gcccggccag gcccgcgagc taccgagacc cgggttccaa tcctcccccc    420

ttccgcaaac gcccgggttc gaggtacctg gcgggcaagg gccgcagcgg agcgaagcgg    480

gctggccatg ggaggctgc ggggacgcgg ggctgcagag agcggcagtg gcacggagcg    540

cgcggctgga agcgaaagca ggcggtgtgg ccaagccccg gcgcacggcc catagggcgc    600

tgggtaccac gacctggggc cgcgcgccag ggccaggcgc agggtacgac gcaacccctc    660

cagcatccct tggggaggag cctccaaccg tctcgtccca gtctgtctgc agtcgctaaa    720

accgaagcgg ttgtccctgt caccggggtc gcttgcggag gcccgagaat gcgcgccacg    780

aacgagcgcc tttccaagcg cagatatttc gcgagcatcc ttgtttatta aacaacctct    840

aggtgaatgg ccgggaagcg cccctcggtc aaggctaagg aaacctcgga gaaactacat    900
```

```
<210> SEQ ID NO 124
<211> LENGTH: 600
<212> TYPE: DNA
<213> ORGANISM: Homo sapiens

<400> SEQUENCE: 124

cagtccagcc gcttgcctca cttcttcccg cttgccttat ctccccgcag acgtggttcc     60

cctgcagccc gaggtgagca gctaccggcg cgggcgcaag aaacgcgtgc cctacactaa    120

ggtgcagctg aaggagctag agaaggaata cgcggctagc aagttcatca ccaaagagaa    180

gcgccggcgc atctccgcca ccacgaacct ctctgagcgc caggtaacca tctggttcca    240

gaaccggcgg gtcaaagaga agaaggtggt cagcaaatcg aaagcgcctc atctccactc    300

cacctgacca cccacccgct gcttgcccca tctatttatg tctccgcttt gtaccataac    360

cgaacccacg gaaagacgct gcgcgggtgc agaagagtat ttaatgttaa ggaaagagaa    420

gaaccgcgcc gcccggaggc agagaggctc catggccgtg ctgctgggcc atccccaact    480

ccctatccca tccccagcct ccacccccat ccagatggga ctcacgtggc ttcaacagct    540

ttggaaatgg gtcccgagtg ggccgtgcga ggaaggctgt cgacctctac tcctccttgc    600
```

```
<210> SEQ ID NO 125
<211> LENGTH: 1500
<212> TYPE: DNA
<213> ORGANISM: Homo sapiens

<400> SEQUENCE: 125
```

```
caagatcgac tttcttagga agggggagag gagggaactc ttcacgaagg gaggtgggag      60

tccacctcag acctctattg gaaggaaatc gagttgttcc gggggactga ggtctcttgc     120

ataaggcatg ggatccttat tattattatt attattttta aatcccccgc ggaggagctc     180

tgggcaaatg aataccgagg cgccgctcta gctggttagg cttgggatgc gataactcag     240

tgccctcttg cagacttgca tagaaataat tactgggttg tcgtggaggg gacacgagac     300

agagggagtt ctccgtaatg tgccttgcgg agagaaaggt ccaagaatgc aattcgtccc     360

agagtggccc ggcaggggcg gggtgcgagt gggtggtgga gtaggggtgg gagtggagag     420

aggtggtttc tgtagagaat aattattgta ccagggcccg ccgaggcacg aggcactcta     480

ttttgttttg taatcacgac gactattatt tttagtctga tcaatgggca caatttctaa     540

gcagcgcagt ggtggatgct cgcaaacttt tgcgcaccgc tggaaaccca ctaggttgag     600

ttgcaaaacg taccgcgtag acgcccctgg tggcgccgag agaagagcta ggcctgccca     660

gcacagagcc ggagagcgtc gggccttccg gaagggtaag ttctccgcca aggggtcccg     720

agggagctgg acgtctgaat ctggacttgc cccagcttc ggggttcgat tctgggtttt     780

gcgcgtcccc aacccccagg gctttccgaa gcatggcctg gctccaggcc cggtcctgta     840

aggactggaa cggcagcaaa atgtgcaggg aggcagtcgg ccggcagagc tgcggcggga     900

gccaaggtca ggcccgcggg gagagcgggc agcttccagc gccggccaca agctcccagg     960

ccagctgggc cgcagacccc tttgcttcca gagagcacaa cccgcgtcct ttctctcagc    1020

caggctgcag tggctgcccc gagcttcgct ttcgtttccc aagctgttaa taacgatatg    1080

tccccaaatc cgaggctcgt gtttgctccc agatgccaag aacgcaaccc gaaatccttc    1140

tcccaaaccc taggtcgacg agatgagttc ctacttgacc tctgagccga ggtgggccgg    1200

aaaccgaggc ctaggccccg ccggggctgc aaggaaaagg ggaaactccg agcgtagcgt    1260

cttttccttg tggttccttt ctccggcatc ccggactgcg ggccctgcag ccacctggac    1320

cggcattcaa aggattctgc aagtccagct tcacagactg gctttcccag acgctccgaa    1380

gcccgcacca cgaacagaat aaaggagaga cgagagatcg caactagatt tgagaatcct    1440

cgttcttttc cccaatcgtt cgggcagtaa actccggagc cggctacagc gcgcatcctc    1500
```

```
<210> SEQ ID NO 126
<211> LENGTH: 500
<212> TYPE: DNA
<213> ORGANISM: Homo sapiens

<400> SEQUENCE: 126

actgtcctcc tccctcaatt gcctattttt tgcccatagc tctaacttaa ccctgtgatc      60

accccagatc gctacttctg acccccatct cctctcccac accaacctcc agcgcgcgaa     120

gcagagaacg agaggaaagt ttgcggggtt cgaatcgaaa atgtcgacat cttgctaatg     180

gtctgcaaac ttccgccaat tatgactgac ctcccagact cggccccagg aggctcgtat     240

taggcaggga ggccgccgta attctgggat caaaagcggg aaggtgcgaa ctcctctttg     300

tctctgcgtg cccggcgcgc ccccctcccg gtgggtgata aacccactct ggcgccggcc     360

atgcgctggg tgattaattt gcgaacaaac aaaagcggcc tggtggccac tgcattcggg     420

ttaaacattg gccagcgtgt tccgaaggct tgtgctgggc ctggcctcca ggagaaccca     480

cgaggccagc gctccccgga                                                500

<210> SEQ ID NO 127
```

```
<211> LENGTH: 900
<212> TYPE: DNA
<213> ORGANISM: Homo sapiens

<400> SEQUENCE: 127

ctcagggaat cacatgtccg cctggcctgg cctggtacca aatgtttata gacaggacga     60

gggtcgctgg aatcgcctcg ctcctttcag cttggcgcta aggcgcgaat ctcgatcctc    120

ctagtatttc tctggcgtct gtctctatct cagtctctgc ttttgtctct ttctccctcc    180

ctccgcccca gtctttccgt ctctttttcc tcgaatgcac gtggaattcg gaattgaaaa    240

ttgaggtcag aatctccctt tttcttccag ttatccgcgc cgctgcccca cgcctagcgg    300

cttggatctg catagacatc tatctacccg caacaagatc cgagctgcag aagcaaacct    360

aatctgtctc cgcaccatcc cctgctctgt agacccactg ccccatccca cgccacatcc    420

ttgaggttca agtagcgact ccagcggatg attcggagaa tgccctgctt tccaaaggcc    480

ccaacccgtg tttttatttt ctttttcctt tgcccgcttg accaactttg gtttctttca    540

gggcccggag gtgcctgcgc cgcgcttggc tttgctttcc gccgccccag gagacccggg    600

actgtggttt ccgctcgcca catcccagcc tggtgcgcac acaagagcct ggcgagcttc    660

cctcgcgcgc ttacagtcaa ctactttggg cctcggtttc cctgctcctt gtagatcaga    720

gaagggacgg gcgaaatgcc tgcgagggag ggttggcgaa tgggttggtt ggtggcaaga    780

ctgcagttct tgtacatgga cgggggttgg ggggtcaaca ctggaagaac tcctgcctga    840

cgccaagagc cacccgcttt ccagctcgtc ccactccgcg gatgtttacc caccttcatg    900

<210> SEQ ID NO 128
<211> LENGTH: 500
<212> TYPE: DNA
<213> ORGANISM: Homo sapiens

<400> SEQUENCE: 128

tttggggcac ccaacccttc ccaagcctcg gttttcccga tcttgtggga tccttgcggc     60

gcgaatgggg ttggaagcac cttggaagct acagagtacc gggtcgggac aatttccggc    120

actgccccag ttcagtggtt tatagaaaat ttctttctct ctctcaggtc cactaagacc    180

gagagagaga gagaagtcga ctctggcaca cccgggcgag gggctgccgg gattcgggag    240

ctggcgcggt tgattttttc cgagaatcct ccacttgggg tgacgtcggg cagcgcgcgc    300

gggccgtgag gttaatgccc aggcttttct ctaaagcgtc cgggaatgat ccggcgaata    360

aaacgggtgt ctgcaaagtt aatgaattgt acaaggaggc tgagggtggg gacttcgacc    420

cggggagcca gaggcggttc tggtggacgc ttccccgtgc gcctaggggt gcgctgggct    480

ttcccagccg aggtctgcag                                                500

<210> SEQ ID NO 129
<211> LENGTH: 2000
<212> TYPE: DNA
<213> ORGANISM: Homo sapiens

<400> SEQUENCE: 129

ccagacagtt aaggtaaaac gttgaagtca agaggaagta gtgagtctgt tgccaactgg     60

atagggttgg tcctgtccca tctaaatgta ttagaattaa gtggctttta aaaatgagct    120

ggtcatcttc agcccacggg ctggccaatt tggaacttaa tgggcctttg cgtcctcctt    180

ccctgagcct ccttttattc cagacttctc agtgtgagtc tgtgcgtccc tccgacgatc    240

tcagggagtg gggtgccttc atctgcctgt tccctgttcc tcaggctgac gctcccgctg    300
```

```
tcctccccgc ctcccctcac tccttttctc cctcccttcc tccttgtggg gaggctcttg    360

gccagggtcc ctgagcccgg gcgggtgctg gcagaggacg cagaaggggt gaggtcacgt    420

ctcccttgag ccccgagccg ctggcttttc agagcctcgc cacaagccgg cggccagagc    480

cccagaccac acagaccgtg cgctcctccg ccctcccggc gccgccggcc tcgcccatgt    540

ctcagtacgc ccctagcccg gacttcaaga gggctttgga cagcagtccc gaggccaaca    600

ctgaagatga caagaccgag gaggacgtgc ccatgcccaa gaactacctg tggctcacca    660

tcgtctcgtg tttttgccct gcgtacccca tcaacatcgt ggctttggtc ttttccatca    720

tggtgagtga atcacggcca gaggcagcct gggaggagag acccgggcgg ctttgagccc    780

ctgcagggga gtccgcgcgc tctctgcggc tcccttcctc acggcccggc ccgcgctagg    840

tgttctttgt cctcgcacct cctcctcacc tttctcgggc tctcagagct ctccccgcaa    900

tcatcagcac ctcctctgca ctcctcgtgg tactcagagc cctgatcaag cttcccccag    960

gctagctttc ctcttctttc cagctcccag ggtgcgtttc ctctccaacc cggggaagtt   1020

cttccgtgga ctttgctgac tcctctgacc ttcctaggca cttgcccggg gcttctcaac   1080

cctcttttct agagccccag tgcgcgccac cctagcgagc gcagtaagct catacccccga   1140

gcatgcaggc tctacgttcc tttccctgcc gctccggggg ctcctgctct ccagcgccca   1200

ggactgtctc tatctcagcc tgtgctccct tctctctttg ctgcgcccaa gggcaccgct   1260

tccgccactc tccggggggt ccccaggcga ttcctgatgc cccctccttg atcccgtttc   1320

cgcgctttgg cacggcacgc tctgtccagg caacagtttc ctctcgcttc ttcctacacc   1380

caacttcctc tccttgcctc cctccggcgc cccctttttta acgcgcccga ggctggctca   1440

cacccactac ctctttaggc ctttcttagg ctccccgtgt gcccccctca ccagcaaagt   1500

gggtgcgcct ctcttactct ttctacccag cgcgtcgtag ttcctccccg tttgctgcgc   1560

actggcccta acctctcttc tcttggtgtc ccccagagct cccaggcgcc cctccaccgc   1620

tctgtcctgc gcccggggct ctcccgggaa tgaactaggg gattccacgc aacgtgcggc   1680

tccgcccgcc ctctgcgctc agacctcccg agctgcccgc ctctctagga gtggccgctg   1740

gggcctctag tccgcccttc cggagctcag ctccctagcc ctcttcaacc ctggtaggaa   1800

cacccgagcg aaccccacca ggagggcgac gagcgcctgc taggccctcg ccttattgac   1860

tgcagcagct ggcccggggg tggcggcggg gtgaggttcg taccggcact gtcccgggac   1920

aacccttgca gttgcgctcc ctcccccacc ggctcacctc gcctgcagct gggccacgga   1980

actccccggc cacagacgca                                                2000
```

<210> SEQ ID NO 130
<211> LENGTH: 600
<212> TYPE: DNA
<213> ORGANISM: Homo sapiens

<400> SEQUENCE: 130

```
ctctctgggc cttaggaaaa tggaaatgac acctgtacct gcccttccag gactgacagg     60

aggggctgct ccatgaaacc tcactgctgc ggtcataatg tcattatctt ttgccttaaa    120

gggatttctt ctgcaccagc acctaaagtg gcagcccctt acccttggcc atcagctgga    180

ccctggtgct ctcctggagc ccaaaacctc tgttttgtgt tgcatcctgc tgaccagcca    240

cagtccacac ccatctgagt gtctgagcag aacagcccag aggccacacc aggatggctt    300

tccaccggtc accttccccc acccactcat aaaccctgcg tctctggggg agagggtggc    360
```

```
gaggtcccct ccccacatag atggaaacac tgaggcctga ttcatggtgc cccctgtgaa    420

gcgcctcatg gccagcaccg gggggcagca ggccagggcg gggacacata cccggttctc    480

gtcgtagatg atctgcacca ggctgcggtg cttcgactcg atgggcggcg gtgacacggg    540

cttctcaggc tcgggcggct tggcagcctc ctcctccagc tgttgctgtg gggagaggca    600
```

<210> SEQ ID NO 131
<211> LENGTH: 400
<212> TYPE: DNA
<213> ORGANISM: Homo sapiens

<400> SEQUENCE: 131

```
cttgaaaact cccagccccc tttgtccaga tggggatgga ggtggccagg ctgccccgtt     60

gattgtgtgc cgaggagccc tccccgggaa ggctgtgatt tatacgcgca ggcttgtcac    120

ggggtgaaag gaagggccac tttttcattt tgatccaatg ttaggtttga aagccaccca    180

ctgctgtaaa ctcagctgga tccgcgggcc gtgattaaac acattgcccg ctttgttgcc    240

gagatggtgt ttcggaaggc gctgtgaatg cacttccctt tgcggggctc acacagacaa    300

gatgtgtgtt gcaaggatga ggcgcctgct cggcctccag cccagggccg ggaagggaga    360

aggtgctgtg cgtcgctgcc tgtgtcgccc gcggctctcc                          400
```

<210> SEQ ID NO 132
<211> LENGTH: 1200
<212> TYPE: DNA
<213> ORGANISM: Homo sapiens

<400> SEQUENCE: 132

```
cgcgtcaggg ccgagctctt cactggcctg ctccgcgctc ttcaatgcca gcgccaggcg     60

ctcaccctgc agagcgtccc gcctctcaaa gaggggtgtg acccgcgagt ttagatagga    120

ggttcctgcc gtggggaaca ccccgccgcc ctcggagctt tttctgtggc gcagcttctc    180

cgcccgagcc gcgcgcggag ctgccggggg ctccttagca cccgggcgcc ggggccctcg    240

cccttccgca gccttcactc cagccctctg ctcccgcacg ccatgaagtc gccgttctac    300

cgctgccaga acaccacctc tgtggaaaaa ggcaactcgg cggtgatggg cggggtgctc    360

ttcagcaccg gcctcctggg caacctgctg gccctggggc tgctggcgcg ctcggggctg    420

gggtggtgct cgcggcgtcc actgcgcccg ctgccctcgg tcttctacat gctggtgtgt    480

ggcctgacgg tcaccgactt gctgggcaag tgcctcctaa gcccggtggt gctggctgcc    540

tacgctcaga accggagtct gcgggtgctt gcgcccgcat tggacaactc gttgtgccaa    600

gccttcgcct tcttcatgtc cttctttggg ctctcctcga cactgcaact cctggccatg    660

gcactggagt gctggctctc cctagggcac cctttcttct accgacggca catcaccctg    720

cgcctgggcg cactggtggc cccggtggtg agcgccttct ccctggcttt ctgcgcgcta    780

cctttcatgg gcttcgggaa gttcgtgcag tactgccccg gcacctggtg ctttatccag    840

atggtccacg aggagggctc gctgtcggtg ctggggtact ctgtgctcta ctccagcctc    900

atggcgctgc tggtcctcgc caccgtgctg tgcaacctcg gcgccatgcg caacctctat    960

gcgatgcacc ggcggctgca gcggcacccg cgctcctgca ccagggactg tgccgagccg   1020

cgcgcggacg ggagggaagc gtcccctcag cccctggagg agctggatca cctcctgctg   1080

ctggcgctga tgaccgtgct cttcactatg tgttctctgc ccgtaattgt gagtccccgg   1140

gccccgaggc agcagggcac tgagactgtc cggccgcgga tgcggggcgg gaagggtgga   1200
```

```
<210> SEQ ID NO 133
<211> LENGTH: 2000
<212> TYPE: DNA
<213> ORGANISM: Homo sapiens

<400> SEQUENCE: 133

cttccgccgc ggtatctgcg tgccctttc tgggcgagcc ctgggagatc cagggagaac      60

tgggcgctcc agatggtgta tgtctgtacc ttcacagcaa ggcttccctt ggatttgagg     120

cttcctattt tgtctgggat cggggtttct ccttgtccca gtggcagccc cgcgttgcgg     180

gttccgggcg ctgcgcggag cccaaggctg catggcagtg tgcagcgccc gccagtcggg     240

ctggtgggtt gtgcactccg tcggcagctg cagaaaggtg ggagtgcagg tcttgccttt     300

cctcaccggg cggttggctt ccagcaccga ggctgaccta tcgtggcaag tttgcggccc     360

ccgcagatcc ccagtggaga aagagggctc ttccgatgcg atcgagtgtg cgcctccccg     420

caaagcaatg cagaccctaa atcactcaag gcctggagct ccagtctcaa aggtggcaga     480

aaaggccaga cctaactcga gcacctactg ccttctgctt gccccgcaga gccttcaggg     540

actgactggg acgcccctgg tggcgggcag tcccatccgc catgagaacg ccgtgcaggg     600

cagcgcagtg gaggtgcaga cgtaccagcc gccgtggaag gcgctcagcg agtttgccct     660

ccagagcgac ctggaccaac ccgccttcca acagctggtg aggccctgcc ctacccgccc     720

cgacctcggg actctgcggg ttggggattt agccacttag cctggcagag aggggagggg     780

gtggccttgg gctgaggggc tgggtacagc cctaggcggt gggggagggg gaacagtggc     840

gggctctgaa acctcacctc ggcccattac gcgccctaaa ccaggtctcc ctggattaaa     900

gtgctcacaa gagaggtcgc aggattaacc aacccgctcc cccgccctaa tcccccccctc     960

gtgcgcctgg ggacctggcc tccttctccg cagggcttgc tctcagctgg cggccggtcc    1020

ccaagggaca ctttccgact cggagcacgc ggccctggag caccagctcg cgtgcctctt    1080

cacctgcctc ttcccggtgt ttccgccgcc ccaggtctcc ttctccgagt ccggctccct    1140

aggcaactcc tccggcagcg acgtgacctc cctgtcctcg cagctcccgg acaccccccaa    1200

cagtatggtg ccgagtcccg tggagacgtg agggggaccc ctccctgcca gcccgcggac    1260

ctcgcatgct ccctgcatga gactcaccca tgctcaggcc attccagttc cgaaagctct    1320

ctcgccttcg taattattct attgttattt atgagagagt accgagagac acggtctgga    1380

cagcccaagg cgccaggatg caacctgctt tcaccagact gcagacccct gctccgagga    1440

ctcttagttt ttcaaaacca gaatctggga cttaccaggg ttagctctgc cctctcctct    1500

cctctctacg tggccgccgc tctgtctctc cacgccccac ctgtgtcccc atctcggccg    1560

gcccggagct cgcccacgcg gacccccgcc ctgccccagc tcagcgctcc ctggcggctt    1620

cgcccgggct cctagcgggg aaaaggaagg ggataactca gaggaacaga cactcaaact    1680

cccaaagcgc atgattgctg ggaaacagta gaaaccagac ttgccttgaa agtgtttaag    1740

ttattcgacg gaggacagag tatgtgagcc tttgccgaac aaacaaacgt aagttattgt    1800

tatttattgt gagaacagcc agttcatagt gggacttgta ttttgatctt aataaaaaat    1860

aataacccgg ggcgacgcca ctcctctgtg ctgttggcgc ggcgggaggg ccggcggagg    1920

ccagttcagg ggtcaggctg gcgtcggctg ccggggctcc gcgtgctgcg ggcggggcgg    1980

gcccggtggg gattgggcgc                                                2000


<210> SEQ ID NO 134
<211> LENGTH: 1000
<212> TYPE: DNA
```

<213> ORGANISM: Homo sapiens

<400> SEQUENCE: 134
agtttgggga gccttttctc catttgagaa aaaacaaact tacagcgagg ggtgaggggt 60
tagggtttgg gattggggaa aatgtgggtg gggagccccc ccaaggaagt gaggaggggg 120
ctgcaaggat tacacctggg catacgtttc cctagaaatc acattcattg tatttttata 180
atttattcta aatctttcat gcgaagaaag tcagtagtga gtgttagtac tggtggccct 240
cctgatcaca cttgcatctc ttgagtgtgc cttaaaggtc ttgggaatgg aaaatataaa 300
aactgcttcg tgatgcgtca tctttatccc ccactccccc acccattcca atatattttc 360
tacttccagc ctaaattcgg ggccccctac cgaggccggc catgatcttg agggcggcat 420
aggggaggcc gcgctctgtc caccccagcc tggtgatgcc gttcgcttct tgtgcccggt 480
attgtgggct acatgccttt ccggcgtacg gagctgagcg tccaggccag tgcccctcaa 540
cctctcagta atgtttaccc gaggccgtcg tgcaatgaga ctattcgcat ggcattgtca 600
acgcggcggc gcgcgcgtct cggccctccg cggcttgcca gactgtcctg caaaccacct 660
cacccgtctc tttggcgcag gagactcagg ctgtaaccgg agaaaacact tcaccctgga 720
accctaactc aggtcctggc aaaagatgcg agaggaagac ttgctctctt aataaatctc 780
ggccgcccgc acatctggcc cctagacctg ctcggtagag gactggctgg tggatgcgcg 840
gtccaggccg tgggcactcg acccacctct attttccttc ccgaggcgcc cctggattac 900
cactttcggt ttgcgcttac atccgggatg tcgaatttcc cagggaatca taattatttt 960
atctataatt tattctaacc ccaaggttcc aagaaaatct 1000

<210> SEQ ID NO 135
<211> LENGTH: 1100
<212> TYPE: DNA
<213> ORGANISM: Homo sapiens

<400> SEQUENCE: 135
acattccttc taaaatgtgg gctttctgtg tacatgggcg cgcattccca ggactcggtt 60
ccctgggtgg aattcaccca ggaatacaat cgattttctg aacctgcgta aggccacagg 120
cagctctgaa aatgaaagcg tttgctaagt gggggagatc tcaccgatcg aacgtttaaa 180
aatggctttg tcttcattca gctctcccga tttattctgt gttttacaaa tagaagctca 240
gagcttctgt cgcccagtcc ttgcatgact catggcggtg gccacacggg tttcagggat 300
aacgggatgt ttagaaaatc gctgcatatc ggagtttcct agcacgttcc atttatactg 360
aacgcaggcg gccgctgaaa atccagcctc gactcttgct aatgactggg taggaccctc 420
ggggtcctgc gacggtgctg gagggtgttc ccggctccga tgtggggagg cctgcgcggg 480
gactaggttc tcgagaggcg agcgggcgcg ccagagaacc cgagactgct gcggggccgg 540
atgcgggatc cctgggctgc ggttctacgc agaaacgcca atggccatgc ctccccagct 600
cctcccagcc ccagtcacta ggccggcgcc tggcccggag atcctcccag agccctggcg 660
gtgccatcat gccggagaag acaagctcgg ccccgctgga attcgctcca aacacagatg 720
ctcatttttg gaatattcta gaaaaataac aagatcttgt ttgtcgttat gattcacggg 780
aggtaactga tgggagggcc atttacatga gggcagacac tgtggggcga aggtgacttc 840
tggacgtagg ctttaaagta ggaacggctc caaattccca atatctccgg ccttaccggt 900
tgcaaatcgg acccctgcgg gaaaaccaga cacttctgtt tcgtggcttt cgggctgcct 960
ccagcccacg caggctcgtt tagtccccgt ggagtcagcc ccgagccttc ctagtcctgg 1020

```
aacaagggct ccaggtcgcg gccgcgggaa gccgccaaga gggcggggag tagggattcc   1080

ctccagctcc gcagggcatc                                               1100
```

<210> SEQ ID NO 136
<211> LENGTH: 1500
<212> TYPE: DNA
<213> ORGANISM: Homo sapiens

<400> SEQUENCE: 136

```
tcctcctcgg cctcagatgt cgtcccacct gcccacgagc agggaacctg gaacccactc     60

tcccggcagt ccccagcggg ttccgccacc cggcggccgc ccctgacacc gagtgggtgg    120

gaggaagagg cagctggcgg ggatgggcca ttgagacctc ttgaaaaata ttaaaagaca    180

ggatgggtag agatttctcc gggagaaagt tcgagggtgc atcgggtcgc ggctgggagg    240

agtacccgaa atgccagcag gagaaatgca acctgtttag gccacacctt caatccccga    300

ggctgtctgg agagactgcg tgcgggggac ttgccggcgt tcccacaccg cgcctgcaat    360

ccactcccgc ggctgcctgg cctctgccac tcgcggcttg aagccagtgg ctctcaagcc    420

ctcggccccg cggcggcccg cgcagccttc acccggcgcc ggcaccacga agcctggccg    480

cagtggactc cccgcagctc gctgcgccct ggcgtctccc gtcgaggagg gagggacgga    540

ggcctgagcc gggagctccc tggcggtggt cgggccgccc cccttgaggc ctgctccccc    600

ctctcggcct cgccaaatcc ctgaaagccc agtccccctt cgtcaccccg ggggcttcta    660

atcactcggt atcgatttcc ctaactcttt tcatcctgtt gaagacacat cttaaaacac    720

tccagcccgg agtgtgctct gggctttatc cacactaata aaatgattta cccttctctc    780

cgcgctctcc tcacagagga aaatcgttcg agccccggct atttgtgtgt gatcagtaaa    840

tatttagtgc gctgacatcc ttagctgggc ttcggatcga ttcggggccc accgggaggt    900

gcgcacggtc cgggcggggc cgcgccgagc tcgccgaggg ggctcctccc gccctcgccg    960

ccggccgctg atttacggcc cctgcaacca gctaaggggg gcgaaagcgc gcctggaaaa   1020

ttggcttttc aacctttac ttttgacatt cagccacttc cccaggctct aattctcgcc   1080

cgcactcctc cctcccgccc tactaagggt tgccctgtgc gccctgcgag cccttccagc   1140

agcaacgcgc ggcgctcgcg ccccctcggc ccggggacca cctatcacag ccctgagccg   1200

cgacgcgggg aggccccggc ccctgctatg ggggtcgcct ccttcgagga gagatgctct   1260

ccgcccgccc acacctctga gggaggagag ggggtggaga agcccagagc tgcatctgct   1320

ggatgacgag ccgctctccc tgctaccctt tctccgaccc gtcggccttt ctcctactct   1380

ggagactgat cctcgacgtc catcgggccg gatggcgtcg ggtggaagcg ttactttcct   1440

cgcagaaaaa ctcctcctct ttcctaagat cagaaaaagc gcttagcttg gaattgttag   1500
```

<210> SEQ ID NO 137
<211> LENGTH: 600
<212> TYPE: DNA
<213> ORGANISM: Homo sapiens

<400> SEQUENCE: 137

```
cctaggcatt ctcagcccgt tttgctggag ggggcatttg aggcctggcc agcttagcca     60

gcctacaagg agtgttactg gggtgaaaac agccagcggg gaccagtctg cttgtggccc    120

gccaggtgcc tgggatgggg aagcagcaaa tgcccacctt cctgcccaac cccctcctcc    180

ctcttcatgg ggggaactgg gggtggcagc ggctgccggg tgcgagcggg ctcaggcctg    240
```

tggccctgcc tgacgttggt ccccatcaag ccatgtgacg agaccaggcc acaagaaaga 300
ggtttcaaca agcgttatcg tttcctggaa ctccaactcg gcgacttccc cgaagaccgg 360
ctgtgcctgg cgggcgggct gcgcacagcg gggacaaggc tgcccccttc ctcctccgct 420
gcctccgcgg ccgcgtctat ctcagtctga ctacctggaa gcagcactcc accctccagc 480
ccagcggccc tcggctcagc tgccaggtca ccggcaaccc cgggagcggt ggggcagggg 540
ctgctccgcc agcctctgtg atgttcaggc cgggctgcac cagcccggga cccctaggtg 600

<210> SEQ ID NO 138
<211> LENGTH: 700
<212> TYPE: DNA
<213> ORGANISM: Homo sapiens

<400> SEQUENCE: 138
gcactggttc ccctttacct gagccaacaa cctaccagga agtttccatc aagatgtcat 60
cagtgcccca ggaaacccct catgcaacca gtcatcctgc tgttcccata acagcaaact 120
ctctaggatc ccacaccgtg acaggtggaa ccataacaac gaactctcca gaaacctcca 180
gtaggaccag tggagcccct gttaccacgg cagctagctc tctggagacc tccagaggca 240
cctctggacc ccctcttacc atggcaactg tctctctgga gacttccaaa ggcacctctg 300 gacccccctgt taccatggca actgactctc tggagacctc cactgggacc actggacccc 360
ctgttaccat gacaactggc tctctggagc cctccagcgg ggccagtgga ccccaggtct 420
ctagcgtaaa actatctaca atgatgtctc caacgacctc caccaacgca agcactgtgc 480
ccttccggaa cccagatgag aactcacgag gcatgctgcc agtggctgtg cttgtggccc 540
tgctggcggt catagtcctc gtggctctgc tcctgctgtg gcgccggcgg cagaagcggc 600
ggactggggc cctcgtgctg agcagaggcg gcaagcgtaa cggggtggtg gacgcctggg 660
ctgggccagc ccaggtccct gaggaggggg ccgtgacagt 700

<210> SEQ ID NO 139
<211> LENGTH: 300
<212> TYPE: DNA
<213> ORGANISM: Homo sapiens

<400> SEQUENCE: 139
tgtccgacag gcacacagag cgccgccagg cacggccctc attcttcacc ccgagctccc 60
gcaaggtcgg cgaggaggct ggagcagcgg gtaggaagcg ggccgaggct cccccgacgc 120
tgggccgcaa ctgtcatcgc agatccctga aaaacgagct ctgtaatcgt tgccgtcagc 180
gggtgtacaa ttgcagcctt atgtttcctg ccgctgttta ccttcctgag cggcgcccag 240
agatgcacac acgctgccct gaagcgggac gtgacctctg ggcacctgtg aggtcctggg 300

<210> SEQ ID NO 140
<211> LENGTH: 500
<212> TYPE: DNA
<213> ORGANISM: Homo sapiens

<400> SEQUENCE: 140
gtcggctcct gcgctcccaa cggggtggcc gtttccttcc tcgcaccctc ttctctcccg 60
gtgcctgcgg tcccaccttc cagatacccc tcggagagtc cagctgagct ctcgccagag 120
ctttcccctt ccaacccgct cgacttgccc agatcccaag ctgggcttct ctctccatcg 180
ccccagaaag tgggtcttgg agaccgaggc aagaatttgg gcctccgctt ctgttccaga 240
ccccggaccc cttgccaaaa tgcggcagat gtgcagattg ggccgcgctt ggttcctggc 300

```
tgggtttatg gagcctgcgg ctgaggcagg ctccgcagac cccgagccag agtgggattt    360

aacggcggcc ggtgcgctgt gcttggtcaa ccccggtaac cgtcacgctg ctagtgatat    420

gaaaaaaacc tgccagcgtt ctgcttttct gccccgctgc agtctttagc acccgccagg    480

attctgtccg agtgtttgga                                                500
```

<210> SEQ ID NO 141
<211> LENGTH: 1000
<212> TYPE: DNA
<213> ORGANISM: Homo sapiens

<400> SEQUENCE: 141

```
tttagtgtgt gcataaaaca tcccagctaa tctcaaatag acttttcctg agcagaggct     60

gaaatttgca agtaatgcaa agaagactcc gggagagcgt cgccgatggt ggagcgggag    120

acgggcgtgg ggagccccac tgcagtgctg ggatcgaagt ggtgctgacc ccaagacctc    180

tcccctcctc ctcccccggg agcttctcca gggttatttg ggaaatgagg gggaactcca    240

atccctgaga aagcgctcag gggcttgctg aggtgagcgc aaatggaagc acaaggccgg    300

gctggccgtg ggctcagtaa ccagtcggct gcccggcttg cgccagcact aaatgctcga    360

tcagaaagag aaaaagaggc gcaataattc caaatttcag gaaaagtcaa atcggagagg    420

ggggacgcag gtctcttcag actgcccatt ctccgggcct cgctgaatgc gggggctcta    480

tccacagcgc gcggggccga gctcaggcag gctggggcga agatctgatt ctttccttcc    540

cgccgccaaa ccgaattaat cagtttcttc aacctgagtt actaagaaag aaaggtcctt    600

ccaaataaaa ctgaaaatca ctgcgaatga caatactata ctacaagttc gttttggggc    660

cggtgggtgg gatggaggag aaagggcacg gataatcccg gagggccgcg gagtgaggag    720

gactatggtc gcggtggaat ctctgttccg ctggcacatc cgcgcaggtg cggctctgag    780

tgctggctcg gggttacaga cctcggcatc cggctgcagg ggcagacaga gacctcctct    840

gctagggcgt gcggtaggca tcgtatggag cccagagact gccgagagca ctgcgcactc    900

accaagtgtt aggggtgccc gtgatagacc gccagggaag ggctggttc ggagggaatt     960

cccgctaccg ggaaggtcgg aactcggggt gatcaaacaa                         1000
```

<210> SEQ ID NO 142
<211> LENGTH: 500
<212> TYPE: DNA
<213> ORGANISM: Homo sapiens

<400> SEQUENCE: 142

```
catggtgctt caggaaggga ggggacgaga gccctgggct tgtggtgtcc acgtggacag     60

ctaatgagga gccttgccga tgaggagcat gcgttcccga cggggcggcc gaatgcggaa    120

ggagccgcca ttctctccgc cctgaccgcg ggattctctg cagcagatga gaaacggcgc    180

tgactcagca gggtccctcc caggccccga gcggtcatct ggtgaccccc gcgcttcccc    240

cacggcccag ccggagaagg gcaaagggaa gtcccggctc caaggcgcac ccagagatgc    300

ggtgcatgtg gcaggatggc ccagccccgt cggcagcccc agcttcctgc ccctggtttc    360

cttcctccca cgggctacag gcctctgatg agctttggaa agcaggaaac acacaggcta    420

gtaactatga atgggtccaa aaaacactcc ttattacttt aaactactta ggaagaagca    480

cagcgttgcc aaacgccaga                                                500
```

<210> SEQ ID NO 143

<211> LENGTH: 1200
<212> TYPE: DNA
<213> ORGANISM: Homo sapiens

<400> SEQUENCE: 143
gcgcgggggg ccggaggatg gcggcctggg ggccctgcgg gggctgtcgg tggccgccag 60
ctgcctggtg gtgctggaga acttgctggt gctggcggcc atcaccagcc acatgcggtc 120
gcgacgctgg gtctactatt gcctggtgaa catcacgctg agtgacctgc tcacgggcgc 180
ggcctacctg gccaacgtgc tgctgtcggg ggcccgcacc ttccgtctgg cgcccgccca 240
gtggttccta cgggagggcc tgctcttcac cgccctggcc gcctccacct tcagcctgct 300
cttcactgca ggggagcgct ttgccaccat ggtgcggccg gtggccgaga gcggggccac 360
caagaccagc cgcgtctacg gcttcatcgg cctctgctgg ctgctggccg cgctgctggg 420
gatgctgcct ttgctgggct ggaactgcct gtgcgccttt gaccgctgct ccagccttct 480
gcccctctac tccaagcgct acatcctctt ctgcctggtg atcttcgccg gcgtcctggc 540
caccatcatg ggcctctatg gggccatctt ccgcctggtg caggccagcg ggcagaaggc 600
cccacgccca gcggcccgcc gcaaggcccg ccgcctgctg aagacggtgc tgatgatcct 660
gctggccttc ctggtgtgct ggggcccact cttcgggctg ctgctggccg acgtctttgg 720
ctccaacctc tgggcccagg agtacctgcg gggcatggac tggatcctgg ccctggccgt 780
cctcaactcg gcggtcaacc ccatcatcta ctccttccgc agcagggagg tgtgcagagc 840
cgtgctcagc ttcctctgct gcgggtgtct ccggctgggc atgcgagggc ccggggactg 900
cctggcccgg gccgtcgagg ctcactccgg agcttccacc accgacagct ctctgaggcc 960
aagggacagc tttcgcggct cccgctcgct cagctttcgg atgcgggagc ccctgtccag 1020
catctccagc gtgcggagca tctgaagttg cagtcttgcg tgtggatggt gcagccaccg 1080
ggtgcgtgcc aggcaggccc tcctggggta caggaagctg tgtgcacgca gcctcgcctg 1140
tatggggagc agggaacggg acaggccccc atggtcttcc cggtggcctc tcggggcttc 1200

<210> SEQ ID NO 144
<211> LENGTH: 600
<212> TYPE: DNA
<213> ORGANISM: Homo sapiens

<400> SEQUENCE: 144
gggcgggttg ccacactgtc ccctttctgc atgggaggaa gggggctcga gaactgagtc 60
agccacacaa aacgaggatg gacagaactc ctgagtagcg agggtgcctg ccgggcgcga 120
ggaggagggg gaagacgagg aagacgagga ggaggaatag ggagcaccac atgacagagg 180
ggctgcctca gaccacaaag cgcttcctca tcctttcctc gccctttgat gccgccggca 240
acgtgactct gcgagcagcg gggcagacgc caggtctccc tcgcaggcgg gaaaggggct 300
ccaaggcggg tgctgccttg ctcgggtcac atggctacgt gggggccttg ctcaaattca 360
cttcctgcct tcattacaaa actgtcaaag gggatcgcac gtttgcaggg tgtcacccaa 420
gcattctggt tttgcaaacg acgctgtgcg gcaggcggtc tgatacctga tgagctcggt 480
gtggcggggt cggcagcatt tcctccgggg ttttgagctc tggccacttc tccttttgtt 540
ccacccaatc tcacccactt ctgggcttcg aggccagagt gtcttaacaa gggggcacgt 600

<210> SEQ ID NO 145
<211> LENGTH: 500
<212> TYPE: DNA
<213> ORGANISM: Homo sapiens

<400> SEQUENCE: 145

```
gagcgagact ttgtctcaaa aaaaaaaaaa accaaataaa ttgaaagctg agaaattcag      60
agcacaagaa gacaagcgcg ccccctcttt tagctgtcaa catggcggag ccgtccctgg     120
tgacgcagcc tccaaaggcc tccctgtgcc ctcctgagac cgcaagaggg aaagtggcag     180
cgacagtgat cgtggtgtct ttgtggcggt tgtgttgacc tcactgaccc ccgaagtgcc     240
gctctagggt ctgtcctcag cggtgacccg gccgggtcga agggcagagt tccgctgtca     300
ctagccctcc acccgtcctg tgtgctggga tgccctcgcg gcgccgtcca cgccaccgcc     360
gccccctctt gtgggttctg tctcctccgt gtctaggatc ctcctgcatc cgtttttcct     420
tcctcccttc tctccctccg tctgtcttgc ccgcacctga ggttgtcgca gaggcgctga     480
gacgggccag caggagctgt                                                 500
```

<210> SEQ ID NO 146
<211> LENGTH: 600
<212> TYPE: DNA
<213> ORGANISM: Homo sapiens

<400> SEQUENCE: 146

```
tgctgtcccg gtcctgtcgc agtcctcaaa gatgctagag tgacagtcct ctaggggtag      60
agatggtcgt cctcccagga gaaggtggcc cggagacttg gaggtgggat caatcctgcc     120
agtcctggat caggaggcct ctgtcgggcg ccgcccccct tcctcctcca tcagcaacag     180
gcggcgccgg ccagcctcat agtcagcctc atccacactg accagcaggc gaacagcctc     240
ccggcccaca gcctctcgca gggcctcagt caggaacacg ccccgcaggg cctgcagcag     300
ggcgccactc aggtagtcgc cccagaaggc gtccagatag gagagctctg agaacttgat     360
gtcacaaacc acagagccca ggtcccttga gcgcagcact gcggtggcct gcccaaacac     420
gtccagctgc cgcgccagcg cctggggccg ccgggatgcc acgccctgct ccaaggctgg     480
cccatgctcg cagtactctg ctcgaacccg gagccggatg tctgcagggg aaggagggat     540
ttgtcaggga gggggccaac actagacaca cttatgggga acgccaccct tcctccctcc     600
```

<210> SEQ ID NO 147
<211> LENGTH: 500
<212> TYPE: DNA
<213> ORGANISM: Homo sapiens

<400> SEQUENCE: 147

```
tgatgcccgg cccccagggg ggcagaggcg ccgccaccat gagcctgggc aagctctcgc      60
ctgtgggctg ggtgtccagt tcacagggaa agaggcggct gactgcagac atgatcagcc     120
acccactcgg ggacttccgc cacaccatgc atgtgggccg tggcggggat gtcttcgggg     180
acacgtcctt cctcagcaac cacggtggca gctccgggag cacccatcgc tcaccccgca     240
gcttcctggc caagaagctg cagctggtgc ggagggtggg ggcgcccccc cggaggatgg     300
catctccccc tgcaccctcc ccggctccac cggccatctc ccccatcatc aagaacgcca     360
tctccctgcc ccagctcaac caggccgcct acgacagcct cgtggttggc aagctcagct     420
tcgacagcag ccccaccagc tccacggacg gccactccag ctacggtgag ggcctgggcc     480
atcttggccc acttttcaga                                                 500
```

<210> SEQ ID NO 148
<211> LENGTH: 110
<212> TYPE: DNA

<213> ORGANISM: Homo sapiens

<400> SEQUENCE: 148

```
tttgggccac gaggcaagtt caaagcggga gacttttgtt ttataaaatg atggtgagca     60

gctccggttt tatgtcaaac atcagggttt cgtgcaggat ataaacattt               110
```

<210> SEQ ID NO 149
<211> LENGTH: 800
<212> TYPE: DNA
<213> ORGANISM: Homo sapiens

<400> SEQUENCE: 149

```
tgcctgagcg cagagcggct gctgctgctg tgatccagga ccagggcgca ccggctcagc     60

ctctcacttg tcagaggccg gggaagagaa gcaaagcgca acggtgtggt ccaagccggg    120

gcttctgctt cgcctctagg acatacacgg gaccccctaa cttcagtccc ccaaacgcgc    180

accctcgaag tcttgaactc cagccccgca catccacgcg cggcacaggc gcggcaggcg    240

gcaggtcccg gccgaaggcg atgcgcgcag gggtcgggc agctgggctc gggcggcggg    300

agtagggccc ggcagggagg cagggaggct gcagagtcag agtcgcgggc tgcgccctgg    360

gcagaggccg ccctcgctcc acgcaacacc tgctgctgcc accgcgccgc gatgagccgc    420

gtggtctcgc tgctgctggg cgccgcgctg ctctgcggcc acggagcctt ctgccgccgc    480

gtggtcagcg gtgagtcagg ggccgtctcc ccgaagaacg agcggggaga ggggaccacg    540

gggcgcggcg ggcagcctgt tctcgggcgg aggctctccg gggcgttgga aacctgcatg    600

gtgtaaggac ccgggaggag gcggggagaa attgattgtg ctgttctcct ccctctcttc    660

tctaacacac acgcagaaaa gtttaaattt ttgtgaagcg cttgcttacg tagctgcgga    720

gcgagcctct gcttcattac gagcggcata gcctttttca ggagtgattt ccactttctt    780

tgtgagagag ttgaccacac                                                800
```

<210> SEQ ID NO 150
<211> LENGTH: 600
<212> TYPE: DNA
<213> ORGANISM: Homo sapiens

<400> SEQUENCE: 150

```
ttcaatttac actcgcacac gcgggtacgt gggtgttcgg ggtagggcac tgatctgggg     60

aaggtctccc ccccgcgacc caactcatct ttgcacattt gcagtcctcc ctcggtgcac    120

tcctggcggg gatctggcca gtgcagcgca ctgggaccga gggcagagcc cgcggagtga    180

ggccaggaga gacttcaggc ctctaaggac acagctgagg ctaaggctga gttgaacgca    240

gcccctcccg cggctcgtcc cctctccagt gtctctcccg taaggtgccg ctcccaacag    300

caatgggtcg agatgtagag gaaacactct gtacgttatt tttccgccca ccctttagcg    360

cctgaggaga cagacagtgt agactttagg gtacaattgc ttcccctctg tcgcggcggg    420

gtggggagcg tgggaagggg acagccgcgc aaggggccag cctgctccag gtttgagcga    480

gagagggaga aggaggtcca cggagagaca agaatctccc tcctcccacg cccaaaagga    540

ataagctgcg gggcacaccg cccgcctcca gatcccccat tcacgttgag ccggggcgcg    600
```

<210> SEQ ID NO 151
<211> LENGTH: 1400
<212> TYPE: DNA
<213> ORGANISM: Homo sapiens

<400> SEQUENCE: 151

```
gcctgaagac catttcttcc tctcttaggg acctgctggt ctccagctga ttcggtccag     60

gaggaaaaac ctcccacttg ctcctctcgg gctccctgca aggagagagt agagacactc    120

ctgccaccca gttgcaagaa gtcgccactt ccccctccag ccgactgaaa gttcgggcga    180

cgtctgggcc gtcatttgaa ggcgtttcct ttctttaag aacaaaggtt ggagcccaag     240

ccttgcggcg cggtgcagga aagtacacgg cgtgtgttga gagaaaaaaa atacacacac    300

gcaatgaccc acgagaaagg gaaaggggaa aacaccaact acccgggcgc tgggcttttt    360

cgacttttcc tttaaaaaga aaaaagtttt tcaagctgta ggttccaaga acaggcagga    420

gggggagaa gggggggggg gttgcagaaa aggcgcctgg tcggttatga gtcacaagtg     480

agttataaaa gggtcgcacg ttcgcaggcg cgggcttcct gtgcgcggcc gagcccgggc    540

ccagcgccgc ctgcagcctc gggaagggag cggatagcgg agccccgagc cgcccgcaga    600

gcaagcgcgg ggaaccaagg agacgctcct ggcactgcag gtacgccgac ttcagtctcg    660

cgctcccgcc cgcctttcct ctcttgaacg tggcagggac gccgggggac ttcggtgcga    720

gggtcaccgc cgggttaact ggcgaggcaa ggcgggggca gcgcgcacgt ggccgtggag    780

cccggcctgg tcccgcgcgc gcctgcgggt gccccctggg gactcagtgg tgtcgcctcg    840

cccgggacca gagattgcgc tggatggatt cccgcgggca gaggcagggg gaaggagggg    900

tgttcgaaac ctaatacttg agcttctttg caaagtttcc ttggatggtt ggggacgtac    960

ctgtataatg gccctggacc agcttccctg ttggagtggc cagagaagtg tgtaaaacac   1020

actagagggg cagggtggaa aaagagactg ccttcaaaac ttgtatcttt tcgatttcat   1080

tttgaaaaat aactacaaat ctattttaat tttacaaagt tagactcata gcattttaga   1140

tatcaatgtc ttcatttaac agaagtgaag atggagcaaa cgctcaatca gcgtctgtat   1200

ttattcgctc ctgttgtgcc agggtgcgtt tttgccgagc ggttgccttt ctttactcac   1260

aaaacccccct tgatgtctgt cctccacgtt ttacgaggga gagccggatc ttttgaagtt  1320

tgtatcatct aaagcaggta tattgggatg actatggata gaatttaacc tgaaaacact   1380

gaagttgaca gctgacaaag                                               1400
```

```
<210> SEQ ID NO 152
<211> LENGTH: 250
<212> TYPE: DNA
<213> ORGANISM: Homo sapiens

<400> SEQUENCE: 152

tgcttcaacc ggaaatgtgg ttgaattacc cttacagtga acctgatcag tggtaacagg     60

agatgctaga acaggaaaag acaagtttcc cctttcctcc ctatcccatc aattactttg    120

aggtgtattt tttctttgca acccctccag agaagtcggc aatgtttaac gagcatgcct    180

gccaagtggc ttgccttata cctcattatg aagtgatact cagggccact aacacatcgc    240

acagcattgc                                                           250
```

```
<210> SEQ ID NO 153
<211> LENGTH: 500
<212> TYPE: DNA
<213> ORGANISM: Homo sapiens

<400> SEQUENCE: 153

tatgattccc tcgatttccc tcaatcttaa ccattgtgga tcacagcagg agggccagaa     60

agtgagcttc agcctggcac cgggacctca gcctctccct taaactttcc ctaatcctcg    120
```

gagctagtgt tactcaagtg actccacagt gttgcccgat cccttcagac atggccttga 180
tgatctccaa aactcatgct acctttgcca gcctaaagca tccactctgt gccccaaaac 240
gtgaatgtca aatacccttc aaggcagaag gctatttcta tttttgtttg tttctgttta 300
aggcaacaat caccaacatt tggtacacat gagccatcct gtgaaacatc aaggcgcttc 360
gttggcagca agtcaacttc ggtttcagaa gaaagctgca ctatttcctg aggttagagg 420
tttaaaccaa aacaagacaa ccacatttta accccaaatc tgccgactga gggtaaccat 480
gatccttcct tcacagcacc 500

<210> SEQ ID NO 154
<211> LENGTH: 150
<212> TYPE: DNA
<213> ORGANISM: Homo sapiens

<400> SEQUENCE: 154
tactaaatca acccaaaccc gagaacccgg tcatggagaa ataaatgata gtaatctatg 60
ctgttcatct gttccatcac tcactcactc tcttgctgaa caagaaaggg ccacccatgt 120
agcaaaccac atgtaaagag ccgggaagac 150

<210> SEQ ID NO 155
<211> LENGTH: 300
<212> TYPE: DNA
<213> ORGANISM: Homo sapiens

<400> SEQUENCE: 155
tattattttg ttcaaagtag acgggtatac taacatctgt gggcaagttt accacacgcc 60
acttaaaaca ggctaacagg gtcatatgcc aaaacgttca ggtttgcatt tttgaaaagc 120
tcagagatct gacagatgtg ttccggccgc gatttaacat gcggctccag tgagaaggaa 180
gcagatatga caaatggttc acttatttca gaactaaaac cccagaggag cagcctgagc 240
caaaaaggga agtgatcaat ggaaaagacg gtcgaatctg ctcacaggca aggcaagggg 300

<210> SEQ ID NO 156
<211> LENGTH: 400
<212> TYPE: DNA
<213> ORGANISM: Homo sapiens

<400> SEQUENCE: 156
gcaggggtga ctggtcctct ctctctgcac ctcgcaggat ttctctggaa gatctgagcc 60
cgagcgtcgt gctgcacatg accgagaagc tgggttacaa gaacagcgac gtgatcaaca 120
ctgtgctctc caaccgcgcc tgccacatcc tggccatcta cttcctctta aacaagaaac 180
tggagcgcta tttgtcaggg gtaagtgcga ccctagaggc gatcgtctct gctgtctgtg 240
gaaaaaagag ctcctacacc caaagtgctt ctcagttgct gacacttgat ccaagctgct 300
aatttaatct aatgtgaggc tgagttttct gaatgtggga taaagtcgta gctaaacctg 360
cttctcaggg agtgcctttt atctgcaatg tttttcaaat 400

<210> SEQ ID NO 157
<211> LENGTH: 10000
<212> TYPE: DNA
<213> ORGANISM: Homo sapiens

<400> SEQUENCE: 157
gtctttcccg ccccccttgtc taaactcaaa accgagtccg ggcgcgcctt gcagggcgcc 60
cgagctctgc agcggcgttg cgggctgaac ccatccggca caaactgcgg gccactggcc 120

```
cctcacacct gggagtttgc ggcgctggcc tgcagcccgg ggcccacgtg gcggaagctt    180
tcccgggcgc gcgctgcgca gccccgcggg gccggggaga caccgctcgg gagtcctccg    240
ctcggctgca gaatctttat cagctgcact ttaccgcagc cctggctagg acgctaggcg    300
gtggagcgcc ctatccaggt gcgccgccgc accatggatc accgcgcccg gtcccgcagt    360
cccgccatgg cctggggagg cccgaagccc ggggacagtg gccggcccat ctccggctcc    420
gcggaccccc ggctcaggcg ggagggcagg cgggtccctg caggccccca gggagcccgg    480
gagcctctct ctggcgtcat tcagtcccgg ggcaacctga agcgcggtag atattggaga    540
gggggcgtct gttgggggga cctggcgtca ttactgatgg ctagcaggga ggagggaacg    600
ggttgtcacc tcggcctcat aaggccgtga gtgagtagtc cagggcctct tcaggcattt    660
ttgaaactgg attaactagg ggggaaattg tagcactgaa gccaccgtga ctgtcttttg    720
cgctgtgtgg aaactccggt aaaactcttt gggcaacagt cttatcacca gctcttcaac    780
gtgtgcagcc cttctggtcc tgtccctgtt ctgggcccca ggaatgcaaa gcaggtccag    840
gcactgtgaa gaccctggcg gtggaggaag aggcttcccg gctgtggagg aagccagacc    900
cttacaacac aagacgagaa ccagacctgc gtgggggagc tctggatgct acaggggctc    960
aaggaggggt ggaggggcct tcccaggcca acccctgaac ggcttggaca agatgctcag   1020
atggacggga ggaacggcgt gtgggatggg ggagctggag gcgggtgggt gggggggga    1080
ggatggggaa agcgctggcc cacccagtgt gggaggggta gaggaaaagc ccgcaggggc   1140
caggttggga ccccgtaggc cgggttagag ggcttggact tgatcctgac aggcgacagg   1200
gagacatatt gctacttatt atgtgcacag tggccagatc tctaaagaaa acaccatccc   1260
ccaccccac ccccatata gtaaaccagg tggtccgccc agtgctccca gggaggtgat     1320
gggaaatccc actccatacc ctgcggtgag gggttccatg ccctccacgt gtgcaactac   1380
tccgggccca gggaaacact gggccccatc cggtaacccc cggcccagtc gggtttccca   1440
gttcacatta taaccaaacg gtcttgccag ctagacagac agacacccct gacctgttta   1500
ccctgatcct ctgctctcag gattaatcac aacttgtcga agggggtggc ttccagtggg   1560
gtggaccgct ctgtcaatgc cagcgtgtgt ctagcatctc ctggggtggg ggtgtgggga   1620
agggaggtgt aggatgaagc cctagaagcc tcaggcaatt gtgatccggt gggctggata   1680
ctgaagccca cccctgcctt gacctcaatt ttcagtatct tcatctgtaa aatgggaaca   1740
acctgccttc ctcctagccc taaaggggct gctgtcaaga ttggctgaga tagctgtttg   1800
caagctgagc tcaatgaaag ttcattgtgt ccccctcagt cctatcccaa tatcgtctca   1860
ctgcaaaggt ggggggcagc ttaacttcaa gggcacttca aggatagcca ggtggctgtc   1920
agcccagctt tccaggatgg gagcaggatc ttgacagaag ggttgactgg gaggggcagt   1980
tgctggtttg ggcttcgtta ggttgcattt ttgtttgttg tcctttcatt tccctggggc   2040
agcacccctt cctgcaagct ccaggccttc ctctggaatg ctcctagagc ccaacctctg   2100
ctggtgcctg agcttaagcc aggccagcta aggggatcct ggattcacac ggcctcacag   2160
tcactcagat tgttagcaga agacaaaaat tacaagggga gggcgtcatg tgattcttac   2220
acaccctcca aatccagcag acaccttgga agccacaggt agcttcaaga aacccatttt   2280
acggatgaga acctgagatg gagaaaggac aactggagat ctctgagtct ctgagcccac   2340
actccctacc tccctgcacc tccaggcact ctgctggcag gatcttgggc aaatgcccac   2400
agctctctga gagtcagttt tcctgtctgt aaaatgggag tcataccttc ctcctatggc   2460
```

```
cggtgagaga ctaaattaaa ctatgtctgt caagacacct gaaactcctg gcacaattta   2520
ggttgccttc aagtggtcac agttgtcatt aggtggaagt caacacccca atcattgtaa   2580
aggtgcccat ataccccaag atccagatta cagctctcac agtttattat atacagcgaa   2640
aaaacacata acacaccttt gcccacattt acatgtattt tacggaccat gtttcacatc   2700
agtccgcatg cacatctgca cgtgtgtgca ttcggcagta tttaccaagc acctgccaag   2760
tgccagggcc tgtcctccgc acccggcgtg aactgtcctg gaccagtccc gggagccgcg   2820
gttctgacca gccgtgctga ccctggacga ctccatgagc tgttttgtga gaaagacacg   2880
ccatttgttt gcagagttct gacttctgag ggtcatgta  gcacatgttt ggtagccaaa   2940
cgctgtcatt cacgaccagg agcgatggct gcaatgcctt tttctttgct ttgctttccg   3000
gtgccgggag ccttgcctcc cgccgccacc cctggtcagc tctgcgcaag aacgtcgttc   3060
tgtttggcag ccaggccgag acgcagcctg aatgtgagca ggaactcgga gaagggaagg   3120
gagagaatca gaaagaaggc ccgggaggga cccgggaagc agtgggaggt ctgcgccctg   3180
gagccccgcg agagcccgcc ggtttggcac gggctcctcc cgggccgccc ggcggtccaa   3240
caaaggccgg ccccgacacg cacccggtct tttgtgggag agaaacacaa agaagaggga   3300
aaaacacgga ggaggccaac agcaccagga cgcgggggcc aaccaggaac tcccggagcc   3360
ggggcccatt agcctctgca aatgagcact ccattcccca ggaaggggcc ccagctgcgc   3420
gcgctggtgg gaaccgcagt gcctgggacc cgcccaggtc gcccaccccg ggcgccgggc   3480
gcaggacccg gacaagtcct ggggacgcct ccaggacgca ccagggcaag cttgggcacc   3540
gggatctaat ttctagttat tcctgggacg gggtggggag gcataggaga cacaccgaga   3600
ggtactcagc atccgattgg caccagggcc aagggagccc aggggcgaca cagacctccc   3660
cgacctccca agctactccg gcgacgggag gatgttgagg gaagcctgcc aggtgaagaa   3720
ggggccagca gcagcacaga gcttccgact ttgccttcca ggctctagac tcgcgccatg   3780
ccaagacggg cccctcgact ttcacccctg actcccaact ccagccactg gaccgagcgc   3840
gcaaagaacc tgagaccgct tgctctcacc gccgcaagtc ggtcgcagga cagacaccag   3900
tgggcagcaa caaaaaaaga aaccgggttc cgggacacgt gccggcggct ggactaacct   3960
cagcggctgc aaccaaggag cgcgcacgtt gcgcctgctg gtgtttatta gctacactgg   4020
caggcgcaca actccgcgcc ccgactggtg gccccacagc gcgcaccaca catggcctcg   4080
ctgctgttgg cggggtaggc ccgaaggagg catctacaaa tgcccgagcc ctttctgatc   4140
cccacccccc cgctccctgc gtcgtccgag tgacagattc tactaattga acggttatgg   4200
gtcatccttg taaccgttgg acgacataac accacgcttc agttcttcat gttttaaata   4260
catatttaac ggatggctgc agagccagct gggaaacacg cggattgaaa aataatgctc   4320
cagaaggcac gagactgggg cgaaggcgag agcgggctgg gcttctagcg gagaccgcag   4380
agggagacat atctcagaac taggggcaat aacgtgggtt tctctttgta tttgtttatt   4440
ttgtaacttt gctacttgaa gaccaattat ttactatgct aatttgtttg cttgttttta   4500
aaaccgtact tgcacagtaa aagttcccca acaacggaag taacccgacg ttcctcacac   4560
tccctaggag actgtgtgcg tgtgtgcccg cgcgtgcgct cacagtgtca agtgctagca   4620
tccgagatct gcagaaacaa atgtctgaat tcgaaatgta tgggtgtgag aaattcagct   4680
cggggaagag attagggact gggggagaca ggtggctgcc tgtactataa ggaaccgcca   4740
acgccagcat ctgtagtcca agcagggctg ctctgtaaag gcttagcaat tttttctgta   4800
ggcttgctgc acacggtctc tggcttttcc catctgtaaa atgggtgaat gcatccgtac   4860
```

```
ctcagctacc tccgtgaggt gcttctccag ttcgggctta attcctcatc gtcaagagtt   4920
ttcaggtttc agagccagcc tgcaatcggt aaaacatgtc ccaacgcggt cgcgagtggt   4980
tccatctcgc tgtctggccc acagcgtgga gaagccttgc ccaggcctga aacttctctt   5040
tgcagttcca gaaagcaggc gactgggacg gaaggctctt tgctaacctt ttacagcgga   5100
gccctgcttg gactacagat gccagcgttg cccctgcccc aaggcgtgtg gtgatcacaa   5160
agacgacact gaaaatactt actatcatcc ggctcccctg ctaataaatg gaggggtgtt   5220
taactacagg cacgaccctg cccttgtgct agcgcggtta ccgtgcggaa ataactcgtc   5280
cctgtaccca caccatcctc aacctaaagg agagttgtga attctttcaa aacactcttc   5340
tggagtccgt cccctccctc cttgcccgcc ctctacccct caagtccctg cccccagctg   5400
ggggcgctac cggctgccgt cggagctgca gccacggcca tctcctagac gcgcgagtag   5460
agcaccaaga tagtggggac tttgtgcctg ggcatcgttt acatttgggg cgccaaatgc   5520
ccacgtgttg atgaaaccag tgagatggga acaggcggcg ggaaaccaga cagaggaaga   5580
gctagggagg agaccccagc cccggatcct gggtcgccag ggttttccgc gcgcatccca   5640
aaaggtgcgg ctgcgtgggg catcaggtta gtttgttaga ctctgcagag tctccaaacc   5700
atcccatccc ccaacctgac tctgtggtgg ccgtattttt tacagaaatt tgaccacgtt   5760
ccctttctcc cttggtccca agcgcgctca gccctccctc catcccccttt gagccgccct   5820
tctcctcccc ctcgcctcct cgggtccctc ctccagtccc tccccaagaa tctcccggcc   5880
acgggcgccc attggttgtg cgcagggagg aggcgtgtgc ccggcctggc gagtttcatt   5940
gagcggaatt agcccggatg acatcagctt cccagccccc cggcgggccc agctcattgg   6000
cgaggcagcc cctccaggac acgcacattg ttccccgccc ccgcccccgc caccgctgcc   6060
gccgtcgccg ctgccaccgg gctataaaaa ccggccgagc ccctaaaggt gcggatgctt   6120
attatagatc gacgcgacac cagcgcccgg tgccaggttc tcccctgagg cttttcggag   6180
cgagctcctc aaatcgcatc cagagtaagt gtccccgccc cacagcagcc gcagcctaga   6240
tcccagggac agactctcct caactcggct gtgacccaga atgctccgat acagggggtc   6300
tggatcccta ctctgcgggc catttctcca gagcgacttt gctcttctgt cctccccaca   6360
ctcaccgctg catctccctc accaaaagcg agaagtcgga gcgacaacag ctctttctgc   6420
ccaagcccca gtcagctggt gagctccccg tggtctccag atgcagcaca tggactctgg   6480
gccccgcgcc ggctctgggt gcatgtgcgt gtgcgtgtgt ttgctgcgtg gtgtcgatgg   6540
agataaggtg gatccgtttg aggaaccaaa tcattagttc tctatctaga tctccattct   6600
ccccaaagaa aggccctcac ttcccactcg tttattccag cccgggggct cagttttccc   6660
acacctaact gaaagcccga agcctctaga atgccacccg caccccgagg gtcaccaacg   6720
ctccctgaaa taacctgttg catgagagca gaggggagat agagagagct taattatagg   6780
tacccgcgtg cagctaaaag gagggccaga gatagtagcg agggggacga ggagccacgg   6840
gccacctgtg ccgggacccc gcgctgtggt actgcggtgc aggcgggagc agcttttctg   6900
tctctcactg actcactctc tctctctctc cctctctctc tctctcattc tctctctttt   6960
ctcctcctct cctggaagtt ttcgggtccg agggaaggag gaccctgcga aagctgcgac   7020
gactatcttc ccctggggcc atggactcgg acgccagcct ggtgtccagc cgcccgtcgt   7080
cgccagagcc cgatgacctt tttctgccgg cccggagtaa gggcagcagc ggcagcgcct   7140
tcactggggg caccgtgtcc tcgtccaccc cgagtgactg cccgccggag ctgagcgccg   7200
```

```
agctgcgcgg cgctatgggc tctgcgggcg cgcatcctgg ggacaagcta ggaggcagtg   7260
gcttcaagtc atcctcgtcc agcacctcgt cgtctacgtc gtcggcggct gcgtcgtcca   7320
ccaagaagga caagaagcaa atgacagagc cggagctgca gcagctgcgt ctcaagatca   7380
acagccgcga gcgcaagcgc atgcacgacc tcaacatcgc catggatggc ctccgcgagg   7440
tcatgccgta cgcacacggc ccttcggtgc gcaagctttc caagatcgcc acgctgctgc   7500
tggcgcgcaa ctacatcctc atgctcacca actcgctgga ggagatgaag cgactggtga   7560
gcgagatcta cgggggccac cacgctggct tccacccgtc ggcctgcggc ggcctggcgc   7620
actccgcgcc cctgcccgcc gccaccgcgc acccggcagc agcagcgcac gccgcacatc   7680
accccgcggt gcaccacccc atcctgccgc ccgccgccgc agcggctgct gccgccgctg   7740
cagccgcggc tgtgtccagc gcctctctgc ccggatccgg gctgccgtcg gtcggctcca   7800
tccgtccacc gcacggccta ctcaagtctc cgtctgctgc cgcggccgcc ccgctggggg   7860
gcgggggcgg cggcagtggg gcgagcgggg gcttccagca ctggggcggc atgccctgcc   7920
cctgcagcat gtgccaggtg ccgccgccgc accaccacgt gtcggctatg ggcgccggca   7980
gcctgccgcg cctcacctcc gacgccaagt gagccgactg gcgccggcgc gttctggcga   8040
caggggagcc aggggccgcg gggaagcgag gactggcctg cgctgggctc gggagctctg   8100
tcgcgaggag gggcgcagga ccatggactg gggtggggc atggtgggga ttccagcatc   8160
tgcgaaccca agcaatgggg gcgcccacag agcagtgggg agtgagggga tgttctctcc   8220
gggacctgat cgagcgctgt ctggctttaa cctgagctgg tccagtagac atcgttttat   8280
gaaaaggtac cgctgtgtgc attcctcact agaactcatc cgacccccga cccccacctc   8340
cgggaaaaga ttctaaaaac ttctttccct gagagcgtgg cctgacttgc agactcggct   8400
tgggcagcac ttcggggggg gagggggtgt tatgggaggg ggacacattg gggccttgct   8460
cctcttcctc ctttcttggc gggtgggaga ctccgggtag ccgcactgca gaagcaacag   8520
cccgaccgcg ccctccaggg tcgtccctgg cccaaggcca ggggccacaa gttagttgga   8580
agccggcgtt cggtatcaga agcgctgatg gtcatatcca atctcaatat ctgggtcaat   8640
ccacaccctc ttagaactgt ggccgttcct ccctgtctct cgttgatttg ggagaatatg   8700
gttttctaat aaatctgtgg atgttccttc ttcaacagta tgagcaagtt tatagacatt   8760
cagagtagaa ccacttgtgg attggaataa cccaaaactg ccgatttcag ggcgggtgc   8820
attgtagtta ttattttaaa atagaaacta ccccaccgac tcatctttcc ttctctaagc   8880
acaaagtgat ttggttattt tggtacctga gaacgtaaca gaattaaaag gcagttgctg   8940
tggaaacagt ttgggttatt tgggggttct gttggctttt taaaattttc ttttttggat   9000
gtgtaaattt atcaatgatg aggtaagtgc gcaatgctaa gctgtttgct cacgtgactg   9060
ccagccccat cggagtctaa gccggctttc ctctattttg gtttattttt gccacgttta   9120
acacaaatgg taaactcctc cacgtgcttc ctgcgttccg tgcaagccgc ctcggcgctg   9180
cctgcgttgc aaactgggct ttgtagcgtc tgccgtgtaa caccottcct ctgatcgcac   9240
cgcccctcgc agagagtgta tcatctgttt tatttttgta aaaacaaagt gctaaataat   9300
atttattact tgtttggttg caaaaacgga ataaatgact gagtgttgag attttaaata   9360
aaatttaaag taaagtcggg ggatttccat ccgtgtgcca ccccgaaaag ggttcagga   9420
cgcgatacct tgggaccgga tttggggatc gttcccccag tttggcacta gagacacaca   9480
tgcattatct ttcaaacatg ttccgggcaa atcctccggg tctttttcac aacttgcttg   9540
tccttatttt tattttctga cgcctaaccc ggaactgcct ttctcttcag ttgagtattg   9600
```

```
agctccttta taagcagaca tttccttccc ggagcatcgg actttgggac ttgcagggtg   9660

agggctgcgc ctttggctgg gggtctgggc tctcaggagt cctctactgc tcgattttta   9720

gatttttatt tcctttctgc tcagaggcgg tctcccgtca ccaccttccc cctgcgggtt   9780

tccttggctt cagctgcgga cctggattct gcggagccgt agcgttccca gcaaagcgct   9840

tggggagtgc ttggtgcaga atctactaac ccttccattc cttttcagcc atctccacta   9900

ccctccccca gcggccaccc ccgccttgag ctgcaaagga tcaggtgctc cgcacctctg   9960

gaggagcact ggcagcgctt tggcctctgt gctctttcct                        10000
```

<210> SEQ ID NO 158
<211> LENGTH: 100
<212> TYPE: DNA
<213> ORGANISM: Homo sapiens

<400> SEQUENCE: 158

```
tttttaatgc tcagagaagt tcgtattact gattcgggaa cactgagttt ttcagctcct     60

gtaaaactat tttcaggttt attttcaagt acattcttta                          100
```

<210> SEQ ID NO 159
<211> LENGTH: 400
<212> TYPE: DNA
<213> ORGANISM: Homo sapiens

<400> SEQUENCE: 159

```
caccctagag gcaaggacgg ggtctgtgtc aagaggcttc ccagagaagt gaaaactctg     60

caggtgcagc cgctgggaga gcatcaagaa gggcagggtg gaggggcagg gggcgaaggg    120

agggggtgaa gcccgcaccc tacccccaca tgaaactgat tccactaccc catctctgca    180

agcgtccaga ggcagagagg ccaacatttc ggggacagct tggaggcggg agatttaggc    240

agggctcctt aaacttttat gtgcatgaaa atcaggccaa tcacggggct cttgagcaaa    300

tggggacgat gattcagcag gtctgggctg aggcctcaga ttctgcactt ctaacaagtt    360

cccaggtggt agtgatgctg ccagtccaaa gaccacactg                          400
```

<210> SEQ ID NO 160
<211> LENGTH: 5000
<212> TYPE: DNA
<213> ORGANISM: Homo sapiens

<400> SEQUENCE: 160

```
tgcttcagtg gggtaaactt gaaccgctga gaagacaagc agggagtcgg tctcgctgag     60

atttttacct gtggttctag gaacgcagag gcatgtgagt gttcaggctt tgcatagacc    120

actaagccac ttctaagaac aaggctacct gagccatttt gcaaaaatat gtacgtgccg    180

aggcttttcc tccccacacc tacctcaact ctttctgccg acacactgca cttttcaagg    240

gaacccaagt ttgggttcgg caagaattgt acgttgcaca ccgtgtgtga taattccagg    300

gaatttcaat cgcatcttgt cttccttcct aagcaaattc ggtgggaacc tggtgtggtg    360

tgatagaaaa agccccgagt tctctgtggt agaccacatc aatttcatgt gccagtctct    420

cagactccgg cttgcctctc tcaaggaagg gaacaatggt ttgcttggct tcactcctct    480

ctttcccccc aatttccaca tgggtatctg gctaaaaatg agttacaggt ttccttctgt    540

gagaattgca tggactgata aagtaccatc ccaggaagaa aacaaagatg ctgtcttccc    600

tttcggctca cagttgccgt tggggaggga acacacgctg taaattatag gcagccagaa    660
```

```
gtgaccgcat tgaccactgc gagtggccca gctatggcaa caggctgaga actctggggg    720
agagccattt gttggcaggg atggtgattc ttctagcatc aagctctaag atgatgacca    780
aacggtatca aaagaaatga tattttgcta cctctccggc ttgggtgaat gatgtggaca    840
gttaacctgg acaatttaaa cctttatgtt gatggatcac ttggatgaaa ttaaccagga    900
aattgccaag atttcacttg gccctctgac atcaaatctc aatattatat taccaaatta    960
gagattctaa agaaccctga gttcctttca ctgaaaggaa ggagtggaaa aacctttcca   1020
gatgatccct tttgagtctt ggtgcgagct caggccctcc ctacactgcc tccgtgaaag   1080
ctaaccgacc cttgttccta acctagcgca ggtcagctga gtgtccatcg ggcacaggag   1140
ccctgggctt gtccgggaga tagccagact cctgctattt cctgatgtct gcatagctca   1200
gcgtgtccct caccatcttt gccgttggcc agtaaggaga gccccagggg ccagcactgc   1260
acactgaaac ccaacctatt gctcaatgga atgcttaaaa atttcctgaa tctgccttcc   1320
tgagttgata aaataggaaa caatacacgt tctgaggggg tactgaaagc agagtaaagc   1380
caggaagatc tttttttct gttattctat acaaatattg cttcctctgc ttgttagcag   1440
cccagaggaa atgcagccag ggagccgttt gcagcttttc accagtggcc ggtgtctctg   1500
tgttaccaac caaacgacgc tgcaagacta gtgactaacg cacgtctgca tgattcaact   1560
tcactaaaat tccctctgct gccagtaaag aagcacttga aaactcttta atttgaaact   1620
tgagcttggt taatgacttg ttttcttctc tttctcttta acttctctct tgccatctcc   1680
aacacacaca cacacacaca cacacacaca cacacacaca cacacacact ctctctctct   1740
ctctctctct ctctctctct ctctcatcaa gttttttaat ttcagggacc cggaaacata   1800
cagccccgtg cattcacaat agcatttgct gtgataaagt ggccggcaag ccctctgcat   1860
tcccctgctc acttagctgt atgaataaat aatgagtcac agatacaatt tgggtgctca   1920
agagagtttg tagccagaaa attaattatt ctcccatccc agcccactcc atctcagctt   1980
tgccaaacca tcaagataca ctttgcaggc actggtcaga gtgcgtgccc cgacgcacac   2040
ggcaatgcct ttgagacatt ttatgttatt atttttgttt gtttaagcac agccctcttt   2100
taccacgaaa gatacacaag acgcacatgc acacacatac tcacacactc acagctcaac   2160
cacagctttg tccatttcaa gaggctggtt tcaaaaatgg agacaggttt tccaccctgg   2220
ctgttcctat tcataagcct gtaatctaac gacttaagct gcgagaatgc ttaactcggg   2280
aaacttctct attgcccttt tccagagaga cctcggtatg ccacaatttg cttcctttct   2340
ctcttgaaag atgctggttg tctctttgca ttgaggctac aaggaaaaac acagcacagc   2400
cccatgctga tgattttaac ctaaccaagt ctgtcagtct cctgtactct ctgccttata   2460
gagacagctg ccttgccact ttggccctga agtccccagg ctggtgcaag gctatctgag   2520
agcctccgcc tcctgcccca cactggcacc agccctcctg gctggctctg tgcatgtgcc   2580
tgctaagccc cagggcaggc tgcattctgg gccacacagc atgccgagtt aaggataact   2640
cagacacagg cattccgggc aagggacagc aaaataaaac ccagggagct tcgtgcaagc   2700
ttcataatct ctaagccttt aaacaagacc agcacaactt actcgcactt gacaaagttc   2760
tcacgcaccg actgaacact ccaacagcat aactaagtat ttattaaaac atttctgaag   2820
agcttccatc tgattagtaa gtaatccaat agacttgtaa tcatatgcct cagtttgaat   2880
tcctctcaca aacaagacag ggaactggca ggcaccgagg catctctgca ccgaggtgaa   2940
acaagctgcc atttcattac aggcaaagct gagcaaaagt agatattaca agaccagcat   3000
gtactcacct ctcatgaagc actgtgggta cgaaggaaat gactcaaata tgctgtctga   3060
```

```
agccatcgct tcctcctgaa aatgcaccct cttctgaagg cgggggactc aatgatttct   3120

tttaccttcg gagcgaaaac caagacaggt cactgtttca gcctcacccc tctagcccta   3180

catctctctt tcttctcccc tctgctggat acctctggga ctccccaagc cctattaaaa   3240

aatgcacctt tgtaaaaaca aatattcaaa ttgttaaaga ttaaaaaaaa aaaaaaagcc   3300

agcgccgcct tggctgtggg ttggtgatgc tcaccacgct gcgaaaccct gtggtttgca   3360

ttcagtgtga ttcgtcctgc ctgctgacca ctatgctggg ttcagacttc tgacactgcc   3420

aggctaccca acttgtggtt ctgtggttgt ttatgaggcc caaagaagtt ttcacacaac   3480

ccaaattaca aatttaactg ttcccctttc cacagcccat ctcaattggt tcttgccaat   3540

catgtgactt aagtgatgtc aatttttttt tttcttttct gagcaatgcc cttccttccc   3600

tccacctgcc ctcccccagg ctgtgcaaga aaatagccga gtagactttg caagaggggg   3660

ggatgtagaa aaaagtgact cagtcactta ttatatctca atggtctttg ctgatttagt   3720

acaactcggc tcctgttgtt atttgtggtt tttggaacta ctgattattt tgataaagat   3780

ttcattgctg cttattcaat agtaattcaa cgctggcatc aagccgctgc tccgacagga   3840

tgtggatccc atcatttaaa atgctaggca tcagctccgg gagagttaag tccttggtaa   3900

cgtctatcat ggcataagtg aaactataaa agggaaaaat aaataaaaag aaatgttttg   3960

gtgagagtct gaccccctaca acgggctggc aactcacagg tattttaaag cctgggaaag   4020

ggaaagaatt ttacttttga aataaaagga ctgttttaat gaaaccaaaa ttatgtggtt   4080

ttattccccc taaatggaca actttagtat gtatctcttt cagtaaagag ataaaatcat   4140

agtacagtct taacacacac acacacacac acacacacac acacacacac acaaattagg   4200

aagctaaagg aaaacaaagc agagagaatt tctgtatttg ggacaaagca gtggttactc   4260

tgcagatgtt tatttgtatt gtcacttggg aaagctccct gtattgcctt tctctagttc   4320

aattcaaatc aataggctaa tttacacctg taggtaaaac tacactttga gcacatgagg   4380

atgccacaat agaaggggaa ccaggaggag acacttctcc tggggctgac taatgaatat   4440

tatatagcgc gtcctctacc ttagaaagac atgcctgttt gaagatgcta aaaacaggat   4500

aattttgtaa gtgggcaaac cactgtggtc acacgtattt cattttccgg ccccactggc   4560

tttacctgct gacaactaaa acgtcatttt gttttgtagt tccaagatga agaaaggctt   4620

attttcctga tttactacct tattcatttg gctctgctct gcctacatcc gccatagcac   4680

tctgcgcacg tgaaatttcg acacataggg tcaagagaac ctgtgtgatg atgggttgta   4740

aatgccagtc ctggattcta agctgcagta gccagcacag gcacttcaga aaggctgaac   4800

tcccacaaca ctccctcggt tttccctcat ccacttaatt tcacacacac aaagacccac   4860

aacgatagta gcttccatgg cacaagtctt tcaaaaggaa cagacacaat ttttacttac   4920

tcctgttttg actaaagcag gaattgaaac tcaacagacc gctttctctt acacttgtga   4980

gaagttagct ggccacatgt                                               5000
```

<210> SEQ ID NO 161
<211> LENGTH: 500
<212> TYPE: DNA
<213> ORGANISM: Homo sapiens

<400> SEQUENCE: 161

```
agggaaaaga gataacgaaa gaaagaaaga aaaaaaaaag ggccggcaat ttcatgtaca     60

tttgttttgg cattcgctga attctagaga tgaaaacaat ctcctgcttt taattcagtc    120
```

```
cacgtgcaac aaagttgtac gttgggagat ctggctttta ataagaacga ttaacaagcg    180

tttttgatca caggaagttg agaagagtcg ctgcttctaa gaatacaata aacattgact    240

agcagttaga cggtccatct ttctctatca gccgtttagc agcctctact ttgatttggg    300

gcaaatgcga gatgggacca ggagagagct ccccacaccc ccaccaccac gtgggcagtg    360

gttctgttcc agagcgcctt ccttcctgtc cagggaggca ggctgctgag gccgtttctg    420

ggcaagaggc cattgtcggg atatttgctt tagatagctt gcagctgggc tgagtgggtg    480

tttcattcag actcaacaca                                                500


<210> SEQ ID NO 162
<211> LENGTH: 700
<212> TYPE: DNA
<213> ORGANISM: Homo sapiens

<400> SEQUENCE: 162

agcctggcgc acccgcccta atttgagtca gggaccctag gcgcctgcag ctccggttcg     60

ggttgagtgc ctcctgtcag gatgtgaagc tgctgtcccc cccgggggcc tccagcactg    120

ctgaggactc agcagtcagc ctctcctccc acttgggctc atttacagag agcatctcca    180

ggaatcagtc atggggaaag gggaaacgcg gagtgacaac acaacacgta gaaagttctc    240

tgccgccttg gtcaggcttg tcagcctcac agcccatcct gctcctgcgg gaggaaaagt    300

gagcagaact cagcccggag atgagccgca ggccggcagc ccctgcctct gccctgcttg    360

ttgtgactgc aatgcaaggc tctctgtagg tgcgggggat tcgggttaaa tgggtctcca    420

gtggtccagc gctcccagca aaggccgacc acaagaatta gcgggctagt tatttaccat    480

aaccatatac aaaaccacaa gcatcagcgt tccctcaaat acatccgaga cgctgtatat    540

ctctttatta aagcctgtca gggtttgtta ttgcacagct tggccttgaa ccccaactaa    600

accaggctgc ttgagcaaag aaccaagcaa tgcaagcatt caggcaggac cattataacc    660

ctgaggccaa aggcagaagc agggagagga gacgtcttcc                          700


<210> SEQ ID NO 163
<211> LENGTH: 500
<212> TYPE: DNA
<213> ORGANISM: Homo sapiens

<400> SEQUENCE: 163

agaccagcct cggtcttcgg cctgcgggtt ctgcaaagtc aggctagctg gctctccgcc     60

tgctccgcac cccggcgagg ttccggtggg gaggggtagg gatggttcag ccccgccccg    120

ctagggcggg gcctgcgcct gcgcgctcag cggccgggcg tgtaacccac gggtgcgcgc    180

ccacgaccgc cagactcgag cagtctctgg aacacgctgc ggggctcccg ggcctgagcc    240

aggtctgttc tccacgcagg tgttccgcgc gccccgttca gccatgtcgt ccggcatcca    300

tgtagcgctg gtgactggag gcaacaaggg catcggcttg gccatcgtgc gcgacctgtg    360

ccggctgttc tcgggggacg tggtgctcac ggcgcgggac gtgacgcggg gccaggcggc    420

cgtacagcag ctgcaggcgg agggcctgag cccgcgcttc caccagctgg acatcgacga    480

tctgcagagc atccgcgccc                                                500


<210> SEQ ID NO 164
<211> LENGTH: 17000
<212> TYPE: DNA
<213> ORGANISM: Homo sapiens

<400> SEQUENCE: 164
```

```
cacgcgcccc ggcctggctg gaggggccaa cccagcgggg cccgcctgcc cgccggcctt     60
tctgtaactt tctctcttta aacttccaat gaatgaacgt gcctcttctt acggatttgt    120
ttagattagg gaatagattc ctcgctgata gcgttgcttt gcaaataaga cctcctatat    180
tattcaaacc aaacgagttt gtgtctttaa aggactatag cagccccatt ctatgttaag    240
ggttggctat tacaattatt atatgcttag ggaaaaaatg taagccccgt agtttgtgct    300
tttcttgatg tacagaaagg tttatcttag gtggataggt tttgttttgt ttcttaaatg    360
ggattttttt ggttcgtgtc tttgaagggc tgtttcgcga cgtcattaat gaactaatcg    420
gttttcagat ttcaagacgg tgtgtaattg atgtaaccac tgaggaattt cagtgcacac    480
cagactaaga ctcttccagc gcaggggatt ccagatgctt cttgggccct ctggaagcca    540
tggggatgtt tccagaccga aaggagggct ttgctgggga gcagatgtgc tgcctctccc    600
cgacccagga ttttgaggcc atgtttccgt taatctggac cgagagccct ctgggagagg    660
gaggcaggtc gtagggggcg ggggtgaggg ggagcgagat gaggtcgtcg ctggacgctg    720
ggctcccttg tcgttgtcct tttccccaga atccatggtc aggcctaggg agccacccct    780
gggtgctcga gatgagtccc caccctcact gaaggtcggt cactggatgt ttgtgtgcat    840
cgtaaggggc ccaccgaagt cccgaagcct tctcagggac cagcgagaaa gaggagcagg    900
cttgggagac agggaaggaa aatgcagggg aaagggctca cccctcgacc ccaggtaaaa    960
ttagaaggaa cgtgtggcaa cccaggtgca gctttggtcg ctcgctcaag gactttgcta   1020
gtcactacca ttaattaatt aatcactatc attaactacc aaggacaccg tttttattcc   1080
cctaaaagcg tcaccttgag gggaatggag aattgggcag cagctatgca aatcctggga   1140
caggagacac tgcctgagga ccctctctca ctcccaatcc cagaacccga agttatcccc   1200
gacaaccaag tccaagcaca tgaaccaaga cgatcagctt caggcagctc cttaccccca   1260
caagcggccc aggaggtggg cattatcccc cacccctggg atttctccat ccctccctct   1320
tctctcctgc gggagagaga gctgtggtca cccagttggg cgcgatggct ctggactaat   1380
ggggtctcta gacccagggc acaaaggcca atctgccagg ggttactgca tgtaatgaga   1440
taatcagaca tgttgaccaa cctaaaagaa aagactctcc cagggagtaa ctcccagtga   1500
aataatttat taaaaaaagc aaaaaagaga cataaatttc tctctactac ttgaggaaac   1560
agcaaacaga acgaattagg gtcttggcct ctgcaggaat aaattatttc cgacttggtc   1620
tggatacctg taattatttg taagctgtgg gtagtaatac tgtaattgtc ccccggtcct   1680
ttctggaagt agcaatgacc ccaaggacaa ttggtgacgt ctccacaggg tttacacatg   1740
gaaaggagtg aaaaatcgag gaattctttc agatagccca gaccaaaaat cctctcagcc   1800
atgaaaaggt catatatgtg atgctgggcc aagcggactt ttctggagta accatatcat   1860
aactgattgc ggatgtagac aagagcgtat aaaccaaata ggcttgaatc aacgcagtcc   1920
tggattttct gttgcctctg cttgctgggg cagtggaagt tcttaaactc cacttcagag   1980
gttggaaatt cttccccctc ccccacctcc ttagtgacaa ggtctctgat ctcctgctgc   2040
cactgcaata gcctctccca tcccgcgggg aacggccgga gttcttccct tgatctctcc   2100
cgagtcggct tccgctgggg atggatcgca ggtaggcgcc ggcgcggcct ggggaagaac   2160
agttgcggag catctgaagc ggaaaatcca agcagatgtg aggcgatccg ggcccgcctc   2220
gttcctcttg ggcctgaat ttcttccaga taagtttcct aatggaacat ttctaagagg   2280
tggggtacga ggcggcttgc tcgcacgcgc agtgggacag actgcgggtg gggacgtact   2340
```

```
gagaggtccg gacctcaatg cgtccgaccc gtctccacac cgcccttttc cagcccccag   2400
tctcctttca ttccctactc ttcaggctcc tttggggcca gtgggtgaac cgccatttag   2460
aacggtgcct cggactcggg ggtcgtgcgc tccatctctg cctcccccct ggggcccgcg   2520
aggctggtcc gggctttctg agctgggcgt tcggctttag gcccaatacc tggaccagga   2580
atttcttctc cccgcgccag aagggaaaga cataggaggt gtcccaatct gcggtcaccg   2640
ccgatgctcc tgaccactct agtgagcacc tgcccggtac ttttccattc caacagagct   2700
tccagcttca tactaactat cccacatacg gcctgtgggt attagctcta agtgtccttt   2760
tccgagggcc cgaggctccc cctccagcag ggagagctcc gggacggccc ccaccaaggg   2820
ttgggtttct tccttcacaa ttccacagag gcatccctgt ccttcctacc tgggaaacct   2880
cgaggtgcgg tgcccgtgta cttctggtac tttgcgtggt gccatcaggg accccagagc   2940
cacagctgcg tgtgtgtgtg gatgtgtgtg tgtgtgtgcg cgcgcgcgcg tgtacggcga   3000
aaggatgtgc ttgggggagc cgagtacaca acgtctgctt gggcagctgc tgggcaggcg   3060
ttgggcctgg aggtatctca cacccacgta tcttccagtc ttcaaacacg gcattgctct   3120
gcctcccgta gcgcgcttcg aacctgcctc gcggacacgt gaacagaggc tgtccctggg   3180
aagataagtg cgctttcccg taaaatccgg gaaatttgcc ttgaggaaag tttccgttct   3240
tgttacttgt cgggtttctc ccacttccac ttagccatgt ttctgcgatc tgggtaatcc   3300
ctttcaagcc caggaggaat tctcccgggt ccataattga gggtcggaag ccgtgggggt   3360
gagaaacgca ttaaatcctc ccgaagccca ggaggtgcca gagcgggctc agggggccgc   3420
ctgcggaagc tgcggcaggg gctgggtccg tagcctctaa ccccttggag ctccttctcc   3480
cagaggcccg gagccggcag ctgtcagcgc agccaggagc gggatcctgg gcgcggaggt   3540
gggtccgact cgccaggctt gggcattgga gacccgcgcc gctagcccat ggccctctgc   3600
tcaagccgct gcaacaggaa agcgctcctg gatccgaaac cccaaaggaa agcgctgtta   3660
ctctgtgcgt ccggctcgcg tggcgtcgcg gtttcggagc accaagcctg cgagccctgg   3720
ccacgatgtg gactccgcaa ggggctaggg acaggcaggg ggagagcccg ggtttgcgca   3780
caccttccag cccctggagg gagcctgctc ggcttcgaac gccttcgaac ttttgacctt   3840
caaaggagtc cctggaaaag gtcaggagcg cctgctgcag gcacggttgc cgaaggccag   3900
gccttcctgg cgcaggggag ggccagggga gggaagcgga tactcagtcg ctgtccgacg   3960
gcgagttttc ggagcagcag gctcatgatc ccgggccagt ggcgagagca gtgacaccga   4020
gaacccaaat ctccgcgccc ccatccgcgg cccggtgtcc tcccggcccc tgctgacctc   4080
caggtcacgc accccactgc tccacggctc tgcagcctgt ggcacacggc cgagagtccc   4140
cacatgatct cgacgccaag gtaaggaatt gccctgcgtc ctctgagcct gtctctggcc   4200
tggggggccg ggaaagctgc actcctggaa gaggtggggt tatgtgaccg ccgctgcagg   4260
ggtgcgcgga ggactcctgg gccgcacacc catttccagg ctgcgggagc cggacagggg   4320
agggcagagg ggggacaaaa ggactcttta ggtccaaaat gaccctgaag gagagtccag   4380
aatgcccagt ggccgcgtct gcaacggagt cttctttctc caattgcctt ctgccccatc   4440
accatgggcc ccacctgcgc cacctgcgcc caccctgtga ccctggctca gcgaccttgg   4500
cccttaatcg cccaacgccg attcctcaaa attccggctg cgctgaatcg ggctgctttt   4560
gccgccgccc cggcagttgg gccctgtttc cgccggcgcc ctgggagagg cctcaccact   4620
cggctgggct ccctggcccc tcccttcccc tggcctgagc gcccctgcgg cctcccgctc   4680
ctcctgagaa ggcgacaatc tctttgcacc ttagtgtttc gaggacagaa agggcagaag   4740
```

```
ggtcacttcg gagccactcg cgccgttttc acgtgtgtgt gtaatggggg gagggggct   4800
cccggctttc ccctttttcag ctcttggacc tgcaacaccg ggagggcgag gacgcgggac   4860
cagcgcaccc tcggaaggct cgatcctccc cggcagggcg cctggccaac gagtcgcgcc   4920
gcctcctctc ggccgcgcct gctggtgacc ttcccgagag ccacaggggc ggcctcggca   4980
cccctccttc cctcgccctc cctgccgccc atcctagctc cggggtccgg cgaccggcgc   5040
tcaggagcgg gtccccgcgg cgcgccgtgt gcactcaccg cgacttcccc gaacccggga   5100
gcgcgcgggt ctctcccggg agagtccctg gaggcagcga cgcggaggcg cgcctgtgac   5160
tccagggccg cggcggggtc ggaggcaaga ttcgccgccc ccgcccccgc cgcggtccct   5220
ccccccctcc gctcccccct ccgggaccca ggcggccagt gctccgcccg aaggcgggtc   5280
tgccataaac aaacgcggct cggccgcacg tggacagcgg aggtgctgcg cctagccaca   5340
catcgcgggc tccggcgctg cgtctccagg cacagggagc cgccaggaag ggcaggagag   5400
cgcgcccggg ccagggcccg gccccagccg cctgcgactc gctcccctcc gctgggctcc   5460
cgctccatgg ctccgcggcc accgccgccc ctgtcgccct ccggtccgga ggggccttgc   5520
cgcagccggt tcgagcactc gacgaaggag taagcagcgc ctccgcctcc gcgccggccg   5580
cccccacccc ccaggaaggc cgaggcagga gaggcaggag ggaggaaaca ggagcgagca   5640
ggaacggggc tccggttgct gcaggacggt ccagcccgga ggaggctgcg ctccgggcag   5700
cggcgggcgg cgccgccggg ttgctcggag ctcaggcccg gcggctgcgg ggaggcgtct   5760
cggaaccccg ggaggccccc cgcacctgcc cgcggcccac tccgcggact cacctggctc   5820
ccggctcccc cttccccatc cccgccgccg cagcccgagc ggggctccgc gggcctggag   5880
cacggccggg tctaatatgc ccggagccga ggcgcgatga aggagaagtc caagaatgcg   5940
gccaagacca ggagggagaa ggaaaatggc gagttttacg agcttgccaa gctgctcccg   6000
ctgccgtcgg ccatcacttc gcagctggac aaagcgtcca tcatccgcct caccacgagc   6060
tacctgaaga tgcgcgccgt cttccccgaa ggtgaggcct caggtgggcg gccggggacg   6120
ctggggagcc cggcggcccc ggcccaggcg ggaagcgcaa gccagcccgc ccagaggggt   6180
tgccgcggcc tggcgtccag agctggggcg tctgagggag gttgcgtgag ggtcttcggc   6240
ttcggcgctg gcttggggcg aggggccagg gccttggcgg cccaggcgac caaaccctct   6300
cctggtccag ggctgggtga gggcgaatta cgaattgttc caggggcagg cagtccccca   6360
gcccgcacgg ccagcgagtt ctttctggtt ttgttctttc tccctttcct ccttccttcc   6420
ttcgccagtg cattctggtt tggtttggat ttttttctct ctttctttcc tttctttctt   6480
tctttctctt tctttttctt tctttcttcc tctttctttc attctcccct tccttccttc   6540
cttggccccc tctctccctc cctccttcct tccttccttt gccaatgcat tggtttgttt   6600
tctttccttt tctgctttcc ttcctttctt tggaagttca ctctggtttt gctttctttc   6660
tttccccatc ccttcctttc tttatccctc cttcccttcc tccttttctt tctacgattc   6720
cctttatttt tccttcattc ctccctcttt ttgtctcttc tggaggaggt gaaggagggt   6780
cagcttcagg cgctgcgagt cagcggggat cacggtgagg cccaagcact gcaggctgag   6840
gccacagagc gaacacttgt gctgagccgg gccctctcgt gaggctgggg tgcgggaagt   6900
ccgggcagga gagacccgcc cccgccgttg ctgagctgag acccggctga aagagagggg   6960
tccgattaat tcgaaaatgg cagacagagc tgagcgctgc cgttcttttc aggattgaaa   7020
atgtgccagt gggccagggg cgctgggacc cgcggtgcgg aagactcgga acaggaagaa   7080
```

```
atagtggcgc gctgggtggg ctgccccgcc gcccacgccg gttgccgctg gtgacagtgg   7140
ctgcccggcc aggcacctcc gagcagcagg tctgagcgtt tttggcgtcc caagcgttcc   7200
gggccgcgtc ttccagagcc tctgctccca gcggggtcgc tgcggcctgg cccgaaggat   7260
ttgactcttt gctgggaggc gcgctgctca gggttctggt gggtcctctg ggcccaggag   7320
ctgggagggc tgcgccggcc tctggagccc cgggagccag tgccgaggta gggagacaac   7380
ttccgccgca gggcgccgga cggtcggggc agagcaggcg acaggtgtcc ctaggccgca   7440
gggcgcttcc atagcgccat ccccaccagg cactctactc gaaatcggaa agctcgacct   7500
tttgcgttcg cctctgccaa gcctgttatt tgtgctggcc gctgggtctg gagctgcgct   7560
tctcggcccc tccccggtgg agcgcagagg gctggtctgc aagcgcggcc tccagccccg   7620
cggctccccg gcccaggagc caggcgcggg ctgacccggg agcacccggc agcggagggg   7680
gctggaagcg gaccctaggc ctctcctgtg ccacccggcc ctaccgcgcg gccgcggggc   7740
gctctcctct cgggcgcagc ggtccttcag cccagggcag gttcctccct ttcctactcg   7800
gaacgtggca aagataccc agtcccagcc cctccagctg agagctgttg cccaaggtcg   7860
tcgctacttg tccgctcaat ggtgacccct tggcagagaa ctagggatga ttccactccg   7920
gttgatgttt taggggaaat taaaagaaca ttcggttttc tgagtctcct tccggggagg   7980
cgtggtggta actggtttgc tgggaagagc cgttccttaa ccgcatgcaa caaagcaggt   8040
gtggaatccg gacgagaggg cactcactgc cttctgcccc ctttggaaat agaaaaagcc   8100
ttcgaagcag caatccaaag atcaaatgat ttgcggtcaa tgatttcaat taaaccagaa   8160
attagtaagg gagggccgag aagacacggc tgctcagaag ctgttcgctg tttgagggat   8220
ttcccggaga gcctgttaaa agatgcgaag tggtgggtgt accgctcagc cacctttaaa   8280
ccggctctgt gcgttctggc tctggaaagc aagtctccag gcatttgggc tcagaattgc   8340
tgggccccga gtttgggcgg gggtggtcct tctgggggtc aggccttgag cagcttgcac   8400
tggtggcagg tttgggagca gttgaggggc ttcctgtgtg tcttttggag ggggtgaccc   8460
tggaagttgg cactctggaa gggagctgtt tggccctaga gttttggaaa gggccctgaa   8520
cctgttcggt ccccctcgga aagggaaggg agcagtggct tagtccctcc ctcctccatt   8580
cgtgcaatgc ctggggtagg ggtagacctg gagccggtgg actcatatcc ttggaattcg   8640
tcaggacagc tgctccgggg ccttggccct cagtcagtct ggggctgagg agtagggaag   8700
ctgggaactt ggggcagagg aagaagatgc gtttagaaag acctccatta tgcaaactgg   8760
agtccattta tgcaaactgg tcacccttcc agtagctcca aagagtggca gtggagtggc   8820
atcttgattg atttaacctc ttctcagggg acctgggtct gcgagggagg atatggctgc   8880
ggggttggaa taggatctgt ctgagctgcc agggtcaggg tggtggccct agggaggttt   8940
tagggccagg gtggtcccgg gctgtggcag gggctctcag atcgcctcgg gctctcagct   9000
gcaaggtgaa aaataccatg aggaattgat ctgccaaggg cggtcttgtc tcaaagcaag   9060
tggattgctg gggtaaagaa tctagagacc agcttaggac tctgggagga agaaaaaaaa   9120
aaaaagaata gcatagtcct aaggaactgc aaggatcacc agattaaccc ttcatacctg   9180
gggaaattaa ggccagacat gacacaggcc tttcccaagg ctctgtagca agggcaatag   9240
caggccagtt gctgccactg cggtcctgtg gggcatgttc tcactccact gcacccagga   9300
ggctgccagc ctctgttcct tttaacatag atctcctcag ttgttaagac agaaagagga   9360
actcagaggg gtccctgtgt gcaaggcaga gggagaccac cagaaccagg gtaagcaccc   9420
cacttggtag ccagttcaag gacttgggga tgttttcaac atttacagcg aggtttgagg   9480
```

```
ccccattgtc atgcagcgct actcggcctt ggtctcctta tctgtaaaat gggcccatta   9540
gcaatgcaca gggttgctgt gatgaagggt gaggtcccac aagcaaaagc tgtgcagtga   9600
ggggggaatc ctaagcattg ttcctatgcc attcacccct tcctgtgagc tccccatatt   9660
ccctggctca aaggagtctt gaatggcagg gatggaggac tcactgcctg gactttgaag   9720
acccctgctt tctgggtgac caccttttct tccctttgac agtgaactaa tacattggag   9780
gtagatagtg ctgggaagag gacaggagac cacggctgac tttggacatg ggctcgaaat   9840
tgataacttg atgagtcttg gagggtggtt aagataagct cggggctggg gcagcgctga   9900
ggtctgatgg tcagccagcc ctccccaaag tgtggccctc cgttctggag ataggggctt   9960
tggaaactgc aaaagcgtcc tggcaggcca gctctggttg ctccctggcc atagctgctc  10020
tgactacagg cagcaggacg caggtcggcc tctgcccatc ggaggtcaga ggcagggcct  10080
ccagcaccag actcagcagt gccactgcaa acctggcaca acaggctggt cccaggactc  10140
agctcagcag tgaagttgga aaccaaggtt gagtctcccc atctcccttt ccccaacccg  10200
aaagacccaa gatgggtgtg ggtgaaagag ggagaaagaa ttgctactcc agaaactgtc  10260
atttgcccac acgaaacgag gtggggttca aggtctgaac tcttccagtg cctgggtgcc  10320
tttgggttta aattcagctg caggtgcccc catcaccact tccacctgag cacaccacga  10380
gaagccaggt tatcttagaa actgtttccc ggaatcaaag cgacttgatt tggagagttg  10440
ggtgaggaga aactcacccc tatacccctc agggcgtcag agatgtgagg caattctcta  10500
cctccgctgg aaaaaatgca gatttattaa aggtcgactg tttagcagaa caacgtagat  10560
tttttacaac gctttccccg tctctgcttt gaagcctgcc aggctgcagc tggggatcca  10620
ggagggaaag cccgcaggcg cagaggggac aatccgggaa gtggtaaagg ggacacccgg  10680
gcacagggcc tgtgctttcg ttgcaggcga ggaagtggag cgcgcgctgc agattcagcg  10740
cggggctaga ggaggggacc tggatccctg aaccccgggg cggaaaggga gcctccgggc  10800
ggctgtgggt gccgcgctcc tcggagccag cagctgctgg ggcggcgtcc gaactcccca  10860
ggtctgcgca cggcaatggg ggcaccgggc cttctgtctg tcctcagaat acgtaggata  10920
cccgcgggcg acaagccggg ccaggctagg agcctccttc cctgcccctc cccatcggcc  10980
gcgggaggct ttcttggggc gtccccacga ccacccccctt ctcacccggt ccccagtttg  11040
gaaaaaggcg caagaagcgg gcttttcagg gaccccgggg agaacacgag ggctccgacg  11100
cgggagaagg attgaagcgt gcagaggcgc cccaaattgc gacaatttac tgggatcctt  11160
ttgtggggaa aggaggctta gaggctcaag ctataggctg tcctagagca actaggcgag  11220
aacctggccc caaactccct ccttacgccc tggcacaggt tcccggcgac tggtgttccc  11280
aagggagccc cctgagccta ccgcccttgc agggggtcgt gctgcggctt ctgggtcata  11340
aacgccgagg tcgggggtgg cggagctgta gaggctgccc gcgcagaaag ctccaggatc  11400
ccaatatgtg cttgcgtgga gcagggagcg gaagaggcag ccggtcctca ccctcctctc  11460
ccgccacgca catatccttc ttgacttcga agtggtttgc aatccgaaag tgagaccttg  11520
agtcctcaga tggccggcaa cgcgccgagg tcacgctccc cagaaacacc cctctcccct  11580
cccctacccc agctccccct ggggcgggtg gtaattgggg gaggagaggc cgcaggcagg  11640
gaaggggtgg gaaagccaga gagggaggca caaagtgatg gcagcccggc aaacactggg  11700
gcttcgggct gggccgcgct cgtttaatcc cacaaaaatc ccattttgga ggtgagaaat  11760
agaggttaga ggtcgggccc ttctggagat cagaccgagg agacgggccc agctggcgtc  11820
```

```
ttaaagcaag gagggggagt cgggaggagg tgagacccct gcacccaggt ggggctccca  11880
aaccgttctg gatttaccac actcccaggt ccgattttcc atggagggct ggggttaggg  11940
actggcacct tcttgttgtt aaccgcattt gatattcaca agaaccctgt gaggagactt  12000
tgtcaccgtt tttagatgcc tgaggttgcc ggaggggcag tgagagaatc gtctaacctg  12060
gtgttcctac cacagtccag gccctgtgtc ctgggctgga cccacagccc ctgccaccac  12120
ccagaggaag gcgcgaagct ggctgcctcc tttacgggtc tcccttaggt gccctcatga  12180
agggggacgg ccacctcaca gtgcaggaac tatctccccg tttgctccca aatagtcttc  12240
ttggtgtggt gctgtctatg gtctgtgacc tgcatctgga gttacccccca ggaccagctt  12300
cggaagagga gggatcgctt ggaggccgtg cagtgtgagg aacggcaggc agggtgtggg  12360
accaacatgc acacactcgc aggtgctggg gccagggagg aatgaggcgc tggctccctt  12420
tccctccatt tctccctggg ggtcccagca acctggccat ccctgacttc caacagcaca  12480
gcgtccccac aggtcctgca gtgctctgca ggggtgcagg gagctcccct ccccccagcc  12540
gcaacctcac cttcctcacc cccacccctc cggcaggaaa ccacaggctg ggttggggac  12600
ccctggtgct ccaagagagc agtgagtgct gggagccgct aaccccgagg cgcctagcac  12660
agactcttct caccccttat ttctgaaata aagcccttcc ttaggtccag atgaggacca  12720
cgtgctcagt gcctcacttt cgtgggagtg tatatcactt tacagtatca agacaatttt  12780
ctttcgttac aaatctttat ttagtctctg cgtttagacc aaagtagatt tttatgggct  12840
gagtgaaaaa acctcgcccg cattggtttc tgatggaaca gctggcagcg ccacggcccc  12900
gggtggggtg gcctagaggc aggggtgctt gggaggaaca tctagcaccc gaccacctcc  12960
accaggtggg aaagggacgt ttgcaccaaa tctccgccgg caaagcagag gctttgggga  13020
attacagaaa aactataatg atctaaaaga gaacaagtta tcttgaactg tgcgggtatt  13080
tgaatcatac agaaaattgt cctgtgtgcc caatgcactt ttgcatgtag agccagggcc  13140
ttcgaggaag ctttcaggag atcccgggca gcggagtctg gtctggagtt tcatttccgt  13200
aggtgcagat ttctccccaa gtcttcccgc catgggcttt gcaagaagcc agggcccaga  13260
ggccacgctc accgttaaca ctgcacaggg caaaggtggc tccaggacaa ctgcccaacc  13320
ccaggaacga cccagcagca gagaaaagga cagctgccag ggtgcctttg tcgctttttg  13380
gaaatcagaa ttcctgggtc cttagttaag tcttacttca ccaaatccca ggaccttcac  13440
attttggttc ttgccattgc taacagttgt aaatgctgcc gccacgaggc ctgggaggaa  13500
ggacccgctg gtgagagcac agggagtgct gctgtgatca cggtggtgat gcggggtgag  13560
cgcgatttcc cgggattaaa aagccaccgc tgcccccgtg gtggaggctg ggggcccccg  13620
aataatgagc tgtgattgta ttcccgggat cgtgtatgtg gaaattagcc acctcctcag  13680
ccaggataag cccctaattc cttgagccca ggaggagaaa ttaaaggtca tcccttttta  13740
aattgaggaa tagtggtttt ttttaacttt ttttttttta ggtttttagt tgccgaatag  13800
ggaagggttt gcgaagccgc tgccctgggc cgaggtgcat tttacgcttc cagaggtcga  13860
ggcctccaga gaccgcgatg cccagggcgt tcccggggag gctgagagac ccagggtgct  13920
ctgggtgact gcacggcgac tcctcgggaa cccactcgtg gctgcccgct tggaagggct  13980
ttgcggcccc gggaacgatc tccaggatct ccacggctgg tcaggttccc cgtccctcgt  14040
atcccgcgct gcccgggggc tcctgccttt ggttcagtgc tcgcggcacc accgcactca  14100
ggacggcagt ggggggctgg ggctggggct gggcctggcc cagcgtgggt tggggcgggg  14160
gacgcgccag cagcgcccgc agctcgctcc gcaggggtcg cagccagggg tcgggagcta  14220
```

```
ggctcgtggg ccgggagacg ccgggcgcgt tgtcctccgg ggaggttggg gtgcaggcgg  14280
tgcaccgacc ctcgccatct ggcgctgcag ccaccagcca cggcgcttag tggagggtct  14340
gcggccaggc tcccggcgga aagattccgg ggagggctcg ggggttgtcc cagcccgcgc  14400
taagcgccgc agcctcgccc ggctttcctg cttcctcgga ctgtgcaggg gaagcctggg  14460
gtctcgcggg gcgcagcagt caggtcgagg gtgcagcagg aggggagtcc tgacgggcag  14520
gtccctcttt cccctggtgc gcaacactgg ttggtagctt ttgcggaggt ggtgaagaag  14580
ggcaggaggc ctgttgagcg gaggagtccg gggatcccta attatgtgac aggagaccct  14640
ttccagttcg gcctgtggcc catccctctc tcaccgccgg cagattggag tctgctctcg  14700
gggagccccc aggtaaaccc ctcacaggga gaaggtttcg gattggaagg aggaccgcgc  14760
tcgtggggcg cctgtgagag ctgggaagcc caaggggtag cgtgtagggg gttttttatg  14820
cgggaggagc tgcctcctgg gcggcgggga ctttctgtct cagcctgtct gcctttggga  14880
aaacaaggag ttgccggaga agcagggaaa gaaaggaggg agggaaggag ggtccttggg  14940
ggaatatttg cgggtcaaat cgatatcccc gtttggccac gagaatggcg atttcaaagc  15000
agattagatt actttgtggc atttcaaata aaacggcaat ttcagggcca tgagcacgtg  15060
ggcgacccgc gggagctgtg ggcctggcag gctcgcacag gcgcccgggc tgccggccgc  15120
tgcggggatt tctcccccag ccttttcttt ttaacagagg gcaaaggggc gacggcgaga  15180
gcacagatgg cggctgcgga gccggggagg cggcggggag acgcgcggga ctcgtgggga  15240
gggctggcag ggtgcagggg ttccgcgtga cctgcccggc tcccaggcat cgggctgggc  15300
gctgcagttt accgatttgc tttcgtccct cgtccaggtt taggagacgc gtggggacag  15360
ccgagccgcg ccgggcccct ggacggcgtc gccaaggagc tgggatcgca cttgctgcag  15420
gtagagcggc ctcgccgggg gaggagcgca gccgccgcag gctcccttcc caccccgcca  15480
ccccagcctc caggcgtccc ttccccagga gcgccaggca gatccagagg ctgccggggg  15540
ctggggatgg ggtggtcccc actgcggagg gatggacgct tagcatgtcg gatgcggcct  15600
gcggccaacc ctaccctaac cctacgtctg cccccacacc ccgccgaagg ccccaggact  15660
ccccaggcca cctgagacct acgccagggg cgcctcccga gcgtggtcaa gtgctttcca  15720
atctcacttc cctcagcagg ttccacccag cgcttgctct gtgccaggcg ccagggctgg  15780
agcagcagaa atgattgggc tgctctgagc tctgaagcat tcggccgctg tgtgtgtgca  15840
aggggcgcaa ggacggagag acagcatcaa taatacaata ttaacaggag cacttgtcca  15900
gagcttactg caagccacat tcagttccgg accttattga cttccccctc ccatctagag  15960
tggattctgg tttttcaatt tgttttgttt tgtttttttgt ttgtttgttt gtttttgaga  16020
cggagtctca ctctgtggcc caggctagag tgcaatggcg cgatctcggc tcactccaac  16080
ctccgcctcc cgggttcaag cgattctccc gcttcagcct cccgagtagc caggattgca  16140
ggcacccgcc atcatgcctg gctaattttt gtagagacag ggtttcaccc aggctggtct  16200
cgatctcctg acctccgatg atccgcccac ctcagccttc caaagtgttg ggattacagg  16260
cgtgagccaa cgcgtcctgc cttgattctg tttttaactc catttttttag aggaggaaat  16320
tgaggcacag agaggttaaa taacatgtct aaggtcacac agcaaggggt ggagcggagt  16380
tagcccactg gcctagctct agagcccacc cggataacca gaacttggtg aggcctccgg  16440
gctcttgctt ggtttggagc caggtgctta gcgccccgag cccggggcca ttcaccctgc  16500
aggagctgca cgcgcccctg acctcggctt ttccctggca gcagaggggc tttgcgggtc  16560
```

```
ggccgggtag ccctgagcac agctcgccac ttccaggtgg gctgttggcg ctggctgggg  16620

acacatcccg atctttcaaa tgccctttac agagcctcat caacgacccg attcattccc  16680

ccctcctgtc atttgtctct gccatcgaaa aatgcctacc gagagctgct ctgcatttcc  16740

gccctctatt ttgtgtttta ctttaaaata ataataaaaa aaatgttggc tgcaggacgc  16800

catgacttag gtcagcgagt cagccgctag ctctgcattt ccaaaaagca gatcttttca  16860

caactctctt gccccaagtg ccctggtgtg gtttattttt taaaatgcat gcctgcggaa  16920

gagaagaccc ggggaatatt cgaaaccccg agcttttaca acataaagcg catggtgtgg  16980

ccgcggcgag taatggcgct                                              17000
```

```
<210> SEQ ID NO 165
<211> LENGTH: 1500
<212> TYPE: DNA
<213> ORGANISM: Homo sapiens

<400> SEQUENCE: 165

caaatcactt gaactcaagt tcaagaccag cctgggcaac atggtgaaac cacatctcta     60

caaaagtaaa gaaaattagc caggcatggt gctgtgtgcc tgtagttcca gctactcctg    120

gggaggtcga ggctgcagtg agccgcaatc acgccacttg tactccagcc tgggcgacag    180

agcaagtccc catctcaaaa aaaaaaaaaa aaaaaaaaaa aaaaggctgg gtgtggtggt    240

cccagatact cagaggctga aaagggagga ttgcttgagc ccaggagttc aaggctgcag    300

tgagctgcga tcacatcaat gcactccatc cagcctgagc aatggagtga gaccctgact    360

atatttaaaa aaaaaaaaaa taggaagaaa caactcaacc acagggctag tatgttactc    420

ggttataaaa tgataaagcc ctaaacagag aattagcccg tttccagaag aggccaagaa    480

cagatgatac agctgaactg aactcctgcc tgtacagctc gttttctaca agattccaga    540

cctggaagat gatggcatcc agccccccatt gaagcacctc gaacaagaaa aacgccgagt    600

ccgaagagcc aggccttgaa cacacgattc ctgtctataa ataactcccc ctggggaata    660

aaaagcagga tccaaggcag gaaacccgag ccgtggaatc tggtaagttc ttaggaaacc    720

cactcacggg cctgagtccc ccgtggaagc ggcgacttcg gcacctggac acccgagtcc    780

ccagagcccc gggcggccgc gcgtccctac ctgcaggcct gataccggcc gcggagcgct    840

cctggccccg ctcccgccag gctccgggac cgctgaaacg cacccagggg ggtgaaggcg    900

tagtcgccaa ggacagcgca gatggcagcg gaggcatggg agccggaacc taccgtggca    960

aagggccagg tcgggacgcc cctcggcgca gccccaaatc ctgcccgcgc cccagccccg   1020

ctcaggccgc gcccctgcca cctctggcca cacgggctga gacgtctggc tcctgcacag   1080

cgcacttccc gctgcccttc tccactggct gctcaggccc tgcctcgcca gcacggcatc   1140

cgcgggggat ccctacctgt cctttagggc ttgcctcata ggtcaaacgt cacctcccag   1200

ggaggtatgg cctgccccct ggccaggtgg gccccttcca cgctcgcctg caacaccacc   1260

cacccacctt gataactgct tgtaaaggtt gtactgcttt ccccccttgag actgcaaacc   1320

ttcaagggca ggaaatgggt ctgttttcct ggcaaaataa tgaagttggc ttaaggtttt   1380

gctgaataaa atgagtgaca gacaaaagta gccaaatttg gcactcctga tgggttattt   1440

gatgaaggag gtgcaatgta tgggcttaac tagttattct ggatttcttt ccccatgtta   1500

<210> SEQ ID NO 166
<211> LENGTH: 200
<212> TYPE: DNA
<213> ORGANISM: Homo sapiens
```

<400> SEQUENCE: 166

```
caaggccggt gcacgcggac ccgaggattc ggtagatgtc cccgaagacc cgctgccgct     60
ctaaggcggt ggaagcgaga ttctccggaa acccagggaa tccgatgctc gcacaggacc    120
aaagcccgag gccgcgggga ccacagaggg acggagaagc cgggactcct cacatcccac    180
atccggcagg ggaagcccag                                                200
```

<210> SEQ ID NO 167
<211> LENGTH: 2000
<212> TYPE: DNA
<213> ORGANISM: Homo sapiens

<400> SEQUENCE: 167

```
ctgataataa agttttacca ttttataatt taaaaatgta aatatggagt tgggcatggt     60
ggttgggagg ctgagaccag aagatcgctt gagcccaggg gtttgagacc agcctgggca    120
acatgcagaa accctgtctc tacaaataaa aaattagcca agcgtggtag cacgcacctg    180
taatcccagc tactcgggag gctgaggcag gagaatcgct tgagcctggg aggtggaggc    240
tgcagtgagc tgagactgta ccactgcact ccagcctggg tgacagagtg aggctctgtc    300
tcaaaaaaac aaaacacaaa aaaacaaaca aaaaaaagca aatatatgta aaaataggaa    360
gtgcggtttc ccaaaatgag gtctgtaaac aactgatcta gaaaatgttc tggaaaaagt    420
aaaaaaggat caggatctga ggtcaactga cctctccctg cgctctggac aggcaaacag    480
gcaaggttcc ctctgaggcc gtagcggctt ctcgtgggcg agtccctgtt cgcaggtgac    540
gtgtggacca cgctcttccg aagcgtctgg cctgtgtgct ctcggggagg ggacgcaggt    600
cagcccacct agccgatggc taacaagtca gtttgttttc tgaacggaag cttaaaccta    660
gaaaagtaac tgggttgggg tgggggtgta gccacatgca gtaaaagcac tgcctgtctg    720
tataacaacg acctgatgaa aaaaggaacg cgtgaaatgg ggagtgttag ggcgtcacaa    780
actccagtgt ggttgaaatg aaagcagaaa gcaaatggca agctggcttc cccttccagc    840
ttttcacaac cctgccttgc tcatggtcag ccccaagcac gggcggaaga aaggactgga    900
ggggagggaa aggggtgggg agcgagggta ccagaggcgt gggaggacgg ggacaaaggg    960
gcagcaaggg accggcggaa aggaaagtcg gcgttagctg gattggaaac agtccagaca   1020
gaacgatggg ctctgctgcc tccgggtggg gcaccaagcg gggagcgggg ccacgaggca   1080
ggggacagtg aagcaccatg cagcgcccac cagccggcag cgcccaccag cctgcgctgc   1140
gctgcacatg gtacccgcgg ccccagctgg ccagtgtgtg gcggagatga gaccctcgtg   1200
aagagactaa gcggccacag caggggggaag ggttgctcac ataaccccat actgctcaca   1260
ctacgaggtt aactgccgtg agatctgcct gcagccagca gaaacccgtt ctaggaaaac   1320
gttgcccagt gacttcagtg agtgccactg acccgggcgc ctccgccccg gcgtccggca   1380
gcagcaccga ttgcgcagga ggcaccttgc aaacaacctt tcctgatccg cgctgcagtt   1440
cccaggccgg ttgcagccgt ttcacagaga ctgcgcacac aaagcgtctc cgtgccctgc   1500
cattcacctt tcgacacagc cgcaacccct cttttcagtg ttaaaacctg gcgccaaaag   1560
gaacatgcga tgtgacgtgt tacctctgcg catgcgccgg gcattcccag cgccccgaac   1620
ctgatgaacg cgcggtgggg accccaggct tccgtgcttt cgttttcctg gaagctacgt   1680
gtcctcagtc tacatattgt tacctggaaa ataaagtttt ctcctttttt cttcctttgt   1740
taacaggcag aaggtgtagg ctgcaggttt cgggcctaag agagggcatg gctggcgaca   1800
```

```
cggagtagac tcctagatga cataacggag gcgagtctgc accggggact cggcattagg   1860

aggaggcaga ggaaaagccc accaccgtgg ccgagggaga tctagcaagc agcttgcagg   1920

gggtgaagtg tgtgcaaagc aggctgagac ctgtccagta tcgaaacacg ccgcggtggt   1980

caagcaggct ttaccatgct                                               2000
```

<210> SEQ ID NO 168
<211> LENGTH: 700
<212> TYPE: DNA
<213> ORGANISM: Homo sapiens

<400> SEQUENCE: 168

```
tgaggctcaa aacaggtgtc tgtgagcttc acaggcggta aggccgtgtc tacatggccg     60

ggacatgcat cccggggctg cccctgccgt gctgcccgag tgcacggggg atgaggacct    120

gacaaggcca ttgatcttgc gggagcttcc tgaactactc cagcgtgaaa atcttccaga    180

aggattctcc acagggcaat gaggcaagaa atttacagct tagcctgatt aatgggccag    240

gcagttaaga gttctttgcc aagctatgag cataatttat agtcatcacg gcaggaggaa    300

aggccacata actcacatcc ttaaagggcc cttagaacaa gagacacgcc ggatcattga    360

aaacgtctcc actcctggcg ccaaaagaga tcggcacgtt tctgggtatt ctggtcaaag    420

aacagggagt ctggattaat atacacggca gaaaaaagcg aagaaaagac acacaggtca    480

tatatttctg actgatattc cgtttgttgt tttcggaggg acttggtatt tatttaacca    540

cattctcact tgacacgccc cctccccaca ccttgtaaat gccttcctct ttagccgagt    600

catttttcat cacatagaat tgaaatgttg ccaggaaggc ggtttatgag attgtagaaa    660

tggcactaga gaaagcagtg tgaaaagagg cctagaacgt                          700
```

<210> SEQ ID NO 169
<211> LENGTH: 600
<212> TYPE: DNA
<213> ORGANISM: Homo sapiens

<400> SEQUENCE: 169

```
tctctacatg ctatctacta aaaacttagg caaggaaatg catcagacca aacaccccac     60

agcacagaga accgaccggc cattgctttc caatctccgc aaacctaacc attgctggaa    120

gaaatcttac tcacagtgca cagacagtag gtattttatt gaagataaac atatagtgga    180

acaaaccaaa ttacccccat ttgagttacg tgagcactca gttctcagcg tggatgtccc    240

acaaatcaag tcaacatttg cgtcccatta ccagcagcca cttgccgagt atctcttcgc    300

ttccactggg actgcctggc atccctgatg ctaaggagcc actgaagagc ctccaaatgt    360

ctgacattca caaacgcatc ttttgctttg acccgaccct tcaacctctc cgagtctgct    420

gccttttctc agacacacat ccaggcaccg ttagggatag ttagagaatc tgaaaattca    480

gaagcgctcc gaaaagcctt tccaaaagta atccacagca ctcaacagtg aatttagaaa    540

ccccaatttt tttctgagtt tgaagttttt aagccttgcg gatggttgga gtaggaaaaa    600
```

<210> SEQ ID NO 170
<211> LENGTH: 1100
<212> TYPE: DNA
<213> ORGANISM: Homo sapiens

<400> SEQUENCE: 170

```
tcagacaagc tctgtgcagt cggaattttt taaagatgca ctgtcacttg aggaagacag     60

gtgatcttcc tgcggcacaa atagaagcaa agagatttct cttcttctct gtagagcaac    120
```

```
acaattgata aatggccgat aatctccacc aaattggcag cagtaggctg cccgaaggca    180

gcaggcatat tcgtctttgt gaattgtttt actatgatgc tgtcacattt ccaggaataa    240

gacggttaaa atgatatatt gttgtggttt ggcatttgca gctttgctct gacttccctg    300

gtaactgcca acatctgcaa attattatgt gcttaaaaaa aaaatcaacc gccaccgcag    360

gctgccccca cggtccctgg ctgggccagg cctcctgcca ggccacaggg cagagttctt    420

ggaccaggag gcagcagggt caaaacccag gttgcctagg aagcccccaa agacagttat    480

ggatagagct gggagcccga aacacatgcg gcagtctctc agtttccagg taccggttct    540

cacatcatcc atgcatgtgt ttgaggaaaa acaaaaaaaa attgatggtt gccaaaaaca    600

aaaatgcttc catatcaaag tttatcagtg tcaatgtcaa gagacttctg gttcgtagac    660

tcattttggc ttgaggccac cagaagtgaa ctctggtttc taaatgcaga agcagaggca    720

ctggccgatc atggaagatg cagggaactg ttcaagaggc ccaagcctgg tgctcagaaa    780

cttggcagga tcaagcatct cgcccaggaa ttcatcccct gcttgtctaa gccggctggc    840

tctcgtgact gactcggaac aacagagcag atgtttgcgt gggaggcaag cctcacccaa    900

catctgtcct gcggcgggaa ggcctgggtg ttcacagata gagctggagt tccccggtgg    960

gtggcacaga caattagctg ggctgcctcc acatgtaatc taattacagg ggaaacaggc   1020

tcaaacaccg ggtgataagc agcgcaactg tttcgggtga ctctgtaatt tttcctccat   1080

taattttctc cataacgcac                                               1100
```

<210> SEQ ID NO 171
<211> LENGTH: 250
<212> TYPE: DNA
<213> ORGANISM: Homo sapiens

<400> SEQUENCE: 171

```
gttgcctggg atatgcttat atcaaaaact tacgtgtcac ttacctagca tttgcatttc     60

actgggcctc ctaaattctg tgtggtaacc gactgccacc ggacatgctg tttacttctc    120

tatcctcacg cagccagttg ccacattcaa cataacactg caaatattgc cggtggatcc    180

tgacttcctc gtggacccta ctgtgtcggg aaaaacaaac aaacgaaccc tggaaggaaa    240

caccatgagt                                                           250
```

<210> SEQ ID NO 172
<211> LENGTH: 600
<212> TYPE: DNA
<213> ORGANISM: Homo sapiens

<400> SEQUENCE: 172

```
tcataaatat ttccaaatgt attcctattt gtctctacag agtctaacag acataaatag     60

cgaattgaag gttctgtctt aaaacccagc agaaagaaaa acaatgacca gaaaaaaaaa    120

acaattgtct ttggcttccc aagaacagca tcggatttca actggaacca cagatggtcc    180

gttgatagaa gcgactactt tttagctctg gaggacgaca aaaggaacca gcttcttcct    240

gtgggtgtca cagcgaggtc gcctggccac atcaggtacc agagcgagcg ccctcacctg    300

ataggccctg tacaacctca gccacagcac tgtcaggagg aacacgcgga actagcaacc    360

taggagggta aaggcggagt tgggagggaa cacgaggcag gcaggtcggc tggctgctga    420

gctacaggct gcactcctag gacgtctacg tgtaattgag aaaaataaga caaaaataac    480

ttactgtgca ggcaattaat tctggttggc atagcgatcc tcttaagtta aagggaatga    540
```

gcatgagatg aagagaagta agaggcagaa agaattatgc aagagcaaca tcagagtgga 600

<210> SEQ ID NO 173
<211> LENGTH: 2000
<212> TYPE: DNA
<213> ORGANISM: Homo sapiens

<400> SEQUENCE: 173
acgccgagcc gcctctgcag gggaaaccga agcagatgtg gtgagataat acatccaacc 60
ctgagtgcta ctctaacctg ccagaggcgg agggttctca gtgagatgaa agcattacag 120
atgcgttaga tctaagggag gggcctgcag atgcgcagct ggcagagaaa ccagggaggg 180
gctgaactgt cagtcgcgac caccagggat ctgaatcagt tcaccgacag ccttggggac 240
attcaccttg ggctccacaa cctgtcagaa atgcccccaa gcccaaaggc gtcgagagaa 300
tggccaggtt gtttcagatt gacacatatc ctaatgtaca agtcagccca cacaccccac 360
gtgcactgag cgtctcttgt tgttcacccc aaataaactc tgccggaact ggggcgggac 420
tcgcaggggc ggagaagggg ggagacgggc agagggcaga agtggatggt gagaagagcc 480
aatggagggg ccccgtgaga gtgagcaagg ctgcacccct aaccgacgtc ctggggctac 540
tgtacaaaca aagaaccaca ggctgggagg ctgaacaaca gacctgcact ctctcgcagc 600
tcggaggctg caggtctgaa atcgaggggc tgacagcgct ggtttcctct ggaggctgcg 660
agggagaaac cgtcccctgc ctctcccagg ctctggggtg agcccttcct ggcatcccgg 720
gctcattgta gatggatcac tccaatctcc atggcttctc agggcttccc tccatgcacc 780
tcaaatctct ctctccttcc ttttgtaagg atgccagtca ttggatttag gttcacctta 840
aatccaggat gatctcatct aaattacatc tgcaaaaaga cccttttttcc aagtaagttg 900 acattcacag gtacctgggg ttaggattgg acatatcttt tgcaggggtg caggggggctg 960 ccactgagcc cgctgcacag ggtgacctgg gccaagggcc cttcactttc acttcctcat 1020
tggcaagctg ccctgtgttt ggactgggtc gaggctgtca accttgctgc ccctcggagt 1080 ccccccctggt gtcccccaaa cagattctaa gctgctttcc tggggctgga ggccaggcat 1140
tgggattttt taaagagctt cccagcaggt gagcagcctt tcatgggtat caggagacct 1200
tcctggcaaa tgtggtgaag gtccttcctc ctgagcgatg ccttagaccc aggagcccag 1260
ggaggctgct cacctgatcg ttaggacagg agcagtggaa acctctggcc tcagaccccc 1320
tggaggaatc cctccctcta agactctggg actggtgcac gcaaggagct atcgtgaaca 1380
ttgctcccaa ctggccgctt gcttgtcccc cggctcccct tggccccagt ggcggctttg 1440
cctgaattag agggcgtgag agccacctgt gtctcagcac tgcaattaaa gcaggaagcc 1500
ctttcggaag cagccgtgtg caccagcctc ccatgggtgg agcagagcaa accacccact 1560
tctgccctct gcccttcttc ccttttctcg acaccctgcg gccccccagt ttcagcagag 1620
tttatttggg gtgaaaaaca agagatgctc agcgcctgtg ggatgtgtgg gctgactcgt 1680
acattaggat gtgtgtcaat ctgaaataac ctggccgtta tatggatgcc ttggggcttg 1740
gggggtttct ggcagtctgt cgagcccgag gtgaatgtcc ccaaggctgc tggtgaatca 1800
gatccctggc gttctccgtt ggcagttcag cccaacagtt tctctgccgg ccgtgcctct 1860
gcaggtccct cctctgatct gattggatta atatttgaat caatagactg agtcaagcag 1920
aatgtgggtg ggcctcatgc aatcagctga agccctgaaa agagcaaaag ggctgcccct 1980
tcccccgagg aggagagaac 2000

```
<210> SEQ ID NO 174
<211> LENGTH: 200
<212> TYPE: DNA
<213> ORGANISM: Homo sapiens

<400> SEQUENCE: 174

gaatgttcaa agaaagagcc ctccttgcct tcctcttctt ccacccctgc cctctgcaga     60

ctggggttct gtagaccccc aaagtaagtc cgccacaccg gaaggaagtg agttacacag    120

gggcccacat gggaaccgct ttttgtcctg tcttggtggg aaaatggcca cgaccccagc    180

ccaggctctg ccacgccaca                                                200


<210> SEQ ID NO 175
<211> LENGTH: 400
<212> TYPE: DNA
<213> ORGANISM: Homo sapiens

<400> SEQUENCE: 175

aggcagcagg gttaggactt caacatacaa cttttggggg gagatgtact tcagcccata     60

acacaccacg tgggaggata acaccgattt cagagcttgc agaggaagcc gccaggaact    120

ccagtgagac atcagccccc aggtgcctgt caggcacgcc gggctgtggg gggcacctgg    180

gcccatctga gtaacggagg cgcatccgca cttcccccag gagtacattt ttagaaccca    240

cagcgccata aaccaaagac aaggagactt cctggtgccc cgtcagcttc tggaggcgac    300

gttctcggct gacagctctg gcagcctccc ctgtaggtga gagacaggta aatgggactc    360

ttgcttccaa aacggaacag ggtaaaaatt ctcaagcgtt                          400


<210> SEQ ID NO 176
<211> LENGTH: 300
<212> TYPE: DNA
<213> ORGANISM: Homo sapiens

<400> SEQUENCE: 176

ttaaagggga gtggttgtat gaagagttcc tcagtcaaag gtgtgcagct gggaagccca     60

ccccacctaa gagggaggtc tgacaaactg tccacactga accactcaga cctgcatcag    120

ggccccgttt cttccataag ccgccaagta cagccctgag tcaactgaac tcaggcctgg    180

gaggcttccc aaagctgact tgactcagct ttgaactgaa atgaccgtac catgacaacc    240

ctgatgaaaa gctaaactga gcccaattat tcaacagtaa aattcagttg gtctcactca    300


<210> SEQ ID NO 177
<211> LENGTH: 450
<212> TYPE: DNA
<213> ORGANISM: Homo sapiens

<400> SEQUENCE: 177

tgctaccagc tgcttgggct tgggcaagtc accctagctc tcagatgtca tctgtaaatg     60

atgacaatgc caatgtggca ctgttctgag agtcagacag aacgtatgtg tgcttcacat    120

atggtgctca tgaagtgcta tcattatcta aggaaaacag aaaacgaagt tcagagtctc    180

tctaaacgca tgacaccaga ccaacaggga gtttcaaaaa ataggtctga agtaaatcaa    240

ttctcctggt ctcaatacac tgaaaacaaa ctattagggg actgaccgaa cccaccttag    300

gaaccacctt acgtcacctt ctgtctctac tgcaaaaccc tcccttaata ctgttcaaat    360

acgctgacaa tccagatcca tatccaatgg aaccagcaat catgcctgtg tgccagcaat    420

gtcagggagg gaagccgatc tctgatgaat                                     450
```

<210> SEQ ID NO 178
<211> LENGTH: 1300
<212> TYPE: DNA
<213> ORGANISM: Homo sapiens

<400> SEQUENCE: 178

```
caagcctgtg gtagggacca ggtcagagta aacaggaaga cagctttcgg ccaggcggtg      60
cacctcggtg ccggtgagtg tgagcgtgtg tgcgtgtgca cgtgtgcaga tgtgtgtgga     120
cgctcccttc tccgcagcag ctcctgaccc cctgcaggtg accctcagcc agccccaggg     180
ctgcccccac tctcccctgt ggacacctac ctcatttggg gtgaagtggg gggactgggg     240
tgtgaggggt gctttggggg gcacacttcg acccctctct ctgcaggcca agtcctgagg     300
ctcagtttcc tcctctgtgc cccggcgacg tggtgcaggc ctcgcgagtg acgtgagggt     360
tcatgaccca ggtgtgggca gccagccctt cacgggaggc cacccacctg gccacagtgc     420
ctgggaattt aggtcgggca ctgccgatat gtcgccttcc acaaggcggg cccgggcctc     480
tgctgaccgt gcaccggtcc tggggctggg taattctgca gcagcagcgc agcccatgcc     540
ggggaatttg cgggcagagg agacagtgag gcccgcgttc tgtgcgggaa ctcccgagct     600
cacagagccc aagaccacac ggctgcatct gcttggctga ctgggccagg cccacgcgta     660
gtaacccgga cgtctctctc tcacagtccc cttgcgtctg gccagggagc tgccaggctg     720
caccccgcgg tggggatcgg gagaggggca gtgtcgccca tccccggaag gctgagcctg     780
gtgcagccag ggagtgaggg ggcgggaagc cggggtgctg ccctgagggt gccccgacac     840
gctctcctgg ggccctgagc ggctgccacg tgcgtccagg gttctggcca cagggtgggc     900
aggggccctg tgctcctcac tggaggcccc tgaggctctg gaactgagac catccacccg     960
ccggccccct ctcgccggct ccggcacccc tgcctactgt gacttcctgc cccggactcg    1020
ctctgccagc ttggggcaaa ccacttccct ctggggtttt cacttccctc tttcccaagt    1080
ggggaaagac cacctgtccc cgacccagaa agggcccctg cccgagggca gcagcagtgc    1140
caggctggca tgtgaggctt ggggcaggcc cggcccccag aggcacaggg cgatgctctg    1200
tgggacgctg tgtcgtttct aagtacaagg tcaggagagg agccccctga ccccggaggg    1260
gaggagaggc agggcaggaa accgccacca tctcagccca                          1300
```

<210> SEQ ID NO 179
<211> LENGTH: 200
<212> TYPE: DNA
<213> ORGANISM: Homo sapiens

<400> SEQUENCE: 179

```
gcccactgtg ggtgtgcccg tgtgtgtggc tgtgaggcgt gagtgcaggc gtgaagtgtc      60
tgggagtggg agcgggcatg agtgtgtgcc acgggcctgc tgttgggtcc ttggaggcca     120
cggttgcccc tgaagggact gcaagctctt ttttgatttg tagttatttg agaagtctat     180
acaggaagaa aattaaaccg                                                 200
```

<210> SEQ ID NO 180
<211> LENGTH: 1000
<212> TYPE: DNA
<213> ORGANISM: Homo sapiens

<400> SEQUENCE: 180

```
agcgcccagc gcagggccgg gacccagagt ggactctacc gtggggctgc ctcaaagaaa      60
tctcagcaaa cacaggaagc cagcccaccc gtgcagccat ggggccagga agcccgccct     120
```

```
ttaccaagtc atttgggcat tttttctctg tgctaacagc ccagatggag ccatagcctc    180

aacctctgtg ttctgataac accaagctgg gacgccggag ccatgcaggg gacagtgccc    240

ggcctgaggc tgcagcctgg gtctggatgc ctttctaatt cagggcctcc tcatggcctg    300

gttccataaa tggtcaaatg cagcctgaca gcgcagcctc ctatcagcgc tgggctccgt    360

accgccacac agcccacata ccccgttccc caggagacgc ccgcaggtgg gcagcgtcac    420

tcccacccgc cgagcacacg ctgtccccgt ctcgtgtccc gaggagccgg aagcagctgc    480

ttcctcccag cctgaaagct gcacctcggg ctgcactcgg ctccccgaac ccgccctccg    540

ctgccctgca attcgccaag ggagctaccc ttcccatata aaaatttcac ctccatttcc    600

ttgtagagaa gaaacatttc tgacagcaag gaagattcta atttgaaaag caagtgattc    660

atctcccggt gccaaacagc agacgcaggc gttaccagtc tgggtggggc gcccgagctg    720

gggacctggg gtcctctggg aggggcaaga aggcagcgat gctggccccc gcctccatct    780

gcccatccca tctgcttcca cacaccgccc tgccgtagct gcttgcagcc cttctctgtc    840

agtttctcca tcttttggtt tggtgataaa tgagagttcc catcgggtgt gccaccctct    900

gtgtgacggg gagcagagaa gaccctgcgt ccaagtcctc ctgggggaag agcgaagatg    960

ctgggaccag ccccagctgt caggggggtct ccaatcccag                        1000
```

<210> SEQ ID NO 181
<211> LENGTH: 300
<212> TYPE: DNA
<213> ORGANISM: Homo sapiens

<400> SEQUENCE: 181

```
cgcacacaca gcacagacgc ctgcatcttc ccatgcgtgg tttctgctct tgcctctctg     60

ggtttttgtt tcacttcggt cgagtttttg gtggtgttga gcggatagcc ggggaagttg    120

gagtcttgtt tgtggccgcc tcgtgctcgt gtctgtatct aagatcctca ggctgctcct    180

ttttgggtaa ggtctgttgc ttctctagga acagtgacgg tggcagagcc cgtggcccct    240

ctctcctgtc ccagagccaa gctgtttcct ctccccactc ccgggcaccc tgcgggcaag    300
```

<210> SEQ ID NO 182
<211> LENGTH: 5000
<212> TYPE: DNA
<213> ORGANISM: Homo sapiens

<400> SEQUENCE: 182

```
aagaggaaat tcccacctaa taaattttgg tcagaccggt tgatctcaaa accctgtctc     60

ctgataagat gttatcaatg acaatggtgc ccgaaacttc attagcaatt ttaatttcgc    120

cttggagctg tggtcctgtg atctcgccct gcctccactg gccttgtgat attctattac    180

cctgttaagt acttgctgtc tgtcacccac acctattcgc acactccttc cccttttgaa    240

actccctaat aaaaacttgc tggtttttgc ggcttgtggg gcatcacaga tcctaccaac    300

gtgtgatgtc tcccccggac gcccagcttt aaaatttctc tcttttgtac tctgtccctt    360

tatttctcaa gccagtcgat gcttaggaaa atagaaaaga acctacgtga ttatcggggc    420

aggtcccccg ataaccccca gctgcagatc gaggcctagt gcgagcacag gtccccccag    480

acccttccca gtgcccacca accggcggcc taggccaggt agaactggca gcgcctcccc    540

tgctgcaaca ccaggctctg gtagaaactt cagaaaacat gcaccggcaa aaccaaggaa    600

gggtggctgc gtcccgggtt cttccgcgca gctgtgtgta cacgcatgca cacacccaca    660
```

```
cgcacacacc cacgtgcaca cccccatgca cacgcaccca cttgcacgcc catgcacgca    720
cacacgcgcg tgcacccatg cgcacgcacc catgcacaca cacgcgcgca cacacccacg    780
tgcgcaccca catgtacaca cccacgtgca cacacccacg cgtacacacc cacgcgcaca    840
caccgctgtc cccagccgtg cagaacgatc ctccctgagt ccccggctcc gacccacacg    900
cagcactcgc taaacgcttc ccacgcagtc gttttgctgg gttgcgcttc acccacttct    960
cagagggggc ggccgaggca gaggtgtcgg ggatcgagca gctccgggcc tcaggggtcg   1020
ccccgccacc gttttccttt cccagatgct gggacggggg cagggagggg ctccccaggc   1080
tgaacccgac taggtcaccc tagaagcgag gcgagcttct cttctgtttt tcttcggcgc   1140
ccctgagccc ctgacagtgc ccaagctgcc catgggattg gattcgccag agcctcctac   1200
gcagacccca cccagggcca aagccaaccc caagccccac caccttggtg gtgtgggatg   1260
aaaagtgagc catcgagaga tggggtcccc ccacccccaa cccctccaag gacaaaggcg   1320
ggctgggaag cacccgcttt cacgtccgcc cctgcccggc tttcctagcg gaattggcgc   1380
cggcatcagt tgggggttgt gggatcagtg aggaatcccg tggggtcgcc tccatttatc   1440
agttgtgtgg ggttgggcga gcacccctag ccccagccca ggcgatcagg gcgcgaagcc   1500
cactggacgc ggatttggga ttaggacggg ggtgacagcc aggaggaccg cacctgccct   1560
ccccactcct gccgctccac ccctgccccc accgcaacac caaggtctcc accaggaaga   1620
tgggggtggg gaaaggacgc ggggtggggg ggggtgcggg gagagaggac acagggtcgg   1680
aagggtgagg ggtagtggca gaggcggagg ccgaggccac gcagctgcgg ggcgcaggga   1740
ggggcagagg aggggcgttc agatgggaac ctagtccaga cccgtcgggg ccctcgtgtg   1800
cggctcgtta tcctggaacc agagaggctg gagacccttg gcttgtctgg agcggaaccg   1860
tagtgtccaa tagagtgtgt ggggctcagc cctaaagcta aacattcttt atttcctgat   1920
gaccatgggg gcggagcggg ggaaaagccc tggccttata gtttagaatt ttataaaagg   1980
aaaggcgtgg ccactgacaa tttgcgcttc aggagtccca gagtgaccgc ctggctcgga   2040
gcagggaatg agggggtcct taactctgag atttgttttc tgagagacaa aggtgatggg   2100
tgaggcggct aagcctctga ttctctatag gtggcggtca ttcatttcag aacatgaatg   2160
gattcagtaa ataaacatga tagaaaaatg ccacaagccc taggcccatt ggagtggact   2220
ggacagtctg ttcccagtgt gtccctcagc ctcggtcccc caccccttccc ggagccctgg   2280
gggtcacaca catccctcct ggctgcctag cctgtgcccc ccgattcccc ccctccccgc   2340
cccgcgcgtg cacacacaca cacacacaca cacacacaca cacacacacc acacagcacg   2400
aggcgacaga gatatgagag agagcgagcg agagaggacg ggagagagag ggagtgcaag   2460
tgtgcgctgg gggtaacccg tgcatgcatg cattgggggt aacaggctgg agctcagatc   2520
cctcccccag cccccagcag gggggactgc aggctcctgg tctgagtggg gagctgggcc   2580
ccctggacag aggactgggc tgcggggtca ggaatgggca cacttcctaa ctgcaggaca   2640
ctctaagggc tttggtcatg cacacgcagc caagagaagg tgtcgctggc acacagcctt   2700
ccaggagcgg acttggagac ctcgccaagg accaggactc cccagcactc acactccctt   2760
aggcgctgaa gtccagagga cagaggttga gggcagagct cctgggagca ccagtggaag   2820
taggagggct gggctggaaa acctccccca acctcctatt gcaaagaggc tccagccagc   2880
agcctccaca ccccagtgat cttttaagat gcaaatctgc gccatcattt atttcctcag   2940
tgccttctcc agctcctggg atgcacactg cccgtcccca ggcccagaga cctgaccacc   3000
ctcattcctc cctcagccca ccctggggtc tctccaccag ctgacagcct tcctgcagtc   3060
```

```
cccteccega atgctgctcc ctgaggccct cctggacacc tgcagggcag gcacagcccg   3120

cgggacctca cagcacttgc tccgggcaga gctgcagttt ggccaagttg ccagctccgt   3180

gtgggcaggg gccctggcct gtggctgcca catcccgggt gggggcacgg cctttcctgg   3240

cgtggatgct gagcaaacgt agggggaagg ggagtgaatg aggagagcca ggtagctcag   3300

gggctgaggc ctcactgagc agggtcccgc gtgaccggtc ccaccgctg acggttcctg    3360

gggtaacact caggacaggg agaggcaatg gaaagagacg tggccgccct cgcatcctgc   3420

agctcccgca ctcccagcct cccagcctcc cacccagccc cccagagccc accagtgacc   3480

ccgcccactg ggtcctcaga tggctcccac gggatctcct gccttgatct cctgtccaca   3540

tggaggtgaa gtgggttgct ctgaatgagg ggtgccgagc ctagggcgca gcccactctc   3600

ctgggtccgc agcatcacgc agcccggacc acaggctcct tacaagaatc ggaagggtcc   3660

ctgcaatcgc ccttcgcact gaggcttcct actgtgtggt gtaaaaacac aggcttgtcc   3720

tcccttgctg cccacggggc tggagccgcc tgaaaatccc agcccacaac ttccccaaag   3780

cctggcagtc acttgaatag ccaaatgagt cctagaaagc gagagacgag aggggaatga   3840

gcgccgaaaa tcaaagcagg ttcccctcct gacaactcca gagaaggcgc atgggccccg   3900

tggcagaccc gaacccccag cctcgcgacc gcctgtgacc tgcgggtcaa ccacccgccg   3960

cggctccacg ccgtgggcac agactcaggg agcaggatga gaaagctgag acggcgcagc   4020

cacggcccgg tgccttcacg cgcacagcga cacagcccca gccagcgggg cccacgctaa   4080

ggcggaatcc cacagaagcc tacagagcga gcgcgcgcct gtgcttccca aaacggaatg   4140

gaaccaaggt gacttctaca gaacgatctg aagccctggc tggcccttat gctagtctct   4200

tgggagcgtt ccaaatgcag ctcaatatta cttacttgac ttttatcttt cctccctggt   4260

tcgtggtatt tataactggg tcatctttta actatttgca acgtagcttc aggggagagg   4320

gggagggctt tataaataac ctgtattatt attatgcagg ttgattctgt tccctgagct   4380

aaagggaaca tgaaaataca tgtctgtgac tcatgccccc ccacccccac tccagggtgt   4440

gctgaggagt ctctcagctg ccccggggtc ctcgagcagg ggagggagaa aggctggcgc   4500

tgcgccctcc atcgcgtgaa gccaggggat tttgctctgc gacaagctga cttggctctc   4560

gtattgtttg cagaatcacc cagttccaag gcagtccctg cgggcaggtg cagctgtgcg   4620

ggagcttcag tcctgtcccc aacacccagg cagtaatggt tccagcacgg aaggtctacc   4680

tacctcccac tgcacagccc gagggctgtc ctggaggcac agccatccgt ccctgggtgg   4740

gcaggcacgt ttatgacccc cacccccacc cccaccccc acgcgagtca gcacgttcca    4800

tactcgggtg atcgtgctca tcccctggtc atgtcatcgg gatctgagtg ccatccgagc   4860

agagagctgt ggcccggtgc cgggggtgga cttcatctat tccagggaac caaggatgca   4920

tgatttgcaa acaaaaccag aagcgcaagc catctcctcg cctcccctga tagccgtgct   4980

gcggagcctg agtgctggag                                               5000
```

<210> SEQ ID NO 183
<211> LENGTH: 400
<212> TYPE: DNA
<213> ORGANISM: Homo sapiens

<400> SEQUENCE: 183

```
tgcgtttagt gtaaaaatat caggtgtggc tgcacggagt gaaaaatcac aggctccacg     60

gagccgggag gcctgctgcc ctgccctctt gctttgatga ggaaatggcg accgcagaag    120
```

gaaatgtagc agcaccggca accggcatcc gtggggccac gccgggctgc ttcccagggc 180
cctccagcca agcagccaca ggaaagagta gatgttgatc ccaagctagg actgaggagt 240
ccgtccctaa gagccgaggg agtcaggtgg gcgaaactgg ccgcatgtct gggtacaact 300
gctcagggtt tctcatctgc tgaatcacca agctaggttc tgaagccagg cgtgagtgag 360
caggactgga gcaggattct gggaacaatc ttttccctcc 400

<210> SEQ ID NO 184
<211> LENGTH: 293
<212> TYPE: DNA
<213> ORGANISM: Homo sapiens

<400> SEQUENCE: 184
aggtggaggt tgcagtgagc cctcctcccc tcctccccct tcccttccca cctcccatgc 60
ccccctttct tcctcccact cccctcccga ggccccgctt attctcccgg cctgtggcgg 120
ttcgtgcact cgctgagctc aggttctggt gaaggtgccc ggagccgggt cccgccttcg 180
gcctgagcta gagccgcgcg ggcggccggc ttcccccaaa ccctgtggga ggggcatccc 240
gaggaggcga ccccagagag tggggcgcgg acaccttccc tggggagggc cag 293

<210> SEQ ID NO 185
<211> LENGTH: 474
<212> TYPE: DNA
<213> ORGANISM: Homo sapiens

<400> SEQUENCE: 185
ccttccagat gttccagaag gagaaggcgg tgctggacga gctgggccga cgcacgggga 60
cccggctgca gcccctgacc cggggcctct tcggagggag ctgagggccg cgttccttct 120
gaaagcggga cgcgggaggg gtggaggctg cggggagccg gggtcgcaca cgaataaata 180
acgaatgaac gtacgagggg aacctcctct tatttccttc acgttgcatc gggtattttt 240
cgttattgta aataaaacgg ttccgagccg tggcatcgag agggcgtctg gagttcaggg 300
aacgcgtggc ccccgcccgg gagcaccgcg cagcgctcgc ctctcgccct tcaagggggt 360
ccctgcccgg agcctgcgcc cccggagagg aaggggctcg aggggcttgg gtgccgcagc 420
gcgtccttcc gtagaaaagg cttgcgtcag tatttcctgc ttttacctcc tgag 474

<210> SEQ ID NO 186
<211> LENGTH: 346
<212> TYPE: DNA
<213> ORGANISM: Homo sapiens

<400> SEQUENCE: 186
cagtatttcc tgcttttacc tcctgagtat tggaatattc gagtaaaccc tggagtttca 60
gcgccagcgc acgcctcttc atcagggcag cgcgtcgcga gcgcgctggt tccccggggc 120
ctcccggcca cggacaccgc tctagccagg gccacggcga ggccgccgag cagcacctca 180
gagacctgcg tgagttctaa agcctggggc tactacaatt ctgctcatct gtttgtcctg 240
tgaaatgatt cagggacatg aaaatgcctt cccactgact tgcgtcctgt cttagcctgg 300
acttgtcccc ttgggaacac gggccaggcc cctctgttcc tgaagt 346

<210> SEQ ID NO 187
<211> LENGTH: 2000
<212> TYPE: DNA
<213> ORGANISM: Homo sapiens

<400> SEQUENCE: 187

```
catacatggt tattagaaaa ggcatctcat ccaaatgtgg tggctcgtgc ttgtaatccc     60
agtgcttcag gaggccaagg gaggaggatt acttgagcct aagagtttga gaccagcctg    120
ggcaacacaa caagaccttg cctctacaaa aaacttaaaa actagctggg tatgatggtg    180
cacacctgta gtcccagcta cttgggaggc ggaggcgggc agatcgcctg aggtcaggag    240
ttcgagacca gcctggccaa catgatgaaa ccccgtctct actaaaaata caaaaattag    300
ccgagtgtgg tggtgcatgc ctgtaatccc agctactcag gaggctgagg caggagaatc    360
acttgaaccc gggaggcgga ggttgccatg agccgagatc acgtcactgc actccagcct    420
gggtgacaga gcacaaaaga caggcatgac tttgtactta actgctcagc tttgtaatca    480
ctgggggccc agatgctcac ttggattcta actttgttgg catctgggcc taaaagccgt    540
gatgcaggtg agcaatgatg cagagggctc tgtgcgcctg gcgggctctg tttgcctgct    600
gggctctgtg cgcctgctgg gctctgtgcg cccgggaagg tgcggccacc ctcacgcgga    660
aggcggccag cggatcccgg tgcgcgcagc tcccagcgct ggggttccag cgccccgcct    720
cttcctatag caaccagcgg gacctgccgt cccccggggc accccgaggg gtctgcgccc    780
gcttctttcc gaaacgggaa ggcgctgggg gctcggcagc cagagggacg ggttcaggga    840
gcgtccggtg agcctaagac gcgcctttgc cggggttgcc gggtgtctgc ctctcactta    900
ggtattagga accgtggcac aaatctgtag gttttcctct gggggtgggc ggaggctcca    960
aaccggacgg ttttctcctg gaggactgtg ttcagacaga tactggtttc cttatccgca   1020
ggtgtgcgcg gcgctcgcaa gtggtcagca taacgccggg cgaattcgga aagcccgtgc   1080
gtccgtggac gacccacttg gaaggagttg ggagaagtcc ttgttcccac gcgcggacgc   1140
ttccctccgt gtgtccttcg agccacaaaa agcccagacc ctaacccgct cctttctccc   1200
gccgcgtcca tgcagaactc cgccgttcct gggaggggaa gcccgcgagg cgtcgggaga   1260
ggcacgtcct ccgtgagcaa agagctcctc cgagcgcgcg gcggggacgc tgggccgaca   1320
ggggaccgcg ggggcagggc ggagaggacc cgccctcgag tcggcccagc cctaacactc   1380
aggaccgcct ccagccggag gtctgcgccc ttctgaggac cctgcctggg ggagcttatt   1440
gcggttcttt tgcaaatacc cgctgcgctt ggacggagga agcgcccacg cgtcgacccc   1500
ggaaacgaag gcctccctga tgggaacgca tgcgtccagg agcctttatt tactcttaat   1560
tctgcccgat gcttgtacgt gtgtgaaatg cttcagatgc ttttgggagc gaggtgttac   1620
ataaatcatg gaaatgcctc ctggtctcac cacacccagg gtgacagctg agatgcggct   1680
tctccagggt ggagcctcct cgttttccag agctgcttgt tgaagtcttc ccagggcccc   1740
tgacttgcac tggaaactgc tcaccttggc atcgggatgt ggagcaagaa atgcttttgt   1800
tttcattcat cctagtgttc ataaaatgga aaacaaataa ggacatacaa aaacattaat   1860
aaaataaatt aatggaacta gatttttcag aaagcacaac aaacacaaaa tccaagtatt   1920
gccatgtcag caacacattc ctactttaag ttttatgaag ttaattggag tagtggagaa   1980
caaaagtgga tgtggggcag                                               2000
```

<210> SEQ ID NO 188
<211> LENGTH: 149
<212> TYPE: DNA
<213> ORGANISM: Homo sapiens

<400> SEQUENCE: 188

```
gctggaccag aaagtgttga gtacctgctc atgcgtgcaa gaggaggagg gaggagcaca     60
```

```
tcactgaact tcacatgaaa ttggataccc gggattagag acagtagagg gttttggtga    120

aatcagatac acattgcaaa gcagcacac                                     149


<210> SEQ ID NO 189
<211> LENGTH: 146
<212> TYPE: DNA
<213> ORGANISM: Homo sapiens

<400> SEQUENCE: 189

ggtcgagttt ttggtggtgt tgagcggata gccggggaag ttggagtctt gtttgtggcc     60

gcctcgtgct cgtgtctgta tctaagatcc tcaggctgct ccttttgggg taaggtctgt    120

tgcttctcta ggaacagtga cggtgg                                         146


<210> SEQ ID NO 190
<211> LENGTH: 133
<212> TYPE: DNA
<213> ORGANISM: Homo sapiens

<400> SEQUENCE: 190

cctcgtgctc gtgtctgtat ctaagatcct caggctgctc ctttttgggt aaggtctgtt     60

gcttctctag gaacagtgac ggtggcagag cccgtggccc ctctctcctg tcccagagcc    120

aagctgtttc ctc                                                       133


<210> SEQ ID NO 191
<211> LENGTH: 95
<212> TYPE: DNA
<213> ORGANISM: Homo sapiens

<400> SEQUENCE: 191

ctgttgcatg agagcagagg ggagatagag agagcttaat tataggtacc cgcgtgcagc     60

taaaaggagg gccagagata gtagcgaggg ggacg                                95


<210> SEQ ID NO 192
<211> LENGTH: 127
<212> TYPE: DNA
<213> ORGANISM: Homo sapiens

<400> SEQUENCE: 192

tgcaggatat ttggcaaggt ttcttactgt tccaagtttt ttttccgaaa acctcccttg     60

aaacttttgt gcttacttgt ggtaacatac ccataatata ccctcttaac catttctacc    120

ggcacag                                                              127


<210> SEQ ID NO 193
<211> LENGTH: 104
<212> TYPE: DNA
<213> ORGANISM: Homo sapiens

<400> SEQUENCE: 193

tgaatcagtt caccgacagc cttggggaca ttcaccttgg gctccacaac ctgtcagaaa     60

tgcccccaag cccaaaggcg tcgagagaat ggccaggttg tttc                     104


<210> SEQ ID NO 194
<211> LENGTH: 127
<212> TYPE: DNA
<213> ORGANISM: Homo sapiens

<400> SEQUENCE: 194

ccgttatatg gatgccttgg ggcttggggg gtttctggca gtctgtcgag cccgaggtga     60
```

-continued atgtccccaa ggctgctggt gaatcagatc cctggcgttc tccgttggca gttcagccca 120
acagttt 127

<210> SEQ ID NO 195
<211> LENGTH: 144
<212> TYPE: DNA
<213> ORGANISM: Homo sapiens

<400> SEQUENCE: 195
ccaggcaaga tggcttatgt ctttaatctc agctgtttgg gaagccaagt ggaaagattg 60
cttgaggcca ggagttcaag accaacctgg ataatgtaag aagacctcgt ctctataaaa 120
aattaaaaat tggctgagca tggt 144

<210> SEQ ID NO 196
<211> LENGTH: 110
<212> TYPE: DNA
<213> ORGANISM: Homo sapiens

<400> SEQUENCE: 196
gacccagacg atacctggaa attatttgct catgtggcag tcactgttga ttgcctaccc 60
aaagccatta ctccttctcc ccacctaaca gaagccgagt tttgttcagc 110

<210> SEQ ID NO 197
<211> LENGTH: 101
<212> TYPE: DNA
<213> ORGANISM: Homo sapiens

<400> SEQUENCE: 197
ccacatcctg gccatctact tcctcttaaa caagaaactg gagcgctatt tgtcaggggt 60
aagtgcgacc ctagaggcga tcgtctctgc tgtctgtgga a 101

<210> SEQ ID NO 198
<211> LENGTH: 88
<212> TYPE: DNA
<213> ORGANISM: Homo sapiens

<400> SEQUENCE: 198
tgagctcaca ggtctggaaa tggtctgaat agaaaggatt ggtctccgga ggaaagcata 60
ctcttcctat taccagaacc ctgtgggg 88

<210> SEQ ID NO 199
<211> LENGTH: 128
<212> TYPE: DNA
<213> ORGANISM: Homo sapiens

<400> SEQUENCE: 199
attctccaca gggcaatgag gcaagaaatt tacagcttag cctgattaat gggccaggca 60
gttaagagtt ctttgccaag ctatgagcat aatttatagt catcacggca ggaggaaagg 120
ccacataa 128

MULTIPLEX DETECTION OF DNA THAT ORIGINATES FROM A SPECIFIC CELL-TYPE

CROSS-REFERENCE TO RELATED APPLICATIONS

This application claims priority to European patent application 14 167 769.0 filed 9 May 2014, the entire disclosure of which is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 27, 2015, is named DFMP-112_SL.txt and is 53 kilobytes in size.

SEQUENCE LISTING

The instant application contains a Substitute Sequence Listing which has been submitted electronically in ASCII format and is hereby incorporated by reference in its entirety. Said ASCII copy, created on Sep. 28, 2017, is named DFMP-112-01_ST25 and is 296,000 bytes in size.

The present invention relates to methods to detect an amount of DNA that originates from cells of a given type, where the sample comprising such DNA in admixture with DNA that does not originate from such cells. Such methods are based on different methylation, at certain regions, of the DNA that originates from the given type of cells compared to the admixed DNA. Such methods have particular application in the detection, from a biological fluid from a pregnant female, of cell free DNA that originates from a foetus or the placenta of a foetus, or the detection, from a biological fluid from and individual, of cell free DNA that originates from cells of a tumour. Accordingly, such methods have diagnostic, prognostic and/or predictive utility for detecting an increased risk of an individual suffering from or developing a medical condition such as preeclampsia or cancer, and/or to aid subsequent diagnostic, prognostic and/or predictive methods such as the detection of chromosomal trisomy in a foetus, including for twin-pregnancies. The present invention also relates to compositions, kits, computer program products and other aspects that are used in, useful for or related to the practice of such methods.

Cell-free DNA (cfDNA), especially that found in plasma or serum, has been the subject of considerable research over the past decade. Despite the original finding of circulating cell-free nucleic acids in the bloodstream being described by Mandel and Metais as early as 1948 (Mandel and Metais 1948, CR Acad Sci Paris 142:241), it took until the mid 1990s for proof that tumours shed DNA into the circulatory system (Sorenson et al 1994, Cancer Epidemiol Biomarkers Prev 3:67; Vassioukhin et al 1994, Br J Haematol 86:774), and until 1997 for the discovery of cfDNA originating from a foetus in the circulatory system of the mother (Lo et al 1997, Lancet 350:485).

Among other forms of characteristics shown by circulating cfDNA, numerous studies have described the presence of methylated circulating cfDNA in the plasma/serum and other body fluids of patients with various types of malignancy and the absence of methylated DNA in normal control patients (for review see Muller and Widschwendter 2003, Expert Rev Mol Diagn 3:443). Although other characteristics of circulating cfDNA exist and are important for diagnostic, prognostic or predictive studies (for example, sequence mutations and micro duplications/deletions), such methylation-based epigenetic characteristics have become an increasingly important source of serologic markers for diagnosis, risk assessment and even for therapy monitoring during follow-up of cancer patients.

Likewise, the use of differences in foetal cfDNA present in the maternal circulation has been the main goal for the development of non-invasive prenatal tests (NIPT). Foetal cfDNA is derived from embryonic cell degradation in material peripheral blood (Lo et al 2000, Clin Chem 46:1301) or from apoptotic placental cells (Smid et al 2006, Prenat Diagn 26:785). It has been demonstrated that foetal cfDNA from maternal plasma is cleared immediately (within a few hours) after pregnancy (Lo et al 1999, Am J Hum Genet 64:218). This finding is of great importance, since the presence of foetal cfDNA from previous pregnancies would otherwise interfere with the correct interpretation of subsequent pregnancies.

It is believed that 60% of tissue-specific differentially methylated regions are methylated in embryonic cells, while during the differentiation of embryonic tissues to adult tissues, they undergo de-methylation (Kawai et al 1993, Nucleic Acids Res 21:5604). Based on the evidence that foetal cfDNA in maternal plasma is of placental origin, epigenetic differences between maternal peripheral (whole) blood and placental DNA have been used to detect a hypomethylated gene sequence (maspin/SERPINB5) in maternal plasma derived from the foetus (Masuzaki et al 2004, J Med Genet 41:289; Fiori et al 2004, Hum Reprod 19:723; Chim et al 2005, Proc Natl Acad Sci USA 102: 14753). Subsequently, a number of additional differential foetal methylation-based epigenetic molecular markers have been described, including the RASSF1A gene on chromosome 3, as well as a marker on chromosome 21 (Chiu et al 2007, Am J. Pathol 170:941; Old et al 2007, Reprod Biomed Online 15:22; Chim et al 2008, Clin Chem 54:500) and others including T-box 3 (TBX3) (Nygren et al 2010, Clin Chem 65:10, WO 2010/033639; WO 2011/034631).

Various methodologies exist for NIPT based on the analysis of foetal cfDNA. For example, foetal sex determination using eg DYS14 (Lo et al 1997; Lancet 350:485), as well as foetal Rhesus D found in maternal circulation in pregnancies in which the mother was Rhesus D negative (Lo 1998, N Eng J Med 339:1734). Also, and of particular relevance, are those using next generation sequencing (NGS) technologies on cfDNA isolated from maternal plasma with the primary aim of detecting the most common chromosomal aneuploidies as commercially available tests (for example, those using random massively parallel sequencing: www.sequenom.com; www.lifecodexx.com; www.verinata.com). Other technologies include targeted approaches, the aim of which is to enrich specific genomic regions of interest before sequencing to reduce the number of sequence tags needed to perform a reliable statistical analysis (eg www.ariosadx.com or www.natera.com), polymorphism analysis or digital PCR (for review, see Go et al 2011, Human Reprod Update 17:372). However, regardless of the specific technology used, current applications of NIPT rely on the qualitative detection of foetal cfDNA to determine the genetic makeup of the foetus. Such an approach leads to an analytic dilemma, because test results from samples that do not contain any or sufficient foetal DNA or are contaminated with maternal cellular DNA can be misleading. The analogous issue arises in diagnostic, prognostic or predicative tests of tumour derived cfDNA from the circulatory system:

the quality of the test result often is dependent on the presence of sufficient, or sufficiently pure, tumour-derived cfDNA in the total DNA from the sample.

The quantitative determination of an amount of DNA originating from such a cell type may, in itself, form a critical part of a diagnostic, prognostic or predicative test. For example, even though studies have demonstrated that the amount of foetal DNA released in maternal circulation increases with pregnancy progression (Lo et al 1998, Am J Hum Genet 62:768), preeclampsia, which results from abnormal trophoblast invasion, is also associated with further elevated foetal cfDNA levels in the maternal circulation. Lo et al (1999, Clin Chem 45:184) demonstrated a fivefold increase in circulating foetal cfDNA concentrations in the plasma of symptomatic preeclamptic women compared with control pregnant subjects, and further studies have investigated if elevated serum foetal cfDNA developed into early-onset preeclampsia (Yu et al 2013, Int J Mol Sci 14:7571), and the potential of cfDNA as a marker for preeclampsia is being increasingly studied (for review, see Hahn et al 2011, Placental 32(Supl):S17). An increased level of circulating cfDNA and/or the level of methylation of such DNA at certain regions is also associated with other medical conditions. For example, hypermethylation of serum cfDNA was found to be common in patients suffering from oesophageal squamous cell carcinoma, and diagnostic accuracy was increased when methylation of multiple genes (RAR-beta, DAPK, CDH1, p16 and RASSF1A) were analysed in combination (Li et al 2011, Epigenetics 6:307). Elevated levels of circulating cfDNA have been reported in patients with acute dengue virus infection (Ha et al 2011, PLoS One 6(10):e25969), in acute Puumala hantavirus infection Outinen et al 2012, PLoS One 7(2):e31455) and high cfDNA has been reported to predict fatal outcome among *Staphylococcus aureus* bacteraemia patients with intensive care unit treatment (Forsblom et al 2014, PLoS One 10; 9(2): e87741.

It is known that foetal cfDNA present in the maternal circulatory system and tumour derived circulating cfDNA is degraded. For example, studies characterising cfDNA in maternal plasma have found that the size of foetal DNA fragments were estimated to be <0.3 kb, whereas that of maternal DNA was >1 kb (Chan et al 2004, Clin Chem 50:88). Follow-up studies have demonstrated that the release of foetal DNA is due to the apoptosis of no more than three nucleosomal complexes, it has also been shown that the average foetal fragment size is 286+/−28 bp with a maximum foetal cfDNA fragment size ranging from 219 to 313 bp (Kimura et al 2011, Nagoya J Med Sci 73:129), and another study has reported that the most significant difference in the size distribution between foetal and total DNA is that foetal DNA exhibits a reduction in a 166-bp peak size and a relative prominence of the 143-bp peak, the latter likely corresponding to the trimming of a ~20-bp linker fragment from a nucleosome to its core particle of ~146 bp (Lo et al 2010, Sci Transl Med 2:61).

In cancer patients, circulating cfDNA in plasma is protein-bound (nucleosomal) DNA and has a short half-life (10 to 15 min) which is removed mainly by the liver (Elshimali et al 2013, Int J Mol Sci 14:18925). Accumulation of cfDNA in the circulation of cancer patients can result from an excessive release of DNA caused by massive cell death, inefficient removal of the dead cells, or a combination of both (Zeerleder 2006, Crit Care 10:142). It should be noted that although cancer patients requiring renal support have higher values of circulating cfDNA, the renal elimination is not the main mechanism of its clearance. The plasma levels of circulating cfDNA do not seem to be dramatically altered in chronic kidney disease, peritoneal dialysis or hemodialysis (Kirsch et al 2008, Ann NY Acad Sci 1137:135).

Although the nucleosome is a very stable protein-DNA complex, it is not static and has been shown to undergo a number of different structural re-arrangements including nucleosome sliding and DNA site exposure. Depending on the context, nucleosomes can inhibit or facilitate transcription factor binding. Also, packaging of DNA into nucleosomes varies depending on the cell cycle stage and by local DNA region (Russell 2010, "iGenetics". 3rd ed. San Francisco: Pearson Benjamin Cummings, pp 24-27). The degree to which chromatin is condensed is associated with a certain transcriptional state. Unpackaged or loose chromatin is more transcriptionally active than tightly packaged chromatin because it is more accessible to transcriptional machinery. By remodeling chromatin structure and changing the density of DNA packaging, gene expression can thus be modulated. Accordingly, and without being bound by theory, the qualitative and/or quantitative level of chromatin packing of a given region of cfDNA may affect its stability, and hence the amount detected in the circulatory system at any given time. Correspondingly, differences between the level of chromatin packing between different DNA regions (for example, due to differences in each regions state of transcription) may influence the relative quantities of DNA from each of these regions when detected as cfDNA, particularly as two studies have investigated in more detail the kinetics of, and reported the rapid, clearance of cfDNA from the circulatory system (Gauthier et al 1996, J Immunol 156:1151; Lo et al 1999, Am J. Hum Genet 64:218).

Various prior art methods have been described to detect, and quantify, cfDNA from a specific cell type. Quantitative analysis of aberrant p16 methylation was described using probe-based real-time quantitative PCR (Lo et al 1999, Cancer res 59:3899). Analogously, differences in the methylation of the placental mapsin gene found in material plasma has been described, and the methylation signature further analysed using MALDI-TOF mass-spectrometry (Chim et al 2005). Total cfDNA and that from male foetuses (only) were accurately and robustly quantified in maternal plasma from 5 to 41 weeks of gestation using a Y-chromosome specific marker (SRY) (Birch et al 2005, Clin Chem 51:2). Hypermethylation of RASSF1A has been proposed as a universal foetal DNA marker to improve the reliability of NIPT, and was studied in a duplex probe-based real-time PCR reaction compared to the non-differentially methylated region on the beta-actin gene (Chan et al 2006, Clin Chem 52:12). A complex method of quantification has been described (Nygren et al 2010; Clin Chem 56:10, WO 2010/033639; WO 2011/034631): starting from a 13-plex competition-PCR reaction (5 differentially methylated regions (DMRs) including TBX3, 3 regions on different genes for total DNA quantification, 3 for quantification of chromosome Y and 2 for restriction enzyme controls), such a complex reaction is subsequently processed for singe-base extension reactions and finally mass-spectrometry is subsequently conducted to both quantify and identify each of the single alleles my mass differences. Also using a complex process starting from methylated DNA immunoprecipitation, and based on SYBR green based quantitative PCR of a plurality of DMRs, has been claimed to be able to accurately quantitate foetal cfDNA and use such quantitation from eg chromosome 21 DMRs, to prenatally diagnose trisomies (Papageorgiou et al 2011, Nat Med 4:510; WO 2012/092592); although technical concerns about such an approach to diagnose trisomies have been raised (Tong et al 2012; Nat Med 18:1327). High-throughout droplet digital PCR (ddPCR) has been described for absolute quantification of DNA copy number from normal and tumorous breast tissues, and also total and foetal cfDNA in maternal plasma using duplex probe-based quantitative PCR of RASSF1/RNaseP and RASSF1/beta-actin (Hindson et al 2011, Anal Chem 83:8604). Separate SYBR green quantitative PCR reactions of RASSF1A, SRY and DYS14 have been evaluated as an assay to detect RASSf1A to facilitate improved diagnostic reliability of NIPT (White et al 2012; PLOS ONE 7(9):e45073). However, generally considered as the "gold standard" for the quantitative measurement of foetal cfDNA against which other assays are often compared, remains the quantification of Y chromosome-specific genes (eg SFY) of male foetuses eg, as used by Yu and co-workers to determine whether the increased foetal cfDNA in maternal serum level of gravitas developed into early-onset preeclampsia (Yu et al 2013, Int J Mol Sci 14:7571).

Accordingly there is a need, from one or more of the above or perspectives, for improved methods to detect, preferably quantitatively, an amount of a species of DNA that originates from a particular cell type, such as a tumour-, foetal- or a placental cell, in particular to so detect cfDNA eg from the circulatory system of an individual.

Accordingly, it is an object of the present invention to provide alternative, improved, simpler, cheaper and/or integrated means or methods that address one or more of these or other problems. Such an object underlying the present invention is solved by the subject matter as disclosed or defined anywhere herein, for example by the subject matter of the attached claims.

Generally, and by way of brief description, the main aspects of the present invention can be described as follows:

In a first aspect, and as may be further described, defined, claimed or otherwise disclosed herein, the invention relates to a method for detecting in a sample from an individual an amount of a species of DNA originating from cells of a given type, which sample comprises said species of DNA in admixture with differently methylated DNA not originating from cells of said type; said method comprising the steps:

(a) treating the DNA present in said sample with a reagent that differentially modifies methylated and non-methylated DNA;
(b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample; and
(c) detecting an amount of total DNA present in said sample using at least one other region that is not differently methylated between said species of DNA and the DNA not originating from cells of said type, the modification of which region(s) by said reagent is insensitive to methylation of DNA, wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

In another aspect, the invention also relates to a method for detecting an increased risk of an individual suffering from or developing a medical condition, said method comprising the steps:

(i) conducting a method of the first aspect of the invention, wherein each of the detection steps comprises quantitative detection; and
(ii) comparing the amount of said species of DNA detected with a threshold amount and/or a reference distribution of amounts, wherein an increase in, or outlying of, the amount of said species of DNA indicates an increased risk of the individual suffering from or developing said medical condition.

In other aspects, the invention also relates to a composition, a kit and a computer program product, in each case as may be described, defined, claimed or otherwise disclosed herein, for use within or in connection with a method of the invention.

The figures show:

Figure 1:
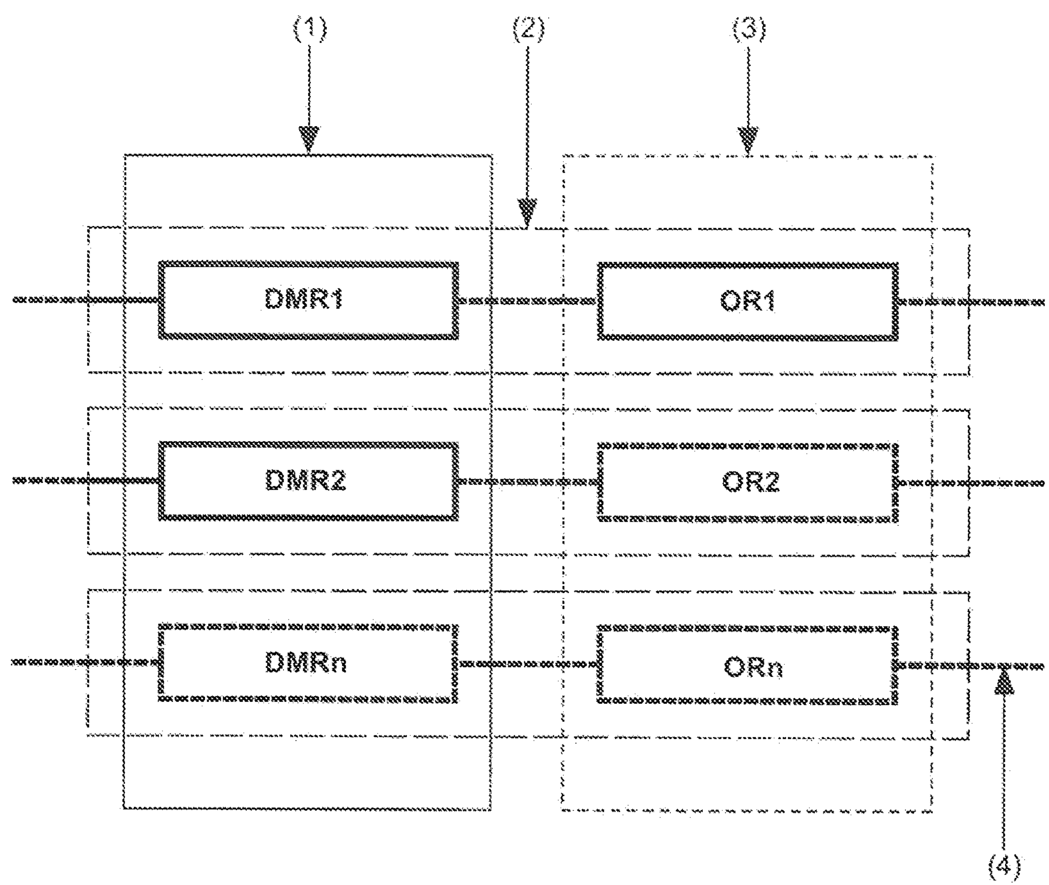
FIG. 1 depicts a schematic representation of the differentially methylated regions ("DMR") and the other regions(s) ("OR") used in the method of the invention.

The present invention, and particular non-limiting aspects and/or embodiments thereof, can be described in more detail as follows:

In a first aspect, the invention relates to a method for detecting in a sample from an individual an amount of a species of DNA originating from cells of a given type, which sample comprises said species of DNA in admixture with differently methylated DNA not originating from cells of said type; said method comprising the steps:

(a) treating the DNA present in said sample with a reagent that differentially modifies methylated and non-methylated DNA;
(b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence f methylated DNA at one or more of said DMRs indicates the presence of said amount of species of DNA in said sample and the absence of methylated DNA at said DMRs indicates the absence of said species of DNA in said sample; and
(c) detecting an amount of total DNA present in said sample using at least one other region that is not differently methylated between said species of DNA and the DNA not originating from cells of said type, the modification of which region(s) by said reagent is insensitive to methylation of DNA, wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

Terms as set forth herein are generally to be understood by their common meaning unless indicated otherwise. Where the term "comprising" or "comprising of" is used herein, it does not exclude other elements. For the purposes of the present invention, the term "consisting of" is considered to be a particular embodiment of the term "comprising of". If hereinafter a group is defined to comprise at least a certain number of embodiments, this is also to be understood to disclose a group that consists of all and/or only of these embodiments. Where used herein, "and/or" is to be taken as specific disclosure of each of the two specified features or components with or without the other. For example "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

In certain embodiments of the present invention, the individual is a human or a non-human animal, where such non-human animal may, in particular embodiments, be selected from the group consisting of: horse, sheep, cow, pig, chicken, mouse and rat. In a more specific embodiment, the individual is a pregnant female human or a human individual suspected of being at increased risk of developing or suffering (or suffering from) a medical condition, such as one or more of the medical conditions disclosed herein. Such a method of the present invention is not intended to be practiced on the human or animal body; for example it is intended to be practiced in an in-vitro manner.

In all aspects of the invention, the cell(s) of a given type may be a cell of a particular organ or tissues of the same individual. For example, the cell may be a tumour cell of the individual. Alternatively, such cell(s) may originate from a different individual or organism. For example, in the case of an individual being a pregnant female, the cell of a given type may be a cell of the foetus, including of the placenta of such foetus, and in other embodiments, the cell type may be an infectious agents such as a bacteria or a protozoa.

In certain embodiments of the present invention, said species of DNA and/or said differently methylated DNA is cell-free DNA, and in particular of such embodiments is circulating cell-free DNA. In one particular embodiment, said species of DNA and the differently methylated DNA that is admixed therewith are both circulating cell-free DNA. The term "cell-free DNA" (or "cfDNA") is art recognised, and includes the meaning of DNA that is found outside of a cell, such as in a biological fluid (eg blood, or a blood fraction) of an individual. "Circulating" is also an art-recognised term, and includes the meaning that an entity or substance (eg cfDNA) is present in, detected or identified in, or isolated from, a circulatory system of the individual, such as the blood system or the lymphatic system. In particular, when cfDNA is "circulating" it is not located in a cell, and hence may be present in the plasma or serum of blood, or it may be present in the lymph of lymphatic fluid.

The term "differentially methylated region" or "DMR" will be recognised by the person of ordinary skill in the art, and is also intended to refer to a region in chromosomal DNA that is differentially methylated (eg at a CpG motif) between said species of DNA and the other DNA with which it is admixed in the sample. For example in one embodiment, the DMRs used in the present invention are differentially methylated between foetal and maternal DNA, or are differentially methylated between tumour-derived and non-tumour-derived DNA from the same individual. In particular embodiments of the present invention, the DMRs are hypermethylated in foetal DNA and hypo methylated in maternal DNA, or are hypermethylated in tumour-derived DNA and hypomethylated in DNA that is derived from non-tumour tissue of the individual. That is, in such regions exhibit a greater degree (ie more) methylation in said species of DNA (eg the foetal or tumour cfDNA) as compared to the other DNA (eg maternal or non-tumour DNA), such as about 10%, 20%, 30%, 40%, 50%, 60%, 70%, 80%, 90% or 100% or, or more of, the sites available for methylation at a given DMR are methylated in said species of DNA as compared to the same sites in the other DNA.

A reagent is used in the present invention that differentially (eg selectively) modifies methylated as compared to non-methylated DNA. For example, treatment of DNA with a reagent comprising bisulphite (bisulfite) converts cytosine residues to uracil, but leaves 5-methylcytosine residues unaffected. Thus, bisulphite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information, including the user of PCR primers and/or probes that can distinguish between such single-nucleotide changes.

Such a reagent may alternatively (or in addition) comprise a restriction enzyme that is sensitive to the DNA methylation states. Cleavage of such a restriction enzyme's recognition sequence may be blocked, or impaired, when a particular base in the enzyme's recognition site is modified, eg methylated. In particular embodiments of all aspects of the invention, the reagent comprises a methylation-sensitive restriction enzyme, such as a methylation-sensitive restriction enzyme disclosed herein; including such embodiments that comprise two, three, four, five or more of such methylation-sensitive restriction enzymes.

Prior to step (a), the sample may be processed to isolate, enrich and/or purify, the DNA present therein. For example, a plasma sample may be processed using a cfDNA isolation process or kit to provide a (non-natural) subsequent solution that comprises an admixture of said species of DNA together with the differentially methylated DNA that does not originate from the cell-type. The step of treating in (a) may comprise the step of adding a separate solution that comprises said reagent (eg a methylation sensitive restriction enzyme) to the admixed DNA of the sample (eg, to a non-natural solution comprising such admixed DNA); and/or may comprise maintaining (or changing to) certain conditions. In particular, when said reagent comprises one or more methylation sensitive restriction enzyme, the step of treating in (a) may comprise incubating the DNA and the enzyme(s) together at about 37° C. for between about 5 min and 300 min, such as between about 30 min and 90 min or about 60 min, and optionally may comprise a step of incubating such mixture at a higher temperature (for example, between about 50° C. and 90° Cm such as about 80° C.) so as to deactivate the enzyme(s). In certain embodiments, the composition formed for a treating step of (a) may be non-naturally occurring. For example, particular salts of components of the solution (or buffer); and/or the mixture of (eg human) cfDNA together with one or more bacterial-derived restriction enzymes (or a non-natural mutant thereof) may be a non-natural composition or mixture.

In contrast, an "other region" ("OR") used in the present invention is not (significantly) differentially methylated between said species of DNA and other DNA with which it is admixed in the sample. For example, under the conditions and nature of the reagent used, there is not detectable difference between modification by such regent at the other region of said species of DNA (eg foetal DNA) as compared to the other region of the admixed DNA (eg the maternal DNA). Such a non-difference may be achieved if the other region comprises no sites for methylation, if there is no difference in the degree of methylation if such sites are present or by the use of a reagent that does not recognise any sites of methylation present in the other region. In particular embodiments, the other region used in the present invention (that is not so differentially methylated) may be non-overlapping with the DMRs used in the present invention. For example, the other region can be located further than about 10 bp, 20 bp, 50 bp, or more than 100 bp, 500 bp, 1 kb or 10 kp, away from either of the DMRs.

One feature of the present invention is that the detection of the various DNA regions, ie the DMRs and the other region(s), occurs in a simplified process. For example, using a single aliquot of DNA from the sample, such DNA regions are detected in a single vessel. This feature simplifies the method, and can provide for more efficient and accurate detection (especially in those embodiments when detection is quantitative). The term "vessel" will be art recognised, and includes embodiments of a vessel (such as a tube, well of a microtitre plate, nano-well, capillary reaction vessel etc) in which a process or procedure comprised in the method occurs, such as a reaction and/or detection process or a step of a method of the present invention. Other such vessels may include droplets in oil/water emulsions, nanoparticles or a hybridisation chamber; as appropriate to the detection technology used. The detectable labels used, in such methods is the same for each DMR and, in certain embodiments, is the same for each other region, provided that the label(s) used for the other region(s) is different (ie, can be separately detected) to the label(s) used for the DMRs. Detectable labels that are "the same", can also include labels while structurally different, are functionally (essentially) similar as they cannot be significantly differentiated by the detection technology employed. For example, structurally different fluorescent dyes may be considered "the same" if their excitation and emission spectra are (substantially or essentially) similar, or overlap to such a degree that they are able to be excited and detected simultaneously with the same wavelength(s). Suitable labels (and detection modalities) are further described elsewhere herein. In addition, the detection of the DMRs and other region(s) is made effectively simultaneously. For example, within the same (reaction/detection) vessel, all such regions (and hence said species of DNA and total DNA) can be detected within less than about 5 s, 1 s, 0.5 s, 100 ms, 10 ms, 1 ms, 100 us, 10 us or 1 us of each other, and for example without transferring the vessel, or the reaction/mixture, to any subsequent vessel, assay or equipment, or for example, without adapting or recalibrating the detection process for either of the DMRs or the other region(s) separately. The use of two different detectable label(s)—one for said DMRs and one for the other region(s)—utilises components, process and/or steps that are non-natural. For example, a composition of two specific labels together with the specific DNA regions would (generally) not be found in nature. In particular, short probes used in quantitative probe-based PCR, while may comprise a DNA sequence that is a fragment of that found in a natural genome, when linked to a one or more labels (such as fluorescent dye) form a specific labelled fragment that is non-natural.

Collectively, the features of the present invention provide for certain advantages over prior art methods. These can include sensitive detection of methylation (and hence the species of DNA to be detected) and/or accurate quantification of the amount of said species of DNA by reference to the amount of total DNA detected within the same assay, from the same aliquot of admixed DNA and effectively simultaneously with the detection of the two or more DMRs, and optionally using a co-located other region.

By way of graphical description, a schematic representation of the general arrangement of the DMRs, the other region(s) and the detectable label(s), as used for the present invention, is presented in FIG. 1. (1) The presence of methylation in DNA at two or more DMRs, DMR1 and DMR2 (and, optionally, up to DMRn), is in each case detected using the same detectable label(s). (2) Optionally, an other region ("OR") is located within the same portion of the genome (eg, between about 20 bp and about 20 kb upstream or downstream of) one of the DMRs. (3) The amount of total DNA detected using at least one OR (OR1, and optionally, OR2 or up to ORn) is detected using different detectable label(s) to those used to detect methylation at the DMRs (optionally, the detectable label(s) used is the same for all the ORs). (4) Optionally, methylation at more than two DMRs is so detected, and/or the amount of total DNA is detected at more than one OR.

In certain embodiments, prior to or as part of the detection that occurs as part of a step (b) and/or a step (c) of any method of present invention, each DNA region comprising said DMRs and/or said other region(s), respectively, is(are) amplified. Amplification of DNA may be conducted using any suitable replication process, and in particular of such embodiments, each of the DMRs and/or an other region, is amplified by a polymerase chain reaction (PCR) using primers suitable designed for each DMR and/or other region. The person of ordinary skill will readily be able to design such PCR primers for use in the method of the invention, for example by use of primer design algorithms and programs such as Clone Manager Professional 9 (Sci-Ed Software), Vector NTI (Life Technologies), or web-based tools such as those found from www.ncbi.nlm.nih.gov/tools/primer-blast/ or molbiol-tools.ca/PCR.htm. Those embodiments of the present invention that comprise PCR amplification can further comprises specific steps that are related to the practice of PCR, such as any of those described herein, or in particular the steps of: (A) providing a reaction mixture comprising a double-stranded target DNA, a pair of primers (for example, a pair of primers disclosed herein) designed to amplify a region of such DNA (such as a DMR or an other region as described herein) wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; (B) heating the reaction mixture to a first predetermined temperature for a first predetermined time to separate the strands of the target DNA from each other; (C) cooling the reaction mixture to a second predetermined temperature for a second predetermined time under conditions to allow the first and second primers to hybridise with their complementary sequences on the first and second strands of the target DNA, and to allow the Taq polymerase to extend the primers; and (D) repeating steps (B) and (C) at least 20 times.

In other embodiments, a detectable label used in step (b) and/or step (c) of a method of the invention is independently selected from the group consisting of: fluorescent, protein, small molecule or radioactive label. For example, fluorescent labels that are the same (including, by having similar or overlapping excitation and/or emission spectra) may be used for the DMRs, and a fluorescent label that has an excitation and/or emission spectra (in particular, a different emission spectrum) may be used for detection of the other region(s). The person of ordinary skill will be able to select appropriate such fluorescent label(s) for use in the present invention from, for example, the group consisting of: FAM, TET, JOE, VIC, HEX, NED, PET, ROX, TAMRA, Quasar and Texas Red. In other embodiments, a detectable label may be a protein or small molecule tag that, for example, can be detected using a specific antibody and ELISA-type detection approaches. The use of the same protein or small molecule for each of the DMRs, and a detectably different protein or small molecule for the other region(s), may also be utilised for the detectable label(s) used in the present invention. Different radioactive labels may be distinguished by their emission energy, penetration/excitation characteristics and particle-type (for example, by distinguishing between alpha and beta particles). Other detectable labels (such as nucleic-acid coded tag) may also be employed in the present invention.

In particular embodiments, the detection in step (b) of a method of the example comprises real-time quantitative probe-based PCR, eg by using at least two labelled probes, each of which is specific for one of said DMRs. PCR amplification of said two or more DMRs in the same reaction can be considered as "multiplex" (or "duplex" if only two DMRs are so amplified). Likewise, the detection in step (c) in the methods of the invention may, in addition or alternatively, comprise real-time quantitative probe-based PCR, such as by using at least one labelled probe specific for one of said other region(s).

The term "probe-based" quantitative PCR is art recognised, and encompasses various embodiments described and marketed under different brand names (such as "TaqMan" PCR of Roche), and uses a (eg fluorescent) reporter probe that is specific for the detection of a given amplicon (eg a DMR or an other region). Probe-based quantitative PCR is distinct from quantitative PCR using double-stranded DNA-binding dues (eg SYBR Green) as reporters, as such double-stranded DNA-binding dyes bind non-specially to any double-stranded amplicon and eg cannot be used to distinguish between detection of the DMRs (ie said species of DNA) from detection of the other region(s) (ie detection of total DNA). As the person of ordinary skill will appreciate, a specific amplicon of PCR may be detected using a single probe or by using multiple probes (such as two or three probes) for an amplicon.

Such probe-based quantitative PCR may be conducted in an analogue-approach, using a machine such as a LightCycler in which the intensity of signal (eg over time) is measured and used to quantitatively determine detection. Alternatively, digital PCR (dPCR), ie, PCR conducted in multiple events so as to determine the number of amplification events as method to quantitate an amount of detected DNA. For example, dPCR that is conducted in nano-wells or droplets (ddPCR).

The person of ordinary skill will be able to design suitable primers and probes (and with suitable labels, eg dyes) for probe-based quantitative PCR detection of the DMRs and/or other regions(s); for example by using primer/probe design software as described elsewhere herein. As will be known, the PCR primers may overlap methylation site(s) specific for the methylation-specific modifying reagent used in the methods, in particular when the reagent comprises one or more methylation sensitive restriction enzyme, such as one (or a combination thereof) as disclosed herein. In particular such embodiments, one or other (or when considered together, both) of the PCR primers for a given DMR may overlap two or three such methylation sites (such as two or three restriction sites for methylation-sensitive restriction enzymes, each of which may comprise, or comprises, a methylation site). Alternatively or in addition, the primers for a DMR may be designed to flank one, two, three or more such methylation sites, such as up to 10, 15, 20, 25 or 50 such methylation sites, in particular flanking restriction sites for one, two, three or more such methylation sites, such as up to 10, 15, 20, 25 or 50 methylation-sensitive restriction enzymes, each of which may comprise, or comprises, a methylation site.

In a particular embodiment, the genomic location of the other region used in the present invention is generally located in the same portion of the genome, such as between about 20 bp and about 20 kb upstream or downstream of (including embodiments within the same gene as) the genomic location of at least one of the DMRs used herein. In certain embodiments, the other region does not overlap with the DMR. The inventors find that detection (and particularly quantification) of the species of DNA is enhanced (eg, in terms of sensitivity, accuracy and/or precision) if the other region is so located in the same portion of the genome as one of the DMRs. Without being bound by theory, it is believed that with such similarly located DMR(s) and other region, the effect of variation in chromatin/nucleosome packing across the genome—and hence stability/degradation of different regions of genomic DNA—is mitigated, such that any difference in stability/degradation of a DMR (ie detecting the species of DNA) as compared to the other region (is detecting total DNA) is less, and hence a relative (and absolute) quantification may be made without it being (significantly) confounded by quantitative differences brought about by (significantly) differential chromatin/nucleosome packing across the genome between a DMR and an other region. The combination of this feature (similarly-located DMR(s) and other region) with another feature of the present invention (the use of at least two DMRs, and the detection in step (b) and the detection in step (c) are made using the same aliquot of DNA of the sample, and in the same reaction/detection vessel, and effectively simultaneously for such DMRs and other region, and using: (x) the same detectable labels(s) for each of said DMRs; and (y) a different detectable label for said other region(s)), is a preferred embodiment of the present invention. The use of such a combination of features in the present invention provides opportunity for efficiency improvements and/or synergistic enchantment of outcome. For example, an improved sensitivity and/or accuracy and/or precision of detection (eg, detection of a quantitative amount) of said species of DNA can be obtained by the use of such a combination; the degree of improvement of which can be synergistic, as compared to the use of each feature alone; eg the enhancement obtained by use of the combined features being greater than the sum of each enhancement obtained by the use of each feature individually.

The present invention includes the use of one other region to provide for the detection of an amount of total DNA in the admixture. However, the present invention also encompasses embodiments that use more than one other region. For example, the invention includes such embodiments wherein said detection in step (c) comprises using at least two of said other regions, such as two, three or four of said other regions. In particular embodiments of all aspects of the present invention, the number of said other regions is the same as the number of DMRs used in step (b). For example, if two DMRs are used then two other regions are used in such an embodiment, and if three DMRs are used then three other regions are used (such as depicted in FIG. 1).

As described elsewhere herein, certain embodiments of the present invention include where the other region is generally located in the same portion of the genome, such as between about 20 bp and about 20 kb upstream or downstream of (including embodiments within the same gene as) the genomic location of at least one of the DMRs used herein. In certain embodiments, the other region does not overlap with the DMR. Accordingly, if multiple other regions are used in the present invention, then embodiments are included where two or more of such other regions are similarly located in the genome to the two or more DMRs. For example, one of said other regions may be located between about 20 bp and about 20 kb upstream or downstream of (including embodiments within the same gene as) a DMR used in step (b) and each other of the said other regions (eg, a second other region) is located between about 2 bp and about 20 kb upstream or downstream of (including embodiments within the same gene as) another of said (eg, non-overlapping) DMRs (eg, the second DMR). In certain embodiments an additional other region, may overlap with a DMR.

An other region used in the present invention, when generally located in the same portion of the genome as a DMR, may be located upstream or downstream of one of said DMRs within a distance selected from the group consisting of: between about 16 kb to 20 bp, 14 kb to 20 bp, 12 kb to 20 bp, 10 kb to 20 bp, 8 kb to 20 bp, 6 kb to 20 bp, 5 kb to 20 bp, 4 kb to 20 bp, 3 kb to 2 bp, 16 kb to 20 bp, 1 kb to 20 bp, 500 bp to 20 bp, 200 bp to 20 bp, 20 kb to 15 kb, 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, 2 kb to 500 bp, 1 kb to 100 bp, 500 bp to 50 bp, 400 bp to 200 bp and 500 bp to 100 bp. In particular embodiments, each other region used in the present invention is so generally located to a different of the DMRs used.

If multiple other regions are used, then the present invention includes embodiments where the detection in step (c) is made using the same detectable label for each of said other regions and/or comprises multiplex real-time quantitative PCR using at least two labelled probes each of which is specific for one of said other regions.

In particular embodiments, all detection steps (ie, those required for all DMRs and all other regions) are conducted in an efficient and effective manner using multiplex quantitative probe-based (eg TaqMan) PCR, in one process step or reaction. For example, the detection in step (c) and said detection in step (b) are made using the same aliquot of DNA of said sample, and in the same reaction/detection vessel, and effectively simultaneously with each other, and by multiplex real-time quantitative PCR using at least one labelled probe specific for each of the said DMRs and other region(s). In particular of such embodiments, the reagent comprises one or more methylation sensitive restriction enzyme, such as one (or a combination thereof) as disclosed herein.

The present invention may also include further procedures, such as one or more control procedures. For example, the present invention can include one or more steps directed to the detection of a third class of DNA region that acts as a control for the modification step (eg, as a control for restriction enzyme digestion). Such embodiments may, for example, also be conducted using multiplex real-time quantitative probe-based PCR wherein such control region is amplified and detected by a third set of primer/probe(s) with a third detectable label used for such class of region.

In one embodiment of the present invention of particular relevance, said species of DNA originates from cells of a foetus and/or the placenta of a foetus and said sample is from a pregnant female. In such embodiments, the sample may be obtained in a non-invasive manner. For example, said species of DNA is circulating cell-free DNA that has been detected from the sample being blood or a blood fraction (such as plasma or serum) that has been obtained from the pregnant female by conventional means such as a blood collection tube.

The present invention includes embodiments where the DMRs are hypermethylated in foetal DNA and hypo methylated in maternal DNA. In certain embodiments, such a DMR may be located in a promoter, enhancer region or an exon or a gene, such as a gene disclosed herein. Alternatively, a DMR may be located in an intron of such a gene, or in a non-coding region of the genome. In particular embodiments of all aspects of the present invention, such genome and/or gene is a human genome or gene. Specifically included in the present invention are embodiments wherein said DMRs comprises at least one, preferably at least two, methylation site(s) specific for said reagent, and at least one of said DMRs is located in a portion of the genome and/or gene (eg a human genome or gene) that is RASSF1A and/or TBX3, or selected from the group consisting of: RASSF1A, TBX3, HLCS, ZFY, CDC42EP1, MGC15523, SOX14 and SPN. Also, embodiments are included wherein said DMRs comprises at least one, preferably at least two, methylation site(s) specific for said reagent, and at least one of said DMRs is located in a region and/or gene selected from the group consisting of: AIRE, SIM2, ERG, VAPA-APCDDI, one disclosed in WO 2011/034631 as being hypermethylated in foetal DNA relative to maternal DNA (eg, SEQ ID NOs: 1-59, 90-163; i.e., SEQ ID NOS: 15-147 of the present application, 176, 179, 180, 184, 188, 189, 190, 191, 193, 195, 198, 199, 200, 201, 202, 203, 205, 206, 207, 208, 209, 210, 211, 212, 213, 214, 221, 223, 225, 226, 231, 232, 233, 235, 239, 241, 257, 258, 259, and/or 261 of WO 2011/034631, i.e., SEQ ID NOS: 148-187 of the present application) and one disclosed in WO 2011/092592 (eg, EP1, EP2, EP3, EP4, EP5, EP6, EP7, EP8, EP9, EP10, EP11 and/or EP12 of WO 2011/092592 (i.e., SEQ ID NOS: 188-199 of the present application), as further investigated in Lim et al 2014, BMC Medical Genomics (7:1).

In particular embodiments of all aspects of the present invention, the two DMRs used are not located in the same portion of the genomic and/or gene. For example, such DMRs may be located on separate chromosomes, or separated by more than about 20 kb, or more than about 15 kb, 10 kb, 8 kb, 6 kb, 4 kb, 2 kb, 1 kb, 500 bp or 200 bp. Alternatively, it is envisioned, that the two (or more) DMRs used in the present invention may, in certain embodiments, be located in the same region or gene (such as one described herein) and, further, may overlap with each other.

In particular embodiments of the present invention, both of said DMRs are (or each, in the case of more than two DMRs are being used, is) located in a portion of the genome and/or gene (preferably that is human) that is RASSF1A and/or TBX3, or is selected from the group consisting of: RASSF1A, TBX3, HLCS, ZFY, CDC42EP1, MGC15523, SOX14 and SPN; and/or at least one of said DMRs is located between about positions 4,700 bp and 5,600 bp of RASSF1A (NCBI Reference Sequence: NG_023270.1: *Homo sapiens* Ras association (RAlGDS/AF-6) domain family member 1 (RASSF1), RefSeqGene on chromosome 3; SEQ ID NO.: 13) or about positions 1,660 bp and 2,400 bp of TBX3 (NCBI Reference Sequence: NG_008315.1: *Homo sapiens* T-box 3 (TBX3), RefSeqGene on chromosome 12; SEQ ID NO.: 14). In a more particular embodiment, two (or more) DMRs are used, and a first DMR comprises one located between about positions 4,700 bp and 5,600 bp of RASSF1A and a second DMR comprises one located between about positions 1,660 bp and 2,400 bp of TBX3.

In particular embodiments, a DMR is located in RASSF1A between about positions 4,900 bp and 5,500 bp, 5,000 bp and 5,400 bp, or 5,100 bp and 5,300 bp of RASSF1A; and/or is located in TBX3 between about positions 1,800 bp and 2,260 bp, 1,920 bp and 2,160 bp or 1,920 bp and 2,080 bp of TBX3.

Figure 2:
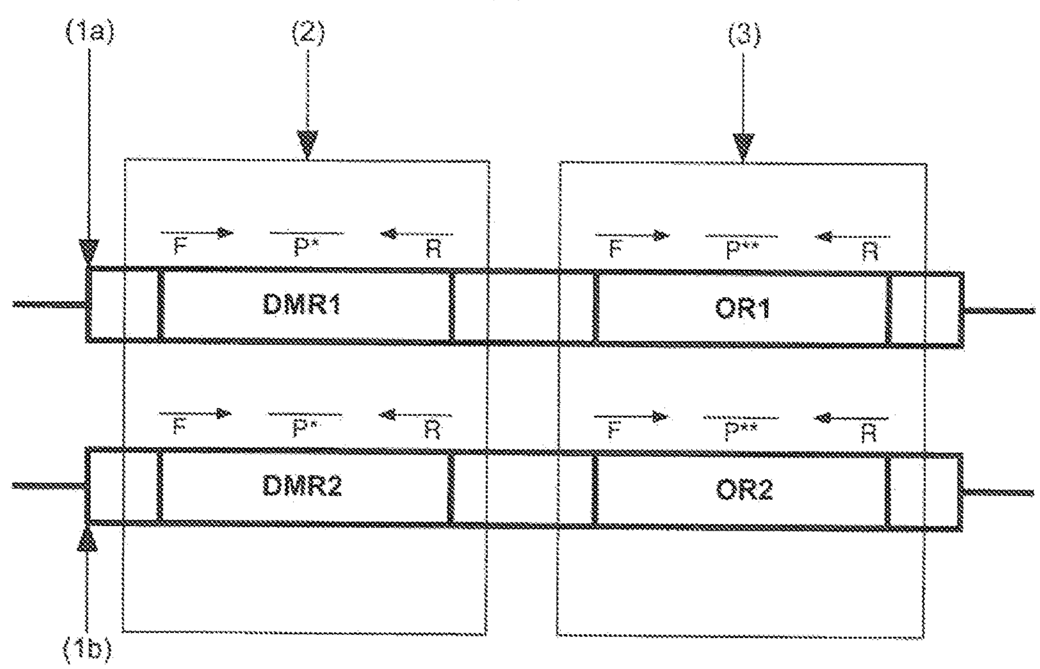
FIG. 2 depicts a schematic representation of the differentially methylated regions ("DMR") and other regions ("OR") used in Example 1.

The general arrangement of the DMRs and other regions ("OR") used in one embodiment of the present invention, is graphically represented by FIG. 2: (1*a*) DMR1 is found in exon 2 of RASSF1A and OR1 is located within exon 4 of RASSF1A, with DMR1 located between positions 50,340,672 bp and 50,340,784 bp and OR1 located between positions 50,331,604 bp and 50,331,702 bp of the RASS1A genomic sequence (NCBI Reference Sequence: NC_000003.12 *Homo sapiens* chromosome 3, GRCh38 Primary Assembly), separating DMR1 and OR1 by a distance of 8,969 bp. (1*b*) DMR2 is found in the promoter region of TBX3, with DMR2 located between positions 114,687,095 bp and 114,687,189 bp and OR2 is located between positions 114,676,384 bp and 114,676,454 bp of the TBX3 genomic sequence (NCBI Reference Sequence: NC_000012.12 *Homo sapiens* chromosome 12, GRCh38 Primary Assembly), separating DMR2 and OR2 by a distance of 10,640 bp. (2) Methylation in DNA at the two DMRs is detected using probe-based quantitative PCR using the respective forward (F) and reverse (R) PCR primers and region-specific probes, each probe labelled with the same labels (P*). (3) Total DNA is detected at two ORs using probe-based quantitative PCR using the respective forward (F) and reverse (R) PCR primers and region-specific probes, each probe labelled with the same labels for the ORs that is different to the labels used for the two DMRs (P**). Details of primer and probe sequences and probe labels are set out in TABLE 1.

The term "methylation site(s)" will be art-recognised, and has a meaning that encompasses, for example, a CpG motif within a short nucleotide sequence (eg one that is 4, 6, 8, 10 or 12 bp in length) that is, preferably, recognised by a methylation-sensitive restriction enzyme, such as one disclosed elsewhere herein.

Analogously, the other region may be located in particular portions and/or genes of the genome, and may be located in a promoter, enhancer region or an exon of a gene, or alternatively, located in an intron of such a gene, or in a non-coding region of the genome. In particular embodiments of all aspects of the present invention, such genome and/or gene is a human genome or gene. In particular embodiments, an other region used in the present invention is located in a (eg human) housekeeping gene (such as GAPDH, beta-actin, ALB, APOE or RNASEP). Alternatively (and in particular when said species of DNA is foetal cfDNA), said other region may be located in the same portion of the genome and/or gene that feature one or more DMRs (such as those RASSF1A, TBX3, HLCS, ZFY, CDC42EP1, MGC15523, SOX14 or SPN), and preferably does not overlap with a DMR used in the invention. In particular embodiments, said other region comprises a portion of the genome without a methylation site specific for said reagent, and said other region is located in the (eg human) genes RASSF1A or TBX3 (eg SEQ ID NOs.: 13 and 14 respectively), and includes more particular embodiments wherein two or more of said other regions are used in detection step (c) and the first other region is located between about positions 14,220 bp and 13,350 bp of such RASSF1A and the second other region is located between about positions 12,400 bp and 13,000 bp of such TBX3. In particular embodiments, an other region is located in RASSF1A between about positions 14,230 bp and 14,340 bp, 14,230 bp and 14,330 bp, 14,230 bp and 14,320 bp, or 14,230 bp and 14,310 bp of such RASSF1A; and/or is located in TBX3 between about positions 12,400 bp and 12,940 bp, 12,700 bp and 12,850 bp or 12,710 bp and 12,790 bp of such TBX3. Alternatively, an other region may be located in an exon such as between about positions 13,790 bp and 13,880 bp, or 14,490 bp and 14,600 bp of such RASSF1A, or between about positions 8,040 bp and 8,180 bp or 6,230 bp and 6,350 bp of such TBX3; or an other region may be located in an intron such as between about positions 10,500 bp and 11,90 bp of such RASSF1A, or between about positions 10,000 bp and 11,000 bp of such TBX3

There is now strong evidence that the level of foetal cfDNA (and/or total cfDNA) present in the circulatory system (eg in plasma) of a pregnant female is a marker of one or more forms of preeclampsia, such as early-onset preeclampsia, mild and/or severe preeclampsia (see Hahn et al 2011, Placenta 32(Supl):S17). The present invention shows particular utility in the efficient, effective, sensitive and/or low-variability detection/quantification of foetal cfDNA present in plasma of pregnant females, and the present invention has particular utility therein. Accordingly, in particular embodiments of the present invention, the individual is a pregnant female and is susceptible to suffering or developing a pregnancy-associated medical condition; particularly where said pregnancy-associated medical condition is preeclampsia. As used herein, an individual "susceptible to" a medical condition may alternatively be described as "is suspected to" or to "be considered at risk of being susceptible to" suffering or developing a medical condition; and in certain embodiments, the present invention is used to screen and/or diagnose the individual for susceptibility to, risk of suffering or developing, or suffering from or developing, a medical condition.

In alternative embodiments, the individual is a pregnant female and is susceptible to (or considered at risk of being susceptible to) suffering or developing a pregnancy-associated medical condition selected from the group consisting of: preterm labour, intrauterine growth retardation and vanishing twin. In particular, the inventors were surprised that the sensitivity of the present invention was such that discrepancies between cfDNA levels determined by the method of the invention and that determined by counts of Y-chromosome sequences as determined by massively parallel sequencing approaches, was useful in identifying one or more cases of a vanishing twin in (mixed-sex) twin pregnancies that previously were believed to be singleton pregnancies, and/or to follow the relative development and health of one or other of such (mixed-sex) twin pregnancies. The present invention may also be utilised in gender determination of twin pregnancies, by consideration of the relative values for foetal cfDNA compared to counts of Y-chromosome sequences determined from cfDNA (eg by using parallel sequencing approaches). In these regards, it should be noted that approaches that use massively-parallel sequencing of random cfDNA in maternal blood typically always count a very low frequency of "Y-chromosome" sequences (such as between about 0.003% and 0.004% of all sequences, or between about 0.0015% and 0.01% or 0.002% and 0.005% of all sequences) in all female pregnancies due to homology of certain Y-chromosome short sequences to other chromosomes. A cut off of "Y-chromosome" sequence counts of about 0.005%, or between about 0.003%, 0.04%, 0.006% or 0.007%, may therefore be employed for female samples.

As described elsewhere herein, there is also increasing evidence that the presence and amount of methylated DNA at certain DMRs is indicative or prognostic of certain medical conditions that are not associated with pregnancy. Accordingly, in another particular embodiment of the present invention, said species of DNA originates from a cell type associated with such a medical condition, particularly in those embodiments where said species of DNA is circulating cell-free DNA and said sample is a blood fraction such as plasma or serum. For example, the medical condition may be a cell proliferative disorder, such as a tumour or cancer. In particular embodiments, the medical condition is a tumour or a cancer of an organ selected from the list consisting of: liver, lung, breast, colon, oesophagus, prostate, ovary, cervix, uterus, testis, brain, bone marrow and blood; and/or said species of DNA may originate from cells of a tumour; particularly where such tumour is a carcinoma or cancer of an organ selected from the group consisting of: liver, lung, breast, colon, oesophagus, prostate, ovary, cervix, uterus, testis, brain, bone marrow and blood.

When used in the context of a medical condition being a tumour or cancer, the present invention includes embodiment wherein said DMRs comprises at least one, preferably at least two, methylation site(s) specific for said reagent, and at least one of said DMR is located in a portion of the genome and/or a gene (in particular, when such genome and/or gene is a human genome or gene) selected from the group consisting of: a tumour suppressor gene, p16, SEPT9, RASSF1A, GSTP1, DAPK, ESR1, APC, HSD17B4 and H1C1. In particular, one of said two or more DMRs may be located in RASSF1A (eg SEQ ID NO. 13) such as located between about positions 4,700 bp and 5,600 bp of such RASSF1A; and/or said other region is located between about positions 14,220 bp and 13,350 bp of such RASSF1A. Other particular locations of the DMRs and/or other region(s) with RASSF1A for use in this embodiment are disclosed elsewhere herein. Furthermore, the person of ordinary skill will now recognise that other DMRs and/or other regions located in other portions of the genome of in other genes may be identified from the relevant scientific literature (eg, for review, see Elshimali 2013). In particular when used in the context of a medical condition being a tumour or cancer, the present invention includes embodiments where at least one other region (preferably two or more) are located in a (eg human) housekeeping gene (such as GAPDH, beta-actin, ALB, APOE or RNASEP). Alternatively for such context, said other region(s) may be located in the same portion of the genome and/or gene that feature one or more DMRs (such as those p16, SEPT9, RASSF1A, GSTP1, DAPK, ESR1, APC, HSD17B4 and H1C1).

In yet another particular embodiment of the present invention, said species of DNA originates from a cell type associated with a medical condition selected from the group consisting of: an infection/infectious disease, a wasting disorder, a degenerative disorder, an (auto)immune disorder, kidney disease, liver disease, inflammatory disease, acute toxicity, chronic toxicity, myocardial infarction, and a combination of any of the forgoing (such as sepsis) and/or with a cell proliferative disorder, particularly in those embodiments where said species of DNA is circulating cell-free DNA and said sample is a blood fraction such as plasma or serum. For example, the medical condition may be an infection/infectious disease, such as one caused by a bacterial, viral or protozoan pathogen, including a pathogen selected from the group consisting of: a retrovirus (such as HIV), a herpes virus (such as HSV, EBV, CMV, HHV or VSV), dengue virus, mycobacteria (eg *Mycobacterium tuberculosis*), and hantavirus. In certain embodiments, the medical condition is sepsis and/or excludes kidney disease.

In all aspects of the present invention, there exist embodiments wherein the sample is a tissue sample or a sample of biological fluid. In particular, the sample is whole blood or a blood fraction (eg, such as plasma or serum). In alternative embodiments, the sample is biological fluid selected from the group consisting of: urine, saliva, sweat, ejaculate, tears, phlegm, vaginal secretion, vaginal wash and colonic wash. In more particular embodiments, the sample is a plasma or serum sample from the individual, or is urine from the individual In other embodiments, the sample is largely (or essentially) free from cells, and/or is not a whole blood and/or ejaculate sample. In certain embodiments, the sample is not ejaculate if the individual is female and the sample is not a vaginal wash if the individual is male.

In all aspects of the present invention, the reagent that differently modifies methylated and non-methylated DNA may comprise bisulphite and/or an agent that selectively digests unmethylated over methylated DNA (for example, such agent may digest unmethylated DNA but not methylated DNA). In particular embodiments, the reagent agent comprises: at least one methylation sensitive enzyme; at least one methylation sensitive restriction enzyme; and/or an agent selected from the group consisting of: AatII, AciI, ACII, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI. In particular embodiments, said reagent is one selected from the group consisting of: BstUI, HhaI and HpaII.

In related embodiments, the reagent may comprise two or more of any of the reagents disclosed herein. For example, it may comprise two, three, four, five or more (eg up to seven, eight or ten) methylation sensitive restriction enzymes, including a reagent comprising or essentially consisting of two or three of the methylation sensitive restriction enzymes selected from the group consisting of: BstUI, HhaI and HpaII The use of bisulphite or methylation-sensitive restriction enzymes to study differential methylation will be well known to the person of ordinary skill, who may apply teachings of standard texts or adaptation of published methods such as Poon et al (2002), Nygren et al (2010) or Yegnasubramanian; et al (2006, Nuc Acid Res 34:319). By way of illustration, the inventors provide examples herein that employ the use of methylation-sensitive restriction enzymes as the reagent that differentially modifies methylated and non-methylated DNA. For further illustration using bisulphite as reagent, it will be apparent to the person of ordinary skill that bisulphite-modified DNA methylation sites may be detected using eg methylation-specific PCR (such as using primers and/or probes that selectively bind to the bisulphite-modified sequences) and/or by the subsequent use of restriction enzymes the recognition site of which is created upon such bisulphite-modification.

In particular embodiments of all aspects of the invention, a quantitative amount of said species of DNA (and/or or said total DNA) is to be detected and/or determined. Accordingly in such embodiments, one or more (eg each) of said detection steps comprises quantitative detection and said detected amount of said species of DNA is expressed as a relative concentration of said species of DNA to the total DNA present in said sample.

If an absolute amount of total DNA is known, then correspondingly an absolute amount (for example, as represented by a concentration such as ug/mL or genome-equivalents such as Eg/mL) of the species of DNA can be determined from such relative concentration. An absolute amount of total DNA for a sample may be determined, for certain embodiments, by including the further steps of: detecting an amount of total DNA in a standard sample of DNA of known amount using the same other region(s) as used in step (c); and comparing the signal detected from said standard sample of DNA to the signal detected in step (c). Such a standard sample of DNA (of known amount/concentration) is readily available from commercial sources, and especially if prepared and analysed using a dilution series, can readily and efficiently be used to determine (by interpolation/estimation from the standard curve) an absolute amount of total DNA present in the sample. Practically, such standard curve may be prepared and analysed essentially as described for the other regions (but in a separate set of standard vessels/reactions), preferably in the same run as the detection of the DMRs/other region(s); and may even use the same reaction master-mix. Accordingly, while the "DMRs" of the DNA control may be detected for such standard DNA, such a signal is not required to generate a standard curve. Accordingly, if the signal from a such a standard DNA sample is used to compare, the in certain embodiments where each of said detection steps comprises quantitative detection, said detected amount of said species of DNA can be expressed as an absolute amount of said species of DNA in said sample.

A determined quantitative amount of said species of DNA has utility in assessing the risk of the individual to certain medial conditions and/or if there is sufficient of such species of DNA in the sample to enable further analysis of such species of DNA to be conducted efficiently, accurately and/or in a cost effective manner.

Accordingly, certain embodiments of the present invention further include the step of: comparing the amount of said species of DNA detected with a threshold amount and/or reference distribution of amounts, wherein an increase in the (or outlying) amount of said species of DNA indicates an increased risk of the individual suffering from or developing a medical condition. Threshold amounts and/or a set of amounts to form a reference distribution may be obtained from published literature and or empirical studies. For example, using published threshold values (Papantoniou et al 2013, Prenat Diag 33:682) if the total cfDNA exceeds an amount of about 7,500 Eg/mL plasma or if the foetal cfDNA fraction exceeds an amount of about 500 Eg/mL plasma, then the woman may be determined to have such an increased risk. Such a risk may instead or additional by assessed by considering: (i) the fold-increase (eg 1.5, 3, 3.5 or 4-fold increase) of foetal cfDNA (determined for such woman compared to a threshold amount), factoring into the determination that for later-term pregnancies a higher fold-increase in foetal cfDNA may be utilized (Zeybek et al 2013, J Obstet Gynaecol Res 39:632); and/or (ii) into which percentile the amount of cfDNA determined from the woman falls, from consideration of a reference distribution of amounts such as those determined from low-risk women or those which did not suffer from or develop preeclampsia, for example if the foetal cfDNA fraction falls within the 90$^{th}$ percentile of such a distribution, then the woman may be considered to have an increased risk of suffering mild or severe preeclampsia (Jakobsen et al 2013, Transfusion 53:1956). Other relevant factors may be considered in determining a suitable threshold amount. For example, a pregnant women who is also suffering from breast cancer, may have a higher bias of methylation of RASSF1A present in her plasma due to both factors.

Analogously, certain embodiments of the present invention further include the step of: comparing the amount of said species of DNA detected with a threshold amount and/or reference distribution of amounts, wherein an amount of said species of DNA in excess to said threshold (or is not an outlier compared to said population) indicates that a diagnosis for an abnormality in the said species of DNA present in said sample may be performed on, preferably a separate aliquot of DNA of, said sample. For example, if foetal cfDNA fraction is greater than about 10%, 9%, 8%, 7%, 6%, 5%, 4%, 3%, 2%, 1% or 0.5% of total cfDNA present in maternal plasma, then there would be sufficient fraction or foetal cfDNA to effectively conduct a subsequent test to investigate one or more characteristics of the foetal cfDNA, for example to investigate the chance of existence of a chromosomal anomaly of mutation comprised within such foetal cfDNA (such as using NIPT based on massively parallel sequencing). In the case of twin pregnancies, the inventors determine that a minimum foetal fraction of cfDNA for NIPT of a twin pregnancy could be considered to be 8%, or about 5%, 6%, 7%, 9% or 10%, and for monochorionic twin pregnancies with concordant genotypes (apart from rare exceptions, Chen et al, 2013, Am J Med Genet A, 161A:1817), a foetal cfDNA fraction of 4%, or about 2%, 3% or 5%, would be sufficient.

Therefore, the present invention also includes embodiments where comprising a further step of: performing on, preferably with a separate aliquot of DNA of, said sample an in-vitro diagnosis for an abnormality in said species of DNA present in said sample; preferably wherein, said species of DNA originates from cells of a foetus and/or the placenta of a foetus, said sample is from a pregnant female and said diagnosis is a prenatal diagnosis. Such diagnosis directed at said species of DNA present may comprise a step that uses a detection technology selected from the group consisting of: DNA sequencing, SNP analysis, digital PCR and hybridization, and in particular embodiments said detection technology is massively parallel sequencing of DNA, such as massively parallel sequencing of random and/or (exon) enriched DNA.

Such a diagnosis or test may be directed at the foetal DNA to identify a genetic mutation or chromosomal abnormality of the foetal DNA. Accordingly in certain embodiments, said species of DNA originates from cells of a foetus and/or the placenta of a foetus, said sample is from a pregnant female and said abnormality is a genetic mutation or a chromosomal abnormality, such as a chromosomal trisomy, associated with a foetal abnormality and/or a congenital disorder. In particular such embodiments, the genetic mutation is selected from the group consisting of: colour blindness, cystic fibrosis, hemochromatosis, haemophilia, phenylketonuria, polycystic kidney disease, sickle-cell and disease, Tay-Sachs disease; and/or the chromosomal abnormality is selected from the group consisting of: a trisomy (such as trisomy 21, trisomy 18, or trisomy 13), a sex-chromosome abnormality (such as Turners syndrome, Klinefelter syndrome, Noonan syndrome, Tripe X syndrome, XXY syndrome, or Fragile X syndrome), a chromosomal deletion (such as Prader-Willi syndrome, Cris-du-chat syndrome, Wolf-Hirschhorn syndrome, or 22q11 deletion syndrome, Duchene muscular dystrophy), Beckwith-Wiedemann syndrome, Canvan syndrome, and neurofibromatosis. In other embodiments, the genetic mutation or chromosomal abnormality may be one or more selected from those having a clinical utility gene cards (CUGCs) of the EuroGentest2 initiative (www.eurogentest.org). In particular embodiments, the chromosomal abnormality is a trisomy (such as trisomy 21, trisomy 18, or trisomy 13), a sex-chromosome abnormality or a chromosomal deletion.

Such diagnosis or test may be directed at a species DNA to identify a genetic mutation or chromosomal abnormality of such DNA that is derived from a cell or cell-type associated with a medical condition. Accordingly in one of such embodiments, said species of DNA originates from cells of a tumour and said abnormality is a genetic mutation or a chromosomal abnormality associated with the diagnosis, prognosis or predictive treatment of a carcinoma or cancer. In particular such embodiments, the genetic mutation is selected from the group consisting of: a mutation in a tumour suppressor gene (such as TP53 (p53), BRCA1, BRCA2, APC or RB1), a mutation in a proto-oncogene (such as RAS, WNT, MYC, ERK, or TRK) and a DNA repair gene (such as HMGA1, HMGA2, MGMT or PMS2); and/or the chromosomal abnormality is a translocation (such as t(9;22)(q34;q11) [ie, Philadelphia chromosome or BCL-ABL], t(8;14)(q24;q32), t(11;14)(q13;q32), t(14;18)(q32;q21), t(10;(various))(q11;(various)), t(2;3)(q13;p25), t(8;21)(q22;q22), t(15;17)(q22;q21), t(12;15)(p13;q25), t(9;12)(p24;p13), t(12;21)(p12;q22), t(11;18)(q21;q21), t(2;5)(p23;q35), t(11;22)(q24;q11.2-12), t(17;22), t(1;12)(q21;p13), t(X;18)(p11.2;q11.2), t(1;19)(q10;p10), t(7,16)(q32-34;p11), t(11,16)(p11;p11), t(8,22)(q24;q11) or t(2;8)(p11;q24)).

A related aspect of the present invention relates to an alternative method for detecting in a sample from an individual an amount of a species of DNA originating from cells of a given type, which sample comprises said species of DNA in admixture with differentially methylated DNA not originating from cells of said type; said method comprising the steps:

(a) treating the DNA present in said sample with a reagent that differentially modifies methylated and non-methylated DNA; and (b) detecting in said sample the presence of methylation in said species of DNA at two or more DMRs that are differently methylated between said species of DNA and the DNA not originating from cells of said type the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample, wherein, said detection in step (b) is made using the same aliquot of DNA of said sample, and in the same reaction/detection vessel, and effectively simultaneously for such DMRs, and using (x) multiplex real-time quantitative PCR; and (y) at least two labelled probes each of which specific for one of said DMRs and that are labelled with the same detectable label(s) for each of said DMRs. Such an alternative method of the present invention is not intended to be practiced on the human or animal body; for example it is intended to be practiced in an in-vitro manner. Further characterisation of any of the features of this alternative method of the present invention (or any combination of such features) can include the characterisations (and their combinations) as described elsewhere herein in respect of the first aspect of the invention. In particular embodiments of this alternative method of the present invention, the reagent comprises one or more methylation sensitive restriction enzyme, such as one (or a combination thereof) as disclosed herein.

In a second aspect, the invention relates to a method for detecting an increased risk of an individual suffering from or developing a medical condition, said method comprising the steps:

(i) conducting a method of the present invention that determines a quantitative amount said species of DNA (and/or total DNA) in the sample; and (ii) comparing the amount of said species of DNA detected with a threshold amount and/or a reference distribution of amounts, wherein an increase in the (or outlying of) amount of said species of DNA (and/or total DNA) indicates an increased risk of the individual suffering from or developing said medical condition.

A third aspect of the invention relates to a composition (eg, one that is useful for, or used in, a method of the present invention), said inventive composition comprising:

two pairs of PCR primers, each pair for amplifying one of said two or more DMRs as set forth anywhere herein;

one pair of PCR primers for amplifying said other region as set forth anywhere herein;

two labelled probes for quantitative probe-based PCR, each of which specific for one of said DMRs, and labelled with the same detectable labels(s) for each of said probe; and one labelled probe for quantitative probe-based PCR specific for said other region and labelled with different detectable label(s) to the probes used for said DMRs.

Such a composition of the present invention may further comprising:

a further pair of PCR primers for amplifying a second other region as set forth anywhere herein; and a further labelled probe for quantitative probe-based PCR specific for said other region and labelled with detectable label(s) that is different to those used probes for said DMRs; and optionally that is the same as that used for the probe(s) specific the first other region.

A fourth aspect of the invention relates to a kit (for example a kit of separate components; such as a kit of holders or vessels, each holding a different component of the kit), such kit comprising a set of primers and probes as comprised in a composition of the present invention. A kit of the present invention may comprise additional components. For example, the kit may additionally comprise: (i) a printed manual or computer readable memory comprising instructions to use said primers and probes, including to use them to practice a method of the present invention and/or to produce or use a composition of the present invention; and/or (ii) one or more other item, component or reagent useful for the practice of a method of the present invention; and/or the production or use of the composition of the present invention, including any such item, component or reagent disclosed herein, such as a reagent that differently modifies methylated and non-methylated DNA as set forth anywhere herein.

A further aspect of the invention relates to a computer program product comprising a computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a given type may be performed, in each case from a sample from an individual comprising a species of DNA originating from cells of a given type in admixture with differently methylated DNA not originating from cells of said type, the DNA in present in said sample being treated with a reagent that differentially modifies methylated and non-methylated DNA as set forth herein; said operation comprising the steps of:

- receiving: (i) one signal representing the essentially simultaneous quantitative detection of methylation at two or more DMRs as set forth in step (b) as described anywhere herein; and (ii) one signal representing the essentially simultaneous quantitative detection of total DNA using at least one other region as set forth in step (c) as described anywhere herein;
- determining a parameter from the signals (i) and (ii), wherein the parameter represents a quantitative amount of said species of DNA (and/or said total DNA);
- comparing the parameter to with a threshold amount and/or reference distribution of amounts; and
- based on such comparison, determining a classification of whether, respectively, (x) an increased risk of an individual suffering from or developing a medical condition exists; and/or (y) a diagnosis for an anomaly in a species of DNA originating from cells of a given type may be performed.

In certain embodiments, a computer program product of the present invention the operation further comprises steps of: receiving a further signal representing the quantitative detection of total DNA in a standard sample of DNA as set forth anywhere else herein; and comparing said signal with the signal representing the essentially simultaneous quantitative detection of total DNA using at least one other region, so as to determine said parameter that represents an absolute quantitative amount of said species of DNA.

In particular embodiments, the computer program product of the present invention is for an operation for determining if a diagnosis for an anomaly in said species of DNA may be performed, and said operation further comprises the step of determining from said parameter a number of random and/or enriched DNA molecules to be sequenced from, preferably from a separate aliquot of DNA of, said sample as part of said diagnosis.

Figure 5:
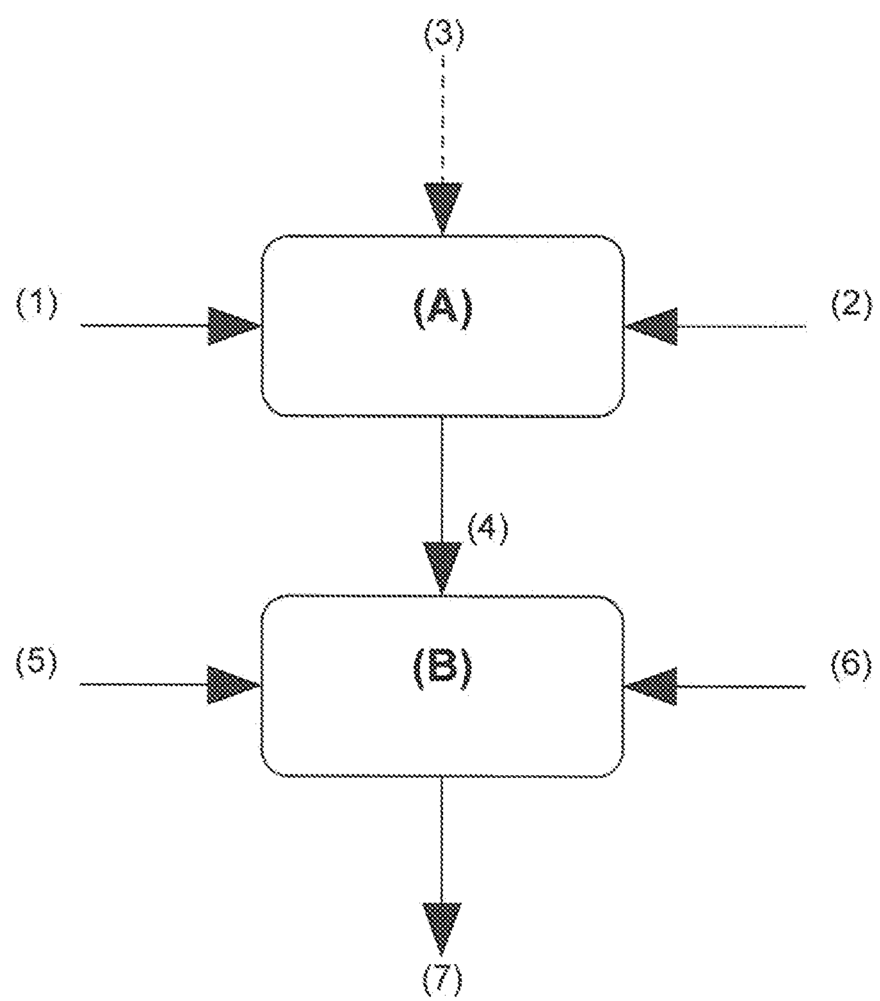
FIG. 5 depicts a schematic representation of the operations conducted by a computer program product of the invention.

One embodiment of operations performed and/or controlled by the computer program product of the invention is depicted in FIG. 5. Operation (A) receives signals (1) and (2) that represent, respectively, the methylation at the DMRs and the total DNA, and optionally signal (3) then represents an amount of total DNA from a standard sample. Operation (A) determines a parameter (4) from signals (1), (2) and optional (3) that represents a relative or absolute amount of DNA (eg from foetal vs total DNA). This parameter (4) is compared by operation (B) against a threshold amount (5) and/or a reference population of amounts (6) so as to classify (7) the risk of an individual suffering from a medical condition and/or if a diagnosis for an anomaly in either of the DNA in the sample may be performed.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

Example 1: Use of the Method of the Invention in NIPT in Multiple Pregnancies, Including in Cases of Vanishing Twins Sample Collection, Processing and DNA Extraction:

36 blood samples from women pregnant with multiple gestations (mono-, di- and trichorionic twin and triplet pregnancies) were collected between Nov. 6, 2012 and Nov. 16, 2013, for research & development (R&D) purposes and as part of routine non-invasive prenatal testing (NIPT) laboratory procedure. One blood sample came from a woman pregnant with triplets, the remaining 35 samples came from twin pregnancies. From each pregnant woman carrying a multiple pregnancy two samples each with 7-10 ml venous blood were collected using Streck cell-free DNA blood collection tubes (Streck). The blood samples were shipped to the diagnostic laboratory with a maximum delivery time of 4 days. Other blood samples from pregnant females analysed herein were similarly collected.

Plasma preparation was performed by centrifugation (1600 g for 10 min at 4° C.) and plasma separation followed by a second centrifugation step (16000 g for 10 min at 4° C.). Extraction of total cell-free DNA (cfDNA) was performed with QIAamp Circulating Nucleic Acid Kit (Qiagen) according to the manufacturer protocol using 3.0-4.0 ml plasma with a final elution volume of 60 ul AVE-buffer (Qiagen).

DNA Quantification:

Foetal cell-free DNA (foetal cfDNA) was detected and quantified in relation to total cell-free DNA (total cfDNA) in order to determine the foetal cfDNA fraction as both a relative concentration and absolute amount using a method of the present invention. From the eluted cell-free DNA, 11 ul were digested with the CpG-methylation sensitive enzymes HhaI (0.4 U/ul), HpaII (0.3 U/ul) and BstUI (0.3 U/ul) in a 22 ul reaction using CutSmart™ Buffer (New England Biolabs). The reaction was incubated for 60 min at 37° C. and 60 min at 60° C. 10 ul from the digestion reaction was used as template DNA for quantitative probe-based PCR (reactions were conducted in duplicate), described briefly as follows.

A 25 ul PCR reaction using a 2-fold concentrated PCR master mix (QuantiFast Multiplex PCR Kit, Qiagen) was conducted. Primers that span CpG methylation sensitive restriction enzyme sites of the respective region that is differentially methylated between foetal and maternal DNA (as a DMR) were used in combination with FAM-labelled probes for such DMRs, and primers that do not span any restriction enzyme sites, an other region that is not differentially methylated between foetal and maternal DNA (as an OR) are used in combination with VIC-labelled probes for such ORs. The sequences of the primers and labelled probes used in this example are described in TABLE 1, and the thermocycler profiles used for the quantitative probe-based (TaqMan) PCR (LightCycler 480 II Instrument; Roche) are described in TABLE 2. In this example, the probes used to detect the presence of the two DMRs, are each labelled with the same detectable fluorescein amidite (FAM) fluorescent moiety, and each with the same minor binding grove (MGB) non-fluorescent quencher (NFQ) moiety, and the probes used to detect the presence of the two ORs, are each labelled with the same detectable VIC (life Technologies) fluorescent moiety, and each with the same MGBNFQ moiety.

TABLE 2

| Thermocycler profiles | | | | |
|---|---|---|---|---|
| Step | Temperature | Time | Cycles | Analysis mode |
| Pre-incubation | 95° C. | 5 min | 1 | None |
| Denaturation | 95° C. | 10 sec | 45 | Quantification |
| Annealing | 60° C. | 10 sec | | None |
| Elongation | 72° C. | 8 sec | | Single |
| Cooling | 40° C. | | | None |

The assay design used in this example on two marker DMRs which are described to be hypomethylated in maternal DNA and hypermethylated in foetal DNA (Nygren, et al, 2010: Clin Chem 56, 1627; Chan et al, 2006: Clin Chem 42, 2211; Chiu et al, 2007: Am J Pathol 170, 941), and two other regions (ORs) not differentially methylated between maternal and foetal DNA which are each located between about 20 bp and 20 kb of their DMR. In particular, the methylation insensitive locus located in RASSF1A is located between 8 kb and 9 kb (8.97 kb) downstream of the methylation sensitive locus located in RASSF1A, and the methylation insensitive locus located in TBX3 is located between 10 kb and 11 kp (10.64 kb) downstream of the methylation sensitive locus located in TBX3. FIG. 2 depicts the respective arrangements and detection modalities of the two DMRs and the two other regions used in this example.

Parallel probe-based quantitative PCR reactions were performed (in separate reactions within the same PCR run) using for template a serial dilution of male genomic DNA (Promega) having known concentrations as a standard. The foetal cfDNA fraction was calculated by relative quantification of signals in the FAM channel (DMR; ie detecting foetal cfDNA) versus the VIC channel (ORs; ie detecting total cfDNA), and the absolute total cfDNA amount was calculated by absolute quantification of signals in the VIC channel obtained from the sample compared to the VIC channel obtained from the dilution series of standard DNA

TABLE 1

| Quantitative (prose based) PCR components | | | | | | |
|---|---|---|---|---|---|---|
| Region | Component | Sequence (5'-3')* | SEQ ID No. | Stock Conc | ul for 1x | Final uM Conc |
| | Master-mix | N/A | | 2x | 12.5 | 1x |
| RASSF1A | DMR1-For | ATT GAG CTG CGG GAG CTG GC | 1 | 100 uM | 0.35 | 1.4 |
| DMR | DMR1-Rev | TGC CGT GTG GGG TTG CAC | 2 | 100 uM | 0.35 | 1.4 |
| | DMR1-Probe | [FAM]-ACC CGG CTG GAG CGT-[MGBNFQ] | 3 | 100 uM | 0.035 | 0.14 |
| RASSF1A | OR1-For | GGT CAT CCA CCA CCA AGA AC | 4 | 100 uM | 0.35 | 1.4 |
| Other | OR1-Rev | TGC CCA AGG ATG CTG TCA AG | 5 | 100 uM | 0.35 | 1.4 |
| region | OR1-Probe | [VIC]-GGG CCT CAA TGA CTT CAC GT-[MGBNFQ] | 6 | 100 uM | 0.035 | 0.14 |
| TBX3 | DMR2-For | GGT GCG AAC TCC TCT TTG TC | 7 | 100 uM | 0.35 | 1.4 |
| DMR | DMR2-Rev | TTA ATC ACC CAG CGC ATG GC | 8 | 100 uM | 0.35 | 1.4 |
| | DMR2-Probe | [FAM]-CCC TCC CGG TGG GTG ATA AA-[MGBNFQ] | 9 | 100 uM | 0.035 | 0.14 |
| TBX3 | OR2-For | TGT TCA CTG GAG GAC TCA TC | 10 | 100 uM | 0.35 | 1.4 |
| Other | OR2-Rev | CAG TCC ATG AGG GTG TTT G | 11 | 100 uM | 0.35 | 1.4 |
| region | OR2-Probe | [VIC]-GAG GTC CCA TTC TCC TTT-[MGBNFQ] | 12 | 100 uM | 0.035 | 0.14 |
| General | DMSO | N/A | | 100% | 0.025 | 0.625 |
| reagents | MgCl2 | N/A | | 50 mM | 2 | 1 |
| | DNA sample | N/A | | | 10 | |
| | Water | | | | — | |
| | Total | | | | 25 | |

*The dyes used for each probe are shown in "[ ]" parentheses of known concentration. Such relative and absolute quantifications were conducted using LightCycler 480 Software release 1.5.0 (Roche).

Maternal Plasma DNA Sequencing and Data Analysis to Identify Foetal Aneuploidy:

DNA sequencing libraries were prepared using NEBNext Ultra™ DNA Library Prep Kit from Illumina. Libraries were prepared according to the manufacturer protocol automated on a Hamilton STARplus robot. Library quality and quantity was measured using a Bioanalyzer instrument (Agilent) and a Qbit Fluorometer (Invitrogen). Based on the library quantification dilutions and equimolar pools of 12 samples per pool were prepared. The pooled samples were sequenced on one lane of an Illumina v3 flow cell on an Illumina HiSeq2000 sequencer. Clonal clusters were generated using TruSeq SR Cluster Kit v3-cBot-HS on a cBot Cluster generation System according to the manufacturer protocol. Bioinformatic analysis to identify foetal chromosomal aneuploidy was carried out as described previously, with z-scores≥3 indicating the presence of a foetal trisomy 21 (Stumm et al 2014, Europ Prenat Diag 34:185). In cases of a positive test result for foetal aneuploidy from this method, the result was confirmed by invasive diagnostic methods.

Results:

Characteristics, % foetal fraction of cfDNA and aneuploidy test results for the blood samples are given in TABLE 3. There were two positive test results indicating foetal trisomy 21. Both were confirmed by karyoptyping after amniocentesis; thus, the false positive rate in this study was 0%. One blood sample represented monochorionic twins with concordant karyoptypes [47, XY, +21] and the other one represent dichorionic twins with discordant karyotypes [47, XY, +21 and 46, XX]. In both samples the foetal fraction was as high as 18.0 and 24.8%, respectively. All other NIPT results were negative for trisomies 21, 18 and 13. There is no evidence for false-negative NIPT results so far in the pregnancies included in this study. Nevertheless, a number of pregnancies are still on-going (with the last birth of the patients expected in mid May 2014) and therefore, the final detection rate is still uncertain.

TABLE 3

Characteristics and NIPT results for the collected blood samples

| Sample | Chr13 z-score | Chr18 z-score | Chr21 z-score | Foetal DNA fraction (%) | Gestational age (p.m.) | No. of foetuses, chorinicity amnionicity | NIPT result |
|---|---|---|---|---|---|---|---|
| LCMPC05 | 1.3 | −1.0 | −0.8 | 16.7 | 11 + 5 | 3, trichorionic, triamniotic | negative |
| LCMPC06 | −0.4 | 1.1 | 8.5 | 18.0 | 13 + 2 | 2, monochorionic, n.a. | T21 positive |
| LCMPC07 | −1.0 | 0.3 | 0.9 | 7.9 | 19 + 0 | 2, dichorionic, diamniotic | negative |
| LCMPC08 | 0.7 | 1.2 | 0.0 | 16.5 | 18 + 1 | 2, dichorionic, diamniotic | negative |
| LCMPC09 | 0.6 | −0.8 | 0.7 | 8.9 | 11 + 5 | 2, monochorionic, diamniotic | negative |
| LCMPC10 | 0.3 | 0.7 | −0.7 | 17.6 | 20 + 4 | 2, dichorionic, diamniotic | negative |
| LCMPC11 | −0.9 | −0.8 | 0.7 | 11.5 | 23 + 0 | 2, dichorionic, diamniotic | negative |
| LCMPC12 | −0.9 | −0.7 | −2.0 | 13.3 | 11 + 1 | 2, monochorionic, diamniotic | negative |
| LCMPC13 | 1.3 | 0.1 | 0.3 | 21.4 | 16 + 0 | 2, dichorionic, diamniotic | negative |
| LCMPC14 | 0.2 | −0.3 | 0.0 | 6.8 | 12 + 5 | 2, n.a., n.a. | negative |
| LCMPC15 | 2.2 | 0.1 | 14.7 | 24.8 | 16 + 0 | 2, dichorionic, diamniotic | T21 positive |
| LCMPC16 | 1.1 | 1.7 | 0.5 | 5.4 | 12 + 5 | 2, n.a., n.a. | negative |
| LCMPC17 | 0.7 | 1.4 | 0.5 | 16.5 | 14 + 2 | 2, n.a., n.a. | negative |
| LCMPC18 | 0.3 | 2.6 | 0.0 | 18.5 | 18 + 3 | 2, n.a., n.a. | negative |
| LCMPC19 | −0.2 | 0.8 | 0.3 | 16.6 | 14 + 0 | 2, dichorionic, diamniotic | negative |
| LCMPC20 | −0.7 | −0.9 | 0.1 | 13.1 | 15 + 4 | 2, dichorionic, diamniotic | negative |
| LCMPC21 | 1.0 | −0.7 | 1.2 | 8.4 | 9 + 3 | 2, dichorionic, diamniotic | negative |
| LCMPC22 | −1.1 | −0.2 | 0.3 | 5.6 | 16 + 2 | 2, monochorionic, n.a. | negative |
| LCMPC23 | −2.2 | 2.2 | −0.8 | 20.6 | 19 + 5 | 2, monochorionic, n.a. | negative |
| LCMPC24 | −1.6 | −0.4 | −0.5 | 14.7 | 22 + 2 | 2, monochorionic, diamniotic | negative |
| LCMPC25 | −0.8 | −0.2 | −1.5 | 12.1 | 11 + 5 | 2, n.a., n.a. | negative |
| LCMPC26 | −0.4 | −0.6 | −1.3 | 7.5 | 13 + 0 | 2, dichorionic, diamniotic | negative |
| LCMPC27 | 0.5 | −0.8 | −0.4 | 16.3 | 12 + 6 | 2, n.a., n.a. | negative |
| LCMPC28 | −1.2 | −0.3 | −0.7 | 19.4 | 10 + 1 | 2, dichorionic, diamniotic | negative |
| LCMPC29 | −0.8 | 0.7 | −0.4 | 14.2 | 13 + 2 | 2, monochorionic, n.a. | negative |
| LCMPC30 | 0.7 | 0.3 | 0.9 | 14.9 | 12 + 2 | 2, monochorionic, monoamniotic | negative |
| LCMPC31 | −0.2 | 0.3 | −0.9 | 19.3 | 19 + 1 | 2, dichorionic, diamniotic | negative |
| LCMPC32 | −1.1 | 2.5 | −2.2 | 11.6 | 20 + 0 | 2, dichorionic, diamniotic | negative |
| LCMPC33 | 0.2 | 2.2 | −1.6 | 8.6 | 11 + 0 | 2, dichorionic, diamniotic | negative |
| LCMPC34 | −1.0 | 1.2 | 0.0 | 15.1 | 15 + 4 | 2, dichorionic, diamniotic | negative |
| LCMPC35 | −0.3 | −0.8 | −0.3 | 19.2 | 12 + 0 | 2, dichorionic, diamniotic | negative |
| LCMPC36 | −1.4 | −0.5 | −0.8 | 13.9 | 12 + 0 | 2, dichorionic, diamniotic | negative |
| LCMPC37 | 1.8 | −0.7 | 0.1 | 13.8 | 17 + 6 | 2, dichorionic, diamniotic | negative |
| LCMPC38 | −0.1 | 1.1 | −0.7 | 13.4 | 13 + 1 | 2, dichorionic, diamniotic | negative |
| LCMPC39 | −1.9 | 0.2 | −2.2 | 15.0 | 17 + 0 | 2, dichorionic, diamniotic | negative |
| LCMPC40 | 0.6 | −0.4 | 0.8 | 16.2 | 18 + 3 | 2, dichorionic, diamniotic | negative |

Figure 3:
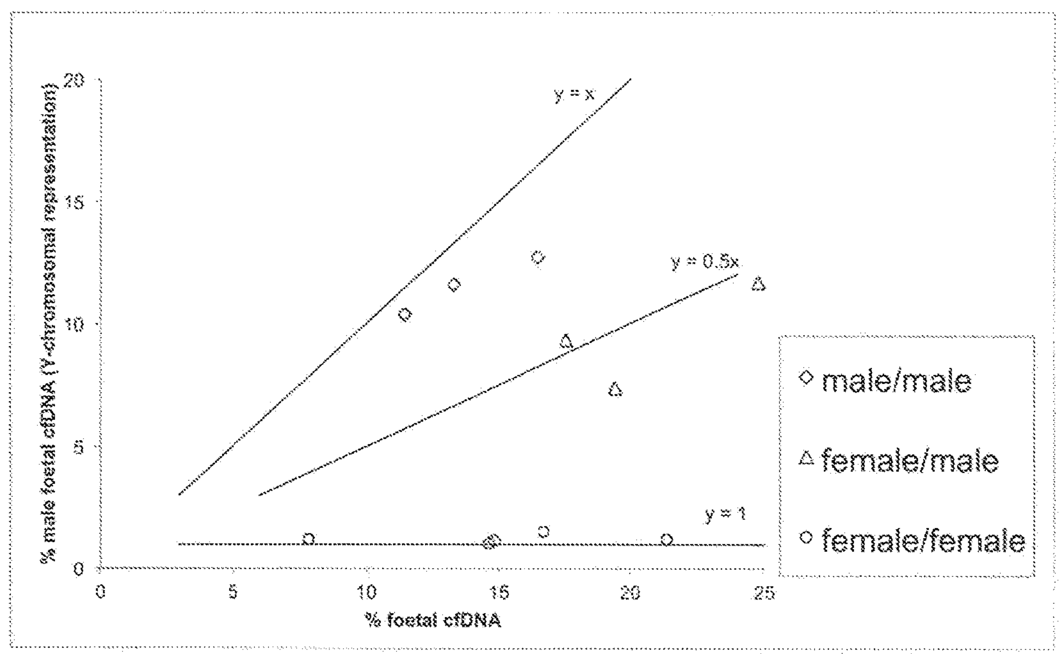
FIG. 3 depicts the correlation of the amount of male specific DNA (Y chromosomal representation) to the foetal cfDNA fraction measured by a method of the present invention (Example 1) for study twin cases with known foetal genders.

The reliable detection of foetal aneuploidy in twin pregnancies by NIPT is dependent on a sufficiently high amount of foetal cfDNA from each foetus in the maternal blood. Different data and considerations have been published on how the lower limit of foetal cfDNA fraction should be defined to ensure that each twin's contribution is above the detection threshold (Leung et al 2013, Prenat Diag 33:675; Qu et al 2007, Am J Pathol 170:941; Struble et al 2013, Fetal Diagn Ther December 7 Epub ahead of print). This is especially important for dichorionic twin pregnancies with discordant karyotypes. In the study described above, supporting information was used for the definition of the minimum foetal cfDNA fraction for twin pregnancies derived from the Y-chromosomal representation, if only one of the two foetuses is male. Using the method of the present invention, the total foetal cfDNA fraction can be determined, which reflects the summary of foetal cfDNA derived from both foetuses. Using the Y-chromosomal representation from the next generation sequencing, the foetal cfDNA amount can be determined for male foetuses (as described in Stumm et al 2014). Thus, in the case of mixed foetal gender the contributing amount of each foetus can be determined by subtraction of the amount of foetal cfDNA determined by the Y-chromosomal representation from the foetal cfDNA fraction measured by method of the present invention. The foetal cfDNA fractions determined by the method of the present invention were compared with the values obtained from Y-chromosomal reads from next generation sequencing for cases with known gender (see FIG. 3). There is a correlation of the amount of male specific cfDNA (y axis) to the foetal cfDNA fraction measured by method of the present invention (x axis). Thus, for twin pregnancies with male/male gender approximately true is: [y=x], for female/male genders it is: [y=0.5x] and for female/female: [y=1]. The genders of cases with similar values are male/male and in case of differing values with low Y-chromosomal representation the genders are female/female. The intermediate cases, which show about half the percentage of foetal fraction as Y-chromosomal representation, are of mixed gender. The data presented in FIG. 3 show that it is not only possible to determine the foetal genders using NIPT results for twin pregnancies, but also that the measurement of the amount of foetal fraction of cfDNA determined by the method of the present invention is surprisingly accurate as compared to frequency counting of Y chromosome sequences. On the other hand, these data support the hypothesis that each foetus of a twin pregnancy contributes roughly about half of the total foetal cfDNA fraction. This leads to the conclusion that for twin pregnancies, twice the amount of foetal cfDNA would be required, and thus a recommended minimum foetal fraction of cfDNA for NIPT of a twin pregnancy could be considered to be 8%.

For monochorionic twin pregnancies with concordant genotypes (apart from rare exceptions, Chen et al 2013, Am J Med Genet A 161A:1817), a foetal cfDNA fraction of 4% would be enough to detect a foetal aneuploidy, just as for single pregnancies. However, for routine laboratory NIPT service one major issue speaks against the implication of such different quality criteria for mono- and dichorionic pregnancies: the determination of chorionicity is dependent on the gestational age and the practical experience of the physician performing the ultrasound examination. The chorionicity is clearly detectable in the first trimester of a multiple pregnancy, but in later stages detection becomes more difficult (Sperling et al 2001, Acta Obstet Gynecol Scand 80:287). Therefore, it is a safer strategy to generally define a minimum foetal cfDNA fraction for twin pregnancies, which is applicable for monochorionic as well as for dichorionic multiple pregnancies.

Identification of Vanishing Twins:

In two cases of NIPT aneuploidy testing in which the foetal cfDNA fraction was measured using the method of the present invention, identified a trisomy 21 (z-scores 13.5 and 3.4 respectively), but also a striking discrepancy between the total foetal cfDNA fraction measured by the method of the invention and the cf-Foetal-DNA amount measured by Y-chromosome representation were observed.

For case A, two analyses of blood samples (first and back-up samples) estimated the total foetal cfDNA fraction measured the method of the present invention was 20.7% and 24.8%, respectively, whereas the foetal cfDNA according to the Y-chromosomal representation from next generation sequencing was 9.2% and 9.3%, respectively. It was speculated, and reported to the physician, that the pregnancy may be a mixed-sex twin pregnancy, who confirmed that a deceased twin had been observed during ultrasound scan at week 10. A further blood sample taken in the third trimester of the pregnancy (38+2) turned out to be negative for trisomy 21 and the foetal cfDNA amount measured by Y-chromosomal representation correlated with the foetal amount measured by QuantYfeX (21.7% and 21.4), which matched the male gender determined by karyotyping of the living foetus. At birth a foetus papyraceus was found in the placental tissue from which a sufficient amount of cells could be isolated for cell culture and following GTG banding, a trisomy 21 positive, female karyotype was confirmed (47, XX, +21).

For case B, a slightly increased Y-chromosomal representation was monitored indicating male specific cf-Foetal-DNA of 3.0% and 2.7% respectively. As the foetal cfDNA fraction estimates measured by the method of the invention were far above that (13.4% and 10.0%) we hypothesized from this discrepancy in the foetal fraction measured, that two foetuses with discordant gender contribute to the foetal fraction and the male foetus being the one affected by trisomy 21. This suggestion was derived from the correlation of Y-chromosome specific foetal cfDNA amount of roughly 3% with the elevated z-score around the cut-off value of 3.0. Since the examination was clearly requested for a singleton pregnancy, the male specific foetal cfDNA was suspected to stem from a vanishing twin—maybe the carrier of a trisomy 21—that was either not recognized or not indicated on the consent form for NIPT. Thus, the result was reported to be indecisive for chromosome 21 and the conflicting data was reported to the responsible physician, including a notice regarding the potential vanishing twin, for further clarification via ultrasound. The responsible physician subsequently confirmed that the pregnancy had started as twin and later continued as a singleton pregnancy. The gender of the living and apparently healthy foetus was confirmed to be female and thus, the foetal cfDNA that caused the increased z-score for trisomy 21 can clearly be assigned to a deceased male foetus. The pregnancy is still on-going and further analysis of placental tissue and blood of the living foetus is not yet possible.

Figure 4:
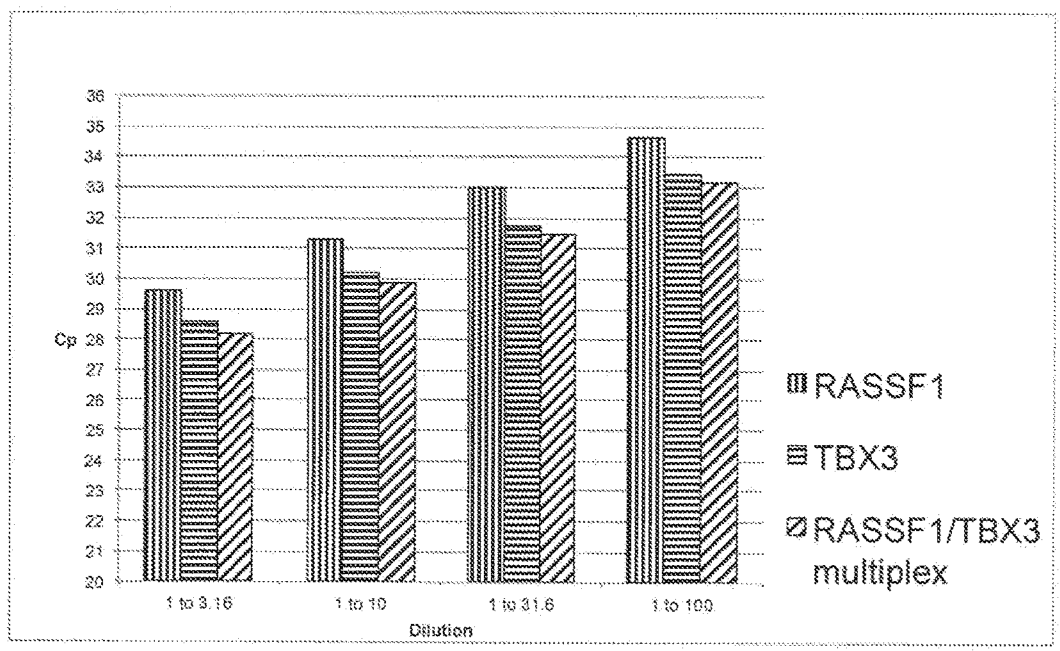
FIG. 4 depicts the improved sensitivity of a method of the invention compared to foetal cfDNA fraction detected using separate reactions of a single DMR. The number of PCR cycles (Cp) required for detection of foetal cfDNA (Example 2) in a sample using either RASSF1A or TBX3 alone as a single DMR, or as a multiplex (using the same labels) of RASSF1A and TBX3.

Example 2: Improved Detection Sensitivity Using Two Differentially Methylated Regions Using the Same Detectable Moiety/Moieties for Each Differentially Methylated Region The inventors were surprised to observe that a complex and multiplex reaction detecting two DMRs using the same detectable moiety/moieties for each of said DMR (as well as two other regions (OR) not differentially methylated) was more sensitive to detect foetal cfDNA fraction than previous detection reactions that each detected—in separate PCR reactions—a single DMR (as well as a single OR) (FIG. 4).

In a method of the present invention, two DMRs (those found in RASSF1A and TBX3, as described in Example 1) were detected (over 4 dilutions) with the same aliquot of DNA and reaction—effectively simultaneously (using quantitative probe-based (TaqMan) PCR) with two ORs (those found in RASSF1A and TBX3, as described in Example 1), using: (x) the same detectable moiety/moieties for each of said DMR; and (y) a detectable moiety/moieties for said at least one OR that is/are different to the detectable moiety/moieties used for said DMRs. In comparison, detection of foetal cfDNA fraction was less sensitive, as shown by detection at higher cycle numbers (Cp), if each DMR (and corresponding OR) was detected independently in separate reactions. The regions/markers, primers/probes and detection methodology was substantially as described in Example 1, except that for the single locus reactions, only the DMR and OR from a given gene (RASSF1A or TBX3) were detected simultaneously in a single reaction.

In contrast, detection of foetal cf DNA fraction using a multiplex reaction of the two DMRs using different detectable moieties (eg FAM for the RASSF1A locus and VIC for the TBX3 locus) is determined to be even less sensitive, and further is difficult to detect simultaneously with any OR; without being bound by theory, believed due to the higher complexity of colour compensation, the limited number of separately detectable fluorescent markers and/or the "bleaching" effects from so many fluorescent markers being present in the same reaction.

Given the exponential nature of quantitative PCR detection, a higher sensitivity of detection (ie lower cycle numbers) would also equate to higher accuracy of quantification, as the correction to standard curves, and interpolation between data points, would be subject to less error than that arising with the amounts of DNA correlating to detection at higher cycle numbers.

Example 3: Detection of an Increased Risk of a Pregnant Woman Suffering From or Developing Preeclampsia (Prophetic Example)

Using a method of the present example, pregnant women are assessed for their risk of suffering from or developing preeclampsia as follows. Firstly, a blood sample is collected from the woman for whom such risk to be assessed and total cfDNA extracted from the plasma of such sample substantially in accordance with the procedures described in Example 1. Secondly, using a method substantially as described in Example 1, a relative and/or absolute amount of foetal cfDNA and total cfDNA present in the plasma is determined, wherein the absolute amount of foetal and/or total cfDNA can be expressed as the amount of genome equivalents ("Eq"). Thirdly, such determined amount of cfDNA and/or total cfDNA is compared to a threshold amount or a reference distribution of amounts, and the women is determined to be at increased risk of suffering from or developing preeclampsia if the amount of foetal cfDNA or total cfDNA exceeds such threshold value and/or is an outlier in such distribution.

For example, using published threshold values (Papantoniou et al 2013, Prenat Diag 33:682) if the total cfDNA exceeds an amount of about 7,500 Eg/mL plasma or if the foetal cfDNA fraction exceeds an amount of about 500 Eg/mL plasma, then the woman is determined to have such an increased risk. Such a risk may instead or additional be assessed by considering: (i) the fold-increase (eg 1.5, 3, 3.5 or 4-fold increase) of foetal cfDNA (determined for such woman compared to a threshold amount), factoring into the determination that for later-term pregnancies a higher fold-increase in foetal cfDNA may be utilised (Zeybek et al 2013, J Obstet Gynaecol Res 39:632); and/or (ii) into which percentile the amount of cfDNA determined from the woman falls, from consideration of a reference distribution of amounts determined from low-risk women or women who did not suffer from or develop preeclampsia, for example if the foetal cfDNA fraction falls within the $90^{th}$ percentile of such a distribution, then the woman is considered to have an increased risk of suffering mild or severe preeclampsia (Jakobsen et al 2013, Transfusion 53:1956).

In this example, t detection of a risk is conducted using a computer program product that performs the operations represented by FIG. 5. Operation (A) receives signals (1) and (2) representing, respectively, foetal and total cfDNA are used by the computer program product to determine a parameter (4) that represents the relative and/or absolute amount of foetal (or total) cfDNA present in the plasma of the woman. This operation may optional receive a signal (3) representing an absolute amount of standard DNA. A second operation (B) compares such determined parameter (4) against a threshold amount (5) and/or a reference population of amounts (6) so as to determine and report (7) whether or not—and based on such comparison—the woman is determined to be at increase risk of suffering or developing preeclampsia.

Example 4: Detection of Tumour-Associated DNA in Samples From Cancer Patients (Prophetic Example)

Methylation of RASSF1A and at least one other DMR such as ER-beta (oestrogen receptor beta), RAR-beta2 (retinoic acid receptor beta 2) and/or Cyclin D2 is used to detect cfDNA derived from a tumour and to assess the risk of women suffering from breast cancer. Specific methylation at such DMRs is a characteristic of tumour-derived cfDNA, and a method of the present invention is used to detect and to quantify the amount tumour derived cfDNA in the plasma of women, and those determined to have elevated (or outlying amounts of tumour-derived cfDNA are determined to be at increased risk from suffering from or developing breast cancer. Essentially, the process described in Example 3 is followed except that DMR2 and OR2 are located in one of ER-beta, RAR-beta2 or Cyclin D2, rather than TBX3. Primers and probes to detect such DMR2 and OR2 for use in this embodiment of the present invention are designable by the person of ordinary skill.

In this example, a similar computer program product as described in Example 3 can be used to assess the risk for a given woman is based on the amount of tumour-derived cfDNA present in her blood, but in this example this parameter is compared against a threshold amount or distribution of amounts that is derived from a study of the amount of tumour-derived cfDNA present in control and breast cancer patients; and those women having an elevated (or outlying) amount of tumour-derived cfDNA are considered to have an increased risk of suffering from or developing breast cancer.

In view of the above, it will be appreciated that the present invention also relates to the following items:

1. A method for detecting in a sample from an individual an amount of a species of DNA originating from cells of a given type, which sample comprises said species of DNA in admixture with differently methylated DNA not originating from cells of said type; said method comprising the steps:
   (a) treating the DNA present in said sample with a reagent that differentially modifies methylated and non-methylated DNA;
   (b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample; and (c) detecting an amount of total DNA present in said sample using at least one other region that is not differently methylated between said species of DNA and the DNA not originating from cells of said type, the modification of which region(s) by said reagent is insensitive to methylation of DNA, wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

2. The method of item 1, wherein prior to or as part of said detection in step (b) and/or step (c), each DNA region comprising said DMRs and/or said other region(s), respectively, is(are) amplified.

3. The method of item 1 or 2, wherein each detectable label used in step (b) and/or step (c) is independently selected from the group consisting of: fluorescent, protein, small molecule or radioactive label.

4. The method of any one of items 1 to 3, wherein said detection in step (b) comprises multiplex real-time probe-based quantitative probe-based PCR using at least two labelled probes each of which specific for one of said DMRs.

5. The method of any one of items 1 to 4, wherein said detection in step (c) comprises real-time quantitative PCR using at least one labelled probe specific for one of said other region(s).

6. The method of any one of items 1 to 5, wherein said other region is located between about 20 bp and about 20 kb upstream or downstream of, and/or within the same gene as, at least one of said DMRs.

7. The method of any one of items 1 to 6, wherein said detection in step (c) comprises using at least two of said other regions; preferably wherein, the number of said other regions is the same as the number of DMRs used in step (b); more preferably wherein, one of said other regions is located between about 20 bp and about 20 kb upstream or downstream of a DMR used in step (b) and each other of the said other regions is located between about 20 bp and about 20 kb upstream or downstream of another of said DMRs.

8. The method of item 7, wherein said detection in step (c) is made using the same detectable label(s) for each of said other regions.

9. The method of item 7 or 8, wherein said detection in step (c) comprises multiplex real-time quantitative probe-based PCR using at least two labelled probes each of which is specific for one of said other regions.

10. The method of any one of items 1 to 9, wherein said detection in step (c) and said detection in step (b) are made using the same aliquot of DNA of said sample, and in the same reaction/detection vessel, and effectively simultaneously with each other, and by multiplex real-time quantitative probe-based PCR using at least one labelled probe specific for each of the said DMRs and other region(s).

11. The method any one of items 1 to 10, wherein said species of DNA originates from cells of a foetus and/or the placenta of a foetus and said sample is from a pregnant female; preferably wherein, said species of DNA is circulating cell-free DNA and said sample is a blood fraction such as plasma or serum.

12. The method of item 11, wherein said DMRs comprises at least one, preferably at least two, methylation site(s) specific for said reagent, and at least one of said DMRs is located in a portion of the genome and/or gene selected from the group consisting of: RASSF1A, TBX3, HLCS, ZFY, CDC42EP1, MGC15523, SOX14 and SPN; preferably wherein, each of said DMRs is located in a portion of the genome and/or gene selected from the group consisting of: RASSF1A, TBX3, HLCS, ZFY, CDC42EP1, MGC15523, SOX14 and SPN; and/or at least one of said DMRs is located between about positions 4,700 bp and 5,600 bp of RASSF1A or about positions 1,660 bp and 2,400 bp of TBX3; more preferably wherein, said two or more DMRs comprise those located between about positions 4,700 bp and 5,600 bp of RASSF1A and about positions 1,660 bp and 2,400 bp of TBX3.

13. The method of item 11 or 12, wherein said other region is located in a portion of the genome and/or gene selected from the group consisting of: GAPDH, beta-actin, ALB, APOE, RNASEP, RASSF1A, TBX3, HLCS, ZFY, CDC42EP1, MGC15523, SOX14 and SPN; preferably wherein, said other region comprises a region without a methylation site specific for said reagent and said locus is located in the genes RASSF1A or TBX3, more preferably wherein, two or more of said other regions are used in detection step (c) and comprise those located between about positions 14,220 bp and 13,350 bp of RASSF1A and about positions 12,400 bp and 13,000 bp of TBX3.

14. The method any one of items 11 to 13, wherein said pregnant female is susceptible to a pregnancy-associated medical condition; preferably wherein, said pregnancy-associated medical condition is selected from the group consisting of: preeclampsia, preterm labour, intrauterine growth retardation and vanishing twin.

15. The method of any one of items 1 to 10, wherein said species of DNA originates from a cell type associated with a medical condition; preferably wherein, said medical condition is one selected from the group consisting of: a cell proliferative disorder, an infection/infectious disease, a wasting disorder, a degenerative disorder, an (auto)immune disorder, kidney disease, liver disease, inflammatory disease acute toxicity, chronic toxicity, myocardial infarction, and a combination of any of the forgoing; more preferably wherein, said species of DNA is circulating cell-free DNA and said sample is a blood fraction such as plasma or serum.

16. The method of item 15, wherein said species of DNA originates from cells of a tumour; preferably wherein, said tumour is a carcinoma or cancer of an organ selected from the group consisting of: liver, lung, breast, colon, oesophagus, prostate, ovary, cervix, uterus, testis, brain, bone marrow and blood.

17. The method of item 16, wherein said DMRs comprises at least one, preferably at least two, methylation site(s) specific for said reagent, and at least one of said DMR is located in a portion of the genome and/or a gene selected from the group consisting of: a tumour suppressor gene, p16, SEPT9, RASSF1A, GSTP1, DAPK, ESR1, APC, HSD17B4 and H1C1; preferably wherein, one of said two or more DMRs is located in RASSF1A; more preferably wherein, one of said two or more DMRs is located between about positions 4,700 bp and 5,600 bp of RASSF1A; and/or more preferably wherein, said other region is located between about positions 14,220 bp and 13,350 bp of RASSF1A.

18. The method of any one of items 1 to 17, wherein said sample is a tissue sample or a sample of biological fluid; preferably wherein, said sample is a sample of biological fluid selected from the group consisting of: whole blood, a blood fraction, urine, saliva, sweat, ejaculate, tears, phlegm, vaginal secretion, vaginal wash and colonic wash; more preferably wherein, said sample is a plasma or serum sample.

19. the method of any one of items 1 to 18, wherein said reagent that differentially modifies methylated and non-methylated DNA comprises bisulphite.

20. The method of any one of items 1 to 18, wherein said reagent that differentially modifies methylated and non-methylated DNA comprises an agent that selectively digests unmethylated over methylated DNA, preferably wherein, said agent comprises:
at least one methylation sensitive enzyme;
at least one methylation sensitive restriction enzyme; and/or
an agent selected from the group consisting of: AatII, AciI, ACII, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI.

21. The method of any one of items 1 to 20, wherein each of said detection steps comprises quantitative detection and said detected amount of said species of DNA is expressed as a relative concentration of said species of DNA to the total DNA in said sample.

22. The method of any one of items 1 to 20, further comprising the steps:
detecting an amount of total DNA in a standard sample of DNA of known amount using the same other regions(s) as used in step (c); and
comparing the signal detected from said standard sample of DNA to the signal detected in step (c).

23. The method of item 22, wherein each of said detection steps comprises quantitative detection and said detected amount of said species of DNA is expressed as an absolute amount of said species of DNA in said sample.

24. The method of item 21 or 23, further comprising the step:
comparing the amount of said species of DNA detected with a threshold amount and/or reference distribution of amounts, wherein: (x) an increase in, or outlying of, the amount of said species of DNA indicates an increased risk of the individual suffering from or developing a medical condition; and/or (y) an amount of said species of DNA in excess to said threshold, or outlying from said distribution, indicates that a diagnosis for an abnormality in the said species of DNA present in said sample may be performed on, preferably a separate aliquot of DNA of, said sample.

25. The method of any one of items 21 to 24, further comprising the step:
performing on, preferably with a separate aliquot of DNA of, said sample, a diagnosis for an abnormality in said species of DNA present in said sample; preferably wherein, said species of DNA originates from cells of a foetus and/or the placenta of a foetus, said sample is from a pregnant female and said diagnosis is a prenatal diagnosis.

26. The method of item 25, wherein said diagnosis comprises a step that uses a detection technology selected from the group consisting of: DNA sequencing, SNP analysis, digital PCR and hybridisation; preferably wherein, said detection technology is massively parallel sequencing of DNA; more preferably wherein said detection technology is massively parallel sequencing of random and/or enriched DNA.

27. The method of item 25 or 26, wherein:
(x) said species of DNA originates from cells of a foetus and/or the placenta of a foetus, said sample is from a pregnant female and said abnormality is a genetic mutation or a chromosomal abnormality, such as a chromosomal trisomy, associated with a foetal abnormality and/or a congenital disorder; preferably wherein:
said genetic mutation is selected from the group consisting of: colour blindness, cystic fibrosis, hemochromatosis, haemophilia, phenylketonuria, polycystic kidney disease, sickle-cell and disease, Tay-Sachs disease; and/or
said chromosomal abnormality is selected from the group consisting of: a trisomy (such as trisomy 21, trisomy 18, or trisomy 13), a sex-chromosome abnormality (such as Turners syndrome, Klinefelter syndrome, Noonan syndrome, Triple X syndrome, XXY syndrome, or Fragile X syndrome), a chromosomal deletion (such as Prader-Willi syndrome, Cris-du-chat syndrome, Wolf-Hirschhorn syndrome, or 22q11 deletion syndrome, Duchene muscular dystrophy), Beckwith-Wiedemann syndrome, Canvan syndrome, and neurofibromatosis; or
(y) said species of DNA originates from cells of a tumour and said abnormality is a genetic mutation or a chromosomal abnormality associated with the diagnosis, prognosis or predictive treatment of a carcinoma or cancer; preferably wherein:
said genetic mutation is selected from the group consisting of: a mutation in a tumour suppressor gene (such as TP53 (p53), BRCA1, BRCA2, APC or RB1), a mutation in a proto-oncogene (such as RAS, WNT, MYC, ERK, or TRK) and a DNA repair gene (such as HMGA1, HMGA2, MGMT or PMS2); and/or
said chromosomal abnormality is a translocation (such as t(9;22)(q34;q11) [ie, Philadelphia chromosome or BCL-ABL], t(8;14)(q24;q32), t(11;14)(q13;q32), t(14;18)(q32;q21), t(10;(various))(q11;(various)), t(2;3)(q13;p25), t(8;21)(q22;q22), t(15;17)(q22;q21), t(12;15)(p13;q25), t(9;12)(p24;p13), t(12;21)(p12;q22), t(11;18)(q21;q21), t(2;5)(p23;q35), t(11;22)(q24;q11.2-12), t(17;22), t(1;12)(q21;p13), t(X;18)(p11.2;q11.2), t(1;19)(q10;p10), t(7,16)(q32-34;p11), t(11,16)(p11;p11), t(8,22)(q24;q11) or t(2;8)(p11;q24)).

28. A method for detecting an increased risk of an individual suffering from or developing a medical condition; said method comprising the steps:
(i) conducting the method of item 21 or 23; and
(ii) comparing the amount of said species of DNA detected with a threshold amount and/or a reference distribution of amounts, wherein an increase in, or outlying of, the amount of said species of DNA indicates an increased risk of the individual suffering from or developing said medical condition.

29. A composition comprising:

two pairs of PCR primers, each pair for amplifying one of said two of more DMRs as set forth in any of items 1 to 28;

one pair of PCR primers for amplifying said other region as set forth in any of items 1 to 28;

two labelled probes as set forth in item 4; and one labelled probe as set forth in item 5.

30. The composition of item 29, further comprising:

a further pair of PCR primers for amplifying a second other region as set forth in any of items 9 to 28; and a further labelled probe as set forth in item 9.

31. A kit comprising:

the primers and probes as set forth in item 29 or 30; and optionally, further comprising: (i) a printed manual or computer readable memory comprising instructions to use said primers and probes to practice a method of any one of items 1 to 28 and/or to produce or use the composition of item 29 or 30; and/or (ii) one or more other item, component or reagent useful for the practice of a method of any one of items 1 to 28 and/or the production or use of the composition of item 29 or 30, including any such item, component or reagent disclosed herein, such as the reagent that differently modifies methylated and non-methylated DNA as set forth in any one of items 1 to 28.

32. A computer program product comprising a computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a given type may be performed, in each case from a sample from an individual comprising a species of DNA originating from cells of a given type in admixture with differently methylated DNA not originating from cells of said type, the DNA in present in said sample being treated with a reagent that differentially modifies methylated and non-methylated DNA as set forth in any one of items 1 to 28; said operation comprising the steps of:

receiving: (i) one signal representing the essentially simultaneous quantitative detection of methylation at two or more DMRs as set forth in step (b) of any one of items 1 to 28; and (ii) one signal representing the essentially simultaneous quantitative detection of total DNA using at least one other region as set forth in step (c) any of items 1 to 28;

determining a parameter from the signals (i) and (ii), wherein the parameter represents a quantitative amount of said species of DNA;

comparing the parameter to with a threshold amount and/or reference distribution of amounts; and based on such comparison, determining a classification of whether, respectively, (x) an increased risk of an individual suffering from or developing a medical condition exists; and/or (y) a diagnosis for an anomaly in a species of DNA originating from cells of a given type may be performed.

33. The computer program product of item 32, wherein said operation further comprises the steps:

receiving a further signal representing the quantitative detection of total DNA in a standard sample of DNA as set forth in item 22; and comparing said signal with the signal set forth in (ii) of item 32, so as to determine said parameter that represents an absolute quantitative amount of said species of DNA.

34. The computer program product of item 32, or 33, wherein said operation is for determining if a diagnosis for an anomaly in said species of DNA may be performed, and further comprises the step of determining from said parameter a number of random and/or enriched DNA molecules to be sequenced from, preferably from a separate aliquot of DNA of, said sample as part of said diagnosis.

35. A method for detecting in a sample from an individual an amount of a species of DNA originating from cells of a given type, which sample comprises said species of DNA in admixture with differentially methylated DNA not originating from cells of said type; said method comprising the steps:

(a) treating the DNA present in said sample with a reagent that differentially modifies methylated and non-methylated DNA; and (b) detecting in said sample the presence of methylation in said species of DNA at two or more DMRs that are differently methylated between said species of DNA and the DNA not originating from cells of said type the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample, wherein, said detection in step (b) is made using the same aliquot of DNA of said sample, and in the same reaction/detection vessel, and effectively simultaneously for such DMRs, and using (x) multiplex real-time quantitative PCR; and (y) at least two labelled probes each of which specific for one of said DMRs and that are labelled with the same detectable label(s) for each of said DMRs; preferably wherein, said reagent comprises agent as set forth in item 20.

The invention claimed is:

1. A method for quantitatively detecting in a sample from an individual an amount of a species of DNA originating from cells of a given type, which sample comprises said species of DNA in admixture with differently methylated DNA not originating from cells of said type; said method comprising the steps:

(a) treating the DNA present in said sample with a reagent that differentially modifies methylated and non-methylated DNA;

(b) quantitatively detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, and wherein the presence of methylated DNA at one or more of said DMRs indicates the presence of said amount of species of DNA in said sample and the absence of methylated DNA at said DMRs indicates the absence of said species of DNA in said sample; and (c) quantitatively detecting an amount of total DNA present in said sample using at least one other region that is not differently methylated between said species of DNA and the DNA not originating from cells of said type, the modification of which region(s) by said reagent is insensitive to methylation of DNA, wherein, said detection in step (b) and said detection in step (c) are made using the same aliquot of DNA of said sample, and in the same reaction/detection vessel, and effectively simultaneously for such DMRs and other region(s), and using: (x) the same detectable label(s) for each of said DMRs; and (y) a different detectable label(s) for said other region(s); and wherein, said detection in step (c) comprises using at least two of said other regions, wherein the number of said other regions is the same as the number of DMRs used in step (b), and wherein one of said other regions is located between about 20 bp and about 20 kb upstream or downstream of a DMR used in step (b) and each other of the said other regions is located between about 20 bp and about 20 kb upstream or downstream of another of said DMRs; and wherein, said detection in step (c) is made using the same detectable label(s) for each of said other regions.

2. The method of claim 1, wherein:

(A) prior to or as part of said detection in step (b) and/or step (c), each DNA region comprising said DMRs and/or said other region(s), respectively, is(are) amplified; and/or (B) each detectable label used in step (b) and/or step (c) is fluorescent; and/or (C) said detection in step (b) comprises multiplex real-time probe-based quantitative PCR using at least two labelled probes each of which is specific for one of said DMRs; and/or (D) said detection in step (c) comprises real-time quantitative PCR using at least one labelled probe specific for one of said other region(s).

3. The method of claim 1, wherein:

said detection in step (c) comprises multiplex real-time quantitative probe-based PCR using at least two labelled probes each of which is specific for one of said other regions.

4. The method of claim 1, wherein said detection in step (c) and said detection in step (b) comprises multiplex real-time quantitative probe-based PCR using at least one labelled probe specific for each of the said DMRs and other regions.

5. The method of claim 1, wherein said species of DNA originates from cells of a fetus and/or the placenta of a fetus and said sample is from a pregnant female, and wherein said species of DNA is circulating cell-free DNA and said sample is a blood fraction.

6. The method of claim 5, wherein:

(A) said DMRs comprise at least one methylation site(s) specific for said reagent, and at least one of said DMRs is located in a portion of the genome and/or gene selected from the group consisting of: RASSF1A, TBX3, HLCS, ZFY, CDC42EP1, MGC15523, SOX14 and SPN; and/or (B) said at least one of said other regions is located in a portion of the genome and/or gene selected from the group consisting of: RASSF1A, TBX3, HLCS, ZFY, CDC42EP1, MGC15523, SOX14 and SPN.

7. The method of claim 6, wherein at least one of said DMRs is located between about positions 4,700 bp and 5,600 bp of RASSF1A or about positions 1,660 bp and 2,400 bp of TBX3.

8. The method of claim 7, wherein said pregnant female is susceptible to a pregnancy-associated medical condition.

9. The method of claim 8, wherein said pregnancy-associated medical condition is preeclampsia.

10. The method of claim 5, further comprising the step of performing on said sample a prenatal diagnosis for an anomaly in the DNA originating from cells of a fetus and/or the placenta of a fetus.

11. The method of claim 10, wherein said anomaly in the DNA originating from cells of a fetus and/or the placenta of a fetus is a chromosomal trisomy.

12. The method of claim 5, wherein one or both of said two or more DMRs is/are located in SEQ ID NOs: 15-199.

13. The method of claim 5, wherein one or both of said two or more DMRs is/are located in SEQ ID NOs: 74-147.

14. The method of claim 1, wherein said species of DNA originates from a cell type associated with a medical condition, wherein said medical condition is one selected from the group consisting of: a cell proliferative disorder, an infection/infectious disease, a wasting disorder, a degenerative disorder, an (auto)immune disorder, kidney disease, liver disease, inflammatory disease, acute toxicity, chronic toxicity, myocardial infarction, and a combination of any of the forgoing, and wherein said species of DNA is circulating cell-free DNA and said sample is a blood fraction.

15. The method of claim 14, wherein said species of DNA originates from cells of a tumor.

16. The method of claim 15, wherein said tumor is a carcinoma or cancer of an organ selected from the group consisting of: liver, lung, breast, colon, oesophagus, prostate, ovary, cervix, uterus, testis, brain, bone marrow and blood.

17. The method of claim 15, wherein said DMRs comprise at least one methylation site(s) specific for said reagent, and at least one of said DMRs is located in a portion of the genome and/or a gene selected from the group consisting of: a tumour suppressor gene, p16, SEPT9, RASSF1A, GSTP1, DAPK, ESR1, APC, HSD17B4 and H1C1.

18. The method of claim 17, wherein at least one of said DMRs is located between about positions 4,700 bp and 5,600 bp of RASSF1A.

19. The method of claim 17, wherein at least one of said other regions is located between about positions 14,220 bp and 13,350 bp of RASSF1A.

20. The method of claim 1, wherein said sample is a tissue sample or a sample of biological fluid, wherein the sample of biological fluid is selected from the group consisting of: whole blood, a blood fraction, urine, saliva, sweat, ejaculate, tears, phlegm, vaginal secretion, vaginal wash and colonic wash.

21. The method of claim 20, wherein said sample is a plasma or serum sample.

22. The method of claim 1, wherein:

(A) said reagent that differentially modifies methylated and non-methylated DNA comprises bisulphate; or (B) said reagent that differentially modifies methylated and non-methylated DNA comprises an agent that selectively digests unmethylated over methylated DNA, wherein said agent comprises:

at least one methylation sensitive enzyme;

at least one methylation sensitive restriction enzyme; and/or an agent selected from the group consisting of: AatII, AciI, AclI, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinPlI, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmlI, PvuI, PvuI-HF, RsrII, SacII, SalI, SalI-HF, SfoI, SgrAI, SmaI, SnaBI, TspMI and ZraI.

23. The method of claim 1:

(A) wherein each of said detection steps comprises quantitative detection and said detected amount of said species of DNA is expressed as a relative concentration of said species of DNA to the total DNA in said sample; or (B) wherein said method further comprises the steps:

detecting an amount of total DNA in a standard sample of DNA of known amount using the same other region(s) as used in step (c); and comparing the signal detected from said standard sample of DNA to the signal detected in step (c); and optionally, wherein each of said detection steps comprises quantitative detection and said detected amount of said species of DNA is expressed as an absolute amount of said species of DNA in said sample.

24. The method of claim 23, further comprising the step:

comparing the amount of said species of DNA detected with a threshold amount and/or reference distribution of amounts, wherein: (x) an increase in, or outlying of, the amount of said species of DNA indicates an increased risk of the individual suffering from or developing a medical condition; and/or (y) an amount of said species of DNA in excess to said threshold, or outlying from said distribution, indicates that a diagnosis for an abnormality in the said species of DNA present in said sample may be performed on a separate aliquot of DNA of said sample.

25. The method of claim 1, wherein two of said DMRs are located on separate chromosomes.

26. The method of claim 1, wherein the other region is located upstream or downstream of one of said DMRs within a distance selected from the group consisting of: between about 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, and 2 kb to 500 bp.

27. The method of claim 1, wherein said reagent that differentially modifies methylated and non-methylated DNA comprises at least one methylation sensitive restriction enzyme.

28. The method of claim 1, wherein:

said essentially simultaneous quantitative detection of said two or more DMRs comprises multiplex real-time probe-based quantitative PCR using at least two labelled probes, each of which is specific for one of said DMRs; and said essentially simultaneous quantitative detection of said at least two other regions comprises multiplex real-time probe-based quantitative PCR using at least two labelled probes, each of which is specific for one of said other regions.

29. A computer program product comprising: a non-transitory computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a given type may be performed, said operation comprising the steps of:

receiving: (i) a first signal representing the essentially simultaneous quantitative detection of methylation at two or more differentially methylated regions (DMRs) in a species of DNA originating from cells of a given type in a sample from an individual comprising a species of DNA originating from cells of a given type in admixture with differently methylated DNA not originating from cells of said type, wherein the sample is treated with a reagent that differentially modifies methylated and non-methylated DNA and wherein detection of said two or more DMRs is made using the same detectable label; and (ii) a second signal representing the essentially simultaneous quantitative detection of total DNA in the sample using at least two other regions of DNA that are not differently methylated between said species of DNA and the DNA not originating from cells of said type, wherein the number of said at least two other regions is the same as the number of DMRs, and wherein one of said other regions is located between about 20 bp and about 20 kb upstream or downstream of one of the DMRs and wherein another of said other regions is located between about 20 bp and about 20 kb upstream or downstream of another of said DMRs; wherein said detection of said other regions is made using the same detectable label, and wherein said detectable label for the other regions is different from the detectable label used to detect the DMRs, and wherein said detections of (i) and (ii) are made using the same aliquot of DNA of said sample and in the same reaction/detection vessel and effectively simultaneously for such DMRs and other regions;

comparing the first signal with the second signal to thereby obtain a parameter, wherein the parameter represents an enhanced quantitative amount of said species of methylated DNA in the sample, wherein said enhanced quantitative amount is more accurate or precise than a quantitative amount of said species of methylated DNA in the sample obtained using an other region(s) located more than 20 kb upstream or downstream of a DMR(s), wherein each DMR and each other region is detected with a different detectable label and/or in a separate reaction/vessel;

comparing the parameter to a threshold amount and/or reference distribution of amounts; and based on such comparison, determining a classification of whether, respectively, (x) an increased risk of an individual suffering from or developing a medical condition exists; and/or (y) a diagnosis for an anomaly in the species of DNA originating from cells of the given type may be performed.

30. The computer program product of claim 29, wherein one of said other regions is located upstream or downstream of one of said DMRs within a distance selected from the group consisting of: between about 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, and 2 kb to 500 bp; and/or another of said other region is located upstream or downstream of another of said DMRs within a distance selected from the group consisting of: between about 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, and 2 kb to 500 bp.

31. The computer program product of claim 29, wherein said species of DNA originates from cells of a fetus and/or the placenta of a fetus and said sample is from a pregnant female, and wherein said species is circulating cell-free DNA and said sample is a plasma or serum sample.

32. The computer program product of claim 31, wherein a classification is determined of whether there is an increased risk of said pregnant female suffering from or developing a pregnancy-associated condition.

33. The computer program product of claim 32, wherein said pregnancy-associated condition is preeclampsia.

34. The computer program product of claim 31, wherein a classification is determined of whether a prenatal diagnosis may be performed for an anomaly in the DNA originating from cells of a fetus and/or the placenta of a fetus.

35. The computer program product of claim 34, wherein said anomaly in the DNA originating from cells of a fetus and/or the placenta of a fetus is a chromosomal trisomy.

36. The computer program product of claim 31, wherein one or both of said two or more DMRs is/are located in SEQ ID NOs: 15-199.

37. The computer program product of claim 31, wherein one or both of said two or more DMRs is/are located in SEQ ID NOs: 74-147.

38. The computer program product of claim 29, wherein said two or more DMRs are located on separate chromosomes.

39. The computer program product of claim 29, wherein said reagent that differentially modifies methylated and non-methylated DNA comprises at least one methylation sensitive restriction enzyme.

40. The computer program product of claim 29, wherein:

said essentially simultaneous quantitative detection of said two or more DMRs comprises multiplex real-time probe-based quantitative PCR using at least two labelled probes, each of which is specific for one of said DMRs; and said essentially simultaneous quantitative detection of said at least two other regions comprises multiplex real-time probe-based quantitative PCR using at least two labelled probes, each of which is specific for one of said other regions.

* * * * *